United States Patent
Wei et al.

(10) Patent No.: US 9,394,329 B2
(45) Date of Patent: Jul. 19, 2016

(54) GLUCOPYRANOSYL DERIVATIVES AND THEIR USES IN MEDICINE

(71) Applicant: Sunshine Lake Pharma Co., Ltd., Dongguan, Guangdong (CN)

(72) Inventors: Yonggang Wei, Dongguan (CN); Jiaping Wen, Dongguan (CN); Guozhi Zhu, Dongguan (CN); Yonghua Lu, Dongguan (CN); Heran Wang, Guangdong (CN); Yincai Wang, Dongguan (CN); Mingyun Yuan, Dongguan (CN); Zheng Gu, Dongguan (CN); Wuyong Wu, Dongguan (CN); Panpan Kang, Dongguan (CN); Zongyuan Zhang, Dongguan (CN); Gang Chen, Dongguan (CN); Pengcho Tang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/435,730

(22) PCT Filed: Sep. 26, 2014

(86) PCT No.: PCT/CN2014/087587
§ 371 (c)(1),
(2) Date: Apr. 14, 2015

(87) PCT Pub. No.: WO2015/043511
PCT Pub. Date: Apr. 2, 2015

(65) Prior Publication Data
US 2015/0266916 A1    Sep. 24, 2015

(30) Foreign Application Priority Data

Sep. 27, 2013 (CN) .......................... 2013 1 0450401

(51) Int. Cl.
| | |
|---|---|
| C07H 15/00 | (2006.01) |
| C07H 15/04 | (2006.01) |
| C07H 9/04 | (2006.01) |
| C07H 7/04 | (2006.01) |
| A61K 45/06 | (2006.01) |
| A61K 31/7034 | (2006.01) |
| A61K 31/7048 | (2006.01) |

(52) U.S. Cl.
CPC ............ *C07H 15/00* (2013.01); *A61K 31/7034* (2013.01); *A61K 31/7048* (2013.01); *A61K 45/06* (2013.01); *C07H 7/04* (2013.01); *C07H 9/04* (2013.01); *C07H 15/04* (2013.01)

(58) Field of Classification Search
None
See application file for complete search history.

(56) References Cited

U.S. PATENT DOCUMENTS

| | | | |
|---|---|---|---|
| 6,414,126 B1 | 7/2002 | Ellsworth et al. | |
| 6,515,117 B2 | 2/2003 | Ellsworth et al. | |
| 7,393,836 B2 | 7/2008 | Eckhardt et al. | |
| 7,662,790 B2 | 2/2010 | Himmelsbach et al. | |
| 7,683,160 B2 | 3/2010 | Eckhardt et al. | |
| 7,772,378 B2 | 8/2010 | Himmelsbach et al. | |
| 7,838,499 B2 | 11/2010 | Chen et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 8,026,347 B2 | 9/2011 | Goodwin et al. | |
| 8,039,441 B2 | 10/2011 | Himmelsbach et al. | |
| 8,080,580 B2 * | 12/2011 | Mascitti ............... | C07D 493/08 514/456 |
| 8,106,021 B2 | 1/2012 | Chen et al. | |
| 8,293,878 B2 | 10/2012 | Goodwin et al. | |
| 8,394,772 B2 | 3/2013 | Bebernitz et al. | |
| 8,609,622 B2 | 12/2013 | Yang et al. | |
| 8,614,195 B2 | 12/2013 | Bebernitz et al. | |
| 8,669,380 B2 | 3/2014 | Mascitti et al. | |

(Continued)

FOREIGN PATENT DOCUMENTS

| | | |
|---|---|---|
| CN | 103570657 A | 2/2014 |
| CN | 103772449 A | 5/2014 |

(Continued)

OTHER PUBLICATIONS

Wolff, Manfred E. "Burger's Medicinal Chemistry, 5ed, Part I", John Wiley & Sons, 1995, pp. 975-977.*

(Continued)

*Primary Examiner* — Traviss C McIntosh, III
(74) *Attorney, Agent, or Firm* — Kam W. Law; Squire Patton Boggs (US) LLP

(57) ABSTRACT

Disclosed are glucopyranosyl derivatives used as sodium dependent glucose cotransporters (SGLTs) inhibitors, intermediates or preparation processes thereof, and pharmaceutical uses thereof, especially glucopyranosyl derivatives represented by Formula (I), or pharmaceutically acceptable salts or all stereoisomers thereof, pharmaceutical compositions containing these derivatives and their uses for treatment of diabetes and diabetes-related diseases.

22 Claims, No Drawings

(56) References Cited

U.S. PATENT DOCUMENTS

| | | | |
|---|---|---|---|
| 8,697,658 | B2 | 4/2014 | Lee et al. |
| 8,722,633 | B2 | 5/2014 | Bebernitz et al. |
| 8,802,637 | B2 | 8/2014 | Chen et al. |
| 8,957,033 | B2 | 2/2015 | Wang et al. |
| 2003/0114390 | A1 | 6/2003 | Washburn et al. |
| 2006/0035841 | A1 | 2/2006 | Eckhardt et al. |
| 2007/0004648 | A1 | 1/2007 | Himmelsbach et al. |
| 2010/0167988 | A1 | 7/2010 | Gant et al. |
| 2011/0059910 | A1 | 3/2011 | Frick et al. |
| 2011/0230403 | A1 | 9/2011 | Palle et al. |
| 2011/0237789 | A1 | 9/2011 | Weber et al. |
| 2011/0269700 | A1 | 11/2011 | Palle et al. |
| 2013/0018005 | A1 | 1/2013 | Bebernitz |
| 2013/0023486 | A1 | 1/2013 | Zhao et al. |
| 2013/0130997 | A1* | 5/2013 | Yang .................. C07H 7/04 514/25 |
| 2013/0165645 | A1 | 6/2013 | Kakinuma et al. |
| 2013/0225487 | A1 | 8/2013 | Mascitti |
| 2013/0324464 | A1 | 12/2013 | Xu et al. |
| 2014/0128331 | A1 | 5/2014 | Wu |
| 2014/0228303 | A1 | 8/2014 | Jain et al. |
| 2014/0256657 | A1 | 9/2014 | Gaul et al. |

FOREIGN PATENT DOCUMENTS

| | | | |
|---|---|---|---|
| WO | 2012003811 | A1 | 1/2012 |
| WO | 2012023582 | A1 | 2/2012 |
| WO | 2012025857 | A1 | 3/2012 |
| WO | 2012119550 | A1 | 9/2012 |
| WO | 2013038429 | A2 | 3/2013 |
| WO | 2013044608 | A1 | 4/2013 |
| WO | 2013178064 | A1 | 12/2013 |
| WO | 2014094544 | A1 | 6/2014 |
| WO | 2014146606 | A1 | 9/2014 |
| WO | 2014187365 | A1 | 11/2014 |
| WO | 2014206349 | A1 | 12/2014 |
| WO | 2015027963 | A1 | 3/2015 |
| WO | 2015032272 | A1 | 3/2015 |

OTHER PUBLICATIONS

Banker, G.S. et al, "Modern Pharmaceutics, 3ed.", Marcel Dekker, New York, 1996, p. 596.*
Adachi et al., Metabolism, vol. 49, No. 8, 2000, 990-995.*
Vincent et al., Discovery of a Clinical Candidate from the Structurally Unique Dioxa-bicyclo[3.2.1]octane Class of Sodium-Dependent Glucose Cotransporter 2 Inhibitors, Journal of Medicinal Chemistry, 2011, vol. 54, Issue 8, p. 2952-2960.
Eng. translation of the abstract of CN103570657.
Eng. translation of the abstract of CN103772449.
Vincent et al., Stereoselective Synthesis of a Dioxa-bicyclo[3.2.1]octane SGLT2 Inhibitor, Organic Letters, 2010, vol. 12, Issue 13, p. 2940-2943.
International Search Report of PCT/CN2014/087587.
Written Opinion of PCT/CN2014/087587.

* cited by examiner

GLUCOPYRANOSYL DERIVATIVES AND THEIR USES IN MEDICINE

CROSS-REFERENCE TO RELATED APPLICATIONS

This is a U.S. national stage application of the International Patent Application No. PCT/CN2014/087587, filed Sep. 26, 2014, which claims priority to Chinese Patent Application No. 201310450401.2, filed Sep. 27, 2013, both of which are incorporated herein by reference in their entirety.

FIELD OF THE INVENTION

This present invention relates to glucopyranosyl derivatives as sodium dependent glucose cotransporters (SGLTs) inhibitors, intermediates or preparation processes thereof, and pharmaceutical uses thereof, especially glucopyranosyl derivatives represented by Formula (I), or pharmaceutically acceptable salts or all stereoisomers thereof, pharmaceutical composition containing these derivatives and their uses for treating diabetes and diabetes-related diseases.

BACKGROUND OF THE INVENTION

Diabetes mellitus is a common chronic disease, characterized by hyperglycemia. The onset of diabetes associates with insulin resistance in peripheral tissue, reduction of insulin in vivo and increase of gluconeogenesis in liver. When the disease cannot be controlled effectively through diet and exercise, insulin or oral hypoglycemic drugs for treatment are needed. At present, hypoglycemic drugs comprise biguanides, sulfonylureas, insulin sensitizers, glinides, α-glucosidase inhibitors and DPP—IV inhibitors, etc. However, these current hypoglycemic drugs have shortcomings Biguanides can cause lactic acidosis. Sulfonylureas can result in severe hypoglycemia. Insulin sensitizers can lead to edema, heart failure and weight gain. α-Glucosidase inhibitors can cause abdominal bloating and diarrhea. DPP—IV inhibitors need to combine with metformin to achieve the desired effect of hypoglycemia. Therefore, there is an urgent need to develop novel, safer, and more effective hypoglycemic agents.

It has been found by research that glucose transporter proteins are a class of carrier proteins embedded in the cell membrane for transporting glucose. Glucose must be in virtue of glucose transporter protein to cross lipid bilayer structure of cell membranes. Glucose transporter proteins are divided into two categories. The first category includes sodium-dependent glucose transporters (SGLTs), and the other category includes glucose transporters (GLUTs). Two major family members of SGLTs are SGLT-1 and SGLT-2. SGLT-1 is mainly distributed in small intestine, kidney, heart and windpipe, predominantly expressed in the intestinal brush border and the distal S3 segment of the renal proximal tubule, and a few expressed in heart and windpipe, and transports glucose and galactose with a sodium to glucose ratio of 2:1. While SGLT-2 is mainly distributed in kidney, predominantly expressed in the distal S1 segment of the renal proximal tubule, and transports glucose with a sodium to glucose ratio of 1:1. In biological bodies, glucose is transported by SGLT through active transport against a concentration gradient with simultaneous energy consumption. While glucose is transported by GLUTs through facilitated diffusion along a concentration gradient without energy consumption in the transport process. Research indicates that normally plasma glucose is filtered in the kidney glomeruli in which 90% of glucose in the early S1 segment of the renal tubule is actively transported to epithelial cells by SGLT-2 and 10% of glucose in the distal S3 segment of the renal tubule is actively transported to epithelial cells by SGLT-1, and then transported to peripheral capillary network by GLUT of epithelial basement membrane accomplishing reabsorption of glucose by renal tubules. Hence, SGLTs is the first stage in regulation of glucose metabolism in cells, and an ideal target for treating diabetes effectively. It has been found by research that the patients with SGLT-2 impairment would excrete large amounts of urine glucose. This provides the factual basis of treating diabetes by reducing glucose uptake through inhibiting SGLT-2 activity. Therefore, inhibiting activity of SGLTs transport protein could block reabsorption of glucose in renal tubules and increase excretion of glucose in urine to normalize the plasma glucose concentration and further control the diabetes and diabetic complications. Inhibiting SGLTs would not influence the normal anti-regulatory mechanism of glucose, which may cause the risk of hypoglycemia. Meanwhile, lowering blood glucose through an increase of renal glucose excretion could promote weight loss in obese patients. It has also been found by research that the mechanism of action of SGLTs inhibitors is independent of pancreatic β cell dysfunction or the degree of insulin resistance. Therefore, the efficacy of SGLTs inhibitors will not decrease with the severe insulin resistance or β-cell failure. SGLTs inhibitors could be used alone or in combination with other hypoglycemic agents. Therefore, SGLTs inhibitors are ideal and novel hypoglycemic agents.

In addition, it has also been found by research that SGLTs inhibitors can be used for treating diabetes-related complications. Such as retinopathy, neuropathy, kidney disease, insulin resistance caused by glucose metabolic disorder, hyperinsulinemia, hyperlipidemia, obesity, and so on. Meanwhile, SGLTs inhibitors also be used in combination with current treatment regimens, such as sulphonamides, thiazolidinedione, metformin, and insulin, etc, which can reduce the dose without impacting on the effectiveness of the medicine, and thereby avoid or educe side effects, and improve patient compliance.

In summary, SGLTs inhibitors, particularly SGLT-2 protein inhibitors, have a good prospect as novel antidiabetic drugs.

SUMMARY OF THE INVENTION

In one aspect, provided herein is a compound having Formula (I) or a stereoisomer, a geometric isomer, a tautomer, a racemate, an N-oxide, a hydrate, a solvate, a metabolite, a pharmaceutically acceptable salt or a prodrug thereof,

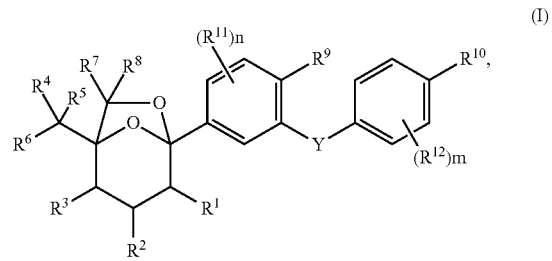

wherein each of $R^1$, $R^2$ and $R^3$ is —OH;
Wherein $R^6$ is —$OR^{6a}$ or —$OC(=O)R^{6b}$; and
each of $R^4$ and $R^5$ is independently —H, alkyl, alkylamino, alkynyl, alkenyl, cyano, cycloalkyl or heterocyclyl, and wherein optionally each of the alkyl, alkylamino, alkynyl, alkenyl, cycloalkyl and heterocyclyl is substituted by one or more substituents independently selected from —H, —F, —Cl, —Br, —I, hydroxy, cyano, amino, alkynyl, alkenyl, carboxy, mercapto, alkylamino, —SR$^{13}$, —C(=O)R$^{13}$, —C(=O)OR$^{13}$, —OC(=O)R$^{13}$, —OC(=O)OR$^{13}$, —NHC(=O)R$^{13}$, —C(=O)NHR$^{13}$, trifluoromethyl, —S(=O)$_2$R$^{13}$, —S(=O)R$^{13}$, aryl, heteroaryl, arylalkyl, heteroarylalkyl, arylalkoxy and heteroarylalkoxy, or R$^4$ and R$^5$, together with the carbon atom to which they are attached, form a ring A, wherein the ring A is a saturated or unsaturated, 3- to 8-membered ring, and wherein the ring A optionally contains one or more atoms or atomic groups independently selected from —NH—, —O—, —S—, —C(=O)— and —S(=O)—, and wherein the ring A is optionally substituted by one or more substituents independently selected from —H, —F, —Cl, —Br and —I; or wherein R$^4$ is —H; and R$^5$ and R$^6$, together with the carbon atom to which they are attached, form a ring B, wherein the ring B is a saturated or unsaturated, 3- to 8-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;

wherein R$^{6a}$ is —H, alkyl, cycloalkyl, heterocyclyl, aryl, heteroaryl, arylalkyl or heteroarylalkyl, and wherein optionally each of the alkyl, cycloalkyl, heterocyclyl, aryl, heteroaryl, arylalkyl and heteroarylalkyl is substituted by one or more substituents independently selected from —H, —F, —Cl, —Br, —I, hydroxy, cyano, amino, alkynyl, alkenyl, carboxy, mercapto, trifluoromethyl, —SR$^{14}$, —C(=O)R$^{14}$, —C(=O)OR$^{14}$, —OC(=O)R$^{14}$, —OC(=O)OR$^{14}$, —NHC(=O)R$^{14}$, —S(=O)$_2$R$^{14}$ and —S(=O)R$^{14}$;

wherein R$^{6b}$ is alkyl, alkoxy, arylalkoxy or heteroarylalkoxy, and wherein optionally each of the alkoxy, arylalkoxy or heteroarylalkoxy is substituted by one or more substituents independently selected from —H, —F, —Cl, —Br, —I, hydroxy, cyano, amino, alkynyl, alkenyl, carboxy and mercapto;

wherein each of R$^7$ and R$^8$ is independently —H, alkyl, alkylamino, alkynyl or alkenyl;

wherein at least one of R$^4$, R$^5$, R$^7$ and R$^8$ is not H;

wherein R$^9$ is —H, —F, —Cl, —Br, —I or C$_{1-6}$ alkyl;

wherein R$^{10}$ is C$_{1-6}$ alkoxy or C$_{1-6}$ haloalkoxy;

wherein Y is methylene, which is optionally substituted by one or more substituents independently selected from —H, —F, —Cl, —Br and hydroxy;

wherein each R$^{11}$ is independently —H, —F, —Cl, —Br, —I or C$_{1-6}$ alkoxy;

wherein n is 1, 2 or 3;

wherein each R$^{12}$ is independently —H, —F, —Cl or —I;

wherein m is 1, 2, 3 or 4; and wherein each R$^{13}$ and R$^{14}$ is independently —H, alkyl, aryl, heteroaryl, cycloalkyl or heterocyclyl, and wherein optionally each of the alkyl, aryl, heteroaryl, cycloalkyl and heterocyclyl is substituted by one or more substituents independently selected from —H, —F, —Cl, —Br, —I, hydroxy, amino, cyano, alkyl, alkoxy, alkylamino, hydroxyalkyl, cycloalkoxy, aryloxy, heteroaryloxy, heterocycloalkoxy, trifluoromethyl, carboxy and —C(=O)O-alkyl.

In some embodiments, provided herein is a compound having Formula (II), or a stereoisomer, a geometric isomer, a tautomer, a racemate, an N-oxide, a hydrate, a solvate, a metabolite, a pharmaceutically acceptable salt or a prodrug thereof,

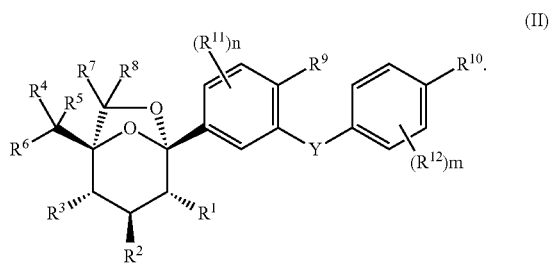

(II)

In some embodiments, provided herein is a compound having Formula (I) or (II), wherein each of R$^4$ and R$^5$ is independently —H, C$_{1-6}$ alkyl, C$_{1-4}$ alkylamino, C$_{2-4}$ alkynyl, C$_{2-4}$ alkenyl, cyano, C$_{3-6}$ cycloalkyl or C$_{2-6}$ heterocyclyl, and wherein optionally each of the C$_{1-6}$ alkyl, C$_{1-4}$ alkylamino, C$_{2-4}$ alkynyl, C$_{2-4}$ alkenyl, C$_{3-6}$ cycloalkyl and C$_{2-6}$ heterocyclyl is substituted by one or more substituents independently selected from —H, —F, —Cl, —Br, —I, hydroxy, cyano, amino, C$_{2-4}$ alkynyl, C$_{2-4}$ alkenyl, carboxy, mercapto, C$_{1-2}$ alkylamino, —SR$^{13}$, —C(=O)R$^{13}$, —C(=O)OR$^{13}$, —OC(=O)R$^{13}$, —OC(=O)OR$^{13}$, —NHC(=O)R$^{13}$, —C(=O)NHR$^{13}$, trifluoromethyl, —S(=O)$_2$R$^{13}$, —S(=O)R$^{13}$, C$_{6-10}$ aryl, C$_{1-9}$ heteroaryl, C$_{6-10}$ aryl-C$_{1-6}$-alkyl, C$_{1-9}$ heteroaryl-C$_{1-6}$-alkyl, C$_{6-10}$ aryl-C$_{1-6}$-alkoxy and C$_{1-9}$ heteroaryl-C$_{1-6}$-alkoxy, or R$^4$ and R$^5$, together with the carbon atom to which they are attached, form a ring A, wherein the ring A is a saturated or unsaturated, 3- to 6-membered ring, and wherein the ring A optionally contains one or more atoms or atomic groups independently selected from —NH—, —O—, —S—, —C(=O)— and —S(=O)—, and wherein the ring A is optionally substituted by one or more substituents independently selected from —H, —F, —Cl, —Br and —I.

In other embodiments, provided herein is a compound having Formula (I) or (II), wherein each of R$^4$ and R$^5$ is independently —H, methyl, ethyl, propyl, allyl, cyano, aminomethyl, methylamino, methylaminomethyl, dimethylaminomethyl, ethylamino, ethynyl, 1-propinyl, 2-propinyl, hydroxymethyl, chloromethyl, cyclopropyl or cyclobutyl, or R$^4$ and R$^5$, together with the carbon atom to which they are attached, form a ring A, wherein the ring A is a saturated or unsaturated, 3- to 4-membered ring, and wherein the ring A optionally contains one or more atoms or atomic groups selected from —NH—, —O—, —S—, —C(=O)— and —S(=O)—, and wherein the ring A is optionally substituted by one or more substituents independently selected from —H, —F, —Cl, —Br and —I.

In some embodiments, provided herein is a compound having Formula (I) or (II), wherein R$^6$ is —OR$^{6a}$ or —OC(=O)R$^{6b}$, or R$^5$ and R$^6$, together with the carbon atom to which they are attached, form a ring B, meanwhile R$^4$ is —H, wherein the ring B is a saturated or unsaturated, 3- to 6-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;

wherein R$^{6a}$ is —H, C$_{1-6}$ alkyl, C$_{3-6}$ cycloalkyl, C$_{2-6}$ heterocyclyl, C$_{6-10}$ aryl, C$_{1-9}$ heteroaryl, C$_{6-10}$ aryl-C$_{1-6}$-alkyl or C$_{1-9}$ heteroaryl-C$_{1-6}$-alkyl, and wherein optionally each of the C$_{1-6}$ alkyl, C$_{3-6}$ cycloalkyl, C$_{2-6}$ heterocyclyl, C$_{6-10}$ aryl, C$_{1-9}$ heteroaryl, C$_{6-10}$ aryl-C$_{1-6}$-alkyl and C$_{1-9}$ heteroaryl-C$_{1-6}$- alkyl is substituted by one or more substituents independently selected from —H, —F, —Cl, —Br, —I, hydroxy, cyano, amino, $C_2$ alkynyl, $C_{2-4}$ alkenyl, carboxy, mercapto, trifluoromethyl, —$SR^{14}$, —$C(=O)R^{14}$, —$C(=O)OR^{14}$, —$OC(=O)R^{14}$, —$OC(=O)OR^{14}$, —$NHC(=O)R^{14}$, —$S(=O)_2R^{14}$ and —$S(=O)R^{14}$; and wherein $R^{6b}$ is $C_{1-6}$ alkyl, $C_{1-6}$ alkoxy, $C_{6-10}$ aryl-$C_{1-6}$-alkoxy or $C_{1-9}$ heteroaryl-$C_{1-6}$-alkoxy, and wherein optionally each of the $C_{1-6}$ alkoxy, $C_{6-10}$ aryl-$C_{1-6}$-alkoxy and $C_{1-9}$ heteroaryl-$C_{1-6}$-alkoxy is substituted by one or more substituents independently selected from —H, —F, —Cl, —Br, —I, hydroxy, cyano, amino, $C_2$ alkynyl, $C_{2-4}$ alkenyl, carboxy and mercapto.

In other embodiments, provided herein is a compound having Formula (I) or (II), wherein $R^6$ is —$OR^{6a}$ or —$OC(=O)R^{6b}$, or wherein $R^4$ is —H, and $R^5$ and $R^6$, together with the carbon atom to which they are attached, form a ring B, wherein the ring B is a saturated or unsaturated, 3- to 6-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;

wherein $R^{6a}$ is —H, methyl, ethyl, iso-propyl, tert-butyl, chloromethyl or dichloromethyl; and wherein $R^{6b}$ is methyl, ethyl, iso-propyl, tert-butyl, methoxy, ethoxy, iso-propoxy or tert-butoxy.

In some embodiments, provided herein is a compound having Formula (I) or (II), wherein each of $R^7$ and $R^8$ is independently —H, $C_{1-4}$ alkyl, $C_{1-4}$ alkylamino, $C_{2-4}$ alkynyl or $C_{2-4}$ alkenyl.

In some embodiments, provided herein is a compound having Formula (I) or (II), wherein each of $R^7$ and $R^8$ is independently —H, methyl, ethyl or isopropyl.

In some embodiments, provided herein is a compound having Formula (I) or (II), wherein $R^{10}$ is methoxy, ethoxy, isopropoxy, difluoromethoxy, trifluoromethoxy, 2,2-difluoroethoxy, 2,2,2-trifluoroethoxy or perfluoroethoxy.

In some embodiments, provided herein is a compound having Formula (I) or (II), wherein each $R^{13}$ and $R^{14}$ is independently —H, $C_{1-6}$ alkyl, $C_{6-10}$ aryl, $C_{1-9}$ heteroaryl, $C_{3-8}$ cycloalkyl or $C_{2-8}$ heterocyclyl, and wherein optionally each of the $C_{1-6}$ alkyl, $C_{6-10}$ aryl, $C_{1-9}$ heteroaryl, $C_{3-8}$ cycloalkyl and $C_{2-8}$ heterocyclyl is substituted by one or more substituents independently selected from —H, —F, —Cl, —Br, —I, hydroxy, amino, cyano, $C_{1-4}$ alkyl, $C_{1-4}$ alkoxy, $C_{1-6}$ alkylamino, $C_{1-6}$ hydroxyalkyl, $C_{3-6}$ cycloalkoxy, $C_{6-10}$ aryloxy, $C_{1-9}$ heteroaryloxy, $C_{2-8}$ heterocyclyloxy, trifluoromethyl, carboxy and —C(=O)O—$C_{1-4}$ alkyl.

In some embodiments, provided herein is a compound having one of the following structures, or a stereoisomer, a geometric isomer, a tautomer, a racemate, an N-oxide, a hydrate, a solvate, a metabolite, a pharmaceutically acceptable salt or a prodrug thereof, but not limited to these compounds:

| Example No. | Structure | Name |
|---|---|---|
| Example 1 | 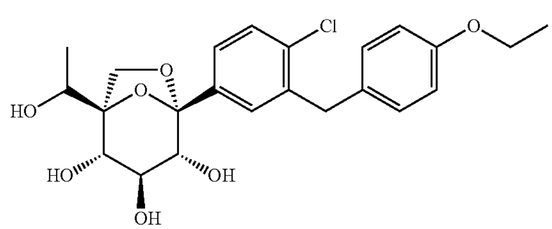 [SMILES: CCOc1ccc(Cc2cc([C@]34OC[C@](C(C)O)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(1-hydroxyethyl)-6,8-dioxabicyclo[3.2.1]octane-2,3,4-triol |
| Example 2 | 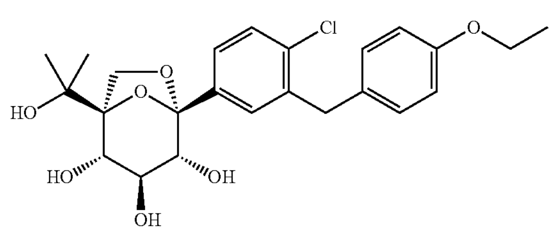 [SMILES: CCOc1ccc(Cc2cc([C@]34OC[C@](C(C)(C)O)(O3)[C@@H](O)[C@H](O)[C@H]4O)ccc2Cl)cc1] | (1S,2S,3S,4R,5S)-5-(4-chloro-3-(4-ethoxybenzyl)phenyl)-1-(2-hydroxypropan-2-yl)-6,8-dioxabicyclo[3.2.1]octane-2,3,4-triol |
| Example 3 | 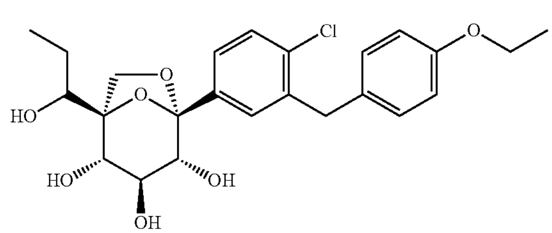 [SMILES: CCOc1ccc(Cc2cc([C@]34OC[C@](C(O)CC)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(1-hydroxypropyl)-6,8-dioxabicyclo[3.2.1]octane-2,3,4-triol |

-continued

| Example No. | Structure | Name |
|---|---|---|
| Example 4 | 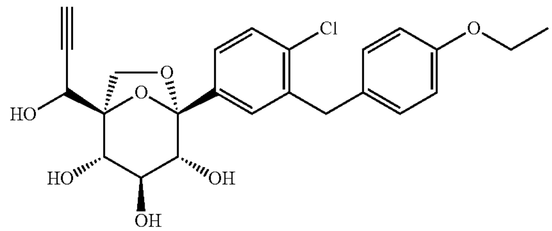 [SMILES: C#CC(O)[C@@]12CO[C@@](c3ccc(Cl)c(Cc4ccc(OCC)cc4)c3)(O1)[C@H](O)[C@@H](O)[C@@H]2O] | (1R,2S,3S,4R,5S)-5-(4-chloro-3-(4-ethoxybenzyl)phenyl)-1-(1-hydroxyprop-2-yn-1-yl)-6,8-dioxabicyclo[3.2.1]octane-2,3,4-triol |
| Example 5 | 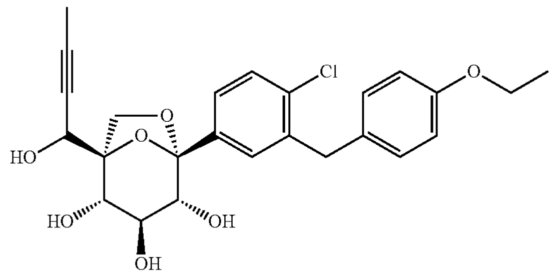 [SMILES: CC#CC(O)[C@@]12CO[C@@](c3ccc(Cl)c(Cc4ccc(OCC)cc4)c3)(O1)[C@H](O)[C@@H](O)[C@@H]2O] | (1R,2S,3S,4R,5S)-5-(4-chloro-3-(4-ethoxybenzyl)phenyl)-1-(1-hydroxy-but-2-yn-1-yl)-6,8-dioxabiyclo[3.2.1]octane-2,3,4-triol |
| Example 6 | 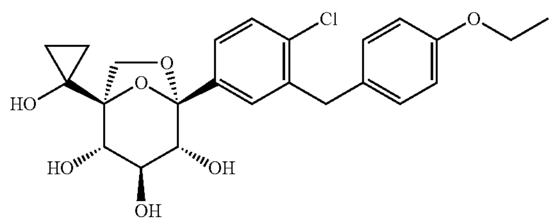 [SMILES: CCOc1ccc(Cc2cc([C@]34OC[C@](C5(O)CC5)(O3)[C@@H](O)[C@H](O)[C@H]4O)ccc2Cl)cc1] | (1S,2S,3S,4R,5S)-5-(4-chloro-3-(4-ethoxybenzyl)phenyl)-1-(1-hydroxy-cyclopropyl)-6,8-dioxabicyclo[3.2.1]octane-2,3,4-triol |
| Example 7 | 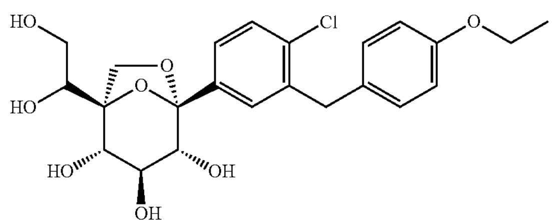 [SMILES: CCOc1ccc(Cc2cc([C@]34OC[C@](C(O)CO)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(1,2-dihydroxyethyl)-6,8-dioxabicyclo[3.2.1]octane-2,3,4-triol |
| Example 8 | 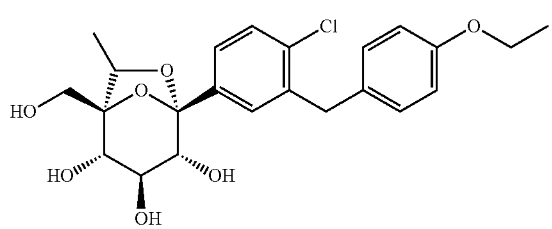 [SMILES: CCOc1ccc(Cc2cc([C@]34OC(C)[C@](CO)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(hydroxymethyl)-7-methyl-6,8-dioxabicyclo[3.2.1]octane-2,3,4-triol |
| Example 9 | 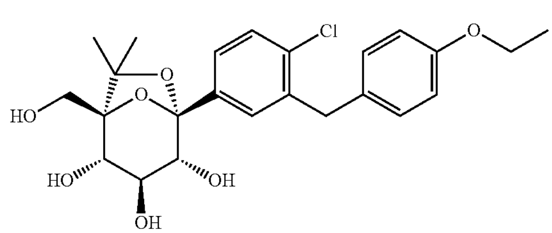 [SMILES: CCOc1ccc(Cc2cc([C@]34OC(C)(C)[C@](CO)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(hydroxymethyl)-7,7-dimethyl-6,8-dioxabicyclo[3.2.1]octane-2,3,4-triol |

-continued

| Example No. | Structure | Name |
|---|---|---|
| Example 10 | 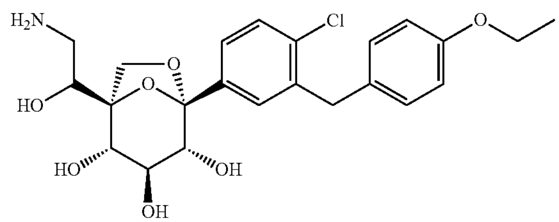 [SMILES: CCOc1ccc(Cc2cc([C@]34OC[C@](C(O)CN)(O3)[C@@H](O)[C@H](O)[C@H]4O)ccc2Cl)cc1] | (1R,2S,3S,4R,5S)-1-(2-amino-1-hydroxyethyl)-5-(4-chloro-3-(4-ethoxybenzyl)phenyl)-6,8-dioxabicyclo[3.2.1]octane-2,3,4-triol |
| Example 11 | 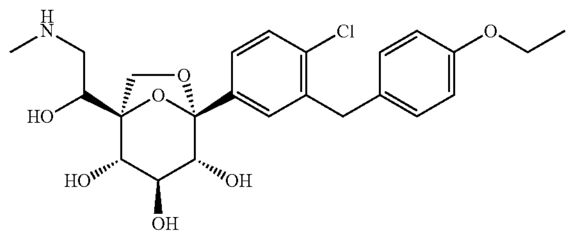 [SMILES: CCOc1ccc(Cc2cc([C@]34OC[C@](C(O)CNC)(O3)[C@@H](O)[C@H](O)[C@H]4O)ccc2Cl)cc1] | (1R,2S,3S,4R,5S)-5-(4-chloro-3-(4-ethoxybenzyl)phenyl)-1-(1-hydroxy-2-(methylamino)ethyl)-6,8-dioxabicyclo[3.2.1]octane-2,3,4-triol |
| Example 12 | 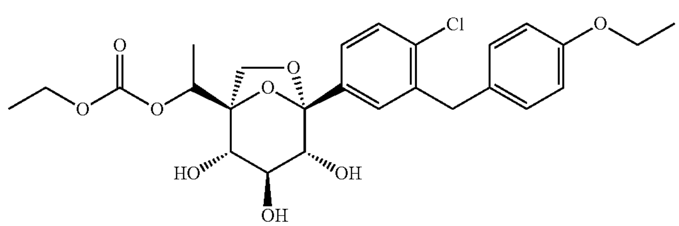 [SMILES: CCOC(=O)OC(C)[C@@]12CO[C@@](c3ccc(Cl)c(Cc4ccc(OCC)cc4)c3)(O1)[C@H](O)[C@@H](O)[C@@H]2O] | 1-((1S,2S,3S,4R,5S)-5-(4-chloro-3-(4-ethoxybenzyl)phenyl)-2,3,4-trihydroxy-6,8-dioxabicyclo[3.2.1]octan-1-yl)ethyl ethyl carbonate |
| Example 13 | 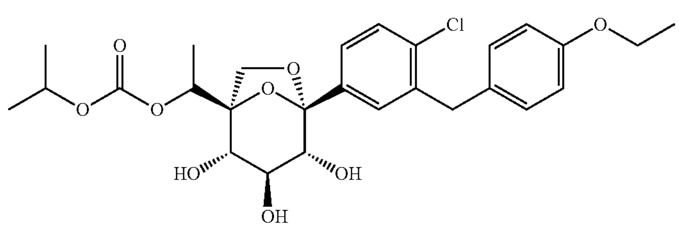 [SMILES: CCOc1ccc(Cc2cc([C@]34OC[C@](C(C)OC(=O)OC(C)C)(O3)[C@@H](O)[C@H](O)[C@H]4O)ccc2Cl)cc1] | 1-((1S,2S,3S,4R,5S)-5-(4-chloro-3-4-ethoxybenzyl)phenyl)-2,3,4-trihydroxy-6,8-dioxabicyclo[3.2.1]octan-1-yl)ethyl isopropyl carbonate |
| Example 14 | 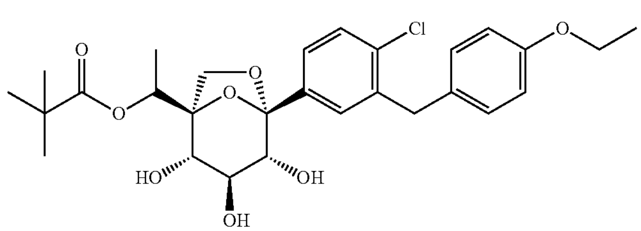 [SMILES: CCOc1ccc(Cc2cc([C@]34OC[C@](C(C)OC(=O)C(C)(C)C)(O3)[C@@H](O)[C@H](O)[C@H]4O)ccc2Cl)cc1] | 1-((1R,2S,3S,4R,5S)-5-(4-chloro-3-(4-ethoxybenzyl)phenyl)-2,3,4-trihydroxy-6,8-dioxabicyclo[3.2.1]octan-1-yl)ethyl pivalate |
| Example 15 | 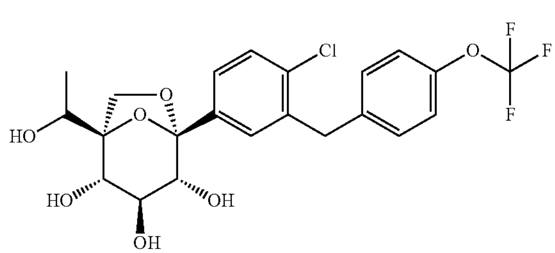 [SMILES: CC(O)[C@@]12CO[C@@](c3ccc(Cl)c(Cc4ccc(OC(F)(F)F)cc4)c3)(O1)[C@H](O)[C@@H](O)[C@@H]2O] | (1R,2S,3S,4R,5S)-5-(4-chloro-3-(4-(trifluoromethoxy)benzyl)phenyl)-1-(1-hydroxyethyl)-6,8-dioxabicyclo[3.2.1]octane-2,3,4-triol |

-continued

| Example No. | Structure | Name |
|---|---|---|
| Example 16 | 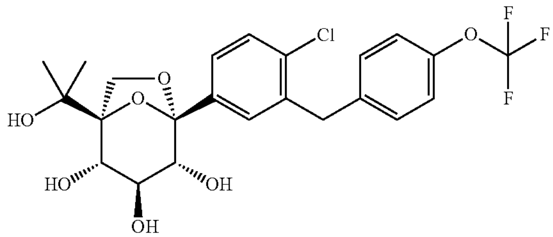 [SMILES: CC(C)(O)[C@@]12CO[C@@](c3ccc(Cl)c(Cc4ccc(OC(F)(F)F)cc4)c3)(O1)[C@H](O)[C@@H](O)[C@@H]2O] | (1S,2S,3S,4R,5S)-5-(4-chloro-3-(4-(trifluoromethoxy)benzyl)phenyl)-1-(2-hydroxypropan-2-yl)-6,8-dioxabicyclo[3.2.1]octane-2,3,4-triol |
| Example 17 | 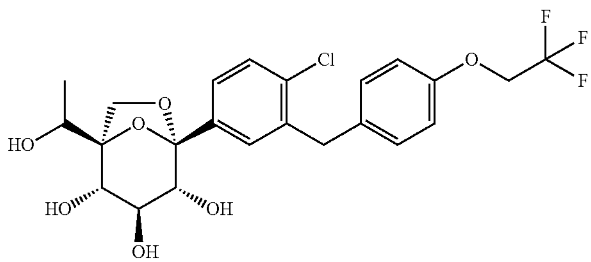 [SMILES: CC(O)[C@@]12CO[C@@](c3ccc(Cl)c(Cc4ccc(OCC(F)(F)F)cc4)c3)(O1)[C@H](O)[C@@H](O)[C@@H]2O] | (1R,2S,3S,4R,5S)-5-(4-chloro-3-(4-(2,2,2-trifluoroethoxy)benzyl)phenyl)-1-(1-hydroxyethyl)-6,8-dioxabicyclo[3.2.1]octane-2,3,4-triol |
| Example 18 | 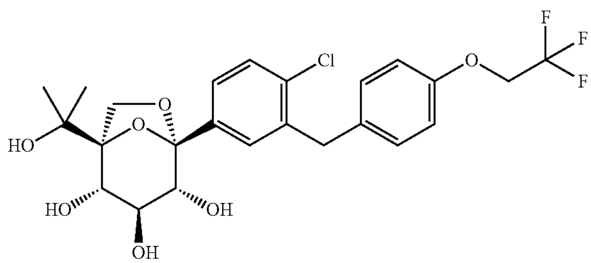 [SMILES: CC(C)(O)[C@@]12CO[C@@](c3ccc(Cl)c(Cc4ccc(OCC(F)(F)F)cc4)c3)(O1)[C@H](O)[C@@H](O)[C@@H]2O] | (1S,2S,3S,4R,5S)-5-(4-chloro-3-(4-(2,2,2-trifluoroethoxy)benzyl)phenyl)-1-(2-hydroxypropan-2-yl)-6,8-dioxabicyclo[3.2.1]octane-2,3,4-triol |
| Example 19 | 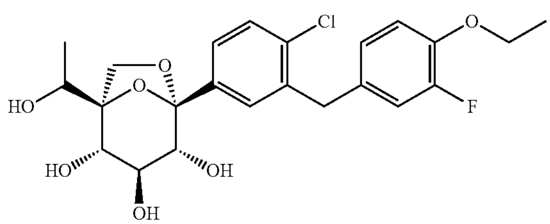 | (1R,2S,3S,4R,5S)-5-(4-chloro-3-(4-ethoxy-3-fluorobenzyl)phenyl)-1-(1-hydroxyethyl)-6,8-dioxabicyclo[3.2.1]octane-2,3,4-triol |
| Example 20 | 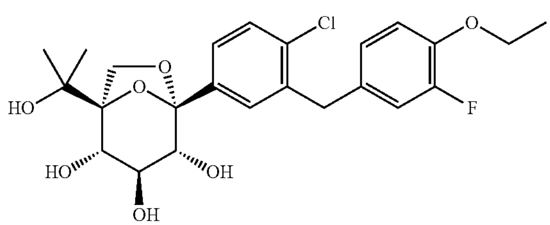 [SMILES: CCOc1ccc(Cc2cc([C@]34OC[C@](C(C)(C)O)(O3)[C@@H](O)[C@H](O)[C@H]4O)ccc2Cl)cc1F] | (1S,2S,3S,4R,5S)-5-(4-chloro-3-(4-ethoxy-3-fluorobenzyl)phenyl)-1-(2-hydroxypropan-2-yl)-6,8-dioxabicyclo[3.2.1]octane-2,3,4-triol |
| Example 21 | 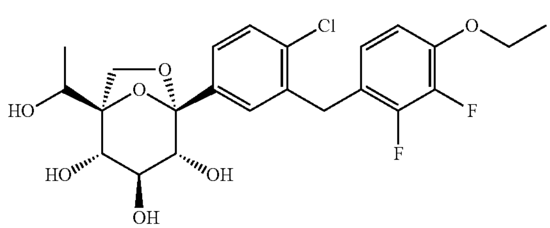 [SMILES: CCOc1ccc(Cc2cc([C@]34OC[C@](C(C)O)(O3)[C@@H](O)[C@H](O)[C@H]4O)ccc2Cl)c(F)c1F] | (1R,2S,3S,4R,5S)-5-(4-chloro-3-(4-methoxy-2,3-difluorobenzyl)phenyl)-1-(1-hydroxyethyl)-6,8-dioxabicyclo[3.2.1]octane-2,3,4-triol |

-continued

| Example No. | Structure | Name |
|---|---|---|
| Example 22 | 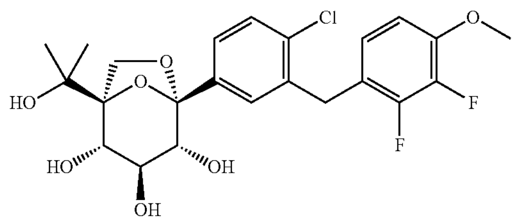 [SMILES: COc1ccc(Cc2cc([C@]34OC[C@](C(C)(C)O)(O3)[C@@H](O)[C@H](O)[C@H]4O)ccc2Cl)c(F)c1F] | (1S,2S,3S,4R,5S)-5-(4-chloro-3-(4-methoxy-2,3-difluorobenzyl)phenyl)-1-(2-hydroxypropan-2-yl)-6,8-dioxabicyclo[3.2.1]octane-2,3,4-triol |
| Example 23 | 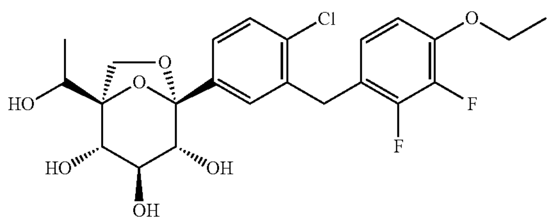 [SMILES: CCOc1ccc(Cc2cc([C@]34OC[C@](C(C)O)(O3)[C@@H](O)[C@H](O)[C@H]4O)ccc2Cl)c(F)c1F] | (1R,2S,3S,4R,5S)-5-(4-chloro-3-(4-ethoxy-2,3-difluorobenzyl)phenyl)-1-(1-hydroxyethyl)-6,8-dioxabicyclo[3.2.1]octane-2,3,4-triol |
| Example 24 | 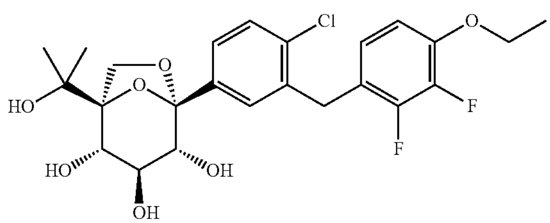 [SMILES: CCOc1ccc(Cc2cc([C@]34OC[C@](C(C)(C)O)(O3)[C@@H](O)[C@H](O)[C@H]4O)ccc2Cl)c(F)c1F] | (1S,2S,3S,4R,5S)-5-(4-chloro-3-(4-ethoxy-2,3-difluorobenzyl)phenyl)-1-(2-hydroxypropan-2-yl)-6,8-dioxabicyclo[3.2.1]octane-2,3,4-triol |
| Example 25 | 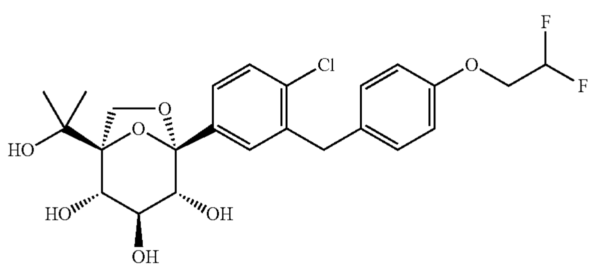 [SMILES: CC(C)(O)[C@@]12CO[C@@](c3ccc(Cl)c(Cc4ccc(OCC(F)F)cc4)c3)(O1)[C@H](O)[C@@H](O)[C@@H]2O] | (1S,2S,3S,4R,5S)-5-(4-chloro-3-(4-(2,2-difluoroethoxy)benzyl)phenyl)-1-(2-hydroxypropan-2-yl)-6,8-dioxabicyclo[3.2.1]octane-2,3,4-triol |
| Example 26 | 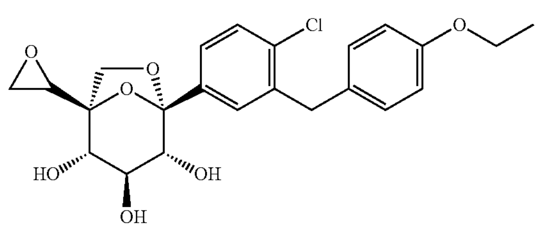 [SMILES: CCOc1ccc(Cc2cc([C@]34OC[C@](C5CO5)(O3)[C@@H](O)[C@H](O)[C@H]4O)ccc2Cl)cc1] | (1S,2S,3S,4R,5S)-5-(4-chloro-3-(4-ethoxybenzyl)phenyl)-1-(oxiran-2-yl)-6,8-dioxabicyclo[3.2.1]octane-2,3,4-triol |
| Example 27 | 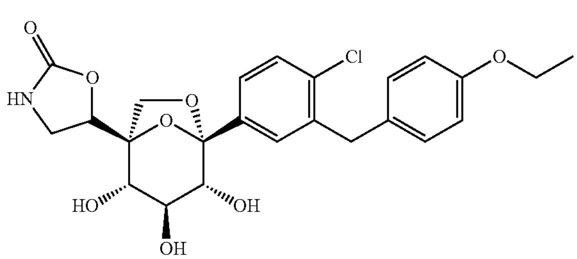 [SMILES: CCOc1ccc(Cc2cc([C@]34OC[C@](C5CNC(=O)O5)(O3)[C@@H](O)[C@H](O)[C@H]4O)ccc2Cl)cc1] | 5-(((1S,2S,3S,4R,5S)-5-(4-chloro-3-4-ethoxybenzyl)phenyl)-2,3,4-trihydroxy-6,8-dioxabicyclo[3.2.1]octan-1-yl)oxazolidin-2-one |

| Example No. | Structure | Name |
|---|---|---|
| Example 28 | 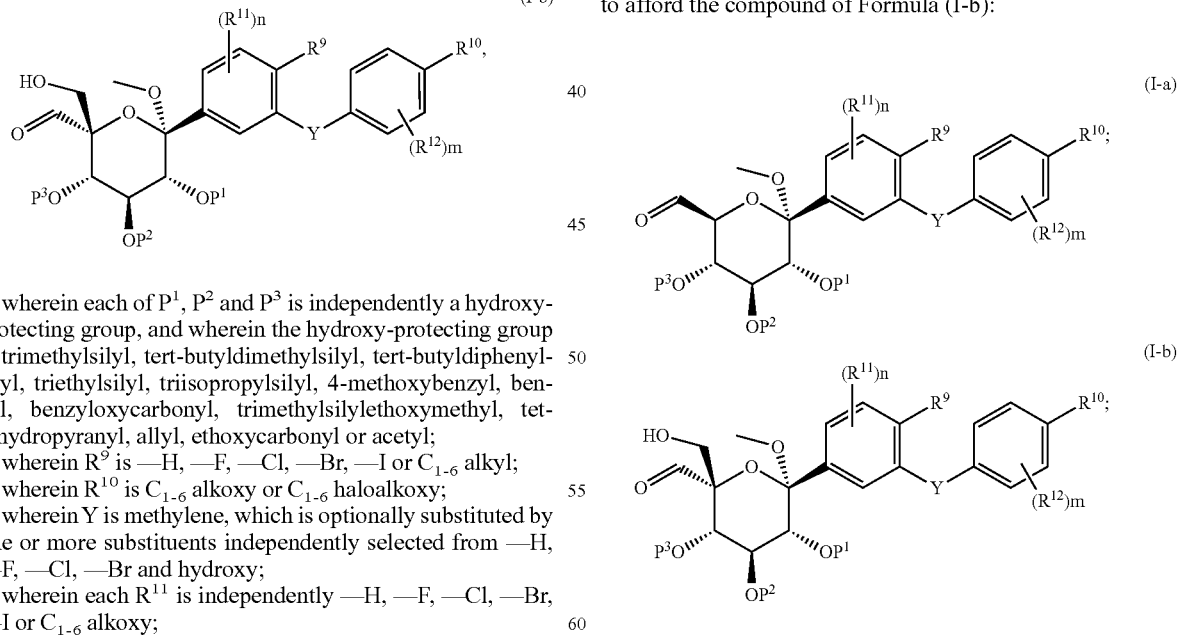 | (1R,2R,3S,4R,5S)-5-(4-chloro-3-(4-ethoxybenzyl)phenyl)-1-(1-hydroxyethyl)-6,8-dioxabicyclo[3.2.1]octane-2,3,4-triol |
| Example 29 | 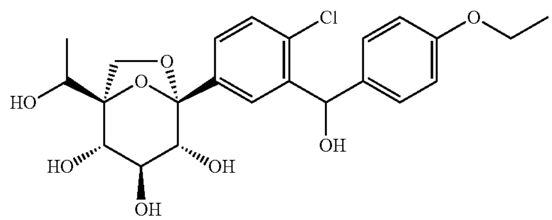 [SMILES: CCOc1ccc(C(O)c2cc([C@]34OC[C@](C(C)O)(O3)[C@@H](O)[C@H](O)[C@H]4O)ccc2Cl)cc1] | (1R,2S,3S,4R,5S)-5-(4-chloro-3-((4-ethoxyphenyl)(hydroxy)methyl)phenyl)-1-(1-hydroxyethyl)-6,8-dioxabicyclo[3.2.1]octane-2,3,4-triol |
| Example 30 | 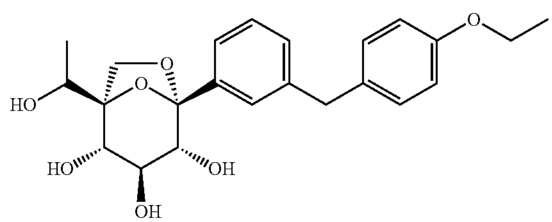 [SMILES: CCOc1ccc(Cc2cccc([C@]34OC[C@](C(C)O)(O3)[C@@H](O)[C@H](O)[C@H]4O)c2)cc1] | (1R,2S,3S,4R,5S)-5-(3-(4-ethoxybenzyl)phenyl)-1-(1-hydroxyethyl)-6,8-dioxabicyclo[3.2.1]octane-2,3,4-triol |

In other aspect, provided herein is a compound having Formula (I-b):

(I-b)

wherein each of $P^1$, $P^2$ and $P^3$ is independently a hydroxy-protecting group, and wherein the hydroxy-protecting group is trimethylsilyl, tert-butyldimethylsilyl, tert-butyldiphenylsilyl, triethylsilyl, triisopropylsilyl, 4-methoxybenzyl, benzyl, benzyloxycarbonyl, trimethylsilylethoxymethyl, tetrahydropyranyl, allyl, ethoxycarbonyl or acetyl;

wherein $R^9$ is —H, —F, —Cl, —Br, —I or $C_{1-6}$ alkyl;
wherein $R^{10}$ is $C_{1-6}$ alkoxy or $C_{1-6}$ haloalkoxy;
wherein Y is methylene, which is optionally substituted by one or more substituents independently selected from —H, —F, —Cl, —Br and hydroxy;
wherein each $R^{11}$ is independently —H, —F, —Cl, —Br, —I or $C_{1-6}$ alkoxy;
wherein n is 1, 2 or 3;
wherein each $R^{12}$ is independently —H, —F, —Cl or I; and
wherein m is 1, 2, 3 or 4.

In some embodiments, wherein $R^9$ is Cl;
wherein $R^{10}$ is $C_{1-4}$ alkoxy or $C_{1-4}$ haloalkoxy;
wherein each $R^{11}$ is independently —H; and
wherein each $R^{12}$ is independently —H or —F.

In other aspect, provided herein is a process for preparing the compound having Formula (I-b), comprising reacting a compound of Formula (I-a) with formaldehyde in the presence of 1,8-diazabicyclo[5.4.0]undec-7-ene in a polar solvent to afford the compound of Formula (I-b):

(I-a)

(I-b)

wherein each of $P^1$, $P^2$ and $P^3$ is independently a hydroxy-protecting group, and wherein the hydroxy-protecting group is trimethylsilyl, tert-butyldimethylsilyl, tert-butyldiphenylsilyl, triethylsilyl, triisopropylsilyl, 4-methoxybenzyl, benzyl, benzyloxycarbonyl, trimethylsilylethoxymethyl, tetrahydropyranyl, allyl, ethoxycarbonyl or acetyl;

wherein $R^9$ is —H, —F, —Cl, —Br, —I or $C_{1-6}$ alkyl;
wherein $R^{10}$ is $C_{1-6}$ alkoxy or $C_{1-6}$ haloalkoxy;
wherein Y is methylene, which is optionally substituted by one or two substituents independently selected from —H, —F, —Cl, —Br and hydroxy;
wherein each $R^{11}$ is independently —H, —F, —Cl, —Br, —I or $C_{1-6}$ alkoxy;
wherein n is 1, 2 or 3;
wherein each $R^{12}$ is independently —H, —F, —Cl or I; and
wherein m is 1, 2, 3 or 4.

In some embodiments, wherein $R^9$ is Cl;
wherein $R^{10}$ is $C_{1-4}$ alkoxy or $C_{1-4}$ haloalkoxy;
wherein each $R^{11}$ is independently —H; and wherein each $R^{12}$ is independently —H or —F.

The polar solvent disclosed herein is water, formamide, dimethyl sulfoxide, acetonitrile, N,N-dimethylformamide, methanol, ethanol, isopropanol or a combination thereof.

The hydroxy protecting group disclosed herein is trimethylsilyl, tert-butyldimethylsilyl, tert-butyldiphenylsilyl, triethylsilyl, triisopropylsilyl, 4-methoxybenzyl, benzyl, benzyloxycarbonyl, trimethylsilylethoxymethyl, tetrahydropyranyl, allyl, ethoxycarbonyl or acetyl.

In other aspect, provided herein is a pharmaceutical composition comprising the compound disclosed herein. In some embodiments, the pharmaceutical composition further comprises a pharmaceutically acceptable carrier, excipient, diluent, adjuvant, vehicle or a combination thereof.

In some embodiments, the pharmaceutical composition further comprises an additional therapeutic agent, wherein the additional therapeutic agent is an anti-diabetic agent other than an SGLT-2 inhibitor, an antihyperglycemic agent, an antiadipositas drug, an antihypertensive agent, an antiplatelet agent, an antiatherosclerotic drug, a lipid-lowering agent, an anti-inflammatory or a combination thereof.

In some embodiments, the anti-diabetic agent other than an SGLT-2 inhibitor or antihyperglycemic agent is a biguanide, a sulfonylurea, a glucosidase inhibitor, a PPAR agonist, an αP2 inhibitor, a PPARα/γ dual agonist, a dipeptidyl peptidase IV (DPP-IV) inhibitor, a meglitinide, insulin, a glucagon-like peptide-1 (GLP-1) inhibitor, a PTP1B inhibitor, a glycogen phosphorylase inhibitor, a glucose-6-phosphatase inhibitor or a combination thereof.

In some embodiments, the lipid-lowering agent is an MTP inhibitor, an HMGCoA reductase inhibitor, a squalene synthase inhibitor, a fibric acid derivative, an ACAT inhibitor, a lipoxygenase inhibitor, a cholesterol absorption inhibitor, an ileal Na(+)/bile acid cotransporter inhibitor, an upregulator of LDL receptor activity, niacin or a derivative thereof, a bile acid sequestrant or a combination thereof.

In some embodiments, the lipid-lowering agent is pravastatin, simvastatin, atorvastatin, fluvastatin, cerivastatin, atavastatin, rosuvastatin or a combination thereof.

In other aspect, provided herein is use of the compound or the pharmaceutical composition disclosed herein in the manufacture a medicament for inhibiting SGLT-2.

In other aspect, provided herein is use of the compound or the pharmaceutical composition disclosed herein in the manufacture a medicament for increasing HDL level.

In other aspect, provided herein is use of the compound or the pharmaceutical composition disclosed herein in the manufacture of a medicament for preventing or treating a disease, lessening a disease symptoms, delaying the progression or onset of a disease, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis or hypertension.

In other aspect, provided herein is a method for inhibiting the activity of SGLT-2, comprising administering to the patient in need thereof a therapeutically effective amount of the compound or the pharmaceutical composition disclosed herein.

In other aspect, provided herein is a method for preventing or treating a disease, lessening a disease symptoms, delaying the progression or onset of a disease or increasing HDL level, comprising administering to the patient in need thereof a therapeutically effective amount of the compound or the pharmaceutical composition disclosed herein, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis or hypertension.

In other aspect, provided herein is a compound or the pharmaceutical composition disclosed herein for use in inhibiting the activity of SGLT-2.

In other aspect, provided herein is a compound or the pharmaceutical composition disclosed herein for use in preventing or treating a disease, lessening a disease symptoms, delaying the progression or onset of a disease or increasing HDL level, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis or hypertension.

The foregoing merely summarizes certain aspects disclosed herein and is not intended to be limiting in nature. These aspects and other aspects and embodiments are described more fully below.

DETAILED DESCRIPTION OF THE INVENTION

The present invention provides glucopyranosyl derivatives, preparation processes and pharmaceutical uses thereof. Skilled in the art can learn from this article to properly improve the process parameters. Of particular note is that all similar substitutions and modifications to the skilled person is obvious, and they are deemed to be included in the present invention.

DEFINITIONS AND GENERAL TERMINOLOGY

Unless otherwise indicated, terms used in the specification and claims have the following definitions.

The term "halogen" refers to fluoro (F), chloro (Cl), bromo (Br), or iodo (I).

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. Some non-limiting examples of the alkyl group include methyl, ethyl, propyl, isopropyl, n-butyl, i-butyl, t-butyl, n-pentyl, 1-methyl-butyl, 2-methyl-butyl, 3-methyl-butyl, neopentyl, 3,3-dimethyl-propyl, n-hexyl and 2-methylpentyl, etc. The alkyl group containing 1 to 6 carbon atoms described herein is a lower alkyl group. The alkyl group is optionally substituted by one or more substituents independently selected from —F, —Cl, —Br, —I, hydroxy, cyano, amino, carboxy and carboxylic ester.

The term "haloalkyl" refers to an alkyl group substituted with one or more halogen atoms. Some non-limiting examples of the haloalkyl group include fluoromethyl, difluoromethyl, trifluoromethyl, perfluoroethyl, 1,1-dichloroethyl and 1,2-dichloropropyl etc.

The term "alkoxy" refers to an alkyl-O-group. Some non-limiting examples of the alkoxy group include methoxy, ethoxy, propoxy, isopropoxy, tert-butoxy, 2-methyl-propoxy and neopentyloxy etc.

The term "haloalkoxy" refers to an alkoxy group substituted with one or more halogen atoms, wherein the alkoxy group is as defined herein. Some non-limiting examples of the haloalkoxy group include difluoromethoxy, trifluoromethoxy, difluoroethoxy and trifluoroethoxy, etc.

The term "hydroxyalkyl" refers to an alkyl group substituted with one or more hydroxy groups, wherein the alkyl group is as defined herein. Some non-limiting examples of the hydroxyalkyl group include hydroxymethyl, 2-hydroxyethyl (—$CH_2CH_2OH$), 1-hydroxyethyl (—$CH_2OHCH_3$), 1,2-dihydroxyethyl, 2,3-dihydroxypropyl, 1-hydroxypropyl, 2-hydroxypropyl, 3-hydroxypropyl and hydroxybutyl, etc.

The term "alkylamino" refers to an amino group substituted with one or two alkyl groups. Some non-limiting examples of the alkylamino group include methylamino, ethylamino, propylamino, isopropylamino, n-butylamino, n-pentylamino, N,N-dimethylamino, N,N-diethylamino, N-ethyl-N-methylamino and N-methyl-n-propylamino, etc.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Some non-limiting examples of the alkenyl group include ethenyl or vinyl (—$CH=CH_2$) and allyl (—$CH_2CH=CH_2$), etc.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is optionally substituted independently with one or more substituents described herein. Some non-limiting examples of the alkynyl group include ethynyl (—C≡CH), 1-propynyl ($CH_3$C≡C—), 2-proynyl (propargyl, —$CH_2$C≡CH), 1-butynyl, 2-butynyl, 1-pentynyl, 2-pentynyl, 3-methyl-1-butynyl, 1-hexynyl, 1-heptynyl and 1-octynyl, etc.

The term "cyclo" refers to a saturated or unsaturated 3-20, or 3-12, or 3-10, or 3-8, or 3-6 membered monocyclic or multiple ring, unless other limited, wherein the multiple ring is fused ring, spiro ring or bridged ring.

The term "cycloalkyl" refers to a saturated or partially saturated monocyclic or polycyclic (include fused ring, bridged ring and/or spiro ring), non-aromatic carbocyclic group containing 3 to n carbon atoms. In some embodiments, n is an integer from 3 to 30, in other embodiments, n is an integer from 3 to 15, in other embodiments, n is an integer from 3 to 10. Some non-limiting examples of the cycloalkyl group include cyclopropyl, cyclobutyl, cyclopentyl, cycloheptyl, cyclopentenyl, cyclohexenyl, cyclohexadienyl, cycloheptatrienyl, norbornyl, norpinanyl, adamantyl, bicycle[3.2.1]octyl and spiro[4.5]decyl, etc. The cycloalkyl group may be optionally substituted by one or more substitents independently selected from halogen, hydroxy, carboxy, cyano, nitro, amino, acyl, alkenyl, alkynyl, carbonyl, mercapto, lower alkyl, cycloalkyl, lower alkylthio, lower alkoxy, lower hydroxyalkyl, lower alkylamino, lower alkylcarbonyl, lower alkyl-thio-lower alkyl, lower alkyl-sulfinyl, lower alkoxycarbonyl and lower alkylaminocarbonyl. In other embodiments, the cycloalkyl group relates to unsubstituted saturated monocyclic ring.

The term "heterocyclyl" refers to a saturated or partially saturated monocyclic or polycyclic (include fused ring, bridged ring and spiro ring), non-aromatic carbocyclic group containing 3 to n carbon atoms and one or more heteroatoms, wherein the heteroatom is independently oxygen, sulfur, nitrogen, phosphorus or silicon. In some embodiments, n is an integer from 3 to 20, in other embodiments, n is an integer from 3 to 15, in other embodiments, n is an integer from 3 to 10, in other embodiments, n is an integer from 3 to 6. Some non-limiting examples of the heterocyclyl group include oxetanyl, tetrahydrofuranyl, pyranyl, pyrrolidinyl, imidazolidinyl, tetrahydrothiophenyl, piperidinyl, piperazinyl, morpholinyl, thiomorpholinyl, imidazolinyl, oxazolidinyl, pyrazolidinyl, pyrrolinyl, oxo-2(1H)-pyridyl and oxazolidin-2-one-5-yl etc. The heterocyclyl group is optionally substituted with one or more substituents independently selected from halogen, hydroxy, carboxy, cyano, nitro, amino, acyl, alkenyl, alkynyl, carbonyl, mercapto, lower alkyl, heteroalkyl, lower alkylthio, lower alkoxy, lower hydroxyalkyl, lower alkylamino, lower alkylcarbonyl, lower alkyl-thio-lower alkyl, lower alkyl-sulfinyl, lower alkoxycarbonyl and lower alkylaminocarbonyl. In other embodiments, the heterocyclyl group relates to unsubstituted saturated monocycle.

The term "aryl" refers to a hydrocarbon cyclic system of a monocyclic ring or multicyclic ring fused (each ring in the system shares an adjacent pair of atoms with another ring in the system) and/or connected (each ring in the system connected with another ring in the system by a single bond or a double bond) together, also refers to a aromatic hydrocarbon monocyclic or multicyclic system of a aromatic monocyclic or multicyclic ring fused to one or more cycloalkyl and/or heterocyclyl. In some embodiments, aryl is a monocyclic system, a multicyclic system having 8 to 16 carbon atoms, benzocycloalkyl or benzoheterocyclyl. Some non-limiting examples of the aryl group include phenyl, 1-naphthyl, 2-naphthyl, anthryl, phenanthrylphenyl, p-aminophenyl, 2-aminophenyl, p-carboxyphenyl, 2-carboxyphenyl, p-trifluoromethylphenyl, o-nitrophenyl, m-nitrophenyl, p-nitrophenyl, o-cyanophenyl, m-cyanophenyl, p-cyanophenyl, 2,6-dinitrophenyl, benzodioxanyl, benzodioxolyl, chromanyl and benzodihydroindolyl etc. The aryl group is optionally substituted by one or more substituents independently selected from halogen, hydroxy, carboxy, cyano, nitro, amino, acyl, alkenyl, alkynyl, carbonyl, mercapto, lower alkyl, cycloalkyl, heterocycloalkyl, lower alkylthio, lower alkoxy, lower hydroxyalkyl, lower alkylamino, lower alkylcarbonyl, lower alkyl-thio-lower alkyl, lower alkyl-sulfinyl, lower alkoxycarbonyl, lower alkylaminocarbonyl, aryl, aryl-lower alkylcarbonyl, aryl-lower alkylthio, aryl-lower alkylsulfinyl, aryl-lower alkyl-sulfinyl-lower alky, aryl-lower alkoxycarbonyl, arylalkylaminocarbonyl and arylalkylaminocarbonyl lower alkyl etc. In other embodiments, the substituent is independently selected from one or two of halogen, cyano, hydroxy, carboxy, amino, lower alkyl, cycloalkyl, heterocycloalkyl and aryl.

The term "aralkyl" or "arylalkyl" refers to an alkyl group substituted by one or more aryl radicals, wherein the aryl and the alkyl are as defined herein. In some embodiments, the aralkyl radical refers to a "lower aralkyl" radical having aryl radical(s) attached to an alkyl radical which have one to six carbon atoms. In other embodiments, the aralkyl radical refers to an alkyl group having one to three carbon atoms attached by aryl radical(s). Some non-limiting examples of such radical include benzyl, diphenylmethyl, phenylethyl, p-tolylmethyl and phenylpropyl, etc. The aralkyl group can be additionally substituted with halo, alkyl, alkoxy, haloalkyl or haloalkoxy.

The term "arylalkoxy" refers to an alkoxy group substituted with one or more aryl groups, wherein the aryl group and the alkoxy group are as defined herein. Some non-limiting examples of the arylalkoxy group include phenylmethoxy, phenylethoxy, (p-tolyl)methoxy and phenylpropoxy, etc.

The term "heteroaryl" refers to an aromatic cyclyl group derivated from an aryl group of which the carbon ring atoms are substituted by one or more heteroatoms independently selected from oxygen, sulfur, selenium, nitrogen, phosphorus and silicon. Some non-limiting examples of the heteroaryl group include furanyl, thiophenyl, pyrrolyl, pyridinyl, quinolinyl, thiazolyl, N-alkylpyrrolyl, pyrimidinyl, pyrazinyl, indolyl, imidazolyl, tetrazolyl, 2-formylfuranyl, 3-formylpyridinyl, 4-methylimidazolyl, 5-methylthiazolyl, 2,5-dimethylfuranyl, 3-acetoxyindolyl, benzopyranyl and benzofuranyl etc. The heteroaryl group is optionally substituted with one or more substituents independently selected from halogen, hydroxy, carboxy, cyano, nitro, amino, acyl, alkenyl, alkynyl, carbonyl, mercapto, lower alkyl, cycloalkyl, heterocycloalkyl, lower alkylthio, lower alkoxy, lower hydroxyalkyl, lower alkylamino, lower alkylcarbonyl, lower alkyl-thio-lower alkyl, lower alkyl-sulfinyl, lower alkoxycarbonyl, lower alkylaminocarbonyl, aryl, aryl-lower alkylcarbonyl, aryl-lower alkylthio, aryl-lower alkyl-sulfinyl, aryl-lower alkyl-sulfinyl-lower alkyl, aryl-lower alkoxycarbonyl, arylalkylaminocarbonyl, arylalkylaminocarbonyl lower alkyl, heteroaryl, heteroaryl-lower alkylcarbonyl, heteroaryl-lower alkylthio, heteroaryl-lower alkyl-sulfinyl, heteroaryl-lower alkyl-sulfinyl-lower alkyl, heteroaryl-lower alkoxycarbonyl, heteroarylalkylaminocarbonyl and heteroarylalkylaminocarbonyl lower alkyl. In other embodiments, the heteroaryl is substituted with one or two of halogen, cyano, hydroxy, carboxy, amino, lower alkyl, cycloalkyl, heterocycloalkyl, aryl and heteroaryl.

The term "heteroarylalkyl" refers to alkyl group substituted with one or more heteroaryl radicals, wherein the heteroaryl radical and the alkyl group are as defined herein. Some non-limiting examples of the heteroarylalkyl group include pyridin-2-ylmethyl, thiazol-2-ylethyl, imidazol-2-ylethyl, pyrimidin-2-ylpropyl and pyrimidin-2-ylmethyl, etc.

The term "heteroarylalkoxy" refers to oxy-containing heteroarylalkyl radicals attached through an oxygen atom to other radicals, wherein the heteroarylalkyl radical is as defined herein. Some non-limiting examples of such radical include pyridin-2-ylmethoxy, thiazol-2-ylethoxy, imidazol-2-ylethoxy, pyrimidin-2-ylpropoxy and pyrimidin-2-ylmethoxy, etc.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "nitro" refers to $-NO_2$.
The term "mercapto" refers to $-SH$.
The term "hydroxy" refers to $-OH$.
The term "amino" refers to $-NH_2$.
The term "cyano" refers to $-CN$.
The term "carboxy" refers to $-C(=O)OH$.

The term "pharmaceutical composition" refers to a mixture of one or more of the compounds described herein, or physiologically/pharmaceutically acceptable salts or prodrugs thereof, and other chemical components, such as physiologically/pharmaceutically acceptable carriers, excipients, diluents, adjuvants, vihicles, and other additional therapeutic agents, such as anti-diabetic agents, antihyperglycemic agents, antiadipositas agents, antihypertensive agents, antiplatelet agents, antiatherosclerotic agents, lipid-lowering agents, anti-inflammatory agents, etc. The purpose of the pharmaceutical composition is to facilitate administration of a compound to an organism.

The term "optional" or "optionally" refers to that the subsequently described event or circumstance may or may not occur, and that the description includes instances where the event or circumstance may or may not occur. For example, "heterocyclic group optionally substituted by an alkyl group" means that the alkyl may or may not be present, and the description includes the situation where the heterocyclic group is substituted by the alkyl group and the situation where the heterocyclic group is not substituted by the alkyl group.

The term "syndrome X", also known as conditions, diseases of metabolic syndrome, the disorders are detailed in Johannsson et al., *J. Clin. Endocrinol. Metab.,* 1997; 82, 727-734, which is incorporated herein by reference.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates, and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nature Reviews Drug Discovery,* 2008, 7, 255-270, and Hecker et al., Prodrugs of Phosphates and Phosphonates, *J. Med. Chem.,* 2008, 51, 2328-2345, all of which are incorporated herein by reference in their entireties.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow Parker et al., McGraw-Hill *Dictionary of Chemical Terms* (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Diastereomeric mixtures can be separated into their individual diastereoisomers on the basis of their physical and chemical differences by methods well known to those skilled in the art, such as by chromatography, crystallization, distillation, or sublimation. Enantiomers can be separated by converting the enantiomeric mixture into a diastereomeric mixture by reacting with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. The intermediates and compounds of the invention may exist in tautomeric forms and all such tautomeric forms are within the scope of the invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons. Unless otherwise stated, structures depicted herein are also meant to include all isomeric (e.g., enantiomeric, diastereomeric, and geometric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Additionally, unless otherwise stated, structures depicted herein are also meant to include compounds that differ only in the presence of one or more isotopically enriched atoms.

The term "pharmaceutically acceptable salt" refers to organic or inorganic salts of a compound disclosed herein. Pharmaceutically acceptable salts are well known in the art. For example, the pharmaceutically acceptable salts are described in detail in Berge et al., *J. Pharmacol Sci*, 1977, 66: 1-19, which is incorporated herein by reference in its entirety. Some non-limiting examples of the pharmaceutically salts include salts of an amino group formed with inorganic acids such as hydrochloric acid, hydrobromic acid, phosphoric acid, metaphosphoric acid, sulfuric acid, nitric acid and perchloric acid or with organic acids such as methanesulfonic acid, ethanesulfonic acid, acetic acid, trifluoroacetic acid, glycolic acid, 2-hydroxyethanesulfonic acid, oxalic acid, maleic acid, tartaric acid, citric acid, succinic acid, malonic acid, benzenesulfonic acid, p-toluenesulfonic acid, malic acid, fumaric acid, lactic acid and lactobionic acid or salts obtained by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, laurate, laurylsulfate, malonate, 2-naphthalenesulfonate, nicotinate, nitrate, oleate, palmitate, pamoate, pectinate, persulfate, 3-phenylpropionate, picrate, pivalate, propionate, stearate, thiocyanate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent include water, isopropanol, ethanol, methanol, DMSO, ethyl acetate, acetic acid, and ethanolamine. The term "hydrate" refers to the complex where the solvent molecule is water.

The Pharmaceutical Compositions of the Compounds in the Invention

The invention features pharmaceutical compositions that include a compound of Formula (I) or Formula (1) to (30), a compound listed herein, or a compound named in Examples 1 to 30, or a stereoisomer, a geometric isomer, a tautomer, a racemate, an N-oxide, a hydrate, a solvate, a metabolite, a pharmaceutically acceptable salt or a prodrug thereof, and a pharmaceutically acceptable carrier, excipient, diluent, adjuvant, vehicle or a combination thereof. The amount of the compound in the compositions disclosed herein is an effective and detectable amount for inhibiting sodium-dependent glucose transporters (SGLTs) activity in biological samples or patients.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, a diluent, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy, 21st ed.*, 2005, Lippincott Williams & Wilkins, Philadelphia, and Swarbrick et al., *Encyclopedia of Pharmaceutical Technology*, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

Compounds disclosed herein can be administered as the sole pharmaceutical agent or in combination with one or more other additional therapeutic (pharmaceutical) agents where the combination causes no unacceptable adverse effects. This may be of particular relevance for the treatment of diabetes, diabetic complications and other related diseases. Some non-limiting examples of these diseases include diabetes mellitus type I, diabetes type II, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis and hypertension. As used herein, the additional therapeutic agents include an anti-diabetic agent other than an SGLT-2 inhibitor, an antihyperglycemic agent, an antiadipositas drug, an antihypertensive agent, an antiplatelet agent, an antiatherosclerotic drug, a lipid-lowering agent, an anti-inflammatory or a combination thereof.

Wherein, the anti-diabetic agents other than an SGLT-2 inhibitor include, but are not limited to, a biguanide (e.g., phenformin and metformin), a sulfonylurea (e.g., acetohexamide, diabinese, glibenclamide, glipizide, gliclazide, glimepiride, glipentide, gliquidone, tolazamide and tolbutamide), a meglitinide, a glinide (e.g., repaglinide, nateglinide), a glucosidase inhibitor (e.g., acarbose, adiposine, camiglibose, emiglitate, miglitol, voglibose, pradimicin and salbostatin), a PPAR agonist (e.g., balaglitazone, ciglitazone, darglitazone, englitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a DPP—IV inhibitor (e.g., sitagliptin, vidagliptin, alogliptin, linagliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal, extract and compounds are disclosed by Zhang, S. et al., *Drug Discovery Today*, 12(9/10), 373-381, 2007), insulin, an insulin mimetic, a glycogen phosphorylase inhibitor, a VPAC2 receptor agonist, a glucokinase activator, a glycogen phosphorylase inhibitor or a glucose-6-phosphatase inhibitor, an αP2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the antihyperglycemic agents include, but are not limited to, a biguanide (e.g., phenformin and metformin), a sulfonylurea (e.g., acetohexamide, diabinese, glibenclamide, glipizide, gliclazide, glimepiride, glipentide, gliquidone, tolazamide and tolbutamide), a meglitinide, a glinide (e.g., repaglinide, nateglinide), a glucosidase inhibitor (e.g., acarbose, adiposine, camiglibose, emiglitate, miglitol, voglibose, pradimicin and salbostatin), a PPAR agonist (e.g., balaglitazone, ciglitazone, darglitazone, englitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a DPP—IV inhibitor (e.g., sitagliptin, vidagliptin, alogliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal, extract and compounds are disclosed by Zhang, S. et al., *Drug Discovery Today*, 12(9/10), 373-381, 2007), insulin, an insulin mimetic, a glycogen phosphorylase inhibitor, a VPAC2 receptor agonist, a glucokinase activator, a glycogen phosphorylase inhibitor or a glucose-6-phosphatase inhibitor, an αP2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the lipid-lowering agents include, but are not limited to, an MTP inhibitor, an HMGCoA reductase inhibitor, a squalene synthase inhibitor, a fabric acid derivative, an ACAT inhibitor, a lipoxygenase inhibitor, a cholesterol absorption inhibitor, an ileal Na(+)/bile acid cotransporter inhibitor, an upregulators of LDL receptor activity, a bile acid sequestrant or niacin and a derivative thereof. In some embodiments, the lipid-lowering agent is selected from pravastatin, simvastatin, atorvastatin, fluvastatin, cerivastatin, atavastatin and rosuvastatin. Wherein, the anti-obesity agents include CB-1 antagonists (such as rimonabant, taranabant, surinabant, otenabant, SLV319 and AVE1625), gut-selective MTP inhibitors (such as dirlotapide, mitratapide and implitapide), CCKa agonists, 5-HT$_{2c}$ agonists (such as lorcaserin), MCR4 agonists, lipase inhibitors (such as cetilistat), PYY$_{3-36}$, opioid antagonist (such as naltrexone), oleoyl-estrone, obinepitide, pramlintide, tesofensine, leptin, liraglutide, bromocriptine, orlistat, exenatide, AOD-9604 and sibutramine.

Wherein, the suitable anti-inflammatory agents include genital tract/urinary tract infection preventatives and treatments. Exemplary agents include cranberries (*Vaccinium macrocarpon*) and cranberry derivatives, such as cranberry juice, cranberry extracts or flavonols of cranberries. Moreover, other suitable anti-inflammatory agents include, but are not limited to, aspirin, non-steroidal anti-inflammatory drugs, glucocorticosteroid, sulfasalazine and selective cyclooxygenase-2 inhibitors, etc.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection and infusion techniques. In some embodiments, the compositions are administered orally, intraperitoneally or intravenously. Sterile injectable forms of the compositions disclosed herein include aqueous and oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, non-volatile oil can be conventionally employed as a solvent or suspending medium.

For this purpose, any bland non-volatile oil includes synthetic mono- or diglycerides. Fatty acids, such as oleic acid and its glyceride derivatives, which are useful in the preparation of injectables, can be used as natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Use of the Compounds and Pharmaceutical Compositions

The amount of the compound or the compound in the compositions disclosed herein is an effective and detectable amount for inhibiting sodium-dependent glucose transporters (SGLTs) activity, especially SGLT-2 activity. SGLT-2 is responsible for reabsorption of D-glucose from kidney spherule filtrate, which inhibits glucose reabsorption in blood vessel and this is beneficial to reduce glucose concentrations in blood. Hence, the compound of the invention would be used for preventing and treating the type II diabetes and related diseases or improving symptoms of these diseases.

Compounds disclosed herein would be useful for, but are not limited to, preventing or treating diabetes or related diseases, or lessening diabetes or related diseases, or delaying the progression or onset of diabetes or related diseases or increasing HDL levels in a patient by administering to the patient a compound or a composition disclosed herein in an effective amount. Such diseases include, but are not limited to, diabetes, especially type II diabetes, and diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis and hypertension.

Moreover, compounds or pharmaceutical compositions disclosed herein also suit for preventing or treating the damage of diabetes in later stages, such as kidney disease, retinopathy, neuropathy, myocardial infarction, peripheral arterial disease, thrombosis, arteriosclerosis, inflammation, immunological diseases, autoimmune diseases such as AIDS, asthma, osteoporosis, cancer, psoriasis, Alzheimer's disease, schizophrenia and infectious diseases.

Besides being useful for human treatment, these compounds are also useful for veterinary treatment of animals such as companion animals, exotic animals and farm animals, including mammals, rodents, and the like. In other embodiments, the animals disclosed herein include horses, dogs, and cats. As used herein, the compounds disclosed herein include the pharmaceutically acceptable derivatives thereof.

An "effective amount" or "effective dose" of the compound or pharmaceutically acceptable composition is an amount that is effective in treating or lessening the severity of one or more of the aforementioned disorders. The compounds and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The compounds and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthetic Procedures

Generally, the compounds disclosed herein may be prepared by methods described herein, wherein the substituents are as defined for Formula (I), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compounds were identified by nuclear magnetic resonance (e.g., $^1$H-NMR and $^{13}$C-NMR). $^1$H-NMR and $^{13}$C-NMR chemical shifts were recorded as ppm ($10^{-6}$). $^1$H-NMR and $^{13}$C-NMR were performed on a Bruker Ultrashield-400 spectrometer. The appropriate solvent was deuterated-chloroform (CDCl$_3$), deuterated-methanol (CD$_3$OD) or deuterated-dimethyl sulfoxide (DMSO-d$_6$).

MS spectra were determined on Agilen-6120 Quadrupole LC/MS mass spectrometer;

The thin-layer silica gel used was Yantai Huanghai HSGF$_{254}$ silica gel plate.

The silica gel used in column chromatography generally was Qingdao Ocean Chemical Factory 300 to 400 mesh silica gel.

The staring materials of the present invention were known or purchased from Shanghai Accela Company, Energy Company, J&K, Chengdu Aiertai Company, Alfa Company and the like, or they could be prepared by the conventional synthesis methods in the prior art.

Unless otherwise stated, the reactions disclosed herein were carried out in a nitrogen atmosphere.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature.

Unless otherwise stated, the room temperature was from 20° C. to 30° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compounds.

The elution system of column chromatography comprised: A: petroleum ether and ethyl acetate, B: dichloromethane and ethyl acetate, C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

HPLC refers to High Performance Liquid Chromatography.

HPLC was determined on Agilent 1200DAD high pressure liquid chromatography spectrometer (Zorbax Eclipse Plus C18 150×4.6 mm chromatographic column).

The test condition of HPLC: the run time was 30 minutes (min); the column temperature was 35° C.; the detection was carried out at the wavelength of 210 nm and 254 nm using PDA detector; the mobile phase was H$_2$O (A) and acetonitrile (B); and the flow rate was 1.0 mL/min.

Scheme

Scheme 1

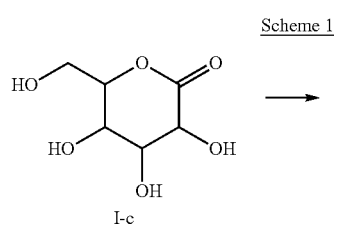

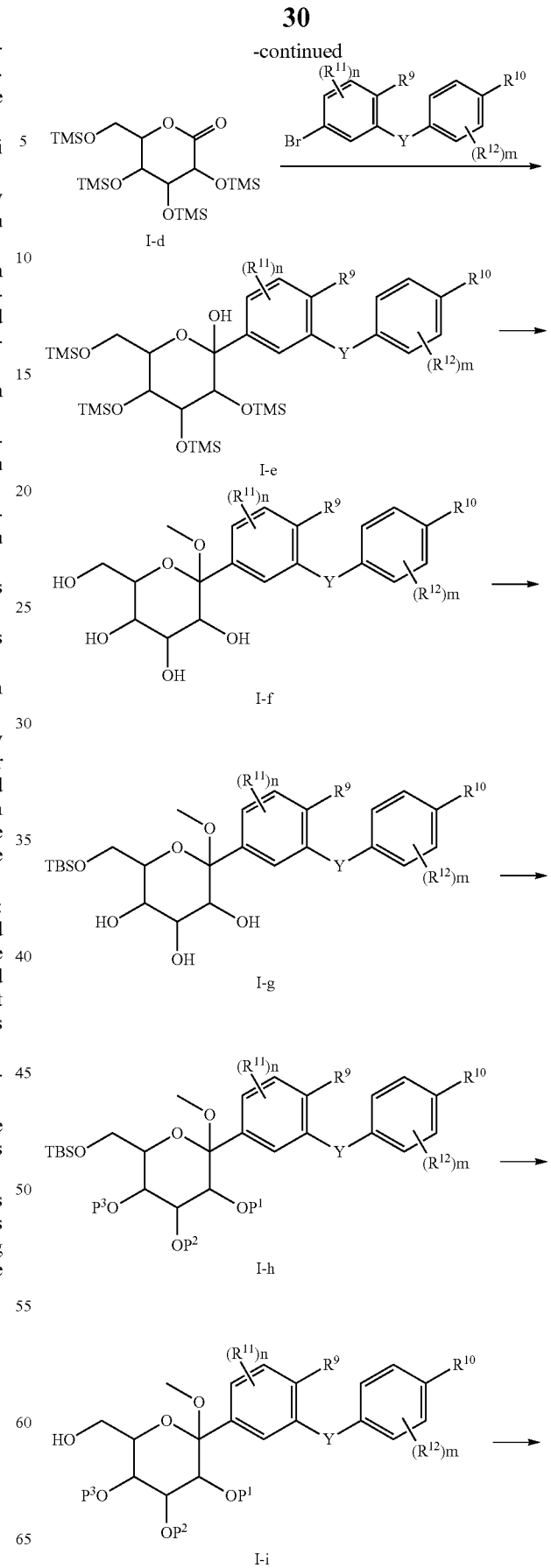

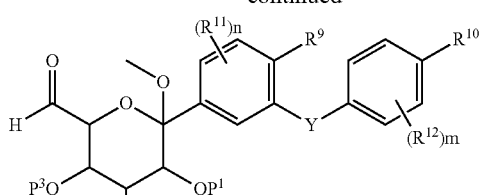

I-j

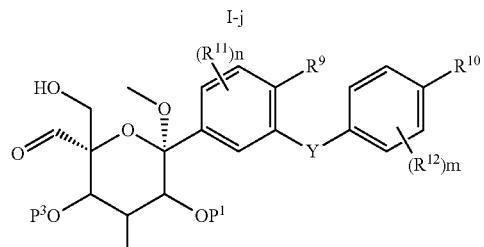

I-k

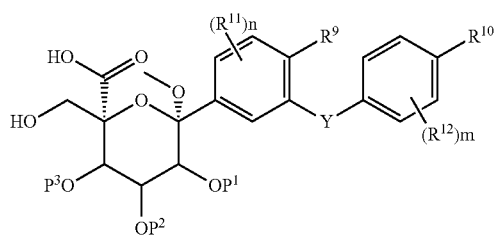

I-q

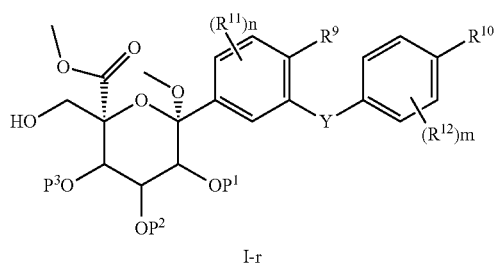

I-r

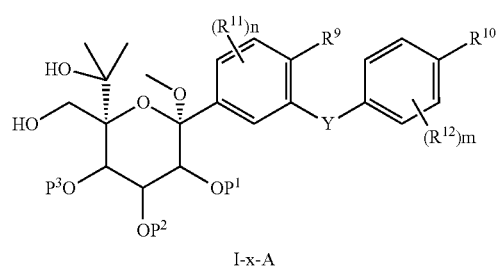

I-x-A

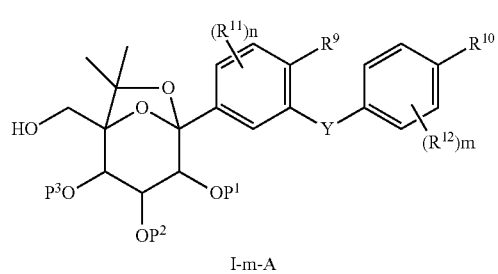

I-m-A

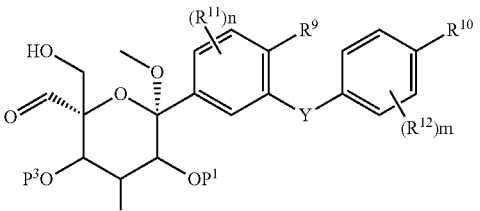

I-A

Compounds of Formula (I-A) can be prepared by a general synthetic procedure illustrated in Scheme 1, wherein each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Compound (I-c) can react with trimethylchlorosilane in the presence of N-methylmorpholine to afford compound (I-d). Coupling reaction of compound (I-d) with bromide fragment (S) in the presence of n-butyllithium can give compound (I-e). Compound (I-e) can react with methanol in the presence of an acid to afford compound (I-f). Compound (I-g) can react with tert-butyldimethylsilyl chloride in the presence of a base to afford compound (I-g). Compound (I-g) can react with benzyl bromide in the presence of a base to afford compound (I-h). Compound (I-h) can react with tetrabutylammonium iodide in a polar solvent to afford compound (I-i). Compound (I-i) can be converted to compound (I-j) in the presence of an oxidizing agent. Compound (I j) can react with methanal in the presence of 1,8-diazabicyclo[5.4.0]undec-7-ene in a polar solvent to afford compound (I-k). Oxidation of compound (I-k) can afford compound (I-q). Compound (I-q) can react with methanol in the presence of an acid to give compound (I-r). Reaction of compound (I-r) with a Grignard reagent can give compound (I-x-A). Cyclization of compound (I-x-A) in the presence of an acid can give compound (I-m-A). The protecting group of compound (I-m-A) can be removed in the presence of an acid or by Pd/C catalysis under $H_2$ to afford compound (I-A).

Scheme 2

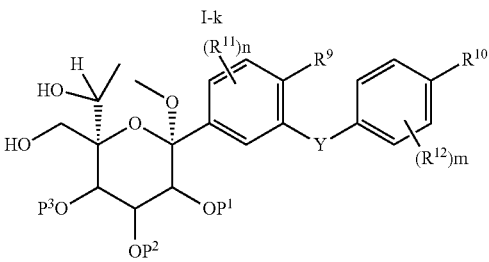

I-k

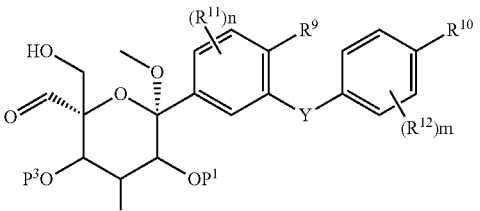

I-x-B

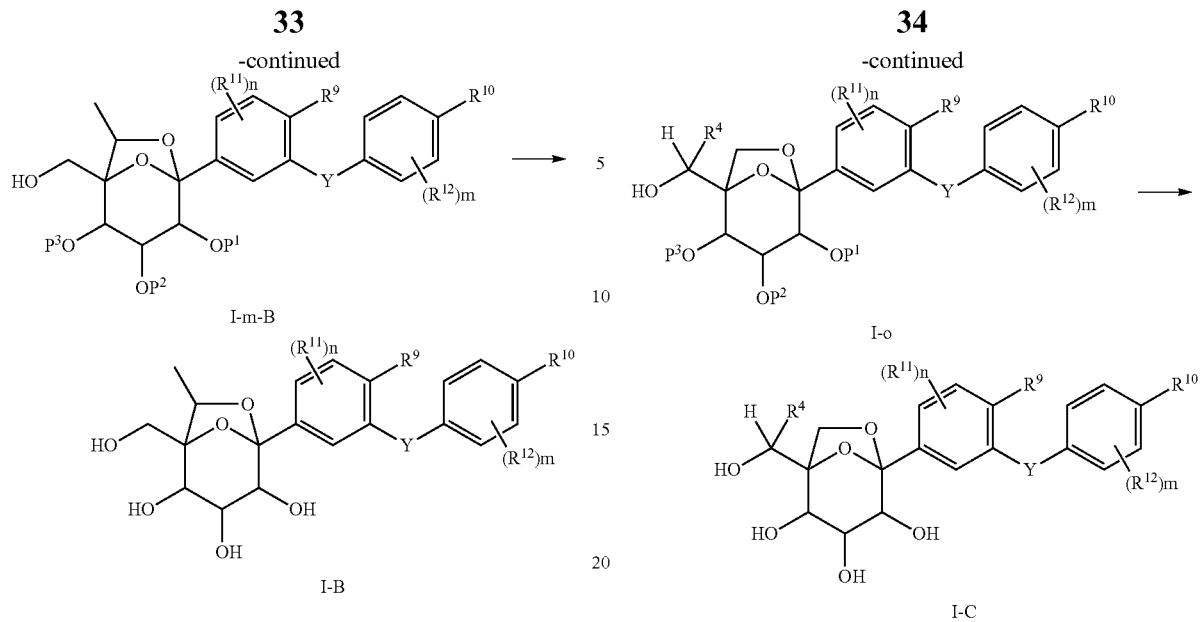

Compounds of Formula (I-B) can be prepared by a general synthetic procedure illustrated in Scheme 2, wherein each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Reaction of compound (I-k) with a Grignard reagent can give compound (I-x-B). Cyclization of compound (I-x-B) in the presence of an acid can give compound (I-m-B). The protecting group of compound (I-m-B) can be removed in the presence of an acid or by Pd/C catalysis under $H_2$ to afford compound (I-B).

Compounds of Formula (I-C) can be prepared by a general synthetic procedure illustrated in Scheme 3, wherein $R^4$ is methyl, ethyl, ethynyl or 1-propinyl; each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Cyclization of compound (I-x-C) in the presence of an acid can give compound (I-m-C). Oxidation of compound (I-m-C) can afford compound (I-n). Reaction of compound (I-n) with a Grignard reagent can give compound (I-o). The protecting group of compound (I-o) can be removed in the presence of an acid or by Pd/C catalysis under $H_2$ to afford compound (I-C).

Scheme 3

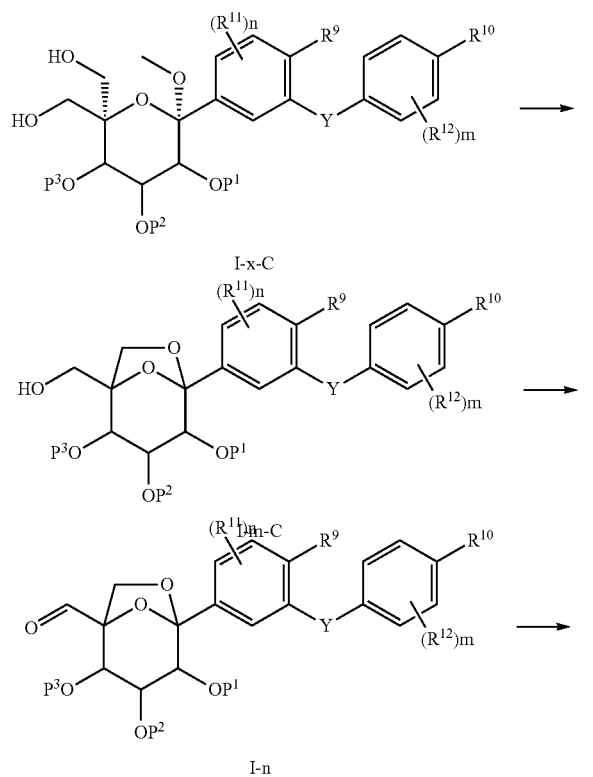

Scheme 4

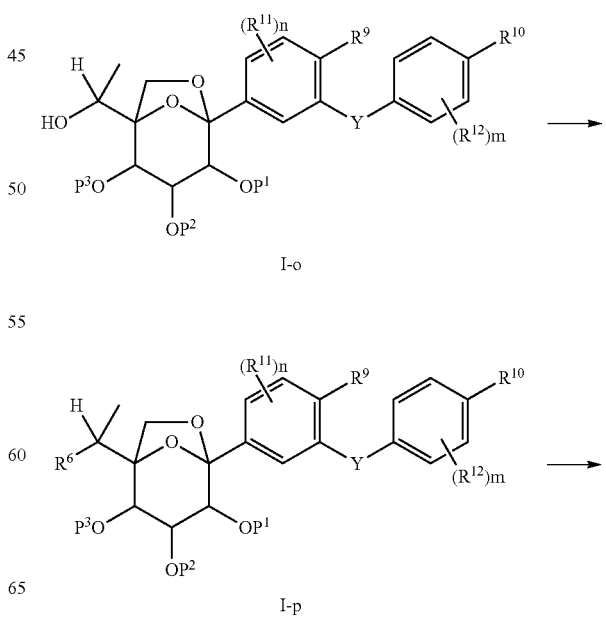

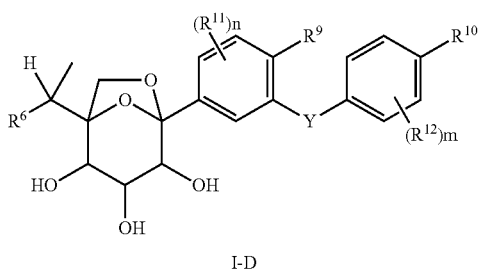

I-D

Compounds of Formula (I-D) can be prepared by a general synthetic procedure illustrated in Scheme 4, wherein $R^6$ is $R^fC(=O)O—$, and wherein $R^f$ is methyl, ethyl, tert-butyl, methoxy, ethoxy, isopropoxy or tert-butoxy; each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Compound (I-o) can react with a halogenating agent under alkaline condition to give compound (I-p). The protecting group of compound (I-p) can be removed in the presence of an acid or by Pd/C catalysis under $H_2$ to afford compound (I-D).

Scheme 5

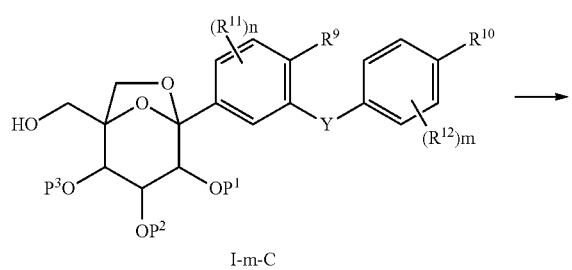

I-m-C

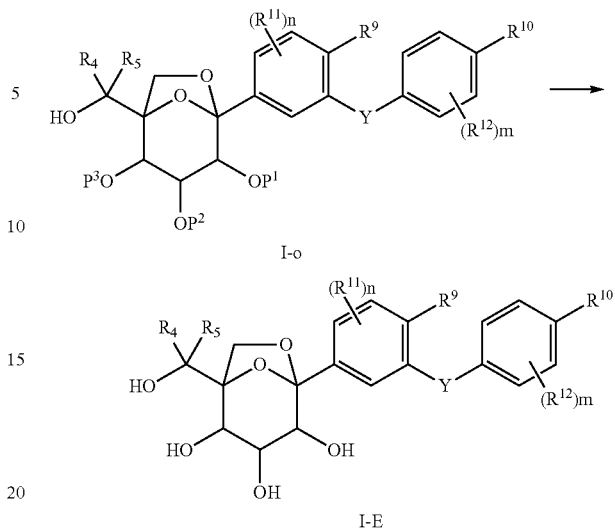

Compounds of Formula (I-E) can be prepared by a general synthetic procedure illustrated in Scheme 5, wherein each of $R^4$ and $R^5$ is independently alkyl, such as methyl; or $R^4$ and $R^5$, together with the carbon atom they are attached to, form a ring, such as cyclopropyl; each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Oxidation of compound (I-m-C) can afford compound (I-s). Compound (I-s) can react with methanol in the presence of an acid to give compound (I-t). Reaction of compound (I-t) with a Grignard reagent can give compound (I-o). Alternatively, compound (I-t) can react with a Grignard reagent in the presence of titanium tetraisopropanolate to afford compound (I-o) ($R^4$ and $R^5$ of which, together with the carbon atom they are attached to, form a ring). The protecting group of compound (I-o) can be removed in the presence of an acid or by Pd/C catalysis under $H_2$ to afford compound (I-E).

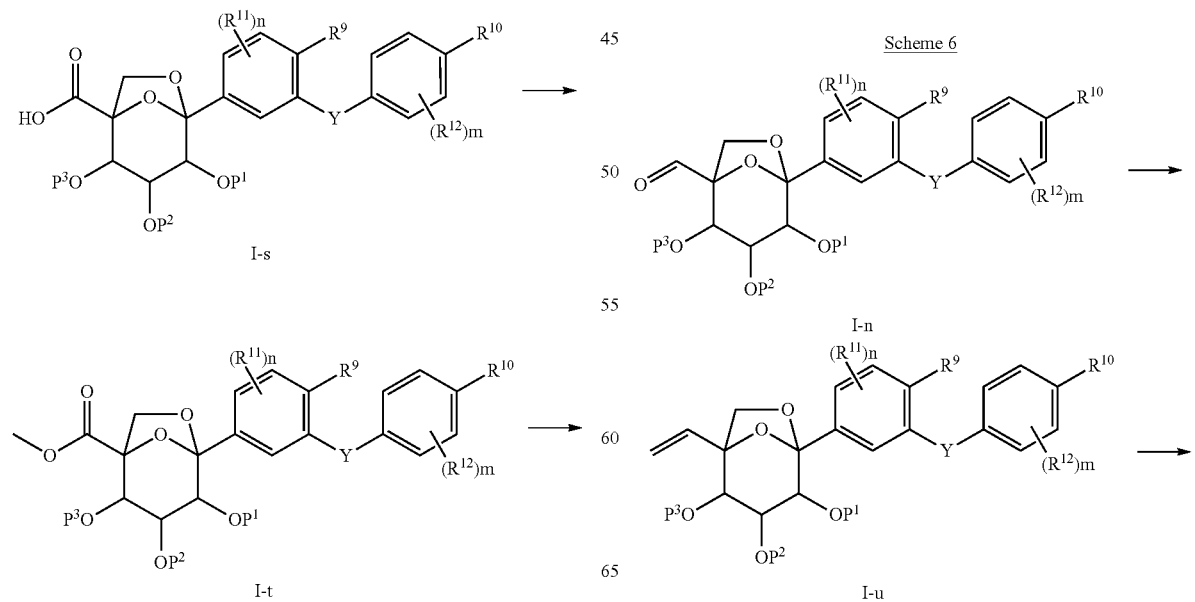

-continued

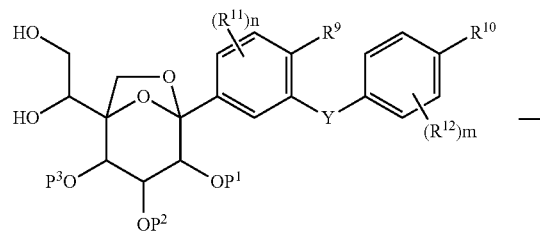

I-o

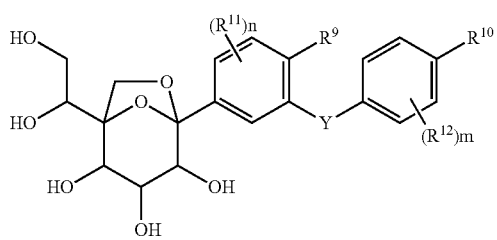

I-F

Compounds of Formula (I-F) can be prepared by a general synthetic procedure illustrated in Scheme 6, wherein each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Compound (I-n) can react with n-butyllithium and methyltriphenylphosphonium bromide to afford compound (I-u). Oxidation of compound (I-u) in the presence of osmium tetraoxide can afford compound (I-o). The protecting group of compound (I-o) can be removed in the presence of an acid or by Pd/C catalysis under $H_2$ to afford compound (I-F).

Scheme 7

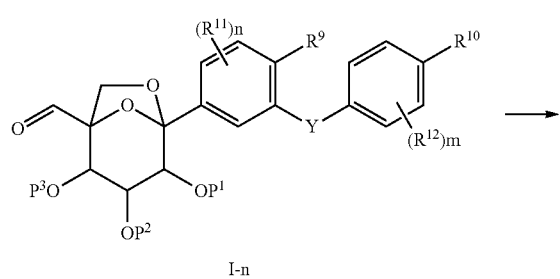

I-n

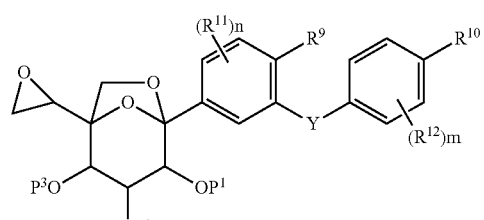

I-v

-continued

[Structure labeled I-o with H2N group]

I-o

[Structure labeled I-p with oxazolidinone]

I-p

[Structure labeled I-J with oxazolidinone and free hydroxyls]

I-J

Compounds of Formula (I-J) can be prepared by a general synthetic procedure illustrated in Scheme 7, wherein each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Compound (I-n) can react with trimethylsulfoxonium iodide under alkaline condition to afford compound (I-v). Compound (I-v) can react with ammonium hydroxide in a polar solvent to afford compound (I-o). Compound (I-o) can react with 1,1'-carbonyldiimidazole in a polar solvent to afford compound (I-p). The protecting group of compound (I-p) can be removed in the presence of an acid or by Pd/C catalysis under $H_2$ to afford compound (I-J).

Scheme 8

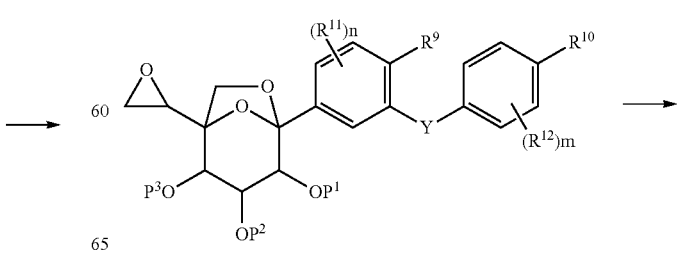

I-v

-continued

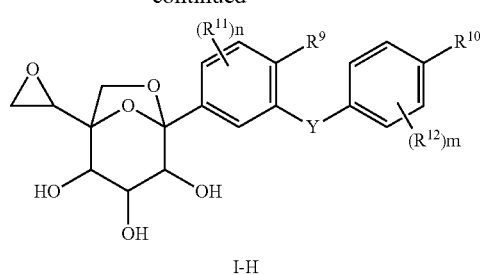

I-H

Compounds of Formula (I-H) can be prepared by a general synthetic procedure illustrated in Scheme 8, wherein each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

The protecting group of compound (I-v) can be removed in the presence of an acid or by Pd/C catalysis under $H_2$ to afford compound (I-H).

Scheme 9

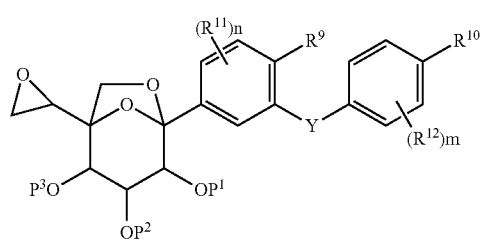

I-v

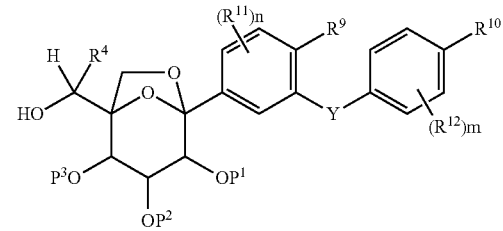

I-o-A

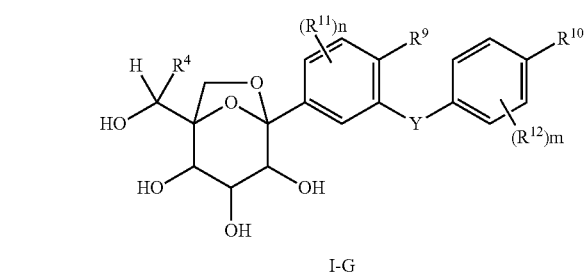

I-G

Compounds of Formula (I-G) can be prepared by a general synthetic procedure illustrated in Scheme 9, wherein $R^4$ is aminomethyl or methylaminomethyl; each of $R^9$, $R^{10}$, $R^{11}$, $R^{12}$, Y, m and n is as defined herein; each of $P^1$, $P^2$ and $P^3$ is independently hydroxy-protecting group, the hydroxy-protecting group is as defined herein.

Compound (I-v) can react with ammonium hydroxide or methylamine in a polar solvent to give compound (I-o-A).

The protecting group of compound (I-o-A) can be removed in the presence of an acid or by Pd/C catalysis under $H_2$ to afford compound (I-G).

Scheme 10

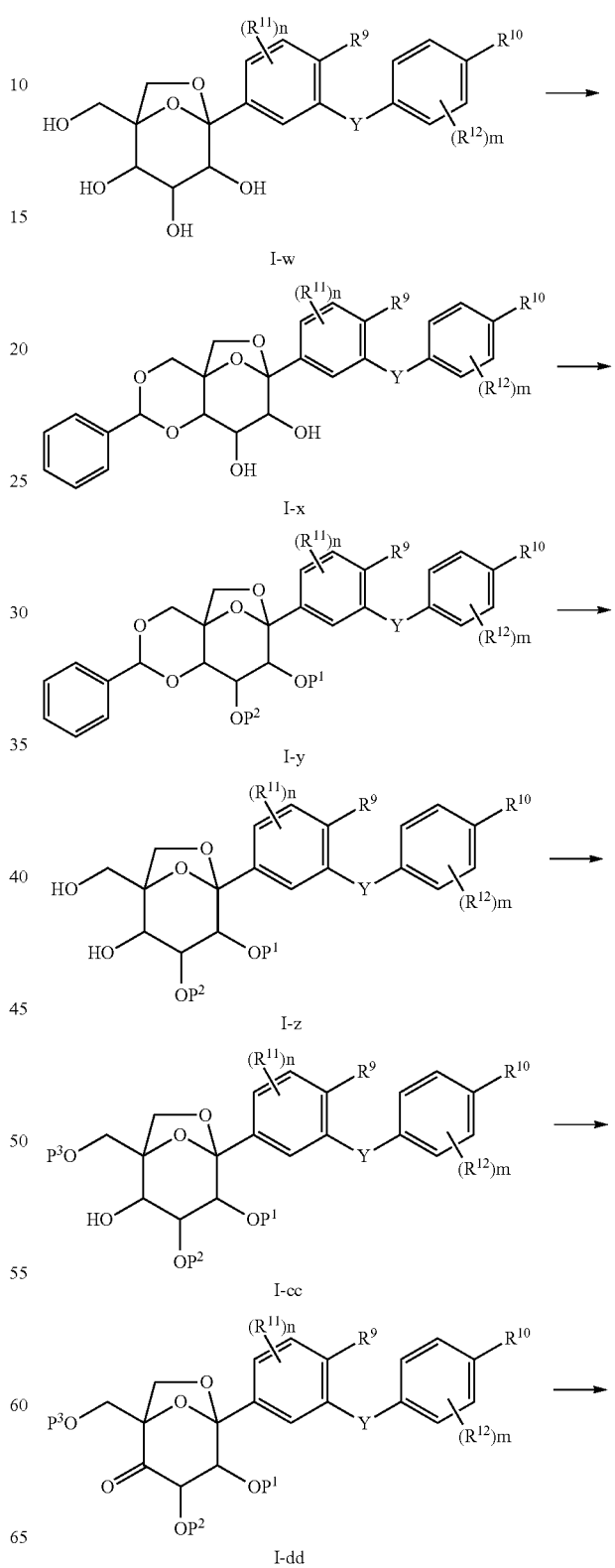

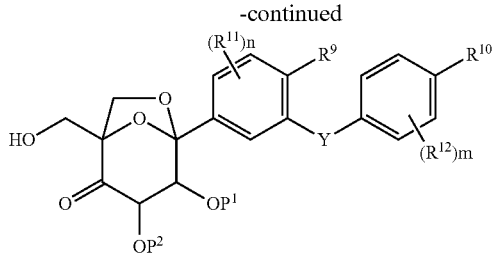

I-ee

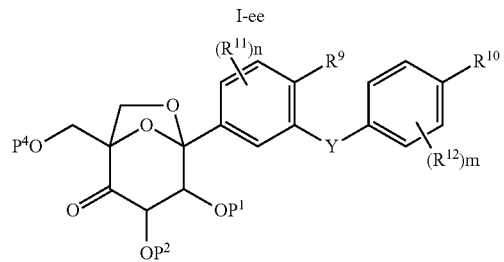

I-ff

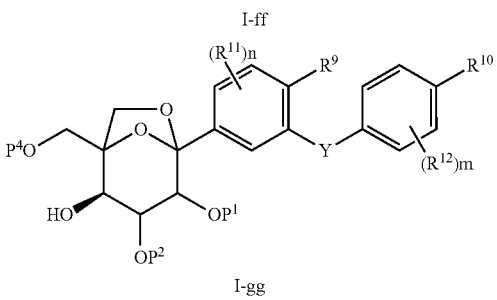

I-gg

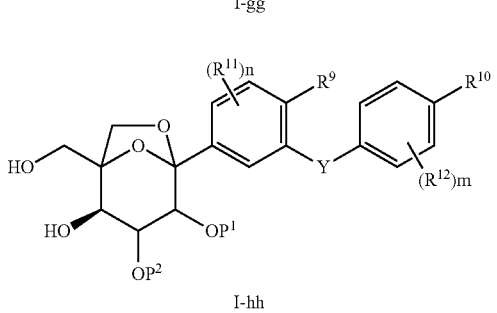

I-hh

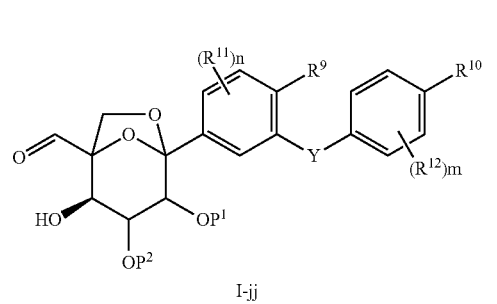

I-jj

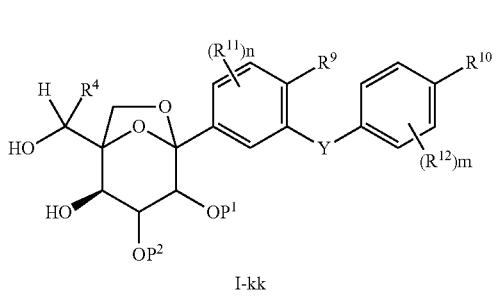

I-kk

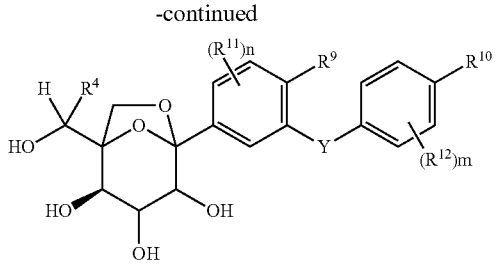

I-H

Compounds of Formula (I-H) can be prepared by a general synthetic procedure illustrated in Scheme 10, wherein $R^4$ is methyl; each of $R^9$, $R^{10}$, $R^{11}$, $R^{12}$, Y, m and n is as defined herein; each of $P^1$, $P^2$, $P^3$ and $P^4$ is independently hydroxy-protecting group, the hydroxy-protecting group is as defined herein.

Compound (I-w) can react with benzaldehyde dimethyl acetal in the presence of an acid to afford compound (I-x). Compound (I-x) can react with benzyl bromide under alkaline condition to afford compound (I-y). The protecting group of compound (I-y) can be removed in the presence of an acid to afford compound (I-z). Compound (I-z) can react with tert-butyldimethylsilyl chloride under alkaline condition to afford compound (I-cc). Oxidation of compound (I-cc) can afford compound (I-dd). The protecting group of compound (I-dd) can be removed to afford compound (I-ee). Compound (I-ee) can react with acetic anhydride under alkaline condition to afford compound (I-ff). Reduction of compound (I-ff) in the presence of sodium borohydride can afford compound (I-gg). The protecting group of compound (I-gg) can be removed to afford compound (I-hh). Oxidation of compound (I-hh) can afford compound (I-jj). Compound (I-jj) can react with methylmagnesium bromide to afford compound (I-kk). The protecting group of compound (I-kk) can be removed in the presence of an acid or by Pd/C catalysis under $H_2$ to afford compound (I-H).

Scheme 11

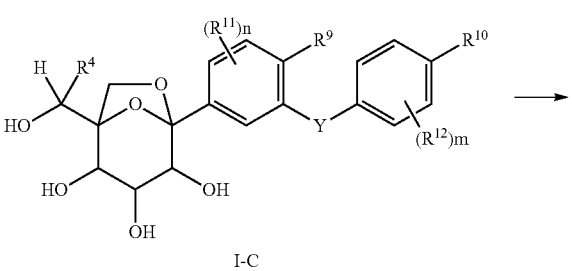

I-C

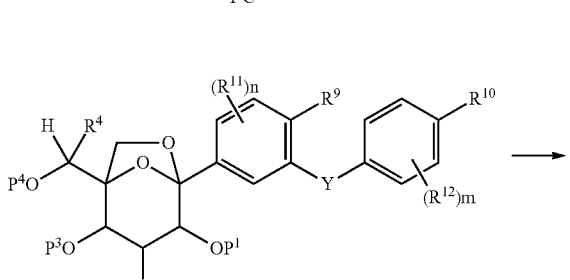

I-mm

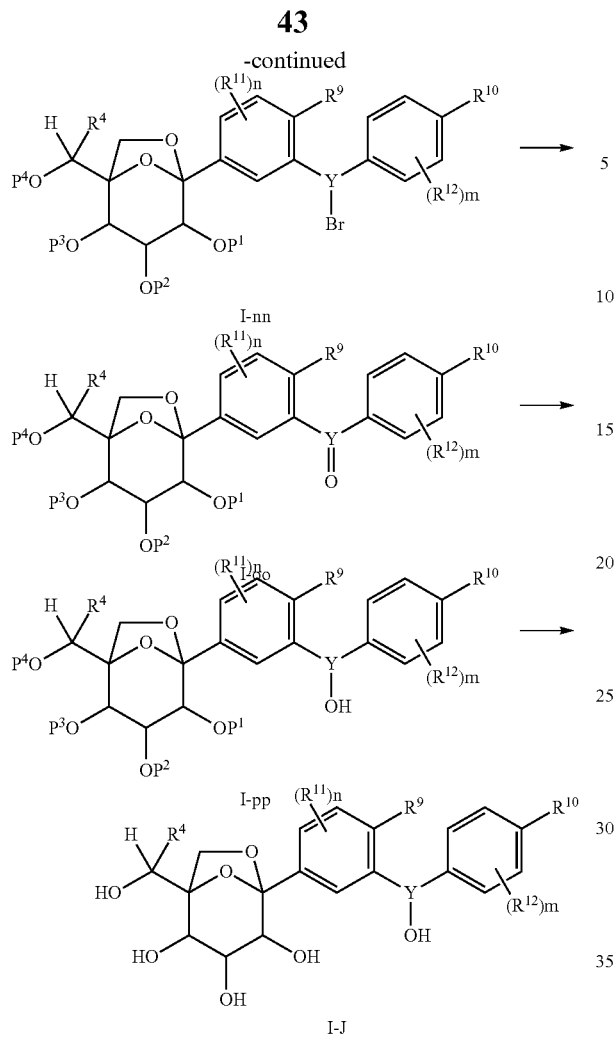

Compounds of Formula (I-J) can be prepared by a general synthetic procedure illustrated in Scheme 11, wherein $R^4$ is methyl; each of $R^9$, $R^{10}$, $R^{11}$, $R^{12}$, Y, m and n is as defined herein; each of $P^1$, $P^2$, $P^3$ and $P^4$ is independently hydroxy-protecting group, the hydroxy-protecting group is as defined herein.

Compound (I-C) can react with acetic anhydride under alkaline condition to afford compound (I-mm) Compound (I-mm) can react with N-bromosuccinimide to afford compound (I-nn). Oxidation of compound (I-nn) can afford compound (I-oo). Compound (I-oo) can react with sodium borohydride to afford compound (I-pp). Compound (I-pp) can react with potassium carbonate in methanol to afford compound (I-J).

Scheme 12

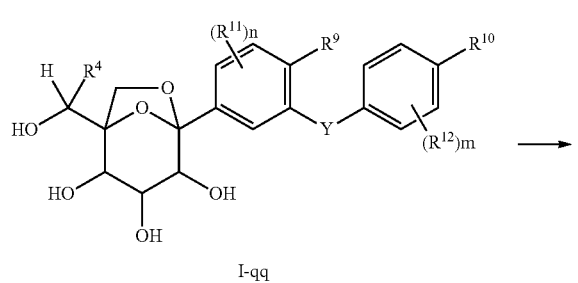

Compounds of Formula (I-rr) can be prepared by a general synthetic procedure illustrated in Scheme 12, wherein $R^4$ is methyl, ethyl, acetenyl or 1-propinyl; each of $R^9$, $R^{10}$, $R^{11}$, $R^{12}$, Y, m and n is as defined herein; $R^9$ is Cl, Br or I.

The group $R^9$ of compound (I-qq) can be removed under alkaline condition in the presence of a Pd/C catalyst to afford compound (I-rr).

EXAMPLE

Example 1

(1R,2S,3S,4R,5S)-5-[4-Chloro-3-[(4-ethoxyphenyl)methyl]phenyl]-1-(1-hydroxyethyl)-6,8-dioxabicyclo[3.2.1]octane-2,3,4-triol 1

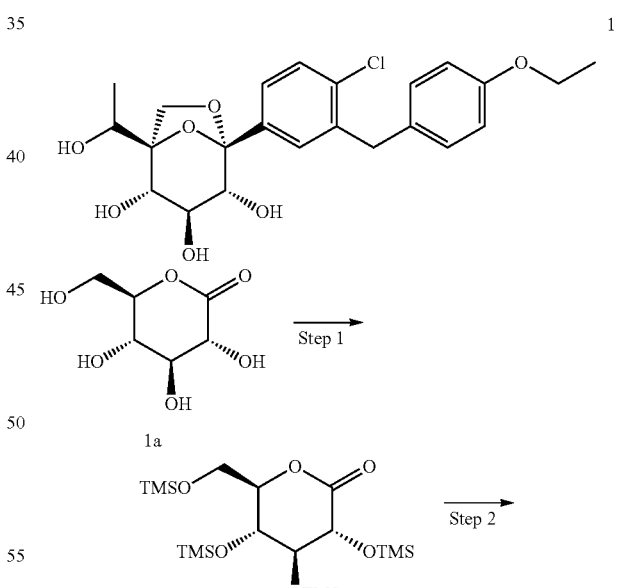

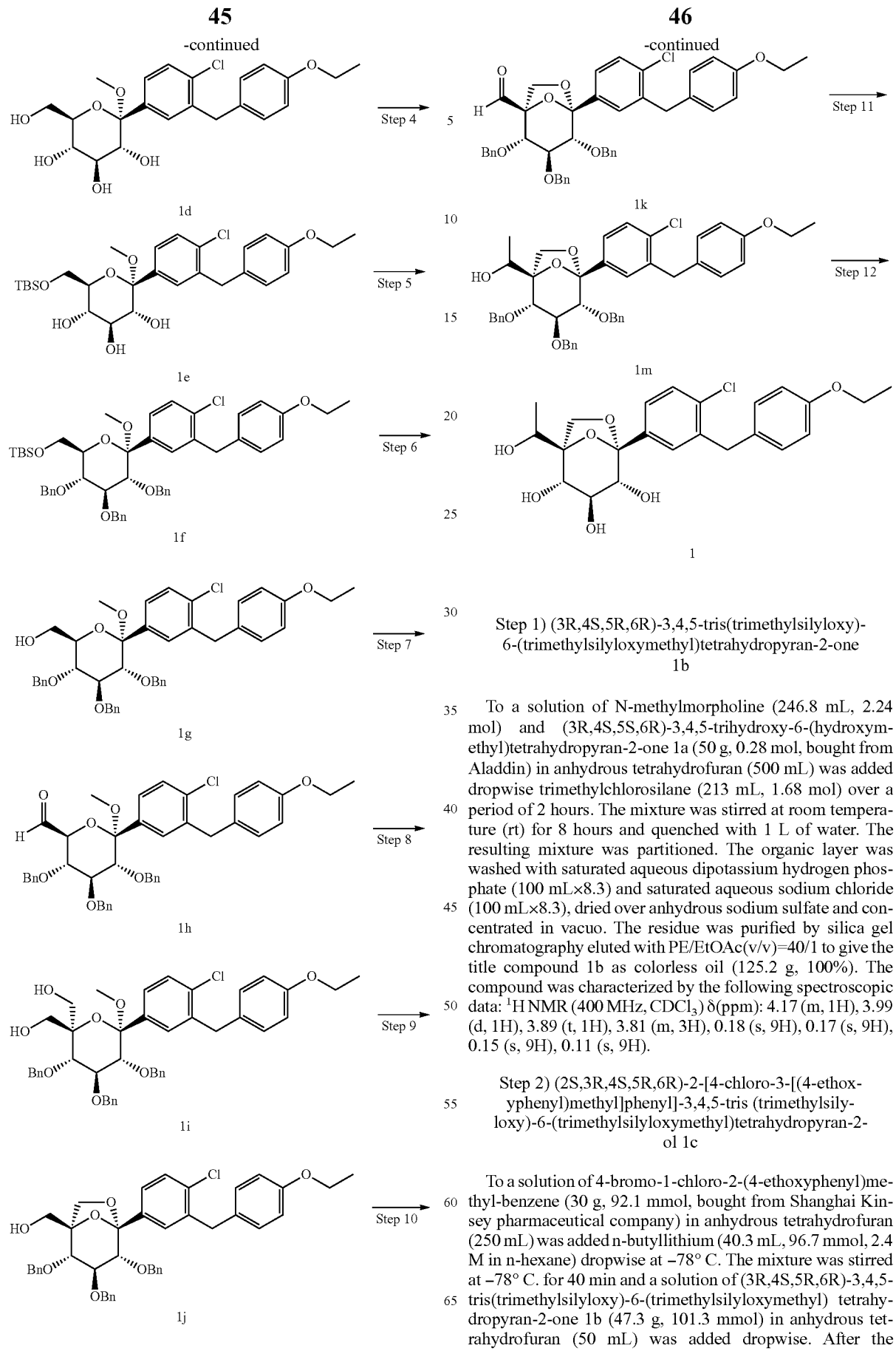

Step 1) (3R,4S,5R,6R)-3,4,5-tris(trimethylsilyloxy)-6-(trimethylsilyloxymethyl)tetrahydropyran-2-one 1b To a solution of N-methylmorpholine (246.8 mL, 2.24 mol) and (3R,4S,5S,6R)-3,4,5-trihydroxy-6-(hydroxymethyl)tetrahydropyran-2-one 1a (50 g, 0.28 mol, bought from Aladdin) in anhydrous tetrahydrofuran (500 mL) was added dropwise trimethylchlorosilane (213 mL, 1.68 mol) over a period of 2 hours. The mixture was stirred at room temperature (rt) for 8 hours and quenched with 1 L of water. The resulting mixture was partitioned. The organic layer was washed with saturated aqueous dipotassium hydrogen phosphate (100 mL×8.3) and saturated aqueous sodium chloride (100 mL×8.3), dried over anhydrous sodium sulfate and concentrated in vacuo. The residue was purified by silica gel chromatography eluted with PE/EtOAc(v/v)=40/1 to give the title compound 1b as colorless oil (125.2 g, 100%). The compound was characterized by the following spectroscopic data: $^1$H NMR (400 MHz, CDCl$_3$) δ(ppm): 4.17 (m, 1H), 3.99 (d, 1H), 3.89 (t, 1H), 3.81 (m, 3H), 0.18 (s, 9H), 0.17 (s, 9H), 0.15 (s, 9H), 0.11 (s, 9H).

Step 2) (2S,3R,4S,5R,6R)-2-[4-chloro-3-[(4-ethoxyphenyl)methyl]phenyl]-3,4,5-tris (trimethylsilyloxy)-6-(trimethylsilyloxymethyl)tetrahydropyran-2-ol 1c To a solution of 4-bromo-1-chloro-2-(4-ethoxyphenyl)methyl-benzene (30 g, 92.1 mmol, bought from Shanghai Kinsey pharmaceutical company) in anhydrous tetrahydrofuran (250 mL) was added n-butyllithium (40.3 mL, 96.7 mmol, 2.4 M in n-hexane) dropwise at −78° C. The mixture was stirred at −78° C. for 40 min and a solution of (3R,4S,5R,6R)-3,4,5-tris(trimethylsilyloxy)-6-(trimethylsilyloxymethyl) tetrahydropyran-2-one 1b (47.3 g, 101.3 mmol) in anhydrous tetrahydrofuran (50 mL) was added dropwise. After the addition, the mixture was further stirred at −78° C. for 5 hours and then quenched with 100 mL of saturated aqueous ammonium chloride. The mixture was allowed to warm up to room temperature and concentrated in vacuo. To the residue was added 150 mL of water. The resulting mixture was extracted with ethyl acetate (150 mL×3). The combined organic layers were washed with saturated aqueous sodium chloride (200 mL), dried over anhydrous sodium sulfate and concentrated in vacuo to give the title compound 1c as pale yellow oil (69.7 g, 100%). This crude product was used in next step without further purification.

Step 3) (2S,3R,4S,5S,6R)-2-[4-chloro-3-[(4-ethoxyphenyl)methyl]phenyl]-6-(hydroxymethyl)-2-methoxy-tetrahydropyran-3,4,5-triol 1d To a solution of (2S,3R,4S,5R,6R)-2-[4-chloro-3-[(4-ethoxyphenyl)methyl]phenyl]-3,4,5-tris(trimethylsilyloxy)-6-(trimethylsilyloxymethyl)tetrahydropyran-2-ol 1c (65.7 g, 92.13 mmol) in methanol (300 mL) was added p-toluenesulfonic acid monohydrate (8.76 g, 46.06 mmol). The mixture was stirred at room temperature for 12 hours, neutralized with saturated aqueous sodium bicarbonate till pH becomes 7 and concentrated in vacuo. To the residue was added 100 mL of water. The resulting mixture was extracted with ethyl acetate (200 mL×3). The combined organic layers were washed with saturated aqueous sodium chloride (200 mL), dried over anhydrous sodium sulfate and concentrated in vacuo. The residue was purified by re-crystallization from toluene/n-hexane(v/v)=1/1 to give the title compound 1d as a white meshy solid (29.0 g, 71.6%). The compound was characterized by the following spectroscopic data: $^1$H NMR (400 MHz, DMSO-d$_6$) δ (ppm): 7.52 (s, 1H), 7.39 (m, 2H), 7.08 (m, 2H), 6.83 (m, 2H), 4.96 (d, 1H), 4.73 (m, 2H), 4.52 (t, 1H), 4.09-3.94 (m, 4H), 3.76-3.72 (m, 1H), 3.61-3.51 (m, 2H), 3.38 (m, 1H), 3.23 (m, 1H), 2.92 (s, 3H), 2.89 (m, 1H), 1.29 (t, 3H).

Step 4) (2S,3R,4S,5S,6R)-6-[(tert-butyl(dimethyl)silyl)oxymethyl]-2-[4-chloro-3-[(4-ethoxyphenyl)methyl]phenyl]-2-methoxy-tetrahydropyran-3,4,5-triol 1e To a solution of (2S,3R,4S,5S,6R)-2-[4-chloro-3-[(4-ethoxyphenyl)methyl]phenyl]-6-(hydroxymethyl)-2-methoxy-tetrahydropyran-3,4,5-triol 1d (82.2 g, 187.4 mmol) in dichloromethane (800 mL) was added imidazole (25.5 g, 374.7 mmol) at room temperature. The mixture was stirred at 0° C. and tert-butyldimethylsilyl chloride (56.7 g, 374.7 mmol) was added. The resulting mixture was further stirred at 0° C. for 2 hours. At 0° C., the mixture was adjusted to pH 7 with saturated aqueous sodium bicarbonate and partitioned. The organic layer was washed with water (100 mL×2) and then saturated aqueous sodium chloride (100 mL×2), dried over anhydrous sodium sulfate and concentrated in vacuo to give the title compound 1e as yellow oil (119 g, 100%). This crude product was used in next step without further purification. The compound was characterized by the following spectroscopic data: $^1$H NMR (400 MHz, CDCl$_3$) δ (ppm): 7.37 (m, 2H), 7.30 (m, 1H), 6.08 (m, 2H), 6.80 (m, 2H), 4.02-3.88 (m, 7H), 3.67 (m, 2H), 3.22 (m, 1H), 3.08 (s, 3H), 1.40 (t, 3H), 0.90 (s, 9H), 0.12 (s, 3H), 0.09 (s, 3H).

Step 5) tert-butyl-dimethyl-[[(2R,3R,4S,5R,6S)-3,4,5-tribenzyloxy-6-[4-chloro-3-[(4-ethoxyphenyl)methyl]phenyl]-6-methoxy-tetrahydropyran-2-yl]methoxy]silane 1f To a suspension of sodium hydride (65.4 g, 1.627 mol, 60% dispersion in Mineral oil) in anhydrous tetrahydrofuran (100 mL) was added dropwise a solution of (2S,3R,4S,5S,6R)-6-[(tert-butyl(dimethyl)silyl)oxymethyl]-2-[4-chloro-3-[(4-ethoxyphenyl)methyl]phenyl]-2-methoxy-tetrahydropyran-3,4,5-triol 1e (150 g, 0.271 mol) in anhydrous tetrahydrofuran (800 mL) at 0° C. The mixture was stirred at 0° C. for 1 hour and then allowed to warm up to room temperature. After benzyl bromide (113 mL, 951.84 mmol) and tetrabutylammonium iodide (3.91 g, 10.6 mmol) were added in turn, the mixture was stirred at 40° C. for 12 hours and cooled to 0° C., and then quenched with 50 mL of water. Most of the solvent was removed in vacuo. To the residue was added 200 mL of water. The resulting mixture was extracted with ethyl acetate (150 mL×3). The combined organic layers were washed with saturated aqueous sodium chloride (200 mL×2), dried over anhydrous sodium sulfate and concentrated in vacuo. The residue was purified by silica gel chromatography eluted with PE/EtOAc(v/v)=20/1 to give the title compound 1f as yellow oil (97 g, 43.5%). The compound was characterized by the following spectroscopic data: $^1$H NMR (400 MHz, CDCl$_3$) δ (ppm): 7.46 (m, 1H), 7.35 (m, 12H), 7.20 (m, 3H), 7.04 (m, 4H), 6.74 (m, 2H), 4.90 (m, 3H), 4.72 (d, 1H), 4.50 (d, 1H), 4.15 (t, 1H), 4.05 (d, 1H), 3.97 (m, 3H), 3.80 (m, 3H), 3.75 (m, 1H), 3.65 (m, 1H), 3.29 (d, 1H), 3.05 (s, 3H), 1.38 (t, 3H), 0.90 (s, 9H), 0.11 (s, 3H), 0.08 (s, 3H).

Step 6) [(2R,3R,4S,5R,6S)-3,4,5-tribenzyloxy-6-[4-chloro-3-[(4-ethoxyphenyl)methyl]phenyl]-6-methoxy-tetrahydropyran-2-yl]methanol 1g To a solution of tert-butyl-dimethyl-[[(2R,3R,4S,5R,6S)-3,4,5-tribenzyloxy-6-[4-chloro-3-[(4-ethoxyphenyl)methyl]phenyl]-6-methoxy-tetrahydropyran-2-yl]methoxy]silane 1f (84.1 g, 102.1 mmol) in tetrahydrofuran (400 mL) was added tetrabutylammonium fluoride (53.4 g, 204.2 mmol) at room temperature. The mixture was stirred at room temperature for 2 hours and quenched with 100 mL of saturated aqueous sodium bicarbonate. The resulting mixture was washed with water (100 mL). The aqueous layer was extracted with ethyl acetate (100 mL×3). The combined organic layers were washed with saturated aqueous sodium chloride (200 mL), dried over anhydrous sodium sulfate and concentrated in vacuo. The residue was purified by silica gel chromatography eluted with PE/EtOAc(v/v)=10/1 to give the title compound 1g as yellow oil (56.3 g, 77.8%). The compound was characterized by the following spectroscopic data: $^1$H NMR (400 MHz, CDCl$_3$) δ (ppm): 7.34 (m, 13H), 7.25 (m, 3H), 7.04 (m, 2H), 6.99 (m, 2H), 6.77 (m, 2H), 4.90 (m, 3H), 4.69 (d, 1H), 4.49 (d, 1H), 4.16 (t, 1H), 4.10 (d, 1H), 4.00 (m, 2H), 3.98 (m, 2H), 3.81 (m, 1H), 3.70 (m, 1H), 3.68 (m, 1H), 3.66 (m, 1H), 3.29 (d, 1H), 3.06 (s, 3H), 1.75 (bs, 1H), 1.38 (t, 3H).

Step 7) (2S,3S,4S,5R,6S)-3,4,5-tribenzyloxy-6-[4-chloro-3-[(4-ethoxyphenyl)methyl]phenyl]-6-methoxy-tetrahydropyran-2-carbaldehyde 1h To a solution of [(2R,3R,4S,5R,6S)-3,4,5-tribenzyloxy-6-[4-chloro-3-[(4-ethoxyphenyl)methyl]phenyl]-6-methoxy-tetrahydropyran-2-yl]methanol 1g (8.65 g, 12.19 mmol) in dichloromethane (300 mL) was added 2-iodoxybenzoic acid (6.83 g, 24.39 mmol) at room temperature. The mixture was refluxed at 45° C. for 36 hours and quenched with 150 mL of water. The mixture was partitioned between dichloromethane and water. The organic layer was washed with saturated aqueous sodium chloride (150 mL×2), dried over anhydrous sodium sulfate and concentrated in vacuo to give the title compound 1l as yellow oil (7.57 g, 87.8%). This crude product was used in next step without further purification. The compound was characterized by the following spectroscopic data: $^1$H NMR (400 MHz, CDCl$_3$) δ (ppm): 9.74 (d, 1H), 7.39-7.19 (m, 16H), 7.03-7.00 (m, 4H), 6.76 (m, 2H), 4.90 (m, 3H), 4.70 (d, 1H), 4.48 (d, 1H), 4.23 (t, 1H), 4.15-4.07 (m, 2H), 3.99-3.75 (m, 5H), 3.31 (d, 1H), 3.07 (s, 3H), 1.38 (t, 3H).

Step 8) [(3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl] methanol To a solution of (2S,3S,4S,5R,6S)-3,4,5-tribenzyloxy-6-[4-chloro-3-[(4-ethoxyphenyl)methyl]phenyl]-6-methoxy-tetrahydropyran-2-carbaldehyde 1h (13.5 g, 19.1 mmol) in an isopropanol/dioxane mixture (95 mL, v/v=18/1) was added sodium hydroxide (1.22 g, 30.56 mmol) in portions at room temperature, and then formaldehyde (38.7 mL, 477.5 mmol, 37 wt % solution) was added. The mixture was stirred at room temperature for 48 hours and adjusted to pH 7 with saturated aqueous ammonium chloride. The resulting mixture was extracted with ethyl acetate (50 mL×3). The combined organic layers were washed with water (25 mL×2) and then saturated aqueous sodium chloride (25 mL×2), dried over anhydrous sodium sulfate and concentrated in vacuo. The residue was purified by silica gel chromatography eluted with PE/EtOAc(v/v)=5/1 to give the title compound 1i as yellow oil (4.63 g, 32.8%). The compound was characterized by the following spectroscopic data: $^1$H NMR (400 MHz, CDCl$_3$) δ (ppm): 7.37 (m, 6H), 7.22 (m, 10H), 7.05 (m, 2H), 7.02 (m, 2H), 6.79 (m, 2H), 4.95 (m, 3H), 4.69 (d, 2H), 4.38 (m, 1H), 4.09 (m, 2H), 4.04-3.96 (m, 4H), 3.83 (m, 3H), 3.66 (m, 1H), 3.25 (m, 1H), 3.06 (s, 3H), 1.72 (t, 1H), 1.39 (t, 3H).

Step 9) [(1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]methanol 1j To a solution of [(3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl]methanol 1i (2.49 g, 3.37 mmol) in dichloromethane (300 mL) was added p-toluenesulfonic acid monohydrate (0.32 g, 1.69 mmol) at room temperature. The mixture was stirred at room temperature for 1 hour and quenched with 30 mL of saturated aqueous sodium bicarbonate. The resulting mixture was extracted with dichloromethane (20 mL×2). The combined organic layers were washed with saturated aqueous sodium chloride (20 mL×2), dried over anhydrous sodium sulfate and concentrated in vacuo. The residue was purified by silica gel chromatography eluted with PE/EtOAc(v/v)=7/1 to give the title compound 1j as pale yellow oil (1.06 g, 44.5%). The compound was characterized by the following spectroscopic data: $^1$H NMR (400 MHz, CDCl$_3$) δ (ppm): 7.45 (d, 1H), 7.40 (m, 12H), 7.30 (m, 3H), 7.09 (m, 2H), 6.91 (m, 2H), 6.78 (m, 2H), 4.88 (m, 3H), 4.78 (d, 1H), 4.29 (m, 2H), 4.11-3.96 (m, 6H), 3.88 (d, 1H), 3.80 (m, 2H), 3.71 (m, 2H), 1.85 (t, 1H), 1.41 (t, 3H).

Step 10) (1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-carbaldehyde 1k To a solution of [(1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]methanol 1j (8.53 g, 12.08 mmol) in dichloromethane (350 mL) was added 2-iodoxybenzoicacid (6.77 g, 24.2 mmol) at room temperature. The mixture was refluxed at 45° C. for 36 hours and quenched with 150 mL of water. The mixture was partitioned between dichloromethane and water. The organic layer was washed with saturated aqueous sodium chloride (150 mL×2), dried over anhydrous sodium sulfate and concentrated in vacuo. The residue was purified by silica gel chromatography eluted with PE/EtOAc (v/v)=10/1 to give the title compound 1k as pale yellow oil (4.94 g, 60.0%).

Step 11) 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 1 m To a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (3.02 g, 4.26 mmol) in tetrahydrofuran (40 mL) was added dropwise methylmagnesium bromide (2.13 mL, 6.39 mmol, 3M in tetrahydrofuran) over a period of 5 min at −10° C. The mixture was stirred at room temperature for 16 hours and quenched with 5 mL of water. The mixture was partitioned. The aqueous layer was extracted with ethyl acetate (10 mL×2). The combined organic layers were washed with saturated aqueous sodium chloride (20 mL×2), dried over anhydrous sodium sulfate and concentrated in vacuo. The residue was purified to give the title compound 1m as pale yellow oil (2.0 g, 65.0%). The compound was characterized by the following spectroscopic data: $^1$H NMR (400 MHz, DMSO-d$_6$) δ (ppm): 7.48 (m, 2H), 7.45 (m, 1H), 7.30 (m, 10H), 7.19 (m, 3H), 7.05 (m, 2H), 6.85 (m, 2H), 6.75 (m, 2H), 5.04 (m, 1H), 4.80 (m, 3H), 4.30 (d, 1H), 4.11 (m, 1H), 4.01 (m, 3H), 3.98 (m, 5H), 3.79 (m, 2H), 1.28 (t, 3H), 1.13 (d, 3H).

Step 12) (1R,2S,3S,4R,5S)-5-[4-chloro-3-[(4-ethoxyphenyl)methyl]phenyl]-1-(1-hydroxyethyl)-6,8-dioxabicyclo[3.2.1]octane-2,3,4-triol 1

To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 1m (1.71 g, 2.36 mmol) in a methanol/tetrahydrofuran mixture (v/v=4/1, 30 mL) were added o-dichlorobenzene (1.74 g, 11.8 mmol) and 10% Pd/C (250 mg, 0.236 mmol) at room temperature. The mixture was stirred under H$_2$ at room temperature for 1.5 hours and filtered. The filtrate was concentrated in vacuo. The residue was purified by preparative HPLC (prep-HPLC) to give the title compound 1 as a white solid (544 mg, 51.3%, HPLC: 99.6%). The compound was characterized by the following spectroscopic data: MS (ESI, pos. ion) m/z: 451.2 [M+H]$^+$; and $^1$H NMR (400 MHz, CDCl$_3$) δ (ppm): 7.35 (m, 1H), 7.29-7.21 (m, 2H), 7.04 (m, 2H), 6.75 (m, 2H), 4.71 (br, 1H), 4.51 (br, 1H), 4.14 (m, 1H), 4.01 (m, 3H), 3.98 (m, 2H), 3.89 (m, 1H), 3.77 (m, 2H), 3.60 (m, 1H), 3.52 (br, 1H), 3.06 (br, 1H), 1.34 (t, 3H), 0.91 (d, 3H).

Example 2

(1S,2S,3S,4R,5S)-5-[4-Chloro-3-[(4-ethoxyphenyl)methyl]phenyl]-1-(2-hydroxypropan-2-yl)-6,8-dioxabicyclo[3.2.1]octane-2,3,4-triol 2

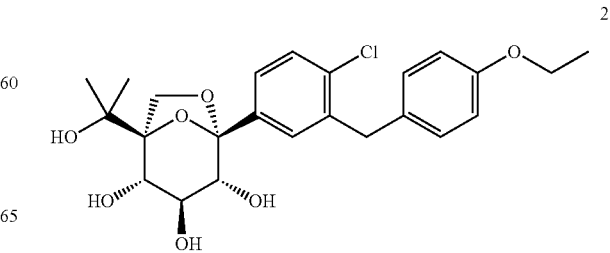

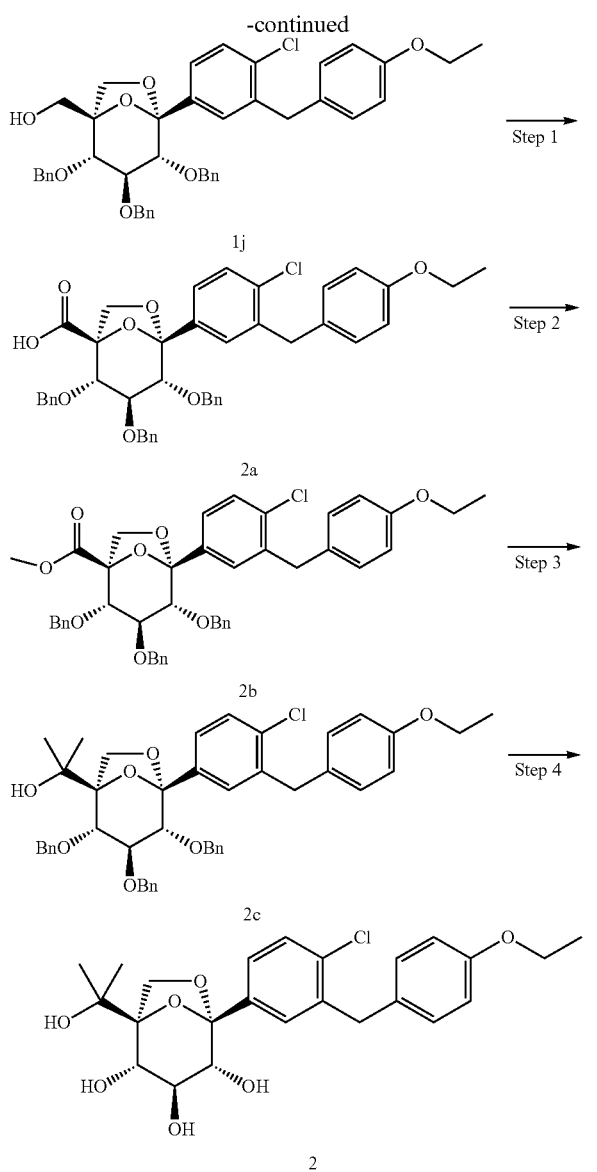

Step 1) (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carboxylic acid 2a To a solution of [(1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]methanol 1j (0.36 g, 0.51 mmol, obtained from the synthetic method described in step 9 of example 1) in tetrahydrofuran (7 mL) were added saturated aqueous sodium bicarbonate (7.4 mL), potassium bromide (12 mg, 0.10 mmol) and 2,2,6,6-tetramethylpiperidinooxy (8 mg, 0.05 mmol) in turn at 0° C., and then sodium hypochlorite (6.7 mL, available chlorine ≥5.5%) was added dropwise over a period of 10 min. The mixture was stirred at 0° C. for 2 hours and acidified with aqueous HCl(1N) till pH becomes 4. The resulting mixture was extracted with ethyl acetate (10 mL×2). The combined organic layers were washed with saturated aqueous sodium chloride (10 mL), dried over anhydrous sodium sulfate and concentrated in vacuo to give the title compound 2a (0.38 g, 100%) as yellow oil. The crude product was used in next step without further purification. The compound was characterized by the following spectroscopic data: $^1$H NMR (400 MHz, DMSO-$d_6$) δ (ppm): 13.92 (s, 1H), 7.52 (s, 1H), 7.45 (dd, 2H), 7.30 (dd, 10H), 7.19 (t, 3H), 7.05 (d, 2H), 6.82 (d, 2H), 6.75 (d, 2H), 4.75 (m, 3H), 4.68 (d, 1H), 4.36 (d, 1H), 4.29 (d, 1H), 4.09 (d, 1H), 4.02 (m, 3H), 3.93 (m, 2H), 3.89-3.82 (m, 2H), 3.76 (d, 1H), 1.28 (t, 3H).

Step 2) methyl (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carboxylate 2b To a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carboxylic acid 2a (0.38 g, 0.53 mmol) in methanol (8 mL) was added concentrated sulphuric acid (56.9 mg, 0.58 mmol) at room temperature. The mixture was stirred at 40° C. for 12 hours and quenched with 0.5 mL of saturated aqueous sodium hydrogen carbonate. Most of the solvent of the mixture was removed in vacuo. To the residue was added water (10 mL). The resulting mixture was extracted with ethyl acetate (10 mL×2). The combined organic layers were washed with saturated aqueous sodium chloride (10 mL×2), dried over anhydrous sodium sulfate and concentrated in vacuo. The residue was purified by silica gel chromatography eluted with PE/EtOAc(v/v)=10/1 to give the title compound 2b as colorless oil (155 mg, 41.4%). The compound was characterized by the following spectroscopic data: $^1$H NMR (400 MHz, CDCl$_3$) δ(ppm): 7.48 (m, 1H), 7.39 (m, 2H), 7.38-7.29 (m, 7H), 7.28-7.23 (m, 3H), 7.19 (m, 3H), 7.08 (m, 2H), 6.91-6.86 (m, 2H), 6.80-6.73 (m, 2H), 4.82 (m, 3H), 4.63 (d, 1H), 4.53 (d, 1H), 4.26 (d, 1H), 4.24-4.16 (m, 2H), 4.09 (d, 1H), 4.05-3.94 (m, 4H), 3.87 (d, 1H), 3.75 (d, 1H), 3.71 (s, 3H), 1.41 (t, 3H).

Step 3) 2-[(1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]propan-2-ol 2c To a solution of methyl (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carboxylate 2b (155 mg, 0.21 mmol) in anhydrous tetrahydrofuran (5 mL) was added dropwise methylmagnesium bromide (0.42 mL, 1.27 mmol, 3M in tetrahydrofuran) at 0° C. The mixture was stirred at 40° C. for 12 hours, quenched with 2 mL of water and filtered. Most of the solvent of the filtrate was removed in vacuo. The resulting mixture was extracted with ethyl acetate (5 mL×2). The combined organic layers were washed with saturated aqueous sodium chloride (5 mL×2), dried over anhydrous sodium sulfate and concentrated in vacuo give the title compound 2c as colorless oil (155 mg, 100%). The crude product was used in next step without further purification. The compound was characterized by the following spectroscopic data: $^1$H NMR (400 MHz, CDCl$_3$) δ(ppm): 7.33 (m, 10H), 7.19 (m, 5H), 7.06 (d, 2H), 6.91 (dd, 2H), 6.74 (m, 2H), 5.05 (d, 1H), 4.94 (d, 1H), 4.75 (d, 2H), 4.32 (d, 1H), 4.19 (d, 1H), 4.05 (m, 5H), 3.97 (m, 2H), 3.80 (d, 1H), 3.69 (d, 1H), 1.38 (t, 3H), 1.28 (s, 3H), 1.24 (s, 3H).

Step 4) (1S,2S,3S,4R,5S)-5-[4-chloro-3-[(4-ethoxyphenyl)methyl]phenyl]-1-(2-hydroxypropan-2-yl)-6,8-dioxabicyclo[3.2.1]octane-2,3,4-triol 2

To a solution of 2-[(1S,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]propan-2-ol 2c (155 mg, 0.21 mmol) in a methanol/tetrahydrofuran mixture (v/v=4/1, 5 mL) were added o-dichlorobenzene (155 mg, 1.06 mmol) and 10% Pd/C (22 mg, 0.02 mmol) in turn at room temperature. The mixture was stirred at room temperature under $H_2$ for 1 hour and filtered. The filtrate was concentrated in vacuo. The residue was purified by silica gel chromatography eluted with PE/EtOAc(v/v)=1/2 to give the title compound 2 as a white solid (90 mg, 91.8%, HPLC: 96.8%). The compound was characterized by the following spectroscopic data: MS (ESI, pos. ion) m/z: 509[M+HCOO]$^-$; and $^1$H NMR (400 MHz, DMSO-d$_6$) δ(ppm): 7.35 (s, 2H), 7.30 (dd, 1H), 7.08 (d, 2H), 6.81 (d, 2H), 5.46 (t, 1H), 5.01 (d, 1H), 4.95 (d, 1H), 4.21 (s, 1H), 3.95 (d, 5H), 3.78 (d, 1H), 3.68 (dd, 1H), 3.43 (dd, 1H), 3.35 (m, 1H), 1.28 (t, 3H), 1.18 (s, 3H), 1.13 (s, 3H).

Example 3

(1S,2S,3S,4R,5S)-5-[4-Chloro-3 [(4-ethoxyphenyl)methyl]phenyl]-1-(1-hydroxypropyl)-6,8-dioxabicyclo[3.2.1]octane-2,3,4-triol 3

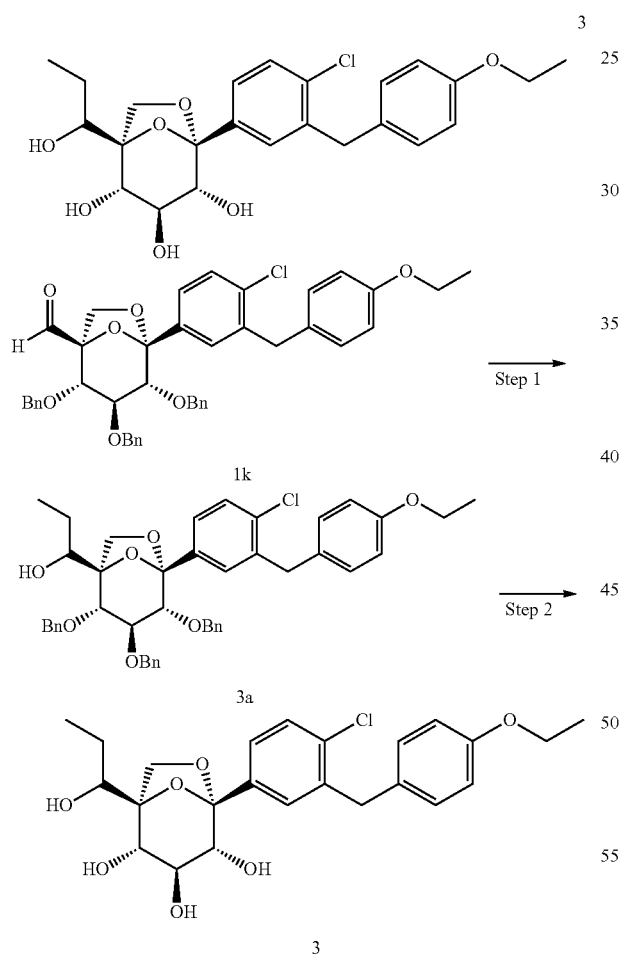

Step 1) 1-[(1S,2S,3S,4R,5S)-2,3,4-tribenzyloxy-5-[4-chloro-3[(4-ethoxyphenyl)methyl]phenyl]-6,8-dioxabicyclo[3.2.1]octane-1-yl]propan-1-ol 3a To a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (0.3 g, 0.43 mmol, obtained from the synthetic method described in step 10 of example 1) in anhydrous tetrahydrofuran (10 mL) was added dropwise ethylmagnesium bromide (1.7 mL, 1.7 mmol, 1M) at 0° C. The mixture was stirred at room temperature for 16 hours, quenched with 2 mL of saturated aqueous ammonium chloride, and extracted with dichloromethane (20 mL×2). The combined organic layers were washed with saturated aqueous sodium chloride (5 mL×2), dried over anhydrous sodium sulfate and concentrated in vacuo. The residue was purified by silica gel chromatography eluted with PE/EtOAc (v/v)=10/1 to give the title compound 3a as colorless oil (48 mg, 16.0%). The compound was characterized by the following spectroscopic data: $^1$H NMR (400 MHz, CDCl$_3$) δ(ppm): 7.40 (m, 1H), 7.31 (m, 10H), 7.18 (m, 5H), 7.07 (m, 2H), 6.90 (m, 2H), 6.75 (m, 2H), 4.93 (m, 2H), 4.77 (m, 2H), 4.29 (d, 1H), 4.21 (d, 1H), 4.03 (m, 3H), 3.96 (m, 4H), 3.81 (m, 1H), 3.65 (m, 2H), 2.23 (d, 1H), 1.51 (m, 2H), 1.38 (t, 3H), 0.93 (t, 3H).

Step 2) (1S,2S,3S,4R,5S)-5-[4-chloro-3 [(4-ethoxyphenyl)methyl]phenyl]-1-(1-hydroxypropyl)-6,8-dioxabicyclo[3.2.1]octane-2,3,4-triol 3

To a solution of 1-[(1S,2S,3S,4R,5S)-2,3,4-tribenzyloxy-5-[4-chloro-3[(4-ethoxyphenyl)methyl]phenyl]-6,8-dioxabicyclo[3.2.1]octane-1-yl]propan-1-ol 3a (42 mg, 0.06 mmol) in a methanol/tetrahydrofuran mixture (v/v=4/1, 5 mL) were added o-dichlorobenzene (41.16 mg, 0.28 mmol) and 10% Pd/C (5.72 mg, 0.006 mmol) in turn. The mixture was stirred at room temperature under $H_2$ for 4 hours and filtered. The filtered cake was washed with a methanol/tetrahydrofuran mixture (v/v=4/1, 10 mL×2). The combined filtrates were concentrated in vacuo. The residue was purified to give the title compound 3 as a pale yellow solid (76.5 mg, 51.0%, HPLC: 94.6%). The compound was characterized by the following spectroscopic data: MS (ESI, pos. ion) m/z: 465.1[M+H]$^+$; and $^1$H NMR (400 MHz, CDCl$_3$) δ(ppm): 7.35 (m, 2H), 7.32 (m, 1H), 7.06 (d, 2H), 6.77 (d, 2H), 4.19 (d, 1H), 4.10 (d, 1H), 3.96 (m, 4H), 3.76 (m, 3H), 3.68 (m, 1H), 1.54 (m, 2H), 1.36 (t, 3H), 0.95 (t, 3H).

Example 4

(1S,2S,3S,4R,5S)-5-[4-Chloro-3 [(4-ethoxyphenyl)methyl]phenyl]-1-(1-hydroxyprop-2-yn-1-yl)-6,8-dioxabicyclo[3.2.1]octane-2,3,4-triol 4

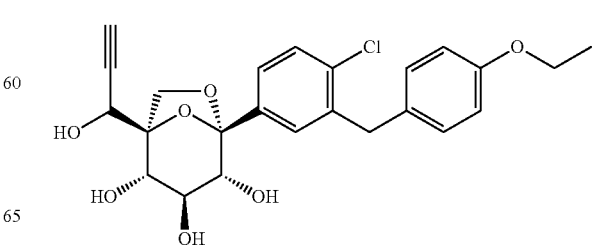

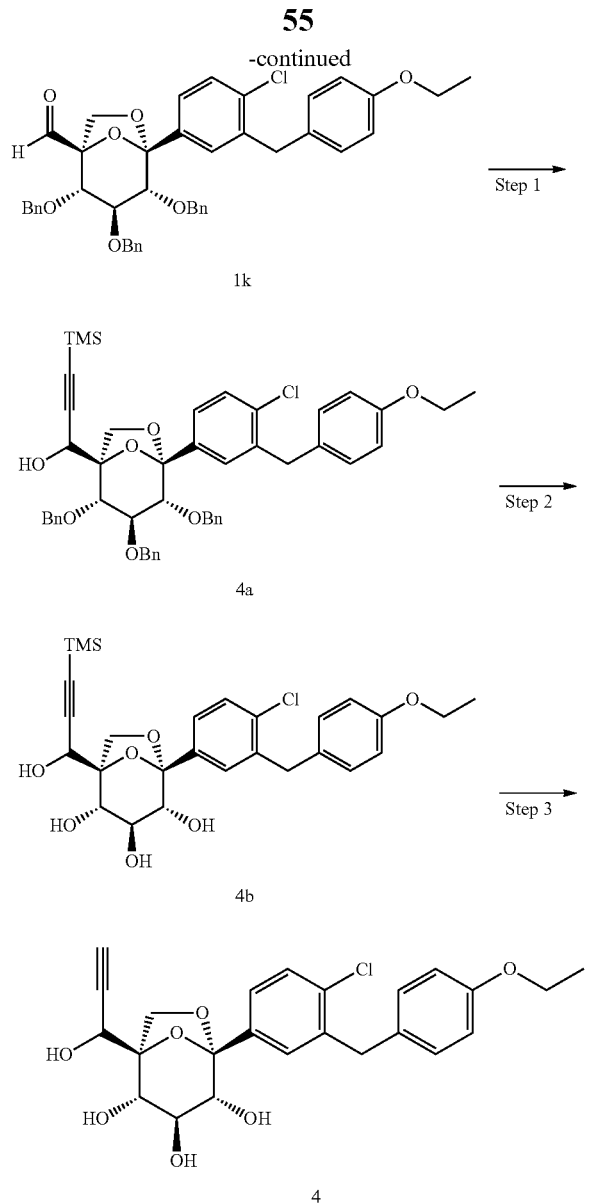

Step 1) 1-[(1S,2S,3S,4R,5S)-2,3,4-tribenzyloxy-5-[4-chloro-3 [(4-ethoxyphenyl)methyl]phenyl]-6,8-dioxabicyclo[3.2.1]octan-1-yl]-3-trimethylsilyl-prop-2-yn-1-ol 4a To a solution of trimethylsilylacetylene (752 mg, 7.66 mmol) in anhydrous tetrahyrofuran (50 mL) was added dropwise n-butyllithium (3.7 mL, 5.93 mmol, 1.6 M in hexane) at −78° C. After the addition, the mixture was stirred at −78° C. for 1 hour, and a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (2.7 g, 3.83 mmol, obtained from the synthetic method described in step 10 of example 1) in anhydrous tetrahydrofuran (20 mL) was added dropwise. After the addition, the mixture was stirred at room temperature for 3 hours and then quenched with 20 mL of water. The resulting mixture was extracted with ethyl acetate (60 mL×3). The combined organic layers were washed with water (30 mL×2) and then saturated aqueous sodium chloride (20 mL×2), dried over anhydrous sodium sulfate and concentrated in vacuo. The residue was purified by silica gel chromatography eluted with PE/EtOAc(v/v)=8/1 to give the title compound 4a as colorless oil (0.65 g, 24.8%). The compound was characterized by the following spectroscopic data: $^1$H NMR (400 MHz, CDCl$_3$) δ(ppm): 7.47 (m, 1H), 7.40 (m, 3H), 7.33 (m, 9H), 7.21 (m, 3H), 7.09 (m, 2H), 6.92 (m, 2H), 6.78 (m, 2H), 4.89 (m, 4H), 4.64 (m, 1H), 4.16 (m, 1H), 4.29 (m, 2H), 4.04 (m, 6H), 3.87 (m, 1H), 3.77 (m, 1H), 2.45 (d, 1H), 1.40 (t, 3H), 0.22 (s, 9H).

Step 2) (1S,2S,3S,4R,5S)-5-[4-chloro-3 [(4-ethoxyphenyl)methyl]phenyl]-1-(1-hydroxy-3-trimethysilyl-prop-2-ynyl)-6,8-dioxabicyclo[3.2.1]octane-2,3,4-triol 4b To a solution of 1-[(1S,2S,3S,4R,5S)-2,3,4-tribenzyloxy-5-[4-chloro-3[(4-ethoxyphenyl)methyl]phenyl]-6,8-dioxabicyclo[3.2.1]octan-1-yl]-3-trimethylsilyl-prop-2-yn-1-ol 4a (0.65 g, 0.81 mmol) in dichloromethane (30 mL) was added dropwise boron trichloride (8.89 mL, 8.89 mmol, 1 M in dichloromethane) at −78° C. The mixture was stirred at −78° C. for 2 hours. After the addition, the reaction mixture was quenched with 5 mL of water and adjusted to pH 6-7 with saturated aqueous sodium hydrogen carbonate. The resulting mixture was extracted with dichloromethane (30 mL×3). The combined organic layers were washed with water (20 mL×2) and then saturated aqueous sodium chloride (20 mL×2), dried over anhydrous sodium sulfate and concentrated in vacuo to give the title compound 4b as red oil (0.43 g, 100%). The crude product was used in next step without further purification. The compound was characterized by the following spectroscopic data: $^1$H NMR (400 MHz, CDCl$_3$) δ(ppm): 7.40 (m, 1H), 7.29 (m, 1H), 7.10 (d, 2H), 6.82 (d, 2H), 4.69 (t, 1H), 4.23 (m, 1H), 4.12 (m, 1H), 4.10 (m, 1H), 4.02 (m, 2H), 3.99 (m, 1H), 3.75 (d, 1H), 3.71 (d, 1H), 2.71 (d, 1H), 2.65 (d, 1H), 1.42 (t, 3H), 0.21 (s, 9H).

Step 3) (1S,2S,3S,4R,5S)-5-[4-chloro-3 [(4-ethoxyphenyl)methyl]phenyl]-1-(1-hydroxyprop-2-yn-1-yl)-6,8-dioxabicyclo[3.2.1]octane-2,3,4-triol 4

To a solution of (1S,2S,3S,4R,5S)-5-[4-chloro-3 [(4-ethoxyphenyl)methyl]phenyl]-1-(1-hydroxy-3-trimethysilyl-prop-2-ynyl)-6,8-dioxabicyclo[3.2.1]octane-2,3,4-triol 4b (0.44 g, 0.82 mmol) in anhydrous methanol (20 mL) was added sodium hydroxide (32.9 mg, 8.2 mmol). The mixture was stirred at room temperature for 10 hours. The reaction mixture was adjusted to pH 6-7 with saturated aqueous ammonium chloride, and extracted with ethyl acetate (40 mL×3). The combined organic layers were washed with water (30 mL×2) and then saturated aqueous sodium chloride (20 mL×2), dried over anhydrous sodium sulfate and concentrated in vacuo. The residue was purified by prep-HPLC to give the title compound 4 (56 mg, 14.7%, HPLC: 84.2%) as colorless oil. The compound was characterized by the following spectroscopic data: MS (ESI, pos. ion) m/z: 461.1[M+H]$^+$; and $^1$H NMR (400 MHz, DMSO-d$_6$) δ(ppm): 7.41 (m, 2H), 7.31 (m, 1H), 7.09 (d, 2H), 6.83 (d, 2H), 5.69 (d, 1H), 5.37 (d, 1H), 5.06 (d, 1H), 4.97 (d, 1H), 4.45 (m, 2H), 3.97 (m, 5H), 3.81 (s, 1H), 3.77 (d, 1H), 3.76 (t, 1H), 3.51 (m, 1H), 1.29 (t, 3H).

Example 5

(1R,2S,3S,4R,5S)-5-[4-Chloro-3 [(4-ethoxyphenyl) methyl]phenyl]-1-(1-hydroxybut-2-yn-1-ye-6,8-dioxabicyclo[3.2.1]octane-2,3,4-triol 5

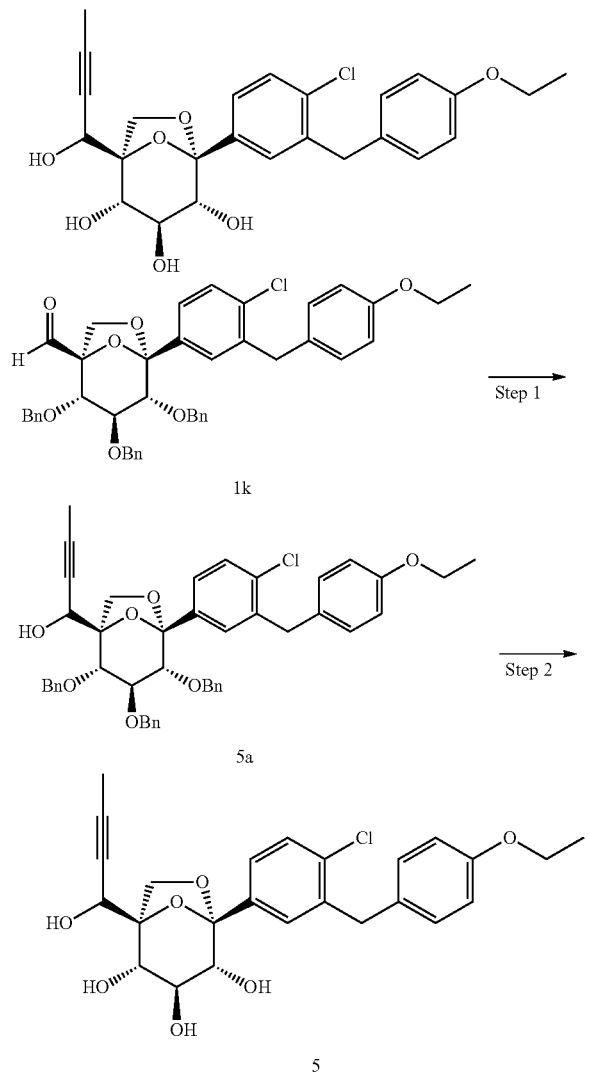

Step 1) 1-[(1R,2S,3S,4R,5S)-2,3,4-tribenzyloxy-5-[4-chloro-3[(4-ethoxyphenyl)methyl]phenyl]-6,8-dioxabicyclo[3.2.1]octan-1-yl]but-2-yn-1-ol 5a To a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (0.2 g, 0.28 mmol, obtained from the synthetic method described in step 10 of example 1) in anhydrous tetrahydrofuran (10 mL) was added dropwise 1-propynylmagnesium bromide (1.1 mL, 0.57 mmol, 0.5 M in tetrahydrofuran) at 0° C. After the addition, the mixture was stirred at room temperature for 4 hours and quenched with 1.5 mL of saturated aqueous ammonium chloride. The resulting mixture was extracted with ethyl acetate (20 mL×3). The combined organic layers were washed with water (10 mL×2) and then saturated aqueous sodium chloride (10 mL×2), dried over anhydrous sodium sulfate and concentrated in vacuo. The residue was purified by silica gel chromatography eluted with PE/EtOAc(v/v)=8/1 to give the title compound 5a as colorless oil (145 mg, 69%). The compound was characterized by the following spectroscopic data: $^1$H NMR (400 MHz, CDCl$_3$) δ(ppm:) 7.45 (m, 1H), 7.37 (m, 2H), 7.32 (m, 8H), 7.28 (m, 2H), 7.16 (m, 3H), 7.07 (d, 2H), 6.88 (m, 2H), 6.74 (m, 2H), 4.90 (m, 1H), 4.85 (m, 1H), 4.81 (m, 1H), 4.57 (m, 1H), 4.37 (t, 1H), 4.29 (m, 1H), 4.23 (m, 1H), 4.17 (m, 1H), 4.09 (m, 1H), 4.02 (m, 2H), 3.96 (m, 3H), 3.84 (d, 1H), 3.73 (d, 1H), 2.35 (d, 1H), 1.84 (s, 3H), 1.38 (t, 3H).

Step 2) (1R,2S,3S,4R,5S)-5-[4-chloro-3 [(4-ethoxyphenyl)methyl]phenyl]-1-(1-hydroxybut-2-ynyl)-6,8-dioxabicyclo[3.2.1]octane-2,3,4-triol 5

To a solution of 1-[(1R,2S,3S,4R,5S)-2,3,4-tribenzyloxy-5-[4-chloro-3[(4-ethoxyphenyl)methyl]phenyl]-6,8-dioxabicyclo[3.2.1]octan-1-yl]but-2-yn-1-ol 5a (0.71 g, 0.95 mmol) in dichloromethane (30 mL) was added dropwsie boron trichloride (9.5 mL, 9.5 mmol, 1 M in dichloromethane) at −78° C. The mixture was stirred at −78° C. for 2 hours. The reaction mixture was then stirred at room temperature for 3 hours and quenched with 5 mL of saturated aqueous sodium bicarbonate. The resulting mixture was extracted with ethyl acetate (50 mL×3). The combined organic layers were washed with water (20 mL×2) and then saturated aqueous sodium chloride (20 mL×2), dried over anhydrous sodium sulfate and concentrated in vacuo. The residue was purified by prep-HPLC to afford title compound as a pale yellow solid (42 mg, 10.0%, HPLC: 91.8%). The compound was characterized by the following spectroscopic data: MS (ESI, pos. ion) m/z: 475[M+H]$^+$; and $^1$H NMR (400 MHz, DMSO-d$_6$) δ(ppm): 7.63 (d, 1H), 7.48 (m, 1H), 7.39 (m, 1H), 7.02 (m, 2H), 6.79 (m, 2H), 5.07 (d, 1H), 5.06 (d, 1H), 4.79 (d, 1H), 4.62 (d, 1H), 4.48 (t, 1H), 4.46 (d, 1H), 3.95 (m, 4H), 3.82 (m, 2H), 3.71 (m, 1H), 3.53 (m, 1H), 1.45 (s, 3H), 1.28 (t, 3H).

Example 6

(1S,2S,3S,4R,5S)-5-[4-Chloro-3 [(4-ethoxyphenyl) methyl]phenyl]-1-(1-hydroxycyclopropyl)-6,8-dioxabicyclo[3.2.1]octane-2,3,4-triol 6

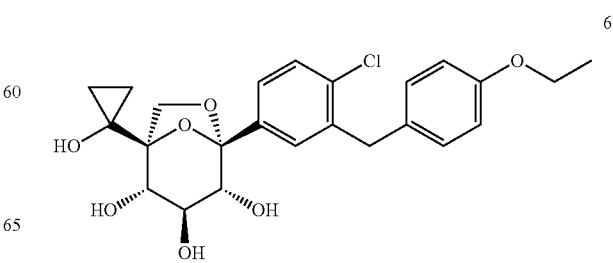

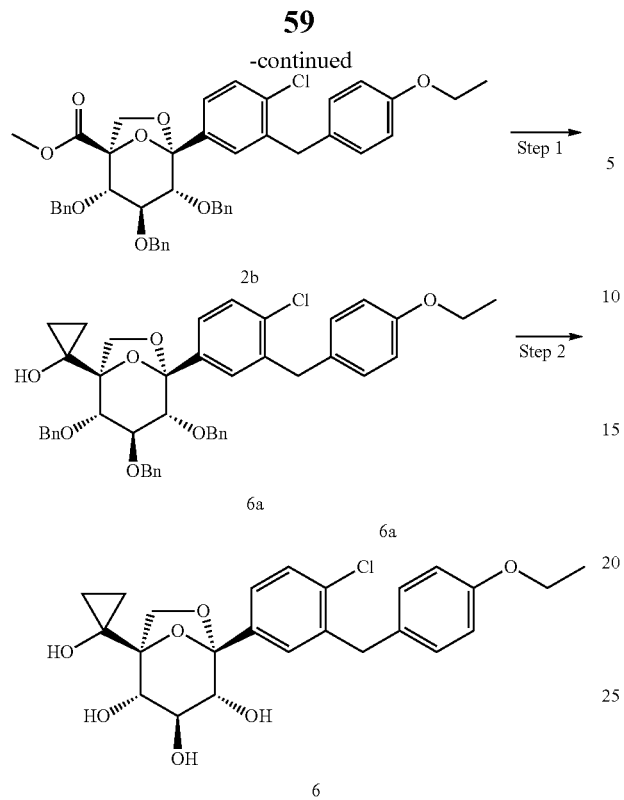

Step 1) 1-[(1S,2S,3S,4R,5S)-2,3,4-tribenzyloxy-5-[4-chloro-3 [(4-ethoxyphenyl)methyl]phenyl]-6,8-dioxabicyclo[3.2.1]octan-1-yl]cyclopropanol 6a To a solution of titanium tetraisopropanolate (54 mg, 0.19 mmol) and methyl (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carboxylate 2b (100 mg, 0.14 mmol, obtained from the synthetic method described in step 2 of example 2) in anhydrous tetrahydrofuran (10 mL) was added dropwise ethylmagnesium bromide (0.38 mL, 0.38 mmol, 1 M in tetrahydrofuran) at room temperature. After the addition, the mixture was stirred at 40° C. for 16 hours and quenched with saturated aqueous ammonium chloride. The resulting mixture was extracted with ethyl acetate (40 mL×2). The combined organic layers were washed with water (20 mL×2) and then saturated aqueous sodium chloride (10 mL×2), dried over anhydrous sodium sulfate and concentrated in vacuo. The residue was purified by silica gel chromatography eluted with PE/EtOAc(v/v)=15/1 to give the title compound 6a as a white solid (15 mg, 15.0%). The compound was characterized by the following spectroscopic data: $^1$H NMR (400 MHz, CDCl$_3$) δ (ppm): 7.31 (m, 13H), 7.17 (m, 3H), 7.06 (m, 2H), 6.88 (m, 2H), 6.75 (m, 2H), 4.99 (d, 1H), 4.93 (d, 1H), 4.84 (m, 2H), 4.71 (s, 1H), 4.42 (m, 1H), 4.22 (d, 1H), 4.05 (m, 3H), 3.99 (m, 3H), 3.80 (d, 1H), 3.62 (t, 1H), 3.26 (s, 1H), 1.38 (t, 3H), 0.78 (m, 1H), 0.63 (m, 2H), 0.59 (m, 1H).

Step 2) (1S,2S,3S,4R,5S)-5-[4-chloro-3 [(4-ethoxyphenyl)methyl]phenyl]-1-(1-hydroxycyclopropyl)-6,8-dioxabicyclo[3.2.1]octane-2,3,4-triol 6

To a solution of 1-[(1S,2S,3S,4R,5S)-2,3,4-tribenzyloxy-5-[4-chloro-3[(4-ethoxyphenyl)methyl]phenyl]-6,8-dioxabicyclo[3.2.1]octan-1-yl]cyclopropanol 6a (75 mg, 0.1 mmol) in a methanol/tetrahydrofuran mixture (v/v=4/1, 5 mL) were added o-dichlorobenzene (74.97 mg, 0.51 mmol) and 10% Pd/C (15 mg, 0.01 mmol) in turn. The mixture was stirred at room temperature under H$_2$ for 4 hours and filtered. The filter cake was washed with a methanol/tetrahydrofuran mixture (v/v=4/1, 10 mL×2). The combined filtrates were concentrated in vacuo. The residue was purified by silica gel chromatography eluted with PE/EtOAc(v/v)=1/4 to give the title compound 6 as colourless oil (24 mg, 50.0%, HPLC: 83.3%). The compound was characterized by the following spectroscopic data: MS (ESI, pos. ion) m/z: 463.1[M+H]$^+$; and $^1$H NMR (400 MHz, DMSO-d$_6$) δ (ppm): 7.38 (m, 2H), 7.29 (m, 1H), 7.10 (m, 2H), 6.84 (m, 2H), 5.27 (s, 1H), 5.19 (d, 1H), 5.02 (d, 1H), 4.95 (d, 1H), 4.06 (m, 1H), 3.99 (m, 3H), 3.96 (m, 1H), 3.80 (t, 1H), 3.41 (m, 2H), 3.29 (m, 1H), 1.31 (t, 3H), 0.55 (m, 4H).

Example 7

(1R,2S,3S,4R,5S)-5-[4-Chloro-3-[(4-ethoxyphenyl)methyl]phenyl]-1-(1,2-dihydroxyethyl)-6,8-dioxabicyclo[3.2.1]octane-2,3,4-triol 7

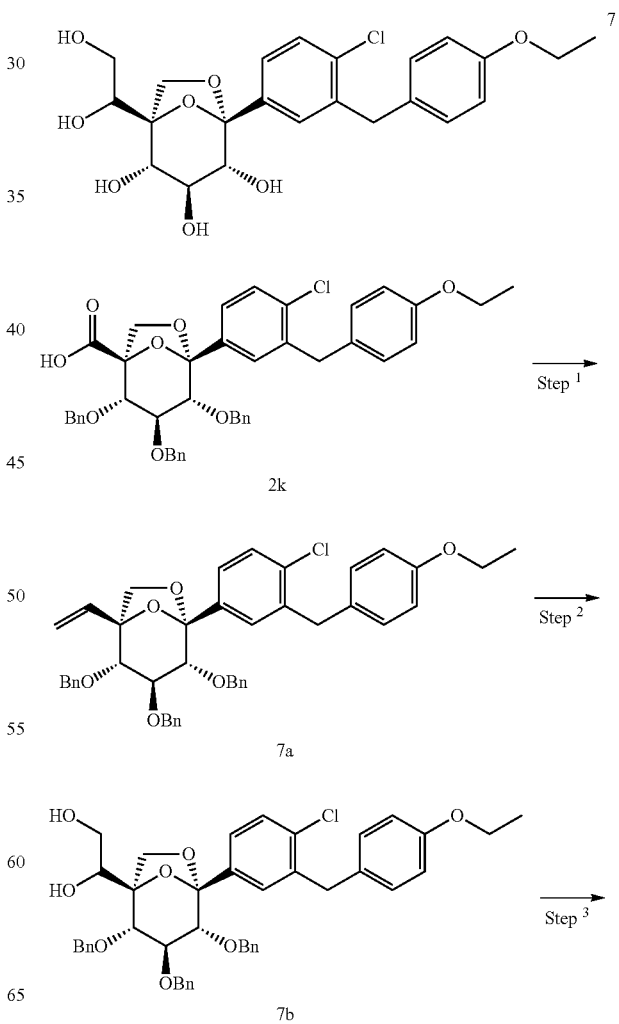

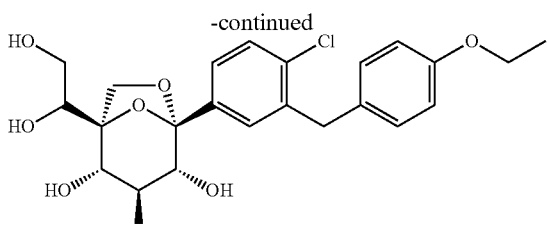

7

Step 1) (1S,2S,3S,4R,5S)-2,3,4-tribenzyloxy-5-[4-chloro-3-[(4-ethoxyphenyl)methyl]phenyl]-1-vinyl-6,8-dioxabicyclo[3.2.1]octane 7a To a solution of methyltriphenylphosphonium bromide (2.53 g, 7.10 mmol) in anhydrous tetrahydrofuran (15 mL) was added dropwise n-butyllithium (2.9 mL, 7.10 mmol, 2.4 M in n-hexane) at −78° C. The mixture was stirred at −78° C. for 30 min, and then a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (1.0 g, 1.42 mmol, obtained from the synthetic method described in step 10 of example 1) in anhydrous tetrahydrofuran (5 mL) was added over a period of 30 min. The mixture was further stirred for 10 min at −78° C. and at room temperature for another 4 hours. The reaction mixture was quenched with 10 mL of saturated aqueous sodium chloride. The resulting mixture was extracted with ethyl acetate (20 mL×3). The combined organic layers were washed with saturated aqueous sodium chloride (20 mL×2), dried over anhydrous sodium sulfate and concentrated in vacuo. The residue was purified by silica gel chromatography eluted with PE/EtOAc(v/v)=15/1 to give the title compound 7a as pale yellow oil (0.45 g, 45.0%). The compound was characterized by the following spectroscopic data: $^1$H NMR (400 MHz, CDCl$_3$) δ (ppm): 7.47 (m, 1H), 7.40 (m, 2H), 7.30 (m, 10H), 7.22 (m, 3H), 7.08 (m, 2H), 6.91 (m, 2H), 6.76 (m, 2H), 6.11 (dd, 1H), 5.45 (dd, 1H), 5.28 (dd, 1H), 4.90 (m, 3H), 4.71 (d, 1H), 4.47 (d, 1H), 4.27 (d, 1H), 4.10 (m, 5H), 3.88 (d, 1H), 3.68 (m, 3H), 1.40 (t, 3H).

Step 2) 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethane-1,2-diol 7b To a solution of (1S,2S,3S,4R,5S)-2,3,4-tribenzyloxy-5-[4-chloro-3-[(4-ethoxyphenyl)methyl]phenyl]-1-vinyl-6,8-dioxabicyclo[3.2.1]octane 7a (1.4 g, 1.99 mmol) in dioxane (20 mL) were added 4-methylmorpholine (1.0 mL, 2.99 mmol) and osmium tetroxide (5 mg, 0.02 mmol) at room temperature in turn. The mixture was stirred at room temperature for 1.5 hours and quenched with 10 mL of saturated aqueous sodium bisulfite. The resulting mixture was extracted with ethyl acetate (20 mL×2). The combined organic layers were washed with water (10 mL×2) and then saturated aqueous sodium chloride (10 mL×2), dried over anhydrous sodium sulfate and concentrated in vacuo. The residue was purified by silica gel chromatography eluted with PE/EtOAc(v/v)=4/1 to give the title compound 7b as colorless thick oil (0.9 g, 61.3%). The compound was characterized by the following spectroscopic data: $^1$H NMR (400 MHz, CDCl$_3$) δ (ppm): 7.41 (m, 1H), 7.36 (m, 12H), 7.21 (m, 3H), 7.09 (d, 2H), 6.91 (m, 2H), 6.79 (m, 2H), 4.88 (m, 4H), 4.37 (dd, 1H), 4.24 (m, 2H), 4.05 (m, 2H), 4.00 (d, 2H), 3.96 (m, 1H), 3.82 (m, 4H), 3.66 (m, 2H), 1.42 (t, 3H).

Step 3) (1R,2S,3S,4R,5S)-5-[4-chloro-3-[(4-ethoxyphenyl)methyl]phenyl]-1-(1,2-dihydroxyethyl)-6,8-dioxabicyclo[3.2.1]octane-2,3,4-triol 7

To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethane-1,2-diol 7b (0.9 g, 1.22 mmol) in a methanol/tetrahydrofuran mixture (v/v=4/1, 15 mL) were added o-dichlorobenzene (0.82 mL, 6.1 mmol) and 10% Pd/C (36 mg, 0.12 mmol) in turn. The mixture was stirred at room temperature under H$_2$ for 5 hours and filtered. The filter cake was washed with a methanol/tetrahydrofuran mixture (v/v=4/1, 10 mL×2). The combined filtrates were concentrated in vacuo. The residue was purified by prep-HPLC to give the title compound 7 as a white solid (94 mg, 9.43%, HPLC: 99.2%). The compound was characterized by the following spectroscopic data: MS (ESI, pos. ion) m/z: 467.3[M+H]$^+$; and $^1$H NMR (400 MHz, DMSO-d$_6$) δ (ppm): 7.40 (m, 2H), 7.29 (dd, 1H), 7.09 (d, 2H), 6.83 (m, 2H), 5.27 (d, 1H), 4.95 (d, 1H), 4.89 (d, 1H), 4.88 (d, 1H), 4.55 (t, 1H), 4.00 (m, 5H), 3.66 (m, 3H), 3.45 (m, 2H), 3.37 (m, 2H), 1.30 (t, 3H).

Example 8

(1R,2S,3S,4R,5S)-5-[4-Chloro-3-[(4-ethoxyphenyl)methyl]phenyl]-1-(hydroxymethyl)-7-methyl-6,8-dioxabicyclo[3.2.1]octane-2,3,4-triol 8

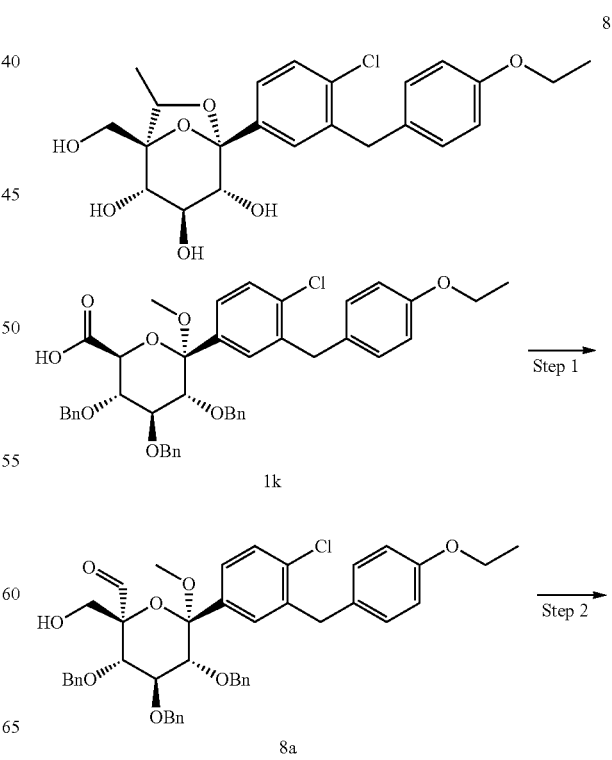

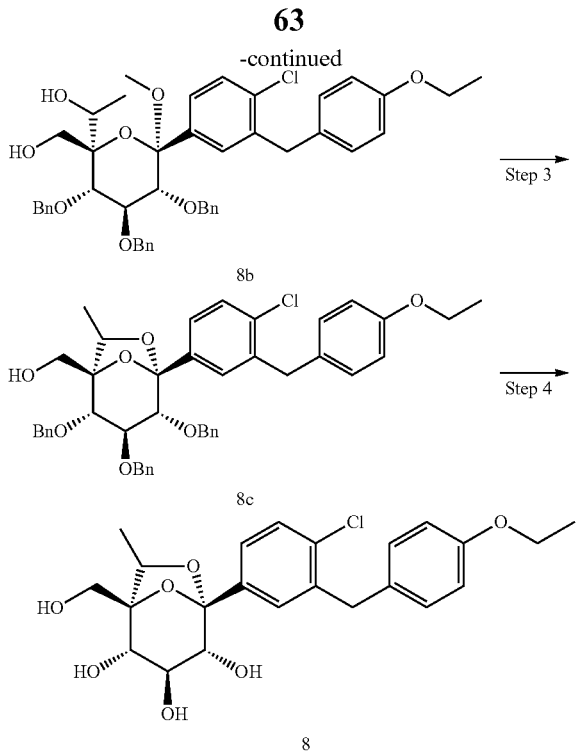

Step 1) (2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-carbaldehyde 8a To a solution of (2S,3S,4S,5R,6S)-3,4,5-tribenzyloxy-6-[4-chloro-3-[(4-ethoxyphenyl)methyl]phenyl]-6-methoxy-tetrahydropyran-2-carbaldehyde 1h (0.82 g, 1.16 mmol, obtained from the synthetic method described in step 7 of example 1) in N,N-dimethylformamide (20 mL) were added 1,8-diazabicyclo[5.4.0]undec-7-ene (0.02 mL, 0.12 mmol) and formaldehyde (1.7 mL, 23.2 mmol, 37% in water) in turn. The mixture was stirred at room temperature for 5 hours and quenched with 10 mL of saturated aqueous sodium bicarbonate. The resulting mixture was filtered. The filtrate was extracted with ethyl acetate (20 mL×1 and 10 mL×3). The combined organic layers were washed with water (10 mL×3) and then saturated aqueous sodium chloride (10 mL×3), dried over anhydrous sodium sulfate and concentrated in vacuo. The residue was purified by silica gel chromatography eluted with PE/EtOAc(v/v)=5/1 to give the title compound 8a as yellow oil (0.56 g, 65.1%). The compound was characterized by the following spectroscopic data: $^1$H NMR (400 MHz, DMSO-$d_6$) δ(ppm): 9.99 (s, 1H), 7.55-7.49 (m, 2H), 7.43 (d, 1H), 7.34-7.24 (m, 13H), 7.07 (dd, 2H), 6.95 (d, 2H), 6.72 (d, 2H), 5.38 (dd, 1H), 4.84 (m, 3H), 4.72 (d, 1H), 4.56-4.43 (m, 2H), 4.16 (d, 1H), 4.01 (d, 1H), 3.92 (q, 2H), 3.81 (m, 3H), 3.57 (dd, 1H), 3.25 (d, 1H), 2.70 (s, 3H), 1.27 (t, 3H).

Step 2) 1-[(2S,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl]ethanol 8b To a solution of (2R,3S,4S,5R,6S)-3,4,5-tribenzyloxy-6-[4-chloro-3-[(4-ethoxyphenyl) methyl]phenyl]-2-(hydroxymethyl)-6-methoxy-tetrahydropyran-2-carbaldehyde 8a (1.38 g, 1.88 mmol) in tetrahydrofuran (30 mL) was added dropwise methylmagnesium bromide (1.9 mL, 5.63 mL) at room temperature. The mixture was stirred at room temperature for 45 min under $N_2$ and quenched with 10 mL of saturated aqueous ammonium chloride. Most of the solvent of the mixture was removed in vacuo. The resulting mixture was extracted with ethyl acetate (10 mL×2). The combined organic layers were washed with saturated aqueous sodium chloride (5 mL×2), dried over anhydrous sodium sulfate and concentrated in vacuo. The residue was purified by silica gel chromatography eluted with PE/EtOAc(v/v)=8/1 to give the title compound 8b as colourless oil (414 mg, 30.0%). The compound was characterized by the following spectroscopic data: $^1$H NMR (400 MHz, DMSO-$d_6$) δ (ppm): 7.55 (m, 1H), 7.46 (d, 1H), 7.40 (d, 1H), 7.35-7.30 (m, 5H), 7.30-7.23 (m, 8H), 7.00 (m, 4H), 6.74 (d, 2H), 5.03 (t, 1H), 4.72 (m, 4H), 4.53 (d, 1H), 4.49 (d, 1H), 4.42 (d, 1H), 4.18 (m, 2H), 4.05 (d, 1H), 3.94 (m, 2H), 3.89 (d, 1H), 3.85-3.77 (m, 2H), 3.73 (m, 1H), 3.43 (d, 1H), 2.92 (s, 3H), 1.28 (t, 3H), 1.23 (d, 3H).

Step 3) [(1S,2S,3S,4R,5S)-2,3,4-tribenzyloxy-5-[4-chloro-3-[(4-ethoxyphenyl)methyl]phenyl]-7-methyl-6,8-dioxabicyclo[3.2.1]octan-1-yl]methanol 8c To a solution of 1-[(2S,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl]ethanol 8b (0.6 g, 0.80 mmol) in dichloromethane (20 mL) was added p-toluenesulfonic acid (27.5 mg, 0.16 mmol). The mixture was stirred at room temperature for 2 hours and quenched with 5 mL of saturated aqueous sodium bicarbonate. The resulting mixture was partitioned. The aqueous layer was extracted with dichloromethane (10 mL×2). The combined organic layers were washed with water (10 mL×2) and then saturated aqueous sodium chloride (10 mL×2), dried over anhydrous sodium sulfate and concentrated in vacuo. The residue was purified by silica gel chromatography eluted with PE/EtOAc(v/v)=10/1 to give the title compound 8c as coloeless oil (258 mg, 44.8%). The compound was characterized by the following spectroscopic data: $^1$H NMR (400 MHz, CDCl$_3$) δ (ppm): 7.41 (s, 1H), 7.34 (m, 4H), 7.31-7.27 (m, 6H), 7.24 (m, 2H), 7.14 (m, 3H), 7.06 (d, 2H), 6.89-6.83 (m, 2H), 6.77-6.72 (m, 2H), 4.86 (m, 3H), 4.74 (d, 1H), 4.32 (dd, 1H), 4.23 (d, 1H), 4.08 (m, 1H), 4.05-3.98 (m, 3H), 3.98-3.89 (m, 3H), 3.77 (d, 1H), 3.68 (d, 1H), 3.64 (d, 1H), 1.56 (d, 3H), 1.38 (t, 3H).

Step 4) (1R,2S,3S,4R,5S)-5-[4-chloro-3-[(4-ethoxyphenyl)methyl]phenyl]-1-(hydroxymethyl)-7-methyl-6,8-dioxabicyclo[3.2.1]octane-2,3,4-triol 8

To a solution of [(1S,2S,3S,4R,5S)-2,3,4-tribenzyloxy-5-[4-chloro-3-[(4-ethoxyphenyl)methyl]phenyl]-7-methyl-6,8-dioxabicyclo[3.2.1]octan-1-yl]methanol 8c (258 mg, 0.37 mmol) in a methanol/tetrahydrofuran mixture (v/v=4/1, 15 mL) were added o-dichlorobenzene (0.21 mL, 1.82 mmol) and 10% Pd/C (19.3 mg, 0.18 mmol) in turn. The mixture was stirred at room temperature under $H_2$ for 4.5 hours and filtered. The filter cake was washed with a methanol/tetrahydrofuran mixture (v/v=4/1, 10 mL×2). The combined filtrates were concentrated in vacuo. The residue was purified by prep-HPLC to give the title compound 8 as white powder (98 mg, 59%, HPLC: 97.2%). The compound was characterized by the following spectroscopic data: MS (ESI, pos. ion) m/z: 451.1[M+H]$^+$; and $^1$H NMR (400 MHz, DMSO-$d_6$) δ(ppm): 7.43-7.36 (m, 2H), 7.30 (d, 1H), 7.09 (d, 2H), 6.82 (d, 2H), 5.15 (d, 1H), 4.99 (d, 1H), 4.92 (d, 1H), 4.74 (t, 1H), 3.96 (m, 5H), 3.76 (dd, 1H), 3.62 (m, 2H), 3.51 (dd, 1H), 3.40 (d, 1H), 1.36 (d, 3H), 1.29 (t, 3H).

Example 9

(1R,2S,3S,4R,5S)-5-[4-chloro-3-[(4-ethoxyphenyl)methyl]phenyl]-1-(hydroxymethyl)-7,7-dimethyl-6,8-dioxabicyclo[3.2.1]octane-2,3,4-triol 9

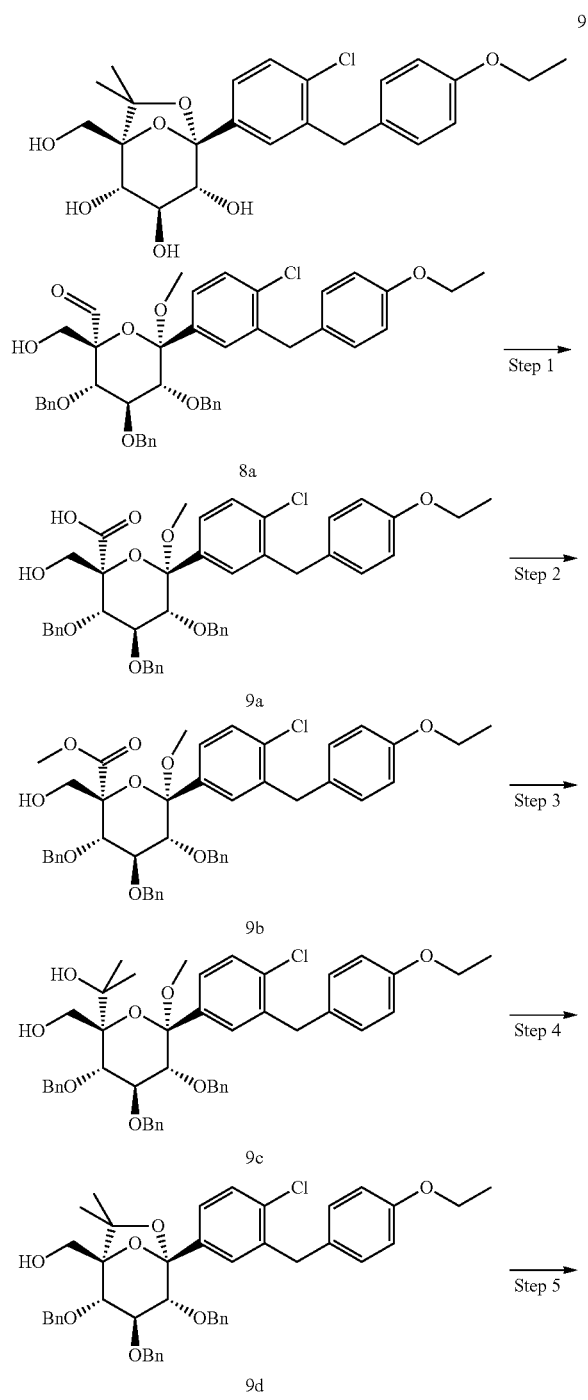

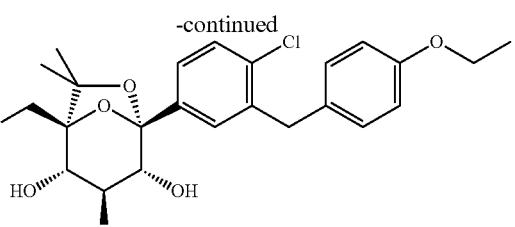

Step 1) (2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-carboxylic acid 9a To a solution of (2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-carbaldehyde 8a (1.40 g, 1.98 mmol, obtained from the synthetic method described in step 1 of example 8) in tert-butanol (10 mL) were added monopotassium phosphate (2.43 g, 17.82 mmol) and 2-methylbut-2-ene (68.88 mg, 97.02 mmol) at room temperature in turn, and then sodium chlorite (1.26 g, 13.90 mmol) and water (5 mL) were added. The mixture was stirred at 35° C. for 24 hours and quenched with 10 mL of saturated aqueous sodium bicarbonate. Tert-butanol was removed in vavuo. The resulting mixture was extracted with ethyl acetate (10 mL×3). The combined organic layers were washed with saturated aqueous sodium chloride (10 mL×2), dried over anhydrous sodium sulfate and concentrated in vacuo to give the title compound 9a as pale yellow oil (1.50 g, 100%). The crude product was used in next step without further purification.

Step 2) methyl (2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-carboxylate 9b To a solution of (2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-carboxylic acid 9a (1.00 g, 1.33 mmol) in N,N-dimethylformamide (20 mL) were added potassium iodide (0.10 mL, 1.60 mmol) and sodium hydroxide (53.20 mg, 1.33 mmol) at room temperature in turn. The mixture was stirred at 60° C. for 15 hours and quenched with 15 mL of saturated aqueous ammonium chloride. The resulting mixture was filtered. The filtrate was extracted with ethyl acetate (20 mL×3). The combined organic layers were washed with saturated aqueous sodium chloride (30 mL×4), dried over anhydrous sodium sulfate and concentrated in vacuo. The residue was purified by silica gel chromatography eluted with PE/EtOAc(v/v)=10/1 to give the title compound 9b as pale yellow oil (0.52 g, 51.0%).

Step 3) 2-[(2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl]propan-2-ol 9c To a solution of methyl (2R,3S,4S,5R,6S)-3,4,5-tribenzyloxy-6-[4-chloro-3-[(4-ethoxyphenye methyl]phenyl]-2-(hydroxymethyl)-6-methoxy-tetrahydropyran-2-carboxylate 9b (0.52 g, 0.68 mmol) in tetrahydrofuran (15 mL) was added methylmagnesium bromide (2.26 mL, 6.78 mmol, 3 M in ethyl ether) at −5° C. under N₂. The mixture was stirred at 60° C. for 21 hours and quenched with 5 mL of water. Most of the solvent of the mixture was removed. To the residue was added 10 mL of water. The resulting mixture was extracted with ethyl acetate (15 mL×2). The combined organic layers were dried over anhydrous sodium sulfate and concentrated in vacuo. The residue was purified by silica gel chromatography eluted with PE/EtOAc(v/v)=10/1 to give the title compound 9c as pale yellow oil (0.23 g, 43.6%).

Step 4) [(1R,2S,3S,4R,5S)-2,3,4-tribenzyloxy-5-[4-chloro-3-[(4-ethoxyphenyl)methyl]phenyl]-7,7-dimethyl-6,8-dioxabicyclo[3.2.1]octan-1-yl]methanol 9d To a solution of 2-[(2R,3S,4S,5R,6S)-3,4,5-tribenzyloxy-6-[4-chloro-3-[(4-ethoxyphenyl)methyl]phenyl]-2-(hydroxymethyl)-6-methoxy-tetrahydropyran-2-yl]propan-2-ol 9c (0.23 g, 0.30 mmol) in dichloromethane (60 mL) was added p-toluenesulfonic acid monohydrate (25.30 mg, 0.13 mmol) at room temperature. The mixture was stirred at room temperature for 21 hours and quenched with 15 mL of saturated aqueous sodium bicarbonate. The mixture was partitioned. The organic layer was washed with saturated aqueous sodium chloride (15 mL×3), dried over anhydrous sodium sulfate and concentrated in vacuo. The residue was purified by silica gel chromatography eluted with PE/EtOAc(v/v)=10/1 to give the title compound 9d as colorless oil (50.00 mg, 28%).

Step 5) (1R,2S,3S,4R,5S)-5-[4-chloro-3-[(4-ethoxyphenyl)methyl]phenyl]-1-(hydroxymethyl)-7,7-dimethyl-6,8-dioxabicyclo[3.2.1]octane-2,3,4-triol 9

To a solution of [(1R,2S,3S,4R,5S)-2,3,4-tribenzyloxy-5-[4-chloro-3-[(4-ethoxyphenyl)methyl]phenyl]-7,7-dimethyl-6,8-dioxabicyclo[3.2.1]octan-1-yl]methanol 9d (50.00 mg, 0.07 mmol) in a methanol/tetrahydrofuran mixture (v/v=4/1, 5 mL) were added o-dichlorobenzene (0.04 mL, 0.35 mmol) and 10% Pd/C (42.40 mg, 0.04 mmol) at room temperature. The mixture was stirred at room temperature under H₂ for 2 hours and filtered. The filtrate was concentrated in vacuo. The residue was purified by silica gel chromatography eluted with EtOAc to give the title compound 9 as colorless oil (13.00 mg, 46.0%, HPLC: 94.04%). The compound was characterized by the following spectroscopic data: MS (ESI, neg. ion) m/z: 509 [M+HCOO]⁻; and ¹H NMR (400 MHz, DMSO-d₆) δ(ppm): 7.40 (m, 2H), 7.29 (dd, 1H), 7.10 (d, 2H), 6.84 (d, 2H), 5.00 (d, 1H), 4.93 (d, 1H), 4.82 (d, 1H), 4.63 (t, 1H), 3.99 (s, 2H), 3.96 (m, 1H), 3.92 (m, 1H), 3.79 (m, 1H), 3.60 (m, 1H), 3.42 (m, 2H), 3.28 (m, 1H), 1.42 (s, 3H), 1.30 (t, 3H), 0.95 (s, 3H).

Example 10

(1R,2S,3S,4R,5S)-1-(2-Amino-1-hydroxy-ethyl)-5-[4-chloro-3-[(4-ethoxyphenyl)methyl]phenyl]-6,8-dioxabicyclo[3.2.1]octane-2,3,4-triol 10

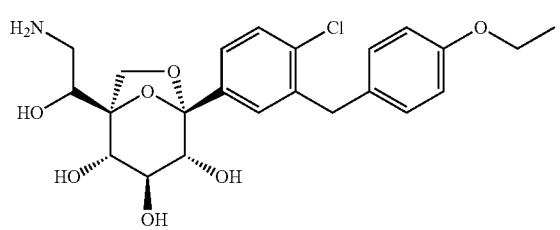

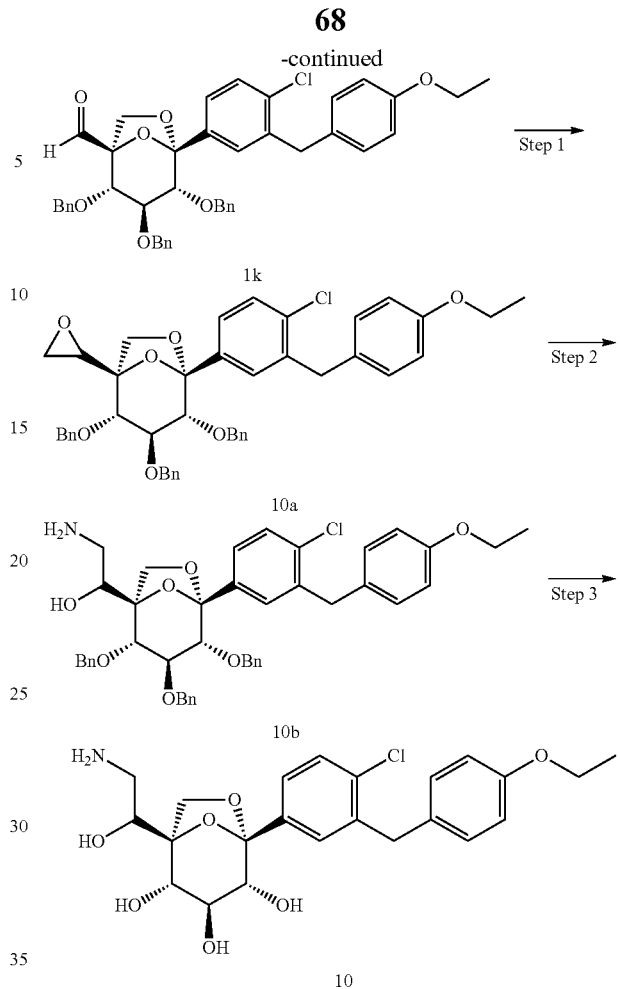

Step 1) (1S,2S,3S,4R,5S)-2,3,4-tribenzyloxy-5-[4-chloro-3-[(4-ethoxyphenyl)methyl]phenyl]-1-(oxiran-2-yl)-6,8-dioxabicyclo[3.2.1]octane 10a To a suspension of sodium hydride (102 mg, 2.55 mol, 60% dispersion in Mineral oil) in anhydrous dimethyl sulfoxide (5 mL) was added a solution of trimethylsulfoxonium iodide (0.61 g, 2.76 mol) in anhydrous dimethyl sulfoxide (5 mL) dropwise at room temperature. The resulting mixture was stirred at room temperature for 40 min, and then a solution of (1S,2S,3S,4R,5S)-2,3,4-tribenzyloxy-5-[4-chloro-3-[(4-ethoxyphenyl)methyl]phenyl]-6,8-dioxabicyclo[3.2.1]octane-1-carbaldehyde 1k (1.5 g, 2.13 mmol, obtained from the synthetic method described in step 10 of example 1) in anhydrous dimethyl sulfoxide (20 mL) was added dropwise. The mixture was further stirred at room temperature for 1h. The resulting mixture was quenched by adding 40 mL of water slowly, and then extracted with ethyl acetate (50 mL×3). The combined organic layers were washed with water (30 mL×2) and saturated brine (30 mL×2) in turn, dried over anhydrous sodium sulfate and filtered. The filtrate was concentrated in vacuo. The residue was purified by silica gel chromatography eluted with PE/EtOAc(v/v)=10/1 to give the title compound 10a as colourless oil (0.96 g, 62.9%).

Step 2) 2-amino-1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 10b To a solution of (1S,2S,3S,4R,5S)-2,3,4-tribenzyloxy-5-[4-chloro-3-[(4-ethoxyphenyl)methyl]phenyl]-1-(oxiran-2- yl)-6,8-dioxabicyclo[3.2.1]octane 10a (0.4 g, 0.56 mmol) in a methanol/tetrahydrofuran mixture (v/v=1/2, 9 mL) was added ammonium hydroxide (2 mL, 10 mmol). The mixture was heated to 55° C. and stirred for 16 hours. The resulting mixture was extracted with ethyl acetate (50 mL×2). The combined organic layers were washed with water (30 mL×2) and saturated brine (30 mL×2) in turn, dried over anhydrous sodium sulfate and filtered. The filtrate was concentrated in vacuo and the residue was purified by silica gel chromatography eluted with PE/EtOAc(v/v)=6/1 to give the title compound 10b as colourless oil (0.21 g, 51.2%). The compound was characterized by the following spectroscopic data: $^1$H NMR (400 MHz, DMSO-$d_6$) δ(ppm): 7.48 (m, 2H), 7.40 (m, 1H), 7.33 (m, 4H), 7.26 (m, 6H), 7.18 (m, 3H), 7.05 (m, 2H), 7.04 (m, 2H), 6.85 (m, 2H), 4.90 (m, 1H), 4.77 (m, 3H), 4.26 (d, 1H), 4.11 (d, 2H), 4.00 (m, 2H), 3.91 (m, 3H), 3.85 (t, 1H), 3.71 (m, 4H), 2.71 (m, 1H), 2.56 (m, 1H), 1.26 (t, 3H).

Step 3) (1R,2S,3S,4R,5S)-1-(2-amino-1-hydroxyethyl)-5-[4-chloro-3-[(4-ethoxyphenyl)methyl]phenyl]-6,8-dioxabicyclo[3.2.1]octane-2,3,4-triol 10

To a solution of 2-amino-1-[(1R,2S,3S,4R,5S)-2,3,4-tribenzyloxy-5-[4-chloro-3-[(4-ethoxyphenyl) methyl]phenyl]-6,8-dioxabicyclo[3.2.1]octan-1-yl]ethanol 10b (205 mg, 0.28 mmol) in a methanol/tetrahydrofuran mixture (v/v=4/1, 25 mL) were added o-dichlorobenzene (0.16 mL, 1.42 mmol) and 10% Pd/C (32 mg, 0.03 mmol) at room temperature. The mixture was stirred at room temperature under $H_2$ for 4 hours and filtered. The filter cake was washed with a tetrahydrofuran/methanol mixture (v/v=1/4, 10 mL×2) and the filtrate was concentrated in vacuo. The residue was purified by silica gel chromatography eluted with EtOAc to give the title compound 10 as colorless oil (36 mg, 25.7%, HPLC: 98.0%). The compound was characterized by the following spectroscopic data: MS (ESI, pos. ion) m/z: 466.0[M+H]$^+$; and $^1$H NMR (400 MHz, DMSO-$d_6$) δ(ppm): 7.73 (s, 2H), 7.42 (m, 2H), 7.31 (m, 1H), 7.09 (m, 2H), 6.82 (m, 2H), 5.52 (d, 2H), 5.02 (d, 2H), 3.95 (m, 5H), 3.72 (d, 1H), 3.61 (d, 1H), 3.48 (m, 2H), 3.14 (m, 1H), 2.69 (m, 1H), 1.28 (t, 3H).

Example 11

(1R,2S,3S,4R,5S)-5-[4-chloro-3-[(4-ethoxyphenyl) methyl]phenyl]-1-[1-hydroxy-2-(methylamino) ethyl]-6,8-dioxabicyclo[3.2.1]octane-2,3,4-triol 11

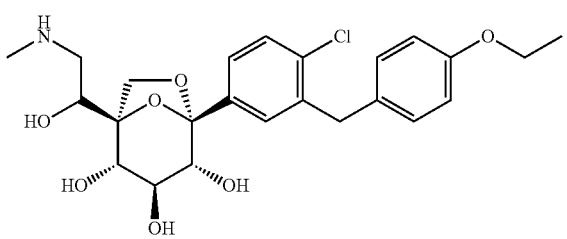

11

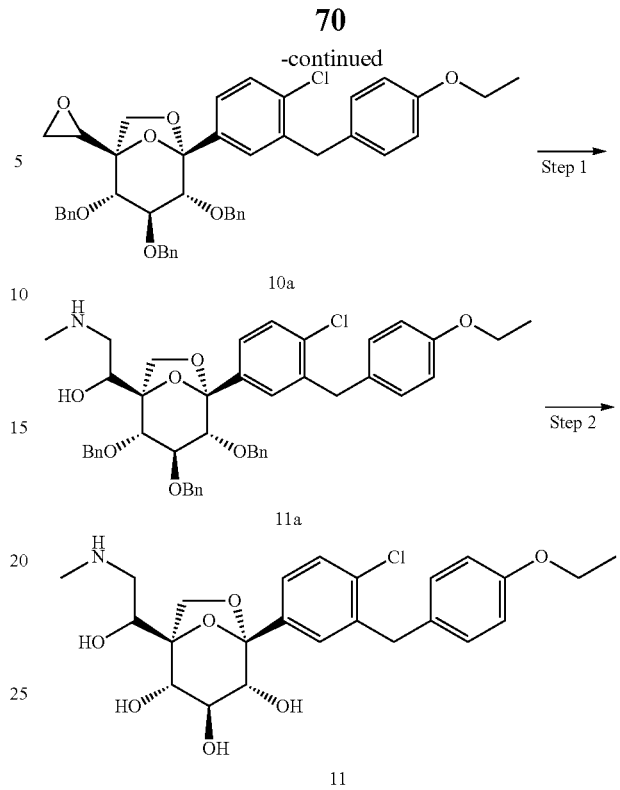

Step 1) 2-(methylamino)-1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 11a To a solution of (1S,2S,3S,4R,5S)-2,3,4-tribenzyloxy-5-[4-chloro-3-[(4-ethoxyphenyl)methyl]phenyl]-1-(oxiran-2-yl)-6,8-dioxabicyclo[3.2.1]octane 10a (50 mg, 0.56 mmol, obtained from the synthetic method described in step 1 of example 10) in a methanol/tetrahydrofuran mixture (v/v=2/1, 9 mL) was added methylamine solution (1 mL, 1.25 mmol). The mixture was heated to 55° C. and stirred for 16 h. The resulting mixture was extracted with ethyl acetate (20 mL×2). The combined organic layers were washed with water (10 mL×2) and saturated brine (10 mL×2) in turn, dried over anhydrous sodium sulfate and filtered. The filtrate was concentrated in vacuo and the residue was purified by silica gel chromatography eluted with EtOAc to give the title compound 11a as a white solid (37.4 mg, 71.6%). The compound was characterized by the following spectroscopic data: $^1$H NMR (400 MHz, DMSO-$d_6$) δ (ppm): 7.41 (m, 2H), 7.40 (m, 1H), 7.32 (m, 3H), 7.26 (m, 6H), 7.17 (m, 3H), 7.04 (d, 2H), 6.85 (m, 2H), 6.73 (m, 2H), 4.87 (m, 1H), 4.75 (m, 3H), 4.26 (m, 1H), 4.11 (m, 2H), 3.97 (m, 2H), 3.92 (m, 3H), 3.82 (m, 2H), 3.72 (m, 3H), 2.65 (m, 1H), 2.55 (m, 1H), 2.22 (s, 3H), 1.27 (t, 3H).

Step 2) (1R,2S,3S,4R,5S)-5-[4-chloro-3-[4(4-ethoxyphenyl)methyl]phenyl]-1-[1-hydroxy-2-(methylamino) ethyl]-6,8-dioxabicyclo[3.2.1]octane-2,3,4-triol 11

To a solution of 2-(methylamino)-1-[(1R,2S,3S,4R,5S)-2,3,4-tribenzyloxy-5-[4-chloro-3-[(4-ethoxyphenyl)methyl] phenyl]-6,8-dioxabicyclo[3.2.1]octan-1-yl]ethanol 11a (0.23 g, 0.31 mmol) in a methanol/tetrahydrofuran mixture (v/v=4/

1, 5 mL) were added o-dichlorobenzene (0.17 mL, 1.53 mmol) and 10% Pd/C (34.5 mg, 0.03 mmol) at room temperature. The mixture was stirred at room temperature under H$_2$ for 4 hours and filtered. The filter cake was washed with a tetrahydrofuran/methanol mixture (v/v=1/4, 5 mL×2) and the filtrate was concentrated in vacuo. The residue was purified by silica gel chromatography eluted with EtOAc to give the title compound 11 as a light yellow solid (150 mg, 100%, HPLC: 87.1%). The compound was characterized by the following spectroscopic data: MS (ESI, pos. ion) m/z: 466.0[M+H]$^+$; and $^1$H NMR (400 MHz, DMSO-d$_6$) δ (ppm): 8.34 (s, 1H), 7.42 (m, 2H), 7.32 (m, 1H), 7.10 (m, 2H), 6.83 (m, 2H), 5.64 (d, 1H), 5.31 (s, 1H), 5.11 (d, 1H), 5.04 (d, 1H), 4.02 (m, 1H), 3.99 (m, 5H), 3.73 (m, 1H), 3.59 (d, 1H), 3.43 (m, 1H), 3.58 (m, 1H), 3.21 (d, 1H), 2.84 (t, 1H), 2.54 (s, 3H), 1.30 (t, 3H).

Example 12

1-[(1S,2S,3S,4R,5S)-5-[4-Chloro-3-[(4-ethoxyphenyl)methyl]phenyl]-2,3,4-trihydroxy-6,8-dioxabicyclo[3.2.1]octan-1-yl]ethyl ethyl carbonate 12

Step 1) ethyl 1-[(1R,2S,3S,4R,5S)-2,3,4-tribenzyloxy-5-[4-chloro-3-[(4-ethoxy phenyl)methyl]phenyl]-6,8-dioxabicyclo[3.2.1]octan-1-yl]ethyl carbonate 12a To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 1m (0.2 g, 0.28 mmol, obtained from the synthetic method described in step 11 of example 1) in dichloromethane (20 mL) were added ethyl chloroformate (0.26 mL, 2.8 mmol), triethylamine (0.78 mL, 5.60 mmol) and 4-dimethyl aminopyridine (cat. 5 mg) in turn at room temperature. The mixture was heated to 30° C. and stirred for 16 hours. The resulting mixture was quenched with 20 mL of saturated ammonium chloride, and then extracted with dichloromethane (40 mL×2). The combined organic layers were washed with saturated brine (20 mL×2), dried over anhydrous sodium sulfate and filtered. The filtrate was concentrated in vacuo and the residue was purified by silica gel chromatography eluted with PE/EtOAc(v/v)=15/1 to give the title compound 12a as a light yellow solid (73.6 mg, 33.5%). The compound was characterized by the following

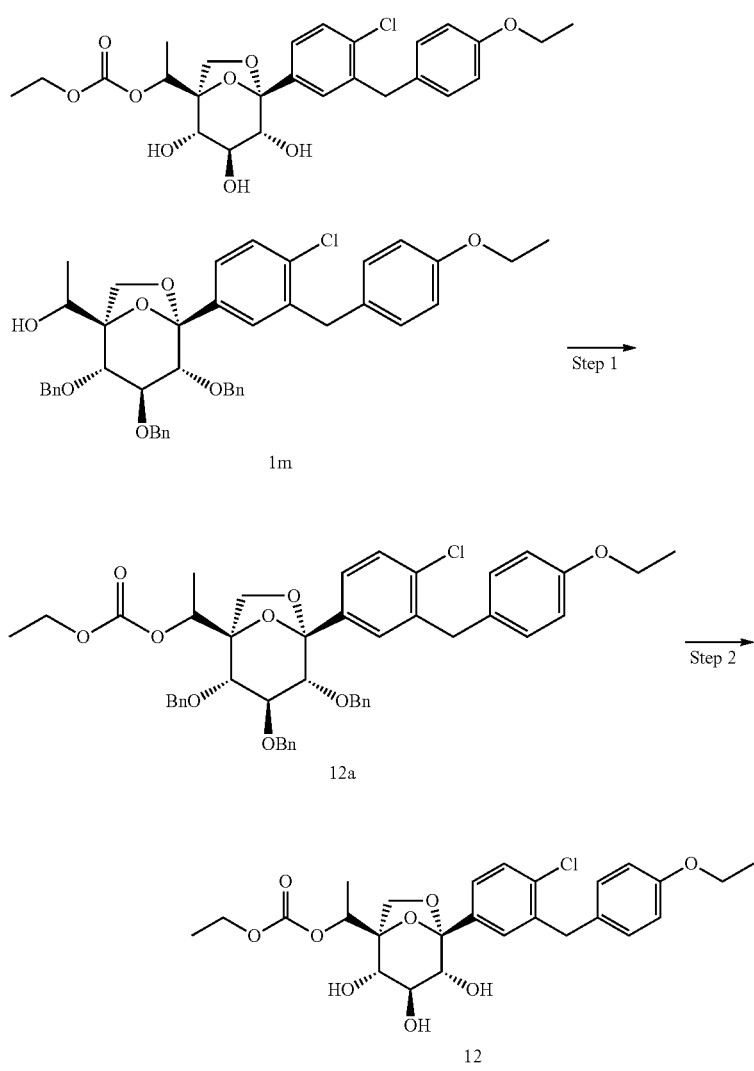

spectroscopic data: $^1$H NMR (400 MHz, CDCl$_3$) δ(ppm): 7.44 (s, 1H), 7.39-7.29 (m, 10H), 7.22 (dd, 5H), 7.08 (d, 2H), 6.91 (d, 2H), 6.77 (d, 2H), 5.10 (m, 1H), 4.97 (d, 1H), 4.90 (s, 1H), 4.81 (d, 2H), 4.33 (s, 1H), 4.21 (s, 1H), 4.20-4.09 (m, 2H), 4.07 (s, 1H), 4.04 (d, 2H), 4.00-3.92 (m, 3H), 3.86-3.76 (m, 2H), 3.66 (d, 1H), 1.41 (t, 3H), 1.29 (m, 6H).

Step 2) 1-[(1S,2S,3S,4R,5S)-5-[4-chloro-3-[(4-ethoxyphenyl)methyl]phenyl]-2,3,4-trihydroxy-6,8-dioxabicyclo[3.2.1]octan-1-yl]ethyl ethyl carbonate 12

To a solution of ethyl 1-[(1R,2S,3S,4R,5S)-2,3,4-tribenzyloxy-5-[4-chloro-3-[(4-ethoxy phenyl) methyl]phenyl]-6,8-dioxabicyclo[3.2.1]octan-1-yl]ethyl carbonate 12a (76.3 g, 0.09 mmol) in a methanol/tetrahydrofuran mixture (v/v=4/1, 10 mL) were added o-dichlorobenzene (0.05 mL, 0.48 mmol) and 10% Pd/C (12 mg, 0.01 mmol) at room temperature. The mixture was stirred at room temperature under H$_2$ for 4 hours and filtered. The filtrate was concentrated in vacuo. The residue was purified by silica gel chromatography eluted with PE/EtOAc(v/v)=1/4 to give the title compound 12 as a light yellow solid (38 mg, 60%, HPLC: 89.7%). The compound was characterized by the following spectroscopic data: MS (ESI, pos. ion) m/z: 523.2 [M+H]$^+$; and $^1$H NMR (400 MHz, DMSO-d$_6$) δ(ppm): 7.40 (m, 2H), 7.29 (m, 1H), 7.09 (s, 2H), 6.83 (m, 2H), 5.59 (d, 1H), 5.13 (d, 1H), 5.02 (d, 1H), 4.93 (m, 1H), 4.14-4.02 (m, 3H), 4.02-3.92 (m, 4H), 3.55 (d, 2H), 3.47-3.37 (m, 2H), 1.31 (m, 6H), 1.19 (t, 3H).

Example 13

1-[(1S,3S,4R,5S)-5-[4-Chloro-3-[(4-ethoxyphenyl)methyl]phenyl]-2,3,4-trihydroxy-6,8-dioxabicyclo[3.2.1]octan-1-yl]ethyl isopropyl carbonate 13

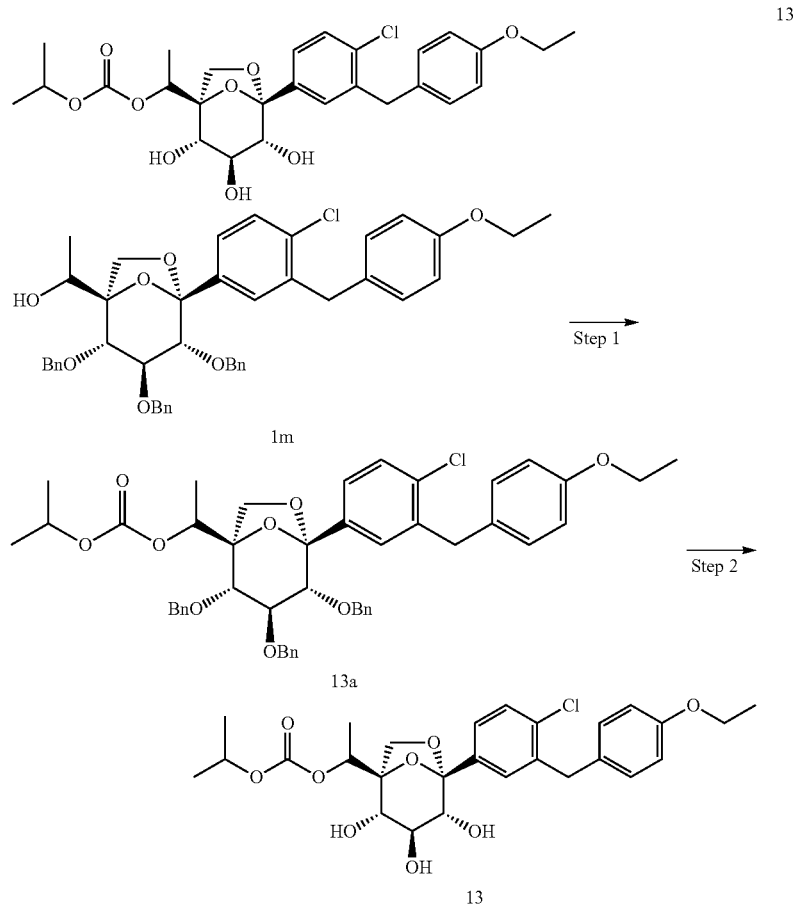

Step 1) isopropyl 1-[(1R,3S,4R,5S)-2,3,4-tribenzyloxy-5-[4-chloro-3-[(4-ethoxy phenyl)methyl]phenyl]-6,8-dioxabicyclo[3.2.1]octan-1-yl]ethyl carbonate 13a To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 1m (0.4 g, 0.56 mmol, obtained from the synthetic method described in step 11 of example 1) in dichloromethane (30 mL) were added isopropyl chloroformate (1.0 mL, 8.34 mmol), triethylamine (1.55 mL, 11.1 mmol) and 4-dimethyl aminopyridine (cat. 5 mg) in turn at room temperature. The mixture was stirred at room temperature for 16 hours. The resulting mixture was quenched with 20 mL of saturated aqueous ammonium chloride, and then extracted with ethyl acetate (40 mL×2). The combined organic layers were washed with saturated brine (20 mL×2), dried over anhydrous brine and filtered. The filtrate was concentrated in vacuo and the residue was purified by silica gel chromatography eluted with PE/EtOAc (v/v)=10/1 to give the title compound 13a as a light yellow solid (244 mg, 54.2%). The compound was characterized by the following spectroscopic data: ¹H NMR (400 MHz, CDCl₃) δ(ppm): 7.41-7.30 (m, 10H), 7.24-7.11 (m, 5H), 7.08 (m, 2H), 6.90 (m, 2H), 6.76 (m, 2H), 5.01-4.80 (m, 3H), 4.79 (m, 3H), 4.32 (d, 1H), 4.21 (d, 1H), 4.05-3.81 (m, 5H), 3.82-3.71 (m, 2H), 3.66 (d, 1H), 1.40 (t, 3H), 1.29 (d, 3H), 1.26 (m, 6H).

Step 2) 1-[(1S,3S,4R,5S)-5-[4-chloro-3-[(4-ethoxyphenyl)methyl]phenyl]-2,3,4-trihydroxy-6,8-dioxabicyclo[3.2.1]octan-1-yl]ethyl isopropyl carbonate 13

To a solution of isopropyl 1-[(1R,3S,4R,5S)-2,3,4-tribenzyloxy-5-[4-chloro-3-[(4-ethoxyphenyl) methyl]phenyl]-6,8-dioxabicyclo[3.2.1]octan-1-yl]ethyl carbonate 13a (244 mg, 0.3 mmol) in a methanol/tetrahydrofuran mixture (v/v=4/1, 10 mL) were added o-dichlorobenzene (0.16 mL, 1.5 mmol) and 10% Pd/C (36 mg, 0.03 mmol) in turn at room temperature. The mixture was stirred at room temperature under H₂ for 4 hours and filtered. The filtrate was concentrated in vacuo. The residue was purified by silica gel chromatography eluted with PE/EtOAc(v/v)=4/1 to give the title compound 13 as a white solid (120 mg, 75.0%, HPLC: 92.3%). The compound was characterized by the following spectroscopic data: MS (ESI, pos. ion) m/z: 537.3[M+H]⁺; and ¹H NMR (600 MHz, DMSO-d₆) δ(ppm): 7.40 (m, 2H), 7.29 (m, 1H), 7.11 (d, 2H), 6.84 (m, 2H), 5.58 (brs, 1H), 5.04 (brs, 2H), 4.93 (m, 1H), 4.73 (m, 1H), 4.50-3.98 (m, 5H), 3.54 (m, 2H), 3.44 (m, 2H), 1.31 (m, 6H), 1.23-1.20 (m, 6H).

Example 14

1-[(1S,2S,3S,4R,5S)-5-[4-Chloro-3-[(4-ethoxyphenyl)methyl]phenyl]-2,3,4-trihydroxy-6,8-dioxabicyclo[3.2.1]octan-1-yl]ethyl pivalate 14

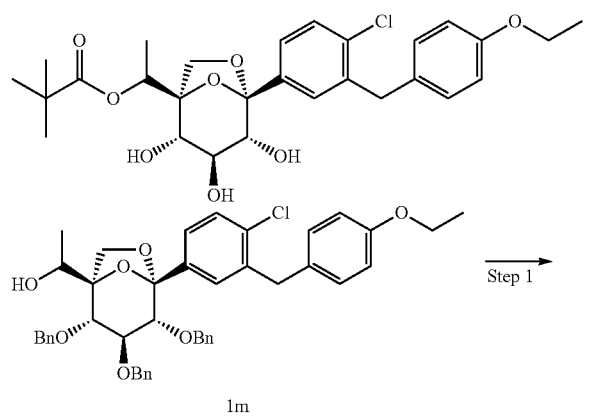

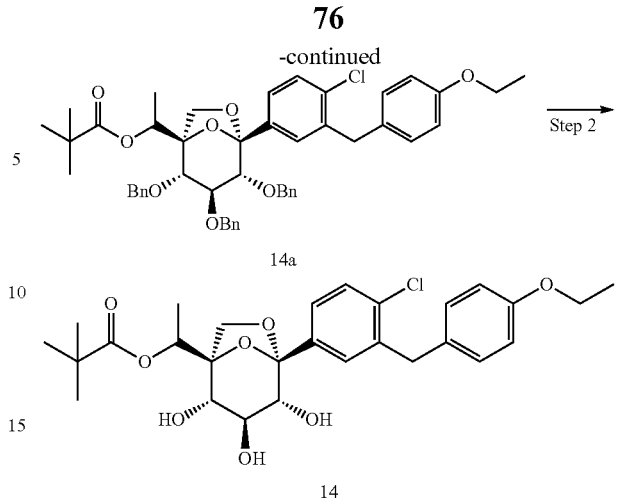

Step 1) 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethyl 2,2-dimethylpropanoate 14a To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethanol 1m (0.4 g, 0.56 mmol, obtained from the synthetic method described in step 11 of example 1) and chloromethyl pivalate (0.36 mL, 2.5 mmol) in tetrahydrofuran (20 mL) was added sodium hydride (77.8 mg, 1.95 mmol, 60% dispersion in Mineral oil) at 0° C. The mixture was heated to 40° C. and stirred for 48 hours. The resulting mixture was quenched with saturated ammonium chloride (20 mL), and then extracted with ethyl acetate (60 mL×3). The combined organic layers were washed with water (50 mL×2) and then saturated brine (50 mL×3), dried over anhydrous sodium sulfate and filtered. The filtrate was concentrated in vacuo and the residue was purified by silica gel chromatography eluted with PE/EtOAc(v/v)=10/1 to give the title compound 14a as light yellow oil (125 mg, 27.8%). The compound was characterized by the following spectroscopic data: ¹H NMR (600 MHz, CDCl₃) δ (ppm): 7.42-7.30 (m, 10H), 7.28-7.15 (m, 6H), 7.07 (m, 2H), 6.91 (m, 2H), 6.76 (m, 2H), 5.20 (m, 1H), 4.98 (d, 1H), 4.89-4.82 (m, 2H), 4.31 (m, 1H), 4.25 (d, 1H), 4.11-3.80 (m, 7H), 3.86 (d, 1H), 3.70 (m, 2H), 1.41 (t, 3H), 1.27 (d, 3H), 1.20 (s, 9H).

Step 2) 1-[(1S,2S,3S,4R,5S)-5-[4-chloro-3-[(4-ethoxyphenyl)methyl]phenyl]-2,3,4-trihydroxy-6,8-dioxabicyclo[3.2.1]octan-1-yl]ethyl-2,2-dimethylpropanoate 14

To a solution of 1-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]ethyl 2,2-dimethyl propanoate 14a (120 mg, 0.15 mmol) in a methanol/tetrahydrofuran mixture (v/v=4/1, 10 mL) were added o-dichlorobenzene (0.08 mL, 0.72 mmol) and 10% Pd/C (19 mg, 0.02 mmol) in turn at room temperature. The mixture was stirred at room temperature under H₂ for 4 hours and filtered. The filtrate was concentrated in vacuo. The residue was purified by silica gel chromatography eluted with PE/EtOAc(v/v)=4/1 to give the title compound 14 as a white solid (62.3 mg, 77.6%, HPLC: 85.3%). The compound was characterized by the following spectroscopic data: MS(ESI, pos. ion) m/z: 580.3[M+HCOO]⁻; and ¹H NMR (600 MHz, DMSO-d₆) δ(ppm): 7.42

(m, 2H), 7.32 (m, 1H), 7.08 (m, 2H), 6.82 (m, 2H), 5.38 (brs, 1H), 5.06 (m, 1H), 4.04 (d, 1H), 3.97 (m, 3H), 3.57 (d, 1H), 3.52 (d, 1H), 3.47 (m, 3H), 1.30 (t, 3H), 1.23 (d, 3H), 1.10 (s, 9H).
Example 15
(1R,2S,3S,4R,5S)-5-[4-Chloro-3-[[4-(trifluoromethoxy)phenyl]methyl]phenyl]-1-(1-hydroxyethyl)-6,8-dioxabicyclo[3.2.1]octane-2,3,4-triol 15
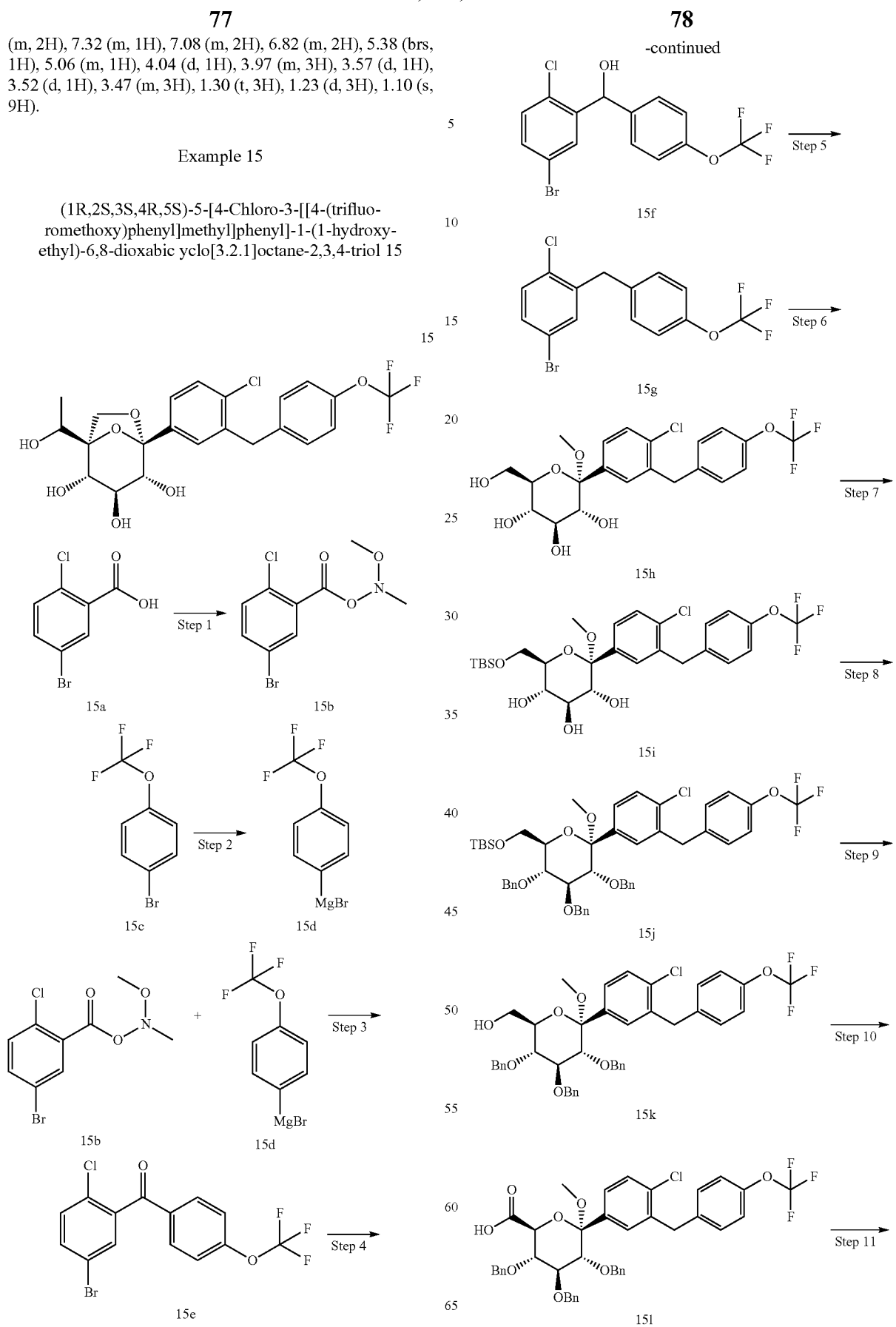

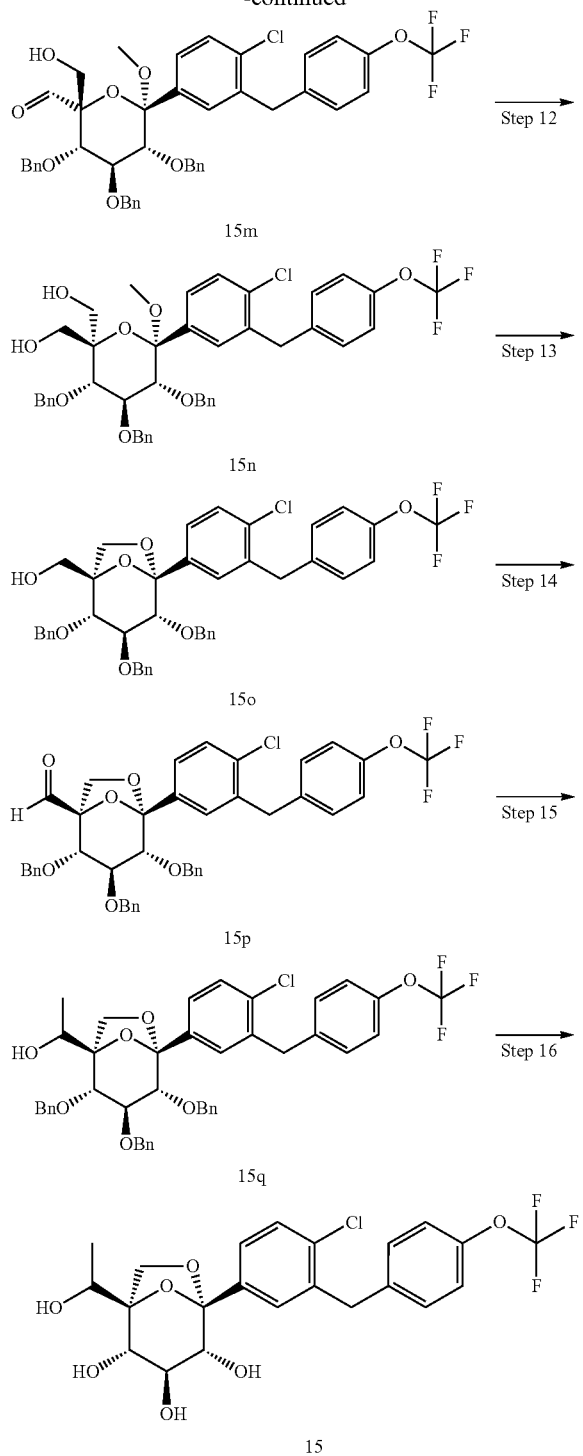

15m

15n

15o

15p

15q

15

Step 1) 1-(5-bromo-2-chlorophenyl)-2-[methoxy(methyl)amino]ethanone 15b

To a solution of N,O-dimethyl hydroxylamine hydrochloride (1.0 g, 10.25 mmol) in dichloromethane (50 mL) was added triethyl amine (3.10 g, 30.75 mmol). The mixture was stirred at room temperature for 10 min followed by adding 5-bromo-2-chloro-benzoic acid 15a (2.41 g, 10.25 mmol, purchased from Beijing yu xiang hui da chemical co., LTD) and bis(2-oxo-3-oxazolidinyl)phosphonic chloride (3.13 g, 12.3 mmol) in turn. The resulting mixture was further stirred for 23 hours. The reaction mixture was quenched with 40 mL of water and extracted with ethyl acetate (40 mL×3). The combined organic layers were washed with saturated brine (50 mL×3), dried over anhydrous sodium sulfate and filtered. The filtrate was concentrated in vacuo to give the title compound 15b as a white solid (2.90 g, 100%). The crude product was used in next step without further purification.

Step 2) bromo-[4-(trifluoromethoxy)phenyl]magnesium 15d

To a dry and oxygen-free flask containing magnesium (0.20 g, 7.97 mmol) and iodine (catalytic, 5 mg) under $N_2$ protection was added a solution of 1-bromo-4-(trifluoromethoxy)benzene 15c (1.60 g, 6.63 mmol, Accela ChemBio Co. Ltd) in anhydrous tetrahydrofuran (30 mL) dropwise. The dropping rate was controlled to keep the mixture slightly boiling. The title compound 15d was obtained as pale brown solution. This material was not further purified.

Step 3) (5-bromo-2-chloro-phenyl)-[4-(trifluoromethoxy)phenyl]methanone 15e

To the solution of 1-(5-bromo-2-chlorophenyl)-2-[methoxy(methyl)amino]ethanone 15b (0.74 g, 2.65 mmol) in dry tetrahydrofuran (10 mL) was added bromo-[4-(trifluoromethoxy)phenyl]magnesium 15d afforded from the last step at 0° C. under $N_2$. The resulting mixture was stirred at 0° C. for 4 hours. The reaction mixture was quenched with 20 mL of saturated brine, and then 20 mL of water and 40 mL of ethyl acetate were added in turn. The mixture was partitioned. The aqueous layer was extracted with ethyl acetate (20 mL×2). The combined organic layers were washed with saturated brine (20 mL×3), dried over anhydrous sodium sulfate and filtered. The filtrate was concentrated in vacuo and the residue was purified by silica gel chromatography eluted with PE/EtOAc(v/v)=50/1 to give the title compound 15e as a white solid (415 mg, 41.1%). The compound was characterized by the following spectroscopic data: $^1$H NMR (400 MHz, CDCl$_3$) δ (ppm): 7.88 (d, 2H), 7.60 (dd, 1H), 7.53 (d, 1H), 7.37 (d, 1H), 7.33 (d, 2H).

Step 4) (5-bromo-2-chloro-phenyl)[4-(trifluoromethoxy)phenyl]methanol 15f

To the solution of (5-bromo-2-chloro-phenyl)-[4-(trifluoromethoxy)phenyl]methanone 15e (5.0 g, 13.0 mmol) in a dry tetrahydrofuran/methanol mixture (v/v=1/1, 20 mL) was added sodium brohydride (0.98 g, 26.0 mmol) in portions at 0° C. After the addition, the mixture was stirred at 0° C. for 40 min. The reaction mixture was quenched with water (5 mL) and extracted with ethyl acetate (50 mL). The water layer was extracted with ethyl acetate (30 mL×2). The combined organic layers were washed with saturated brine (30 mL×2), dried over anhydrous sodium sulfate and filtered. The filtrate was concentrated in vacuo to give the title compound 15f as pale yellow oil (5.0 g, 99.5%). This material was not further purified.

Step 5) 4-bromo-1-chloro-2-[[4-(trifluoromethoxy)phenyl]methyl]benzene 15g

To a solution of (5-bromo-2-chloro-phenyl)-[4-(trifluoromethoxy)phenyl]methanol 15f (5.0 g, 13.0 mmol) in dichloromethane (50 mL) was added triethyl silicane (4.57 g, 39.0 mmol) at 0° C., and then boron fluoride ethyl ether (3.72 g, 26.0 mmol) was added slowly. The resulting mixture was allowed to warm up to room temperature and further stirred for 16 hours. The reaction mixture was quenched with saturated aqueous sodium bicarbonate (10 mL), and then separated. The aqueous layer was extracted with dichloromethane (20 mL×2). The combined organic layers were washed with saturated brine (30 mL×2), dried over anhydrous sodium sulfate and filtered. The filtrate was concentrated in vacuo and the residue was purified by silica gel chromatography eluted with PE to give the title compound 15g as colourless oil (3.69 g, 77.0%). The compound was characterized by the following spectroscopic data: $^1$H NMR (400 MHz, CDCl$_3$) δ (ppm): 7.34 (dd, 1H), 7.31 (d, 1H), 7.28 (s, 1H), 7.22 (d, 2H), 7.17 (d, 2H), 4.08 (s, 2H).

Step 6) (2S,3R,4S,5S,6R)-2-[4-chloro-3-[[4-(trifluoromethoxy)phenyl]methyl]phenyl]-6-(hydroxymethyl)-2-methoxy-tetrahydropyran-3,4,5-triol 15h To a solution of 4-bromo-1-chloro-2-[[4-(trifluoromethoxy)phenyl]methyl]benzene 15g (3.69 g, 9.67 mmol) in anhydrous tetrahydrofuran (60 mL) was added n-butyllithium (6 mL, 14.5 mmol, 2.4 M in hexane) dropwise at −78° C. The mixture was stirred at −78° C. for 30 min and a solution of (3R,4S,5R,6R)-3,4,5-tris(trimethylsilyloxy)-6-(trimethylsilyloxymethyetetrahydropyran-2-one 1b (6.77 g, 14.5 mmol, obtained from the synthetic method described in step 1 of example 1) in anhydrous tetrahydrofuran (40 mL) was added dropwise. After the addition, the mixture was further stirred at −78° C. until 4-bromo-1-chloro-2-[[4-(trifluoromethoxy) phenyl]methyl]benzene 15g was consumed. And then a solution of methanesulfonic acid (2.79 g, 29.0 mmol) in methanol (40 mL) was added to the reaction mixture and the resulting mixture was warmed up to room temperature and stirred for 18 hours. The reaction mixture was quenched with saturated aqueous sodium bicarbonate (40 mL), and then concentrated in vacuo to remove most of the solvent. The residue was extracted with ethyl acetate (10 mL). The aqueous layer was extracted with ethyl acetate (50 mL×2). The combined organic layers were washed with saturated brine (50 mL×3), dried over anhydrous sodium sulfate and filtered. The filtrate was concentrated in vacuo to give the title compound 15h as a pale yellow solid (4.71 g, 97.9%). This material was not further purified.

Step 7) (2S,3R,4S,5S,6R)-6-[[tert-butyl(dimethyl)silyl]oxymethyl]-2-[4-chloro-3-[[4-(trifluoromethoxy)phenyl]methyl]phenyl]-2-methoxy-tetrahydropyran-3,4,5-triol 15i To a solution of (2S,3R,4S,5S,6R)-2-[4-chloro-3-[[4-(trifluoromethoxy)phenyl]methyl]phenyl]-6-(hydroxymethyl)-2-methoxy-tetrahydropyran-3,4,5-triol 15h (1.0 g, 2.09 mmol) in dichloromethane (15 mL) were added imidazole (0.57 g, 8.39 mmol), tert-butyldimethylsilyl chloride (0.63 g, 4.19 mmol) and 4-dimethylaminopyridine (26 mg, 0.21 mmol) in turn at 0° C. The mixture was warmed up to room temperature and stirred for 1.5 hours. The reaction mixture was adjusted with saturated aqueous sodium bicarbonate to pH 7 and partitioned. The aqueous layer was extracted with dichloromethane (20 mL×2). The combined organic layers were washed with saturated brine (20 mL×2), dried over anhydrous sodium sulfate and filtered. The filtrate was concentrated in vacuo to give the title compound 15i as yellow oil (1.37 g, 100%). This material was not further purified.

Step 8) tert-butyl-dimethyl-[[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methoxy]silane 15j To a solution of (2S,3R,4S,5S,6R)-6-[[tert-butyl(dimethyl)silyl]oxymethyl]-2-[4-chloro-3-[[4-(trifluoromethoxy)phenyl]methyl]phenyl]-2-methoxy-tetrahydropyran-3,4,5-triol 15i (1.37 g, 1.69 mmol) in anhydrous tetrahydrofuran (15 mL) was added sodium hydride (0.20 g, 8.45 mmol, 60% dispersion in Mineral oil) at 0° C. The mixture was stirred at 0° C. for 15 min, and then benzyl bromide (1.45 g, 8.45 mmol) and tetrabutylammonium iodide (0.06 g, 0.17 mmol) were added in turn. The mixture was further stirred at room temperature for 20 hours. The reaction mixture was quenched with water (10 mL) and extracted with ethyl acetate (20 mL). The aqueous layer was extracted with ethyl acetate (20 mL×3). The combined organic layers were washed with saturated brine (20 mL×3), dried over anhydrous sodium sulfate, filtered. The filtrate was concentrated in vacuo to give the title compound 15j as yellow oil (1.9 g, 100%). This material was not further purified.

Step 9) [(2R,3R,4S,5R,6S)-3,4,5-tribenzyloxy-6-[4-chloro-3-[[4-(trifluoromethoxy) phenyl]methyl]phenyl]-6-methoxy-tetrahydropyran-2-yl]methanol 15k To a solution of tert-butyl-dimethyl-[[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methoxy]silane 15j (5.27 g, 6.43 mmol) in tetrahydrofuran (35 mL) was added tetrabutylammonium fluoride (9.64 mL, 9.64 mmol, 1 M in tetrahydrofuran) at room temperature. The mixture was stirred at 45° C. for 48 hours. The reaction mixture was quenched with water (10 mL) and partitioned. The aqueous layer was extracted with ethyl acetate (20 mL×2). The combined organic layers were washed with saturated sodium chloride (20 mL×2), dried over anhydrous sodium sulfate and filtered. The filtrate was concentrated in vacuo and the residue was purified by silica gel chromatography eluted with PE/EtOAc(v/v)=8/1 to give the title compound 15k as yellow oil (1.70 g, 35.3%). The compound was characterized by the following spectroscopic data: $^1$H NMR (400 MHz, CDCl$_3$) δ (ppm): 7.45-7.30 (m, 13H), 7.26-7.17 (m, 3H), 7.14 (d, 2H), 7.08 (d, 2H), 7.01 (d, 2H), 4.99-4.87 (m, 3H), 4.71 (d, 1H), 4.56 (d 1H), 4.25-4.11 (m, 2H), 3.95 (m, 3H), 3.75 (m, 3H), 3.33 (d, 1H), 3.09 (s, 3H).

Step 10) (2S,3S,4S,5R,6S)-3,4,5-tribenzyloxy-6-[4-chloro-3-[[4-(trifluoromethoxy) phenyl]methyl]phenyl]-6-methoxy-tetrahydropyran-2-carbaldehyde 15l To a solution of [(2R,3R,4S,5R,6S)-3,4,5-tribenzyloxy-6-[4-chloro-3.4-[[4-(trifluoromethoxy) phenyl]methyl]phenyl]-6-methoxy-tetrahydropyran-2-yl]methanol 15k (100 mg, 0.13 mmol) in dichloromethane (5 mL) was added 2-iodoxybenzoic acid (112 mg, 0.4 mmol) at room temperature. The mixture was refluxed for 24 hours. The reaction mixture was quenched with saturated aqueous sodium bicarbonate (3 mL) and partitioned. The aqueous layer was extracted with dichloromethane (10 mL×2). The combined organic layers were washed with saturated aqueous sodium chloride (10 mL×2), dried over anhydrous sodium sulfate and filtered. The filtration was concentrated in vacuo to give the title compound 15I as yellow oil (101 mg, 100%). This material was not further purified.

Step 11) (2R,3S,4S,5R,6S)-3,4,5-tribenzyloxy-6-[4-chloro-3-[[4-(trifluoromethoxy) phenyl]methyl]phenyl]-2-(hydroxymethyl)-6-methoxy-tetrahydropyran-2-carbaldehyde 15m To a solution of (2S,3S,4S,5R,6S)-3,4,5-tribenzyloxy-6-[4-chloro-3-[[4-(trifluoromethoxy) phenyl]methyl]phenyl]-6-methoxy-tetrahydropyran-2-carbaldehyde 15l (100 mg, 0.13 mmol) in tetrahydrofuran (5 mL) were added formaldehyde (72.3 mg, 2.47 mmol, 37 wt % solution) and 1,8-diazabicyclo[5.4.0]undec-7-ene (16.3 mg, 0.11 mmol) in turn at room temperature. The mixture was stirred at room temperature for 48 hours, and then ethyl acetate (20 mL) and water (5 mL) were added. The resulting mixture was partitioned. The aqueous layer was extracted with ethyl acetate (10 mL×2). The combined organic layers were washed with saturated aqueous sodium chloride (10 mL×2), dried over anhydrous sodium sulfate and filtered. The filtrate was concentrated in vacuo to give the title compound 15m as yellow oil (108 mg, 100%). This material was not further purified.

Step 12) [(3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-yl]methanol 15n To a solution of (2R,3S,4S,5R,6S)-3,4,5-tribenzyloxy-6-[4-chloro-3-[[4-(trifluoromethoxy) phenyl]methyl]phenyl]-2-(hydroxymethyl)-6-methoxy-tetrahydropyran-2-carbaldehyde 15m (1.26 g, 1.59 mmol) in anhydrous methanol (30 mL) was added sodium borohydride (120 mg, 23.18 mmol) in portions at 0° C. The mixture was warmed up to room temperature and stirred for 30 min. The reaction mixture was quenched with water (5 mL) and extracted with ethyl acetate (20 mL×2). The combined organic layers were washed with saturated aqueous sodium chloride (10 mL×2), dried over anhydrous sodium sulfate and filtered. The filtrate was concentrated in vacuo to give the title compound 15n as yellow oil (570 mg, 46.0%). The compound was characterized by the following spectroscopic data: $^1$H NMR (400 MHz, CD$_3$OD) δ(ppm): 7.58 (dd, 1H), 7.54 (d, 1H), 7.39 (d, 1H), 7.32 (m, 5H), 7.25 (m, 8H), 7.16 (d, 2H), 7.09 (m, 4H), 4.94 (d, 1H), 4.90 (d, 1H), 4.80 (s, 1H), 4.76 (d, 1H), 4.63 (t, 1H), 4.24 (t, 1H), 4.14 (dd, 2H), 4.07 (s, 3H), 4.00-3.93 (m, 2H), 3.77 (d, 1H), 3.37 (dd, 1H), 3.18 (s, 3H).

Step 13) [(1S,2S,3S,4R,5S)-2,3,4-tribenzyloxy-5-[4-chloro-3-[[4-(trifluoromethoxy) phenyl]methyl]phenyl]-6,8-dioxabicyclo[3.2.1]octan-1-yl]methanol 15o To a solution of [(3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-yl]methanol 15n (0.57 g, 0.72 mmol) in dichloromethane (30 mL) was added trifluoroacetic acid (0.22 mL, 2.88 mmol) at room temperature. The mixture was stirred at room temperature for 20 hours. The reaction mixture was quenched with saturated aqueous sodium bicarbonate (10 mL) and extracted with dichloromethane (10 mL×2). The combined organic layers were washed with saturated aqueous sodium chloride (10 mL×2), dried over anhydrous sodium sulfate and filtered. The filtrate was concentrated in vacuo and the residue was purified by silica gel chromatography eluted with PE/EtOAc(v/v)=10/1 to give the title compound 15o as pale yellow oil (475 mg, 88.3%). The compound was characterized by the following spectroscopic data: $^1$H NMR (400 MHz, DMSO-d$_6$) δ(ppm): 7.59 (d, 1H), 7.48 (s, 2H), 7.36-7.23 (m, 12H), 7.17 (m, 5H), 6.84 (d, 2H), 5.22 (t, 1H), 4.78 (m, 4H), 4.32 (d, 1H), 4.12 (m, 3H), 3.95 (d, 1H), 3.87 (m, 1H), 3.78 (m, 3H), 3.59 (dd, 1H), 3.52 (d, 1H).

Step 14) (1S,2S,3S,4R,5S)-2,3,4-tribenzyloxy-5-[4-chloro-3-[[4-(trifluoromethoxy) phenyl]methyl]phenyl]-6,8-dioxabicyclo[3.2.1]octane-1-carbaldehyde 15p To a solution of [(1S,2S,3S,4R,5S)-2,3,4-tribenzyloxy-5-[4-chloro-3-[[4-(trifluoromethoxy)phenyl]methyl]phenyl]-6,8-dioxabicyclo[3.2.1]octan-1-yl]methanol 15o (0.7 g, 0.94 mmol) in ethyl acetate (30 mL) was added 2-iodoxybenzoic acid (0.79 g, 2.81 mmol) at room temperature. The mixture was refluxed for 24 hours and filtered. The filtrate was washed with saturated aqueous sodium bicarbonate (10 mL×2) and saturated aqueous sodium chloride (10 mL×2) in turn, dried over anhydrous sodium sulfate and filtered. The filtrate was concentrated in vacuo to give the title compound 15p as yellow oil (0.71 g, 100%). This material was not further purified.

Step 15) 1-[(1R,2S,3S,4R,5S)-2,3,4-tribenzyloxy-5-[4-chloro-3-[[4-(trifluoromethoxy) phenyl]methyl] phenyl]-6,8-dioxabicyclo[3.2.1]octan-1-yl]ethanol 15q To a solution of (1S,2S,3S,4R,5S)-2,3,4-tribenzyloxy-5-[4-chloro-3-[[4-(trifluoromethoxy) phenyl]methyl]phenyl]-6,8-dioxabicyclo[3.2.1]octane-1-carbaldehyde 15p (0.71 g, 0.95 mmol) in dry tetrahydrofuran (15 mL) was added dropwise methylmagnesium bromide (0.64 mL, 1.91 mmol, 3M in tetrahydrofuran) under N$_2$ at 0° C. After the addition, the mixture was warmed up to room temperature and stirred for 3 hours. The reaction mixture was quenched with saturated aqueous ammonium chloride (3 mL). To the mixture was added 20 mL of saturated aqueous sodium chloride and the resulting mixture was partitioned. The aqueous layer was extracted with ethyl acetate (20 mL×2). The combined organic layers were washed with saturated aqueous sodium chloride (30 mL×2), dried over anhydrous sodium sulfate and filtered. The filtrate was concentrated in vacuo and the residue was purified by silica gel chromatography eluted with PE/EtOAc(v/v)=15/1 to give the title compound 15q as colourless oil (104 mg, 14.3%). The compound was characterized by the following spectroscopic data: $^1$H NMR (400 MHz, CDCl$_3$) δ(ppm): 7.45 (s, 1H), 7.40 (s, 2H), 7.38-7.29 (m, 9H), 7.25-7.14 (m, 6H), 7.06 (d, 2H), 6.92 (d, 2H), 4.97 (dd, 2H), 4.81 (d, 2H), 4.29 (d 2H), 4.13-4.07 (m, 3H), 4.06 (s, 3H), 3.84 (d 1H), 3.69 (d, 1H), 3.58 (s, 1H), 1.21 (d, 3H).

Step 16) (1R,2S,3S,4R,5S)-5-[4-chloro-3-[[4-(trifluoromethoxy)phenyl]methyl]phenyl]-1-(1-hydroxyethyl)-6,8-dioxabicyclo[3.2.1]octane-2,3,4-triol 15

To a solution of 1-[(1R,2S,3S,4R,5S)-2,3,4-tribenzyloxy-5-[4-chloro-3-[4-[4-(trifluoromethoxy) phenyl]methyl]phenyl]-6,8-dioxabicyclo[3.2.1]octan-1-yl]ethanol 15q (102 mg, 0.13 mmol) in a methanol/tetrahydrofuran mixture (v/v=4/1, 10 mL) were added o-dichlorobenzene (95 mg, 0.65 mmol) and 10% Pd/C (41 mg, 0.39 mmol) at room temperature. The mixture was stirred under H$_2$ at room temperature for 2 hours and filtered. The filtrate was concentrated in vacuo and the residue was purified by silica gel chromatography eluted with PE/EtOAc(v/v)=1/5 to give the title compound 15 as a white solid (18 mg, 28.2%, HPLC: 96.2%). The compound was characterized by the following spectroscopic data: MS (ESI, pos. ion) m/z: 535.2[M+HCOO]⁻; and ¹H NMR (400 MHz, DMSO-d₆) δ(ppm): 7.47 (d, 1H), 7.42 (d, 1H), 7.37-7.26 (m, 5H), 5.27 (d, 1H), 4.92 (m, 2H), 4.61 (d, 1H), 4.12 (s, 2H), 4.01 (dd, 1H), 3.81 (dd, 1H), 3.54 (d, 1H), 3.47-3.37 (m, 3H), 1.17 (d, 3H).

Example 16

(1S,2S,3S,4R,5S)-5-[4-Chloro-3-[[4-(trifluoromethoxy)phenyl]methyl]phenyl]-1-(1-hydroxy-1-methyl-ethyl)-6,8-dioxabicyclo[3.2.1]octane-2,3,4-triol 16

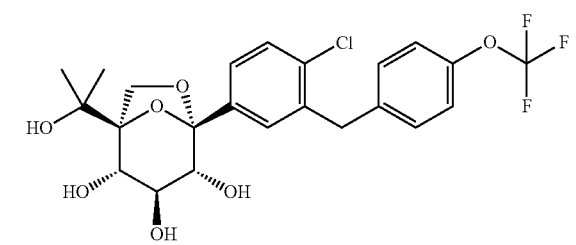

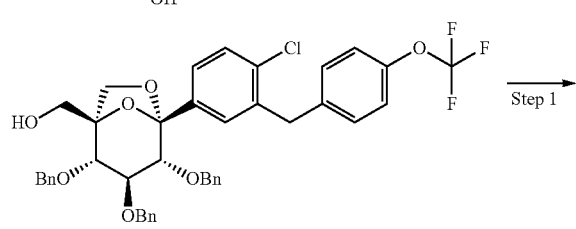

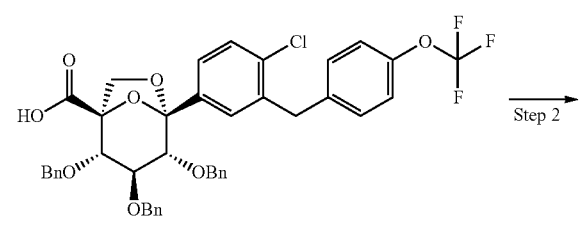

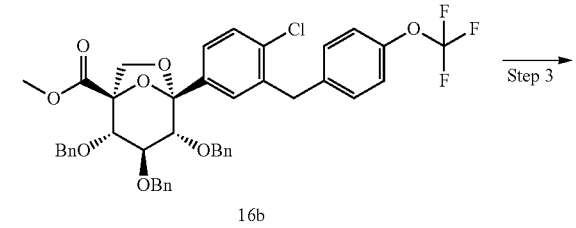

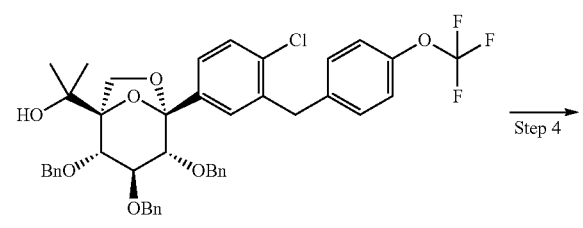

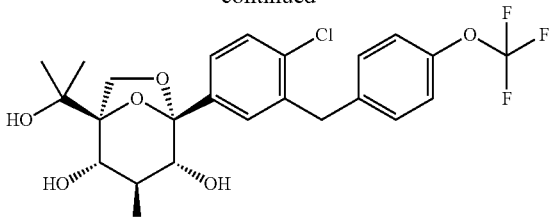

Step 1) (1S,2S,3S,4R,5S)-2,3,4-tribenzyloxy-5-[4-chloro-3-[[4-(trifluoromethoxy)phenyl]methyl]phenyl]-6,8-dioxabicyclo[3.2.1]octane-1-carboxylic acid 16a To a solution of [(1S,2S,3S,4R,5S)-2,3,4-tribenzyloxy-5-[4-chloro-3-[[4-(trifluoromethoxy) phenyl]methyl]phenyl]-6,8-dioxabicyclo[3.2.1]octan-1-yl]methanol 15o (0.45 g, 0.60 mmol, obtained from the synthetic method described in step 13 of example 15) in tetrahydrofuran (8 mL) were added sodium bicarbonate (0.56 g, 6.62 mmol), potassium bromide (14.3 mg, 0.12 mmol) and 2,2,6,6-tetramethylpiperidinooxy (9.38 mg, 0.06 mmol) in turn at 0° C., and then sodium hypochlorite (19 mL, available chlorine ≥5.5%) was added dropwise over a period of 10 min. The mixture was warmed up to room temperature and stirred for 1 hour, and then acidified with aqueous HCl (1 N) till pH becomes 4. The resulting mixture was extracted with ethyl acetate (10 mL×2). The combined organic layers were washed with saturated aqueous sodium chloride (10 mL), dried over anhydrous sodium sulfate and filtered. The filtrate was concentrated in vacuo to give the title compound 16a (0.50 g, 100%) as yellow oil. This material was not further purified.

Step 2) methyl(1S,2S,3S,4R,5S)-2,3,4-tribenzyloxy-5-[4-chloro-3-[[4-(trifluoro methoxy)phenyl]methyl]phenyl]-6,8-dioxabicyclo[3.2.1]octane-1-carboxylate 16b To a solution of (1S,2S,3S,4R,5S)-2,3,4-tribenzyloxy-5-[4-chloro-3-[[4-(trifluoromethoxy) phenyl]methyl]phenyl]-6,8-dioxabicyclo[3.2.1]octane-1-carboxylic acid 16a (0.49 g, 0.64 mmol) in tetrahydrofuran (2 mL) were added methanol (8 mL) and concentrated sulphuric acid (0.24 mL) at room temperature. The mixture was stirred at 45° C. for 20 hours. The reaction mixture was neutralized with saturated aqueous sodium bicarbonate till pH becomes 7 and extracted with ethyl acetate (10 mL×3). The combined organic layers were washed with saturated aqueous sodium chloride (10 mL×2), dried over anhydrous sodium sulfate and filtered. The filtrate was concentrated in vacuo and the residue was purified by silica gel chromatography eluted with PE/EtOAc(v/v)=20/1 to give the title compound 16b as a white solid (322 mg, 66.5%). The compound was characterized by the following spectroscopic data: ¹H NMR (400 MHz, CDCl₃) δ(ppm): 7.48 (d, 1H), 7.44-7.38 (m, 2H), 7.32 (m, 7H), 7.26 (m, 3H), 7.21 (d, 1H), 7.16 (m, 4H), 7.05 (d, 2H), 6.87 (d, 2H), 4.90-4.81 (m, 2H), 4.79 (d, 1H), 4.63 (d, 1H), 4.53 (d, 1H), 4.32 (d, 1H), 4.20 (dd, 2H), 4.10 (t, 2H), 4.02 (dd, 1H), 3.89 (d, 1H), 3.74 (d, 1H), 3.71 (s, 3H).

Step 3) 2-[(1S,2S,3S,4R,5S)-2,3,4-tribenzyloxy-5-[4-chloro-3-[[4-(trifluoromethoxy) phenyl]methyl] phenyl]-6,8-dioxabicyclo[3.2.1]octan-1-yl]propan-2-ol 16c To a solution of methyl(1S,2S,3S,4R,5S)-2,3,4-tribenzyloxy-5-[4-chloro-3-[[4-(trifluoromethoxy) phenyl]methyl] phenyl]-6,8-dioxabicyclo[3.2.1]octane-1-carboxylate 16b (0.33 g, 0.43 mmol) in anhydrous tetrahydrofuran (15 mL) was added dropwise methylmagnesium bromide (0.64 mL, 1.92 mmol, 3 M in tetrahydrofuran) at 0° C. The mixture was stirred at room temperature for 30 min. The reaction mixture was quenched with water (2 mL) and filtered. The filtrate was concentrated in vacuo to remove most of the solvent. The resulting mixture was extracted with ethyl acetate (10 mL×3). The combined organic layers were washed with saturated aqueous sodium chloride (10 mL×2), dried over anhydrous sodium sulfate and filtered. The filtrate was concentrated in vacuo. The residue was purified by silica gel chromatography eluted with PE/EtOAc(v/v)=15/1 to give the title compound 16c as pale yellow oil (242 mg, 72.6%). This material was not further purified. The compound was characterized by the following spectroscopic data: $^1$H NMR (400 MHz, CDCl$_3$) δ(ppm): 7.36 (m, 11H), 7.26-7.19 (m, 4H), 7.19-7.13 (m, 3H), 7.06 (d, 2H), 6.94 (d, 2H), 5.07 (d, 1H), 4.96 (d, 1H), 4.78 (dd, 2H), 4.35 (d, 1H), 4.28 (d, 1H), 4.09 (dd, 5H), 3.83 (d, 1H), 3.71 (d, 1H), 1.30 (s, 3H), 1.26 (s, 3H).

Step 4) (1S,2S,3S,4R,5S)-5-[4-chloro-3-[[4-(trifluoromethoxy)phenyl]methyl]phenyl]-1-(1-hydroxy-1-methyl-ethyl)-6,8-dioxabicyclo[3.2.1]octane-2,3,4-triol 16

To a solution of 2-[(1S,2S,3S,4R,5S)-2,3,4-tribenzyloxy-5-[4-[4-(trifluoromethoxy) phenyl]methyl]phenyl]-6,8-dioxabicyclo[3.2.1]octan-1-yl]propan-2-ol 16c (0.24 mg, 0.31 mmol) in a methanol/tetrahydrofuran mixture (v/v=4/1, 15 mL) were added o-dichlorobenzene (0.18 mL, 1.55 mmol) and 10% Pd/C (72 mg, 0.09 mmol) at room temperature. The mixture was stirred at room temperature under H$_2$ for 30 min and filtered. The filtrate was concentrated in vacuo and the residue was purified by silica gel chromatography eluted with PE/EtOAc(v/v)=1/1 to give the title compound 16 as a white solid (142 mg, 90.7%, HPLC: 97.9%). The compound was characterized by the following spectroscopic data: MS (ESI, pos. ion) m/z: 549 [M+HCOO]$^-$; and $^1$H NMR (400 MHz, DMSO-d$_6$) δ(ppm): 7.47 (d, 1H), 7.42 (d, 1H), 7.36 (dd, 2.1 Hz, 1H), 7.30 (m, 4H), 5.50 (d, 1H), 5.05 (d, 1H), 5.00 (d, 1H), 4.24 (s, 1H), 4.11 (s, 2H), 4.07-3.99 (m, 1H), 3.81 (d, 1H), 3.75-3.66 (m, 1H), 3.50-3.43 (m, 1H), 3.29-3.21 (m, 1H), 1.20 (s, 3H), 1.16 (s, 3H).

Example 17

(1R,2S,3S,4R,5S)-5-[4-Chloro-3-[[4-(2,2,2-trifluoroethoxy)phenyl]methyl]phenyl]-1-(1-hydroxyethyl)-6,8-dioxabicyclo[3.2.1]octane-2,3,4-triol 17

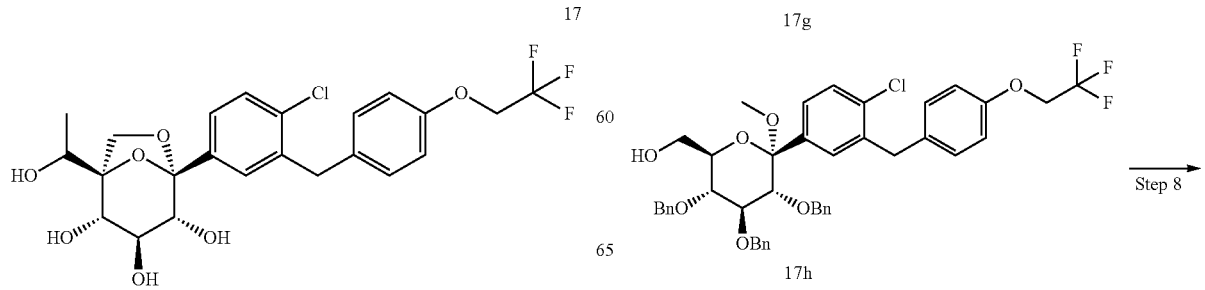

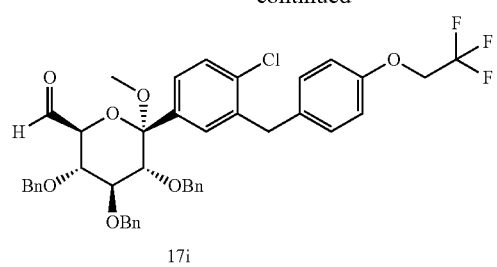

17i

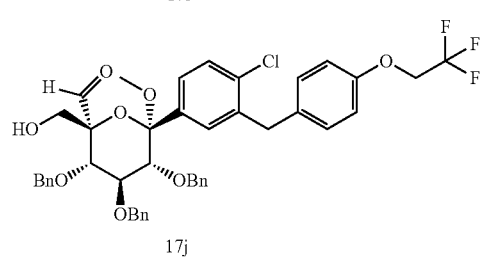

17j

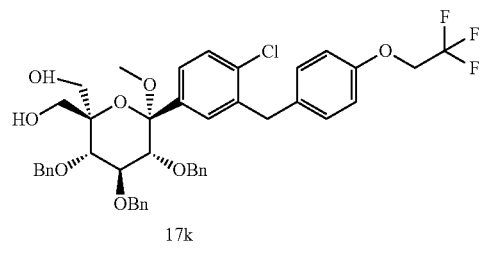

17k

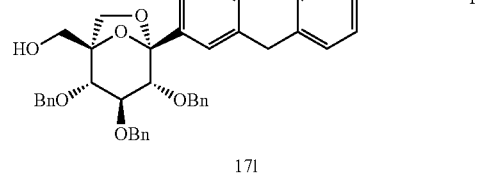

17l

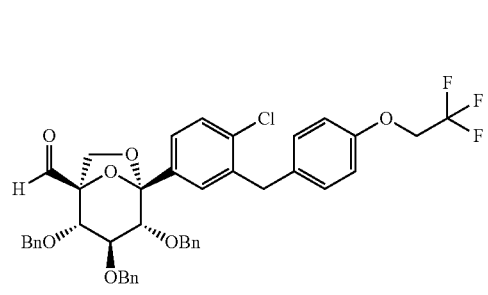

17m

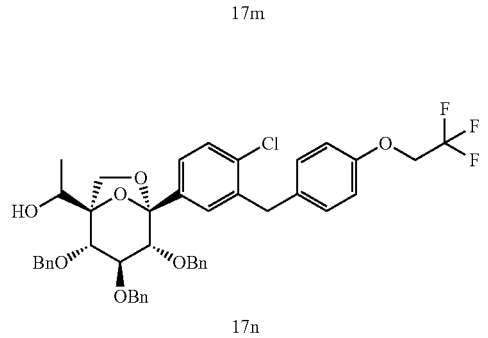

17n

Step 9 →
Step 10 →
Step 11 →
Step 12 →
Step 13 →
Step 14 →

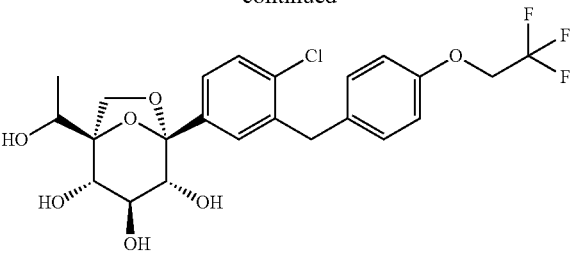

17

Step 1) 4-[(5-bromo-2-chloro-phenyl)methyl]phenol 17b

To a solution of 4-bromo-1-chloro-2-[(4-ethoxyphenyl)methyl]benzene 17a (5.0 g, 15.35 mmol, purchased from Shanghai Caerulum Pharma Discovery Co., Ltd.) in dichloromethane (50 mL) was added a solution of boron tribromide (1.7 mL, 16.89 mmol) in dichloromethane (10 mL) dropwise. The mixture was stirred at room temperature for 30 min. The reaction mixture was neutralized with saturated aqueous sodium bicarbonate till pH becomes 7 and extracted with dichloromethane (50 mL×2). The combined organic layers were washed with saturated aqueous sodium chloride (30 mL×2), dried over anhydrous sodium sulfate and filtered. The filtrate was concentrated in vacuo to give the title compound 17b as a pale yellow solid (5.16 g, 100%). This material was not further purified.

Step 2) 4-bromo-1-chloro-2-[[4-(2,2,2-trifluoroethoxy)phenyl]methyl]benzene 17c To a solution of 4-[(5-bromo-2-chloro-phenyl)methyl]phenol 17b (23.4 g, 78.7 mmol) in N,N-dimethylformamide (30 mL) was added potassium carbonate (54.0 g, 394.0 mmol) at room temperature. The mixture was warmed up to 90° C. and stirred for 30 min, and then 2,2,2-trifluoroethyl-p-toluensulfonate (20 g, 78.7 mmol) was added. The reaction mixture was warmed up to 140° C. and stirred for 12 hours. The mixture was cooled to room temperature and filtered. The filtrate was concentrated in vacuo and the residue was partitioned between ethylacetate (200 mL) and water (200 mL). The aqueous layer was extracted with ethyl acetate (100 mL×2). The combined organic layers were washed with saturated aqueous sodium chloride (30 mL×2), dried over anhydrous sodium sulfate and filtered. The filtrate was concentrated in vacuo and the residue was purified by silica gel chromatography eluted with PE to give the title compound 17c as a white solid (26.0 g, 87.2%, HPLC: 97.45%). The compound was characterized by the following spectroscopic data: $^1$H NMR (400 MHz, CDCl$_3$) δ(ppm): 7.54 (d, 1H), 7.45 (m, 1H), 7.40 (d, 1H), 7.18 (d, 2H), 7.00 (d, 2H), 4.80-4.64 (m, 2H), 4.01 (s, 2H).

Step 3) (2S,3R,4S,5R,6R)-2-[4-chloro-3-[[4-(2,2,2-trifluoroethoxy)phenyl]methyl]phenyl]-3,4,5-tris(trimethylsilyloxy)-6-(trimethylsilyloxymethyltetrahydropyran-2-ol 17d To a solution of 4-bromo-1-chloro-2-[[4-(2,2,2-trifluoroethoxyl)phenyl]methyl]benzene 17c (26.0 g, 68.5 mmol) in anhydrous tetrahydrofuran (200 mL) was added n-butyllithium (30 mL, 72.0 mmol, 2.5 M in hexane) dropwise at −78° C. under N$_2$. The mixture was stirred at −78° C. for 1 hour and a solution of (3R,4S,5R,6R)-3,4,5-tris(trimethylsilyloxy)-6-(trimethylsilyloxymethyetetrahydropyran-2-one 1b (38.4 g, 82.2 mmol, obtained from the synthetic method described in step 1 of example 1) in anhydrous tetrahydrofuran (50 mL) was added dropwise. After the addition, the mixture was further stirred at −78° C. for 5 hours and quenched with saturated aqueous ammonium chloride (80 mL), and then partitioned. The aqueous layer was extracted with ethyl acetate (80 mL×3). The combined organic layers were washed with saturated aqueous sodium chloride (200 mL), dried over anhydrous sodium sulfate and filtered. The filtrated was concentrated in vacuo to give the title compound 17d as pale yellow oil (52.6 g, 100%). This material was not further purified.

Step 4) (2S,3R,4S,5S,6R)-2-[4-chloro-3-[[4-(2,2,2-trifluoroethoxyl)phenyl]methyl]phenyl]-6-(hydroxymethyl)-2-methoxy-tetrahydropyran-3,4,5-triol 17e To a solution of (2S,3R,4S,5R,6R)-2-[4-chloro-3-[[4-(2,2,2-trifluoroethoxyl)phenyl]methyl]phenyl]-3,4,5-tris(trimethylsilyloxy)-6-(trimethylsilyloxymethyl)tetrahydropyran-2-ol 17d (45.0 g, 58.0 mmol) in anhydrous methanol (120 mL) was added methylsulfonic acid (11.3 mL, 174 mmol). The mixture was stirred at room temperature for 16 hours. The reaction mixture was neutralized with saturated aqueous sodium bicarbonate till pH becomes 7 and concentrated in vacuo to remove most of the solvent. The residue was partitioned between water (200 mL) and ethyl acetate (200 mL). The aqueous layer was extracted with ethyl acetate (100 mL×2). The combined organic layers were washed with saturated aqueous sodium chloride (200 mL), dried over anhydrous sodium sulfate and filtered. The filtrate was concentrated in vacuo and the residue was purified by re-crystallization from a toluene/n-hexane mixture (v/v)=1/1 to give the title compound 17e as yellow solid powder (12.5 g, 54.3%). The compound was characterized by the following spectroscopic data: MS (ESI, pos. ion) m/z: 537.1 [M+HCOO]−.

Step 5) (2S,3R,4S,5S,6R)-6-[[tert-butyl(dimethyl)silyl]oxymethyl]-2-[4-chloro-3-[[4-(2,2,2-trifluoroethoxy)phenyl]methyl]phenyl]-2-methoxy-tetrahydropyran-3,4,5-triol 17f To a solution of (2S,3R,4S,5S,6R)-2-[4-chloro-3-[[4-(2,2,2-trifluoroethoxyl)phenyl]methyl]phenyl]-6-(hydroxymethyl)-2-methoxy-tetrahydropyran-3,4,5-triol 17e (3.5 g, 7.1 mmol) in dichloromethane (60 mL) were added imidazole (0.97 g, 14.2 mmol) and tert-butyldimethylsilyl chloride (2.14 g, 14.2 mmol) in turn at 0° C. The mixture was warmed up to room temperature and stirred for 2 hours. The reaction mixture was adjusted with saturated aqueous sodium bicarbonate to pH 7 and partitioned. The organic layer was washed with saturated aqueous sodium chloride (50 mL), dried over anhydrous sodium sulfate and filtered. The filtrate was concentrated in vacuo to give the title compound 17f as light yellow oil (4.8 g, 100%). This material was not further purified.

Step 6) tert-butyl-dimethyl-[[(2R,3R,4S,5R,6S)-3,4,5-tribenzyloxy-6-[4-chloro-3-[[4-(2,2,2-trifluoroethoxyl)phenyl]methyl]phenyl]-6-methoxy-tetrahydropyran-2-yl]methoxy]silane 17g To a suspension of sodium hydride (1.90 g, 47.4 mmol, 60% dispersion in Mineral oil) in anhydrous tetrahydrofuran (50 mL) was added a solution of (2S,3R,4S,5S,6R)-6-[[tert-butyl (dimethyl)silyl]oxymethyl]-2-[4-chloro-3-[[4-(2,2,2-trifluoro ethoxy)phenyl]methyl]phenyl]-2-methoxy-tetrahydropyran-3,4,5-triol 17f (4.8 g, 7.91 mmol) in anhydrous tetrahydrofuran (50 mL) slowly at 0° C. The mixture was stirred at 0° C. for 1 hour and warmed to room temperature. Then benzyl bromide (5.6 mL, 47.4 mmol) and tetrabutylammonium iodide (0.3 g, 0.79 mmol) were added in turn. The mixture was warmed up to 40° C. and further stirred for 12 hours. The reaction mixture was quenched with water (50 mL) and partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel chromatography eluted with PE/EtOAc(v/v)=20/1 to give the title compound 17g as orange-yellow oil (1.6 g, 23.0%). This material was not further purified.

Step 7) [(2R,3R,4S,5R,6S)-3,4,5-tribenzyloxy-6-[4-chloro-3-[[4-(2,2,2-trifluoro ethoxy)phenyl]methyl]phenyl]-6-methoxy-tetrahydropyran-2-yl]methanol 17h To a solution of tert-butyl-dimethyl-[[(2R,3R,4S,5R,6S)-3,4,5-tribenzyloxy-6-[4-chloro-3-[[4-(2,2,2-trifluoroethoxyl)phenyl]methyl]phenyl]-6-methoxy-tetrahydropyran-2-yl]methoxy]silane 17g (23.7 g, 27.01 mmol) in tetrahydrofuran (100 mL) was added tetrabutylammonium fluoride (54.0 mL, 54.02 mmol, 1 M in tetrahydrofuran) at room temperature. The mixture was stirred at room temperature for 1 hour and then 40° C. for 12 hours. The reaction mixture was cooled to room temperature, and then 50 mL of saturated aqueous sodium bicarbonate and 100 mL of water were added. The resulting mixture was partitioned. The aqueous layer was extracted with ethyl acetate (80 mL×3). The combined organic layers were dried over anhydrous sodium sulfate and filtered. The filtrate was concentrated in vacuo and the residue was purified by silica gel chromatography eluted with PE/EtOAc(v/v)=10/1 to give the title compound 17h as orange-yellow oil (5.5 g, 27.0%, HPLC: 84.7%). The compound was characterized by the following spectroscopic data: 1H NMR (600 MHz, CDCl$_3$) δ (ppm): 7.39-7.30 (m, 12H), 7.21 (m, 4H), 7.07 (d, 2H), 7.00 (d, 2H), 6.80 (d, 2H), 4.98-4.86 (m, 3H), 4.70 (d, 1H), 4.50 (d, 1H), 4.34-4.24 (m, 2H), 4.11 (m, 2H), 3.95-3.86 (m, 3H), 3.80 (m, 1H), 3.73 (m, 1H), 3.70 (s, 1H), 3.30 (d, 1H), 3.07 (s, 3H).

Step 8) (2S,3S,4S,5R,6S)-3,4,5-tribenzyloxy-6-[4-chloro-3-[[4-(2,2,2-trifluoro ethoxy)phenyl]methyl]phenyl]-6-methoxy-tetrahydropyran-2-carbaldehyde 17i To a solution of [(2R,3R,4S,5R,6S)-3,4,5-tribenzyloxy-6-[4-chloro-3-[[4-(2,2,2-trifluoroethoxyl) phenyl]methyl]phenyl]-6-methoxy-tetrahydropyran-2-yl]methanol 17h (5.5 g, 7.2 mmol) in dichloromethane (200 mL) was added 2-iodoxybenzoic acid (4.1 g, 14.4 mmol) at −5° C. The mixture was stirred at −5° C. for 1 hour, and then refluxed at 45° C. for 16 hours. The reaction mixture was cooled to room temperature and filtered. The filtrate was concentrated in vacuo to give the title compound 17i as pale yellow oil (5.3 mg, 96.3%). This material was not further purified.

Step 9) (2R,3S,4S,5R,6S)-3,4,5-tribenzyloxy-6-[4-chloro-3-[[4-(2,2,2-trifluoro ethoxy)phenyl]methyl]phenyl]-2-(hydroxymethyl)-6-methoxy-tetrahydropyran-2-carbaldehyde 17j To a solution of (2S,3S,4S,5R,6S)-3,4,5-tribenzyloxy-6-[4-chloro-3-[[4-(2,2,2-trifluoroethoxyl) phenyl]methyl]phenyl]-6-methoxy-tetrahydropyran-2-carbaldehyde 17i (5.5 g, 7.2 mmol) in N,N-dimethyl formamide (40 mL) were added formaldehyde (10.0 mL, 144.0 mmol, 37 wt % solution) and 1,8-diazabicyclo[5.4.0]undec-7-ene (1.1 g, 7.2 mmol) in turn at room temperature. The mixture was stirred at room temperature for 16 hours, and then 60 mL of water was added. The resulting mixture was extracted with ethyl acetate (30 mL×3). The combined organic layers were dried over anhydrous sodium sulfate and filtered. The filtrate was concentrated in vacuo to give the title compound 17i as pale yellow oil (4.6g, 80.7%). This material was not further purified.

Step 10) [(3S,4S,5R,6S)-3,4,5-tribenzyloxy-6-[4-chloro-3-[[4-(2,2,2-trifluoro ethoxy)phenyl]methyl]phenyl]-2-(hydroxymethyl)-6-methoxy-tetrahydropyran-2-yl]methanol 17k To a solution of (2R,3S,4S,5R,6S)-3,4,5-tribenzyloxy-6-[4-chloro-3-[[4-(2,2,2-trifluoroethoxyl) phenyl]methyl]phenyl]-2-(hydroxymethyl)-6-methoxy-tetrahydropyran-2-carbaldehyde 17j (4.80 g, 6.04 mmol) in methanol (50 mL) was added sodium borohydride (326 mg, 8.62 mmol) at −5° C. The mixture was stirred for 30 min at −5° C. The reaction mixture was quenched with saturated aqueous ammonium chloride (15 mL) and concentrated in vacuo to remove most of the solvent. To the residue was added water (50 mL). The mixture was extracted with ethyl acetate (30 mL×3). The combined organic layers were dried over anhydrous sodium sulfate and filtered. The filtrate was concentrated in vacuo and the residue was purified by silica gel chromatography eluted with PE/EtOAc(v/v)=10/1 to give the title compound 17k as light yellow oil (2.7 g, 56.3%, HPLC: 89.2%). This material was not further purified. The compound was characterized by the following spectroscopic data: $^1$H NMR (600 MHz, DMSO-$d_6$) δ(ppm): 7.53 (d, 2H), 7.40 (d, 1H), 7.33 (d, 2H), 7.31-7.22 (m, 12H), 7.08-7.01 (m, 4H), 6.89 (d, 2H), 4.90 (s, 1H), 4.85-4.74 (m, 3H), 4.71-4.63 (m, 3H), 4.52 (d, 1H), 4.30 (s, 1H), 4.05 (m, 3H), 3.99-3.85 (m, 3H), 3.79 (m, 2H), 3.54 (d, 1H), 3.19 (d, 1H), 3.09 (s, 3H).

Step 11) [(1S,2S,3S,4R,5S)-2,3,4-tribenzyloxy-5-[4-chloro-3-[[4-(2,2,2-trifluoro ethoxy)phenyl]methyl]phenyl]-6,8-dioxabicyclo[3.2.1]octan-1-yl]methanol 17l To a solution of [(3S,4S,5R,6S)-3,4,5-tribenzyloxy-6-[4-chloro-3-[[4-(2,2,2-trifluoroethoxyl)phenyl]methyl]phenyl]-2-(hydroxymethyl)-6-methoxy-tetrahydropyran-2-yl]methanol 17k (3.60 g, 4.53 mmol) in dichloromethane (400 mL) was added p-toluenesulfonic acid monohydrate (0.43 g, 2.27 mmol) at 0° C. The mixture was stirred at room temperature for 6 hours. The reaction mixture was neutralized with saturated aqueous sodium bicarbonate to pH 7 and 40 mL of water was added. The resulting mixture was partitioned. The aqueous layer was extracted with dichloromethane (20 mL×3). The combined organic layers were dried over anhydrous sodium sulfate and filtered. The filtrate was concentrated in vacuo and the residue was purified by silica gel chromatography eluted with PE/EtOAc(v/v)=20/1 to give the title compound 17l as orange-yellow oil (3.70 g, 81.6%).

Step 12) (1S,2S,3S,4R,5S)-2,3,4-tribenzyloxy-5-[4-chloro-3-[[4-(2,2,2-trifluoro ethoxy)phenyl]methyl]phenyl]-6,8-dioxabicyclo[3.2.1]octane-1-carbaldehyde 17m To a solution of [(1S,2S,3S,4R,5S)-2,3,4-tribenzyloxy-5-[4-chloro-3-[[4-(2,2,2-trifluoroethoxyl) phenyl]methyl]phenyl]-6,8-dioxabicyclo[3.2.1]octan-1-yl]methanol 17l (2.3 g, 3.02 mmol) in dichloromethane (100 mL) was added 2-iodoxybenzoic acid (1.70 g, 6.04 mmol) at room temperature. The mixture was refluxed for 20 hours, then cooled to room temperature and filtered. The filtrate was washed with saturated aqueous sodium chloride (50 mL) and concentrated in vacuo. The residue was purified by silica gel chromatography eluted with PE/EtOAc(v/v)=10/1 to give the title compound 17m as pale yellow viscous oil (1.85 g, 80.4%, HPLC: 76.76%). This material was not further purified.

Step 13) 1-[(1R,2S,3S,4R,5S)-2,3,4-tribenzyloxy-5-[4-chloro-3-[[4-(2,2,2-trifluoroethoxyl)phenyl]methyl]phenyl]-6,8-dioxabicyclo[3.2.1]octan-1-yl]ethanol 17n To a solution of (1S,2S,3S,4R,5S)-2,3,4-tribenzyloxy-5-[4-chloro-3-[[4-(2,2,2-trifluoroethoxyl)phenyl]methyl]phenyl]-6,8-dioxabicyclo[3.2.1]octane-1-carbaldehyde 17m (1.85 g, 2.43 mmol) in dry tetrahydrofuran (40 mL) was added dropwise methylmagnesium bromide (1.22 mL, 3.66 mmol, 3M in ethyl ether) under $N_2$ at −10° C. The mixture was stirred at −10° C. for 15 min and then room temperature for 3 hours. The reaction mixture was quenched with saturated aqueous ammonium chloride (40 mL) and extracted with ethyl acetate (50 mL×3). The combined organic layers were washed with saturated aqueous sodium chloride (15 mL×3), dried over anhydrous sodium sulfate and filtered. The filtrate was concentrated in vacuo and the residue was purified by silica gel chromatography eluted with PE/EtOAc (v/v)=15/1 to give the title compound 17n as pale yellow oil (1.3 g, 69.1%). The compound was characterized by the following spectroscopic data: $^1$H NMR (600 MHz, CDCl$_3$) δ(ppm): 7.41 (d, 1H), 7.36 (m, 4H), 7.30 (m, 5H), 7.24 (m, 3H), 7.20 (d, 1H), 7.16 (t, 2H), 7.09 (d, 2H), 6.89 (d, 2H), 6.76 (d, 2H), 4.97 (m, 1H), 4.90 (d, 1H), 4.81-4.73 (m, 2H), 4.37 (d, 1H), 4.29-4.20 (m, 3H), 4.08-3.98 (m, 3H), 3.96 (d, 1H), 3.89 (d, 1H), 3.79 (m, 1H), 3.72 (t, 1H), 3.66 (m, 1H), 1.25 (d, 3H).

Step 14) (1R,2S,3S,4R,5S)-5-[4-chloro-3-[[4-(2,2,2-trifluoroethoxyl)phenyl]methyl]phenyl]-1-(1-hydroxyethyl)-6,8-dioxabicyclo[3.2.1]octane-2,3,4-triol 17

To a solution of 1-[(1R,2S,3S,4R,5S)-2,3,4-tribenzyloxy-5-[4-chloro-3-[[4-(2,2,2-trifluoroethoxyl) phenyl]methyl]phenyl]-6,8-dioxabicyclo[3.2.1]octan-1-yl]ethanol 17n (350.0 mg, 0.45 mmol) in a methanol/tetrahydrofuran mixture (v/v=4/1, 15 mL) were added o-dichlorobenzene (0.25 mL, 2.25 mmol) and 10% Pd/C (50.0 mg, 0.04 mmol) at room temperature. The mixture was stirred at room temperature under $H_2$ for 3 hours and filtered. The filtrate was concentrated in vacuo and the residue was purified by silica gel chromatography eluted with PE/EtOAc(v/v)=3/1 to give a few white solid. Then the solid was further purified by prep-HPLC to give the title compound 17 as a white solid (70.5 mg, 30.7%, HPLC: 90.5%). The compound was characterized by the following spectroscopic data: MS (ESI, pos. ion) m/z: 505.20 [M+H]$^+$; and $^1$H NMR (600 MHz, DMSO-$d_6$) δ(ppm): 7.41 (m, 2H), 7.31 (d, 1H), 7.15 (d, 2H), 6.97 (d, 2H), 5.31 (m, 1H), 4.85 (m, 2H), 4.68 (m, 2H), 4.64 (d, 1H), 4.02 (m, 1H), 3.98 (d, 2H), 3.83 (q, 1H), 3.76 (d, 1H), 3.54 (m, 1H), 3.43 (m, 2H), 1.16 (d, 3H).

Example 18

(1S,2S,3S,4R,5S)-5-[4-Chloro-3-[[4-(2,2,2-trifluoro-ethoxyl)phenyl]methyl]phenyl]-1-(1-hydroxy-1-methyl-ethyl)-6,8-dioxabicyclo[3.2.1]octane-2,3,4-triol 18

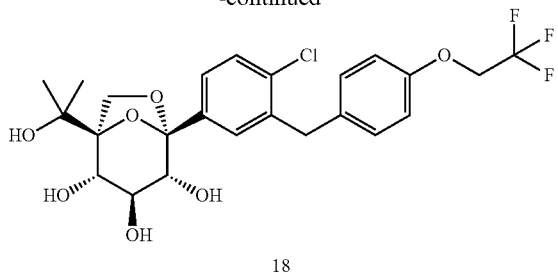

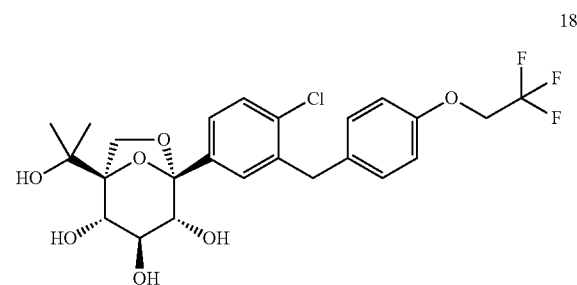

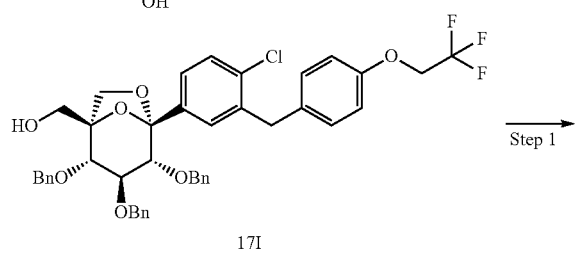

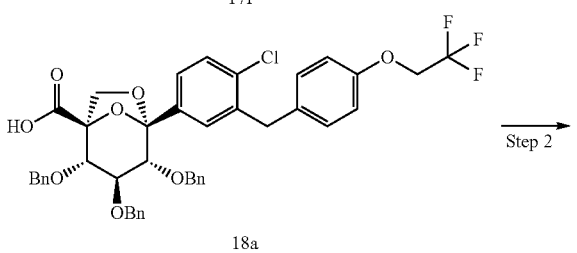

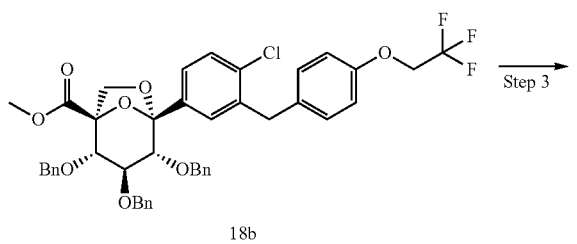

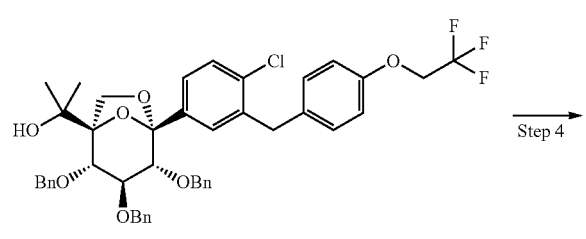

Step 1) (1S,2S,3S,4R,5S)-2,3,4-tribenzyloxy-5-[4-chloro-3-[[4-(2,2,2-trifluoro ethoxy)phenyl]methyl]phenyl]-6,8-dioxabicyclo[3.2.1]octane-1-carboxylic acid 18a To a solution of [(1S,2S,3S,4R,5S)-2,3,4-tribenzyloxy-5-[4-chloro-3-[[4-(2,2,2-trifluoroethoxyl) phenyl]methyl]phenyl]-6,8-dioxabicyclo[3.2.1]octan-1-yl]methanol 17I (1.1 g, 1.45 mmol, obtained from the synthetic method described in step 11 of example 17) in dichloromethane (20 mL) were added sodium bicarbonate (1.58 g, 18.85 mmol), potassium bromide (172.0 mg, 1.45 mmol) and 2,2,6,6-tetramethylpiperidinooxy (22.0 mg, 0.14 mmol) in turn at 0° C., and then sodium hypochlorite (10 mL, 11.80 mmol, 3.5% available chlorine) was added dropwise. The mixture was stirred at 0° C. for 30 min and then room temperature for 1.5 hours. The reaction mixture was acidified with aqueous HCl until pH becomes 4 and partitioned. The aqueous layer was extracted with ethyl acetate (30 mL×3). The combined organic layers were washed with saturated aqueous sodium chloride (50 mL), dried over anhydrous sodium sulfate and filtered. The filtrate was concentrated in vacuo to give the title compound 18a (0.74 g, 66.0%) as pale yellow oil. This material was not further purified.

Step 2) methyl(1S,2S,3S,4R,5S)-2,3,4-tribenzyloxy-5-[4-chloro-3-[[4-(2,2,2-trifluoro ethoxy)phenyl]methyl]phenyl]-6,8-dioxabicyclo[3.2.1]octane-1-carboxylate 18b To a solution of (1S,2S,3S,4R,5S)-2,3,4-tribenzyloxy-5-[4-chloro-3-[[4-(2,2,2-trifluoroethoxyl)phenyl]methyl]phenyl]-6,8-dioxabicyclo[3.2.1]octane-1-carboxylic acid 18a (0.74 g, 0.95 mmol) in methanol (40 mL) was added concentrated sulphuric acid (0.75 mL, 13.8 mmol) at 0° C. The mixture was warmed up to room temperature and stirred for 12 hours, and then adjusted with saturated aqueous sodium bicarbonate to pH 8 and concentrated in vacuo to remove most of the solvent. To the residue was added water (50 mL). The resulting mixture was extracted with ethyl acetate (50 mL×3). The combined organic layers were washed with saturated aqueous sodium chloride (80 mL), dried over anhydrous sodium sulfate and filtrated. The filtrate was concentrated in vacuo to give the title compound 18b as orange-yellow oil (0.6 g, 81.1%). This material was not further purified. The compound was characterized by the following spectroscopic data: $^1$H NMR (600 MHz, CDCl$_3$) δ(ppm): 7.45 (d, 1H), 7.41-7.35 (m, 2H), 7.34-7.27 (m, 6H), 7.24 (m, 4H), 7.20 (t, 1H), 7.15 (t, 2H), 7.08 (d, 2H), 6.85 (d, 2H), 6.76 (d, 2H), 4.82 (m, 2H), 4.77 (d, 1H), 4.61 (d, 1H), 4.51 (d, 1H), 4.25 (m, 3H), 4.17 (t, 2H), 4.07 (d, 1H), 3.99 (m, 2H), 3.84 (d, 1H), 3.72 (d, 1H), 3.69 (s, 3H).

Step 3) 2-[(1S,2S,3S,4R,5S)-2,3,4-tribenzyloxy-5-[4-chloro-3-[[4-(2,2,2-trifluoro ethoxy)phenyl]methyl]phenyl]-6,8-dioxabicyclo[3.2.1]octan-1-yl]propan-2-ol 18c To a solution of methyl(1S,2S,3S,4R,5S)-2,3,4-tribenzyloxy-5-[4-chloro-3-[[4-(2,2,2-trifluoroethoxyl)phenyl]methyl]phenyl]-6,8-dioxabicyclo[3.2.1]octane-1-carboxylate 18b (310.0 mg, 0.39 mmol) in anhydrous tetrahydrofuran (30 mL) was added dropwise methylmagnesium bromide (0.56 mL, 1.68 mmol, 3M in ethyl ether) at −10° C. under $N_2$. The mixture was stirred at room temperature for 2 hours, then quenched with saturated aqueous ammonium chloride to pH 7 and partitioned. The aqueous layer was extracted with ethyl acetate (30 mL×3). The combined organic layers were washed with saturated aqueous sodium chloride (30 mL), dried over anhydrous sodium sulfate and filtered. The filtrate was concentrated in vacuo and the residue was purified by silica gel chromatography eluted with PE/EtOAc(v/v)=20/1 to give the title compound 18c as a white solid (180.0 mg, 58.1%). This material was not further purified. The compound was characterized by the following spectroscopic data: 1H NMR (600 MHz, DMSO-$d_6$) δ(ppm): 7.50 (d, 1H), 7.48 (d, 1H), 7.42 (m, 1H), 7.29 (m, 8H), 7.25 (m, 2H), 7.19 (d, 3H), 7.11 (d, 2H), 6.88 (m, 4H), 4.91 (d, 1H), 4.84 (d, 1H), 4.77 (m, 2H), 4.66 (m, 2H), 4.28 (d, 1H), 4.14 (d, 1H), 4.08 (m, 1H), 4.01 (m, 2H), 3.91 (t, 1H), 3.74 (m, 3H), 1.19 (s, 3H), 1.13 (s, 3H).

Step 4) (1S,2S,3S,4R,5S)-5-[4-chloro-3-[[4-(2,2,2-trifluoroethoxyl)phenyl]methyl]phenyl]-1-(1-hydroxy-1-methyl-ethyl)-6,8-dioxabicyclo[3.2.1]octane-2,3,4-triol 18

To a solution of 2-[(1S,2S,3S,4R,5S)-2,3,4-tribenzyloxy-5-[4-chloro-3-[[4-(2,2,2-trifluoroethoxyl) phenyl]methyl] phenyl]-6,8-dioxabicyclo[3.2.1]octan-1-yl]propan-2-ol 18c (156 mg, 0.20 mmol) in a methanol/tetrahydrofuran mixture (v/v=4/1, 15 mL) were added o-dichlorobenzene (0.11 mL, 0.99 mmol) and 10% Pd/C (21.0 mg, 0.02 mmol) at room temperature. The mixture was stirred at room temperature for 2 hours under $H_2$ and filtered. The filtrate was concentrated in vacuo. The residue was purified by silica gel chromatography eluted with PE/EtOAc(v/v)=1/1 to give the title compound 18 as pale yellow oil (62.5 mg, 62.5%, HPLC: 95.60%). The compound was characterized by the following spectroscopic data: MS (ESI, pos. ion) m/z: 563.3 [M+CHOO]⁻; and ¹H NMR (600 MHz, DMSO-$d_6$) δ(ppm): 7.43 (d, 1H), 7.39 (d, 1H), 7.33 (d, 1H), 7.15 (q, 2H), 6.97 (q, 2H), 4.70 (q, 2H), 4.02 (m, 3H), 3.80 (d, 1H), 3.70 (d, 1H), 3.45 (m, 2H), 1.20 (s, 3H), 1.15 (s, 3H).

Example 19

(1R,2S,3S,4R,5S)-5-[4-Chloro-3-[(4-ethoxy-3-fluoro-phenyl)methyl]phenyl]-1-(1-hydroxyethyl)-6,8-dioxabicydo[3.2.1]octane-2,3,4-triol 19

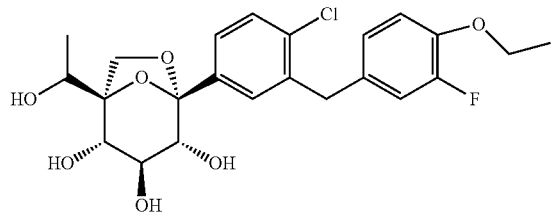

19

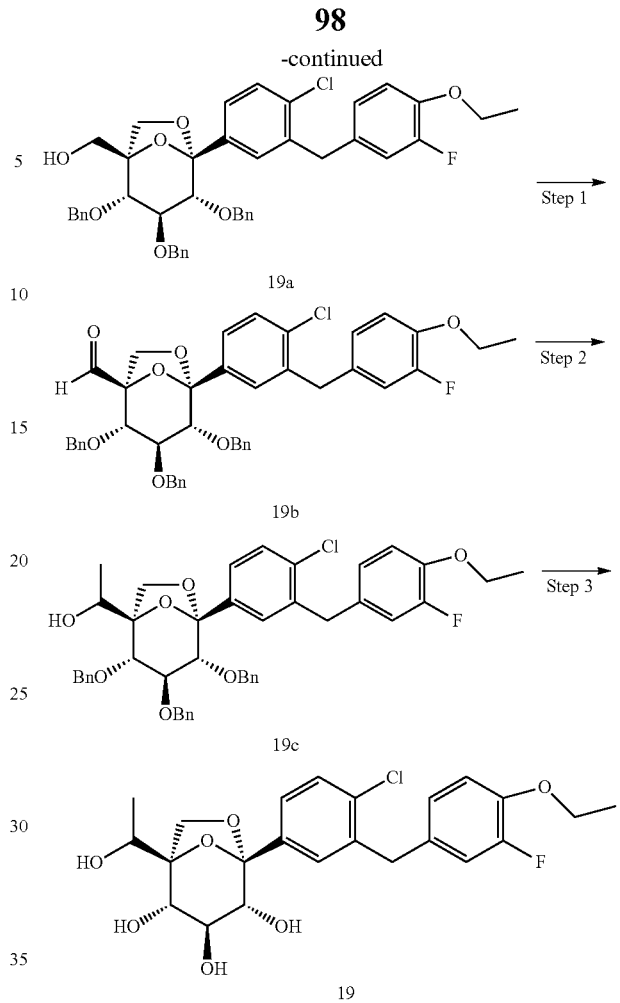

Step 1) (1S,2S,3 S,4R,5 S)-2,3,4-tribenzyloxy-5-[4-chloro-3-[(4-ethoxy-3-fluoro-phenyl)methyl]phenyl]-6,8-dioxabicyclo[3.2.1]octane-1-carbaldehyde 19b To a solution of [(1S,2S,3S,4R,5S)-2,3,4-tribenzyloxy-5-[4-chloro-3-[(4-ethoxy-3-fluoro-phenyl) methyl]phenyl]-6,8-dioxabicyclo[3.2.1]octane-1-yl]methanol 19a (3.48 g, 4.8 mmol, purchased from Shanghai Caerulum Pharma Discovery Co., Ltd.) in dichloromethane (100 mL) was added 2-iodoxybenzoic acid (2.68 g, 9.6 mmol) at room temperature. The mixture was refluxed for 16 hours and filtered. The filtrate was partitioned and the organic layer was adjusted with saturated aqueous sodium bicarbonate to pH 7. The mixture was extracted with dichloromethane (250 mL×2). The combined organic layers were washed with water (100 mL×2) and saturated brine (100 mL×2) in turn, dried over anhydrous sodium sulfate and filtered. The filtrate was concentrated in vacuo. The residue was purified by silica gel chromatography eluted with PE/EtOAc(v/v)=10/1 to give the title compound 19b as yellow oil (3 g, 86.4%). The compound was characterized by the following spectroscopic data: ¹H NMR (400 MHz, DMSO-$d_6$) δ(ppm): 9.79 (s, 1H), 7.50 (m, 3H), 7.25 (m, 13H), 7.02 (d, 1H), 6.95 (m, 1H), 6.87 (d, 1H), 6.81 (m, 2H), 4.71 (m, 4H), 4.29 (m, 1H), 4.17 (m, 1H), 4.00 (m, 5H), 3.75 (m, 3H), 3.41 (m, 1H), 1.29 (t, 3H).

Step 2) 1-[(1R,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octane-1-yl]ethanol 19c To a solution of (1S,2S,3S,4R,5S)-2,3,4-tribenzyloxy-5-[4-chloro-3-[(4-ethoxy-3-fluoro-phenyl) methyl]phenyl]-6,8-dioxabicyclo[3.2.1]octane-1-carbaldehyde 19b (3 g, 4.15 mmol) in dry tetrahydrofuran (50 mL) was added methylmagnesium bromide (2 mL, 6.22 mmol, 3M in ethyl ether) dropwise at 0° C. The mixture warmed up to room temperature and stirred for 5 hours. The reaction mixture was quenched with saturated aqueous ammonium chloride (10 mL) and extracted with ethyl acetate (100 mL×2). The combined organic layers were washed with water (50 mL×2) and then saturated aqueous sodium chloride (50 mL×2) in turn, dried over anhydrous sodium sulfate and filtered. The filtrate was concentrated in vacuo to give the title compound 19c as yellow oil (2.16 g, 70.4%).

Step 3) (1R,2S,3S,4R,5S)-5-[4-chloro-3-[(4-ethoxy-3-fluoro-phenyl)methyl]phenyl]-1-(1-hydroxyethyl)-6,8-dioxabicyclo[3.2.1]octane-2,3,4-triol 19

To a solution of 1-[(1R,2S,3S,4R,5S)-2,3,4-tribenzyloxy-5-[4-chloro-3-[(4-ethoxy-3-fluoro-phenyl) methyl]phenyl]-6,8-dioxabicyclo[3.2.1]octane-1-yl]ethanol 19c (2.16 g, 2.92 mmol) in a methanol/tetrahydrofuran mixture (v/v=4/1, 20 mL) were added o-dichlorobenzene (1.64 mL, 14.6 mmol) and 10% Pd/C (0.5 g, 0.42 mmol) in turn at room temperature. The mixture was stirred at room temperature for 3 hours under $H_2$ and filtered. The filter cake was washed with a tetrahydrofuran/methanol mixture (v/v=1/4, 10 mL×2). The filtrate was concentrated in vacuo. The residue was purified by prep-HPLC to give the title compound 19 as a white solid (0.5 g, 36.5%, HPLC: 96.7%). The compound was characterized by the following spectroscopic data: MS (ESI, pos. ion) m/z: MS (ESI, pos. ion) m/z: 469.2[M+H]$^+$; and $^1$H NMR (400 MHz, DMSO-d$_6$) δ(ppm): 7.42 (m, 1H), 7.39 (s, 1H), 7.31 (dd, 1H), 7.05 (d, 1H), 7.02 (m, 1H), 6.92 (d, 1H), 5.27 (d, 1H), 4.98 (d, 1H), 4.89 (d, 1H), 4.60 (d, 1H), 4.02 (m, 2H), 3.99 (m, 3H), 3.84 (m, 1H), 3.76 (d, 1H), 3.53 (m, 1H), 3.43 (m, 1H), 3.38 (m, 1H), 1.31 (t, 3H), 1.16 (d, 3H).

Example 20

(1S,2S,3S,4R,5S)-5-[4-Chloro-3-[(4-ethoxy-3-fluoro-phenyl)methyl]phenyl]-1-(1-hydroxy-1-methyl-ethyl)-6,8-dioxabicyclo[3.2.1]octane-2,3,4-triol 20

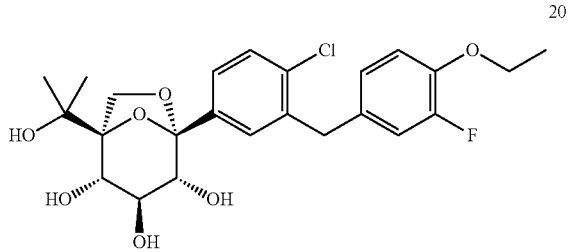

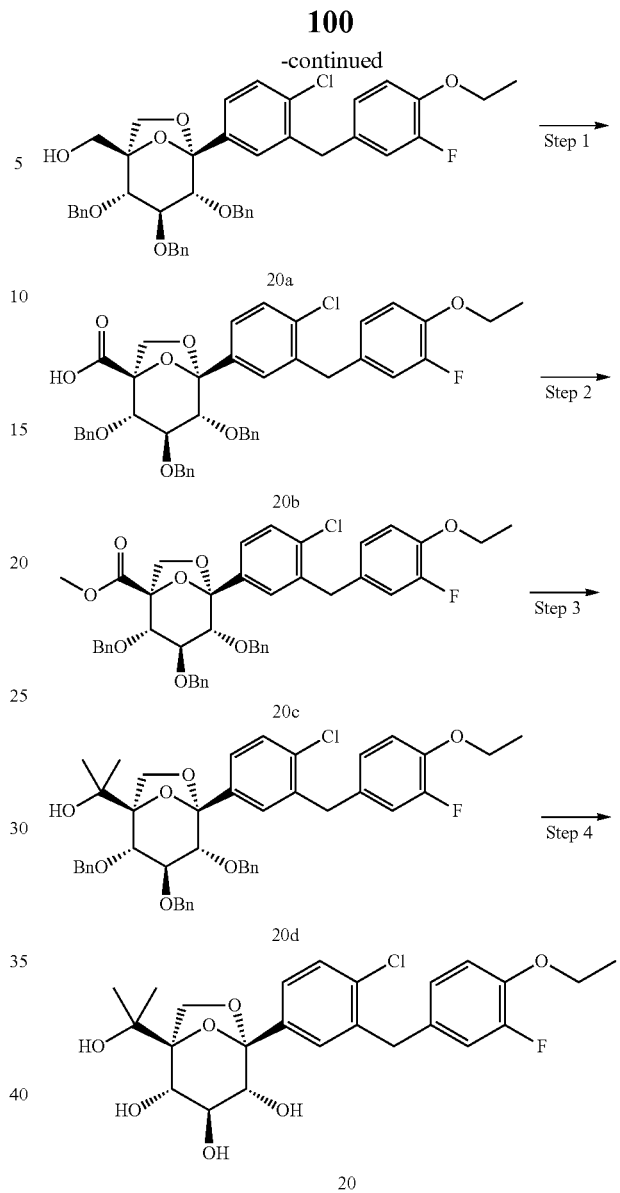

Step 1) (1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octane-1-carboxylic acid 20b To a solution of [(1S,2S,3S,4R,5S)-2,3,4-tribenzyloxy-5-[4-chloro-3-[(4-ethoxy-3-fluoro-phenyl) methyl]phenyl]-6,8-dioxabicyclo[3.2.1]octane-1-yl]methanol 20a (1.0 g, 1.38 mmol, purchased from Shanghai Caerulum Pharma Discovery Co., Ltd.) in tetrahydrofuran (20 mL) were added saturated aqueous sodium bicarbonate (20 mL), potassium bromide (33 mg, 0.28 mmol) and 2,2,6,6-tetramethylpiperidinooxy (22 mg, 0.14 mmol) in turn at 0° C., and then sodium hypochlorite (18 mL, available chlorine ≥5.5%) was added dropwise over a period of 20 min. The mixture was stirred at 0° C. for 40 min and acidified with aqueous HCl (1 N) till pH becomes 4. The resulting mixture was extracted with ethyl acetate (30 mL×2). The combined organic layers were washed with saturated brine (20 mL×2), dried over anhydrous sodium sulfate and filtered. The filtrate was concentrated in vacuo to give the title compound 20b (1.20 g, 117.6%) as yellow oil. This material was not further purified.

Step 2) methyl (1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octane-1-carboxylate 20c To a solution of (1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octane-1-carboxylic acid 20b (1.20 g, 1.38 mmol) in methanol (30 mL) was added concentrated sulphuric acid (150 mg, 1.53 mmol) at room temperature. The mixture was stirred at room temperature for 12 hours and then 40° C. for 6 hours. The reaction mixture was quenched with saturated aqueous sodium bicarbonate (3 mL) at 0° C. and concentrated in vacuo to remove most of the solvent. To the residue was added water (20 mL). The resulting mixture was extracted with ethyl acetate (20 mL). The combined organic layers were washed with saturated brine (10 mL×2), dried over anhydrous sodium sulfate and filtered. The filtrate was concentrated in vacuo and the residue was purified by silica gel chromatography eluted with PE/EtOAc(v/v)=1/1 to give the title compound 20c as colorless semi-solid (0.48 g, 46.2%). The compound was characterized by the following spectroscopic data: $^1$H NMR (400 MHz, CDCl$_3$) δ(ppm): 7.43 (d, 1H), 7.36 (p, 2H), 7.27 (m, 10H), 7.15 (m, 3H), 6.86 (dd, 3H), 6.78 (m, 2H), 4.82 (q, 2H), 4.75 (d, 1H), 4.60 (d, 1H), 4.50 (d, 1H), 4.26 (d, 1H), 4.17 (dd, 2H), 4.00 (m, 5H), 3.85 (d, 1H), 3.71 (d, 1H), 3.68 (s, 3H), 1.40 (t, 3H).

Step 3) 2-[(1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octan-1-yl]propan-2-ol 20d To a solution of methyl(1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octane-1-carboxylate 20c (0.48 g, 0.64 mmol) in anhydrous tetrahydrofuran (6 mL) was added dropwise methylmagnesium bromide (1.2 mL, 3.60 mmol, 3M in ethyl ether) at 0° C. The mixture was stirred at 40° C. for 12 hours. The reaction mixture was quenched with saturated aqueous ammonium chloride (2 mL). The mixture was partitioned between ethyl ether (20 mL) and water (20 mL). The organic layer was washed with saturated brine (10 mL×2), dried over anhydrous sodium sulfate and filtered. The filtrate was concentrated in vacuo to give the title compound 20d as a white solid (0.47g, 97.9%). This material was not further purified. The compound was characterized by the following spectroscopic data: $^1$H NMR (400 MHz, CDCl$_3$) δ(ppm): 7.39 (s, 1H), 7.36 (m, 2H), 7.28 (m, 8H), 7.21 (m, 2H), 7.15 (m, 3H), 6.88 (m, 3H), 6.79 (dd, 1H), 6.74 (t, 1H), 5.03 (d, 1H), 4.92 (d, 1H), 4.73 (d, 2H), 4.30 (d, 1H), 4.20 (d, 1H), 4.00 (m, 7H), 3.79 (d, 1H), 3.67 (d, 1H), 1.39 (t, 3H), 1.26 (s, 3H), 1.22 (s, 3H).

Step 4) (1S,2S,3S,4R,5S)-5-[4-chloro-3-[(4-ethoxy-3-fluoro-phenyl)methyl]phenyl]-1-(1-hydroxy-1-methyl-ethyl)-6,8-dioxabicyclo[3.2.1]octane-2,3,4-triol 20

To a solution of 2-[(1S,2S,3S,4R,5S)-2,3,4-tribenzyloxy-5-[4-chloro-3-[(4-ethoxy-3-fluoro-phenyl) methyl]phenyl]-6,8-dioxabicyclo[3.2.1]octan-1-yl]propan-2-ol 20d (0.46 g, 0.61 mmol) in a methanol/tetrahydrofuran mixture (v/v=6/1, 7 mL) were added o-dichlorobenzene (0.45 g, 3.05 mmol) and 10% Pd/C (64 mg, 0.06 mmol) at room temperature. The mixture was stirred at room temperature for 30 min under H$_2$ and filtered. The filtrate was concentrated in vacuo. The residue was purified by silica gel chromatography eluted with PE/EtOAc(v/v)=1/2 to give the title compound 20 as a white solid (0.26 g, 88.1%, HPLC: 97.6%). The compound was characterized by the following spectroscopic data: MS (ESI, pos. ion) m/z: 505.2 [M+Na]$^+$; and $^1$H NMR (400 MHz, CD$_3$OD) δ(ppm): 7.45 (d, 1H), 7.39 (m, 2H), 6.95 (d, 1H), 6.90 (m, 2H), 4.20 (d, 1H), 4.06 (dd, 5.9 Hz, 4H), 3.97 (dd, 1.4 Hz, 1H), 3.90 (dd, 1H), 3.66 (t, 1H), 3.53 (d, 1H), 1.38 (t, 3H), 1.33 (s, 3H), 1.28 (s, 3H).

Example 21

(1R,2S,3S,4R,5S)-5-[4-Chloro-3-[(2,3-difluoro-4-methoxy-phenyl)methyl]phenyl]-1-(1-hydroxy-ethyl)-6,8-dioxabicyclo[3.2.1]octane-2,3,4-triol 21

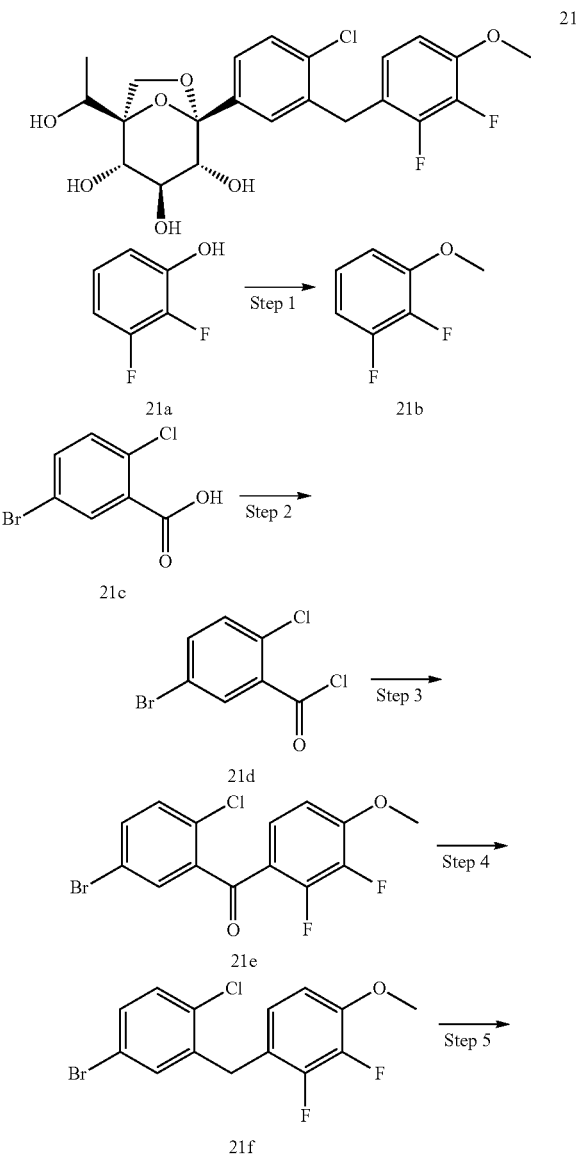

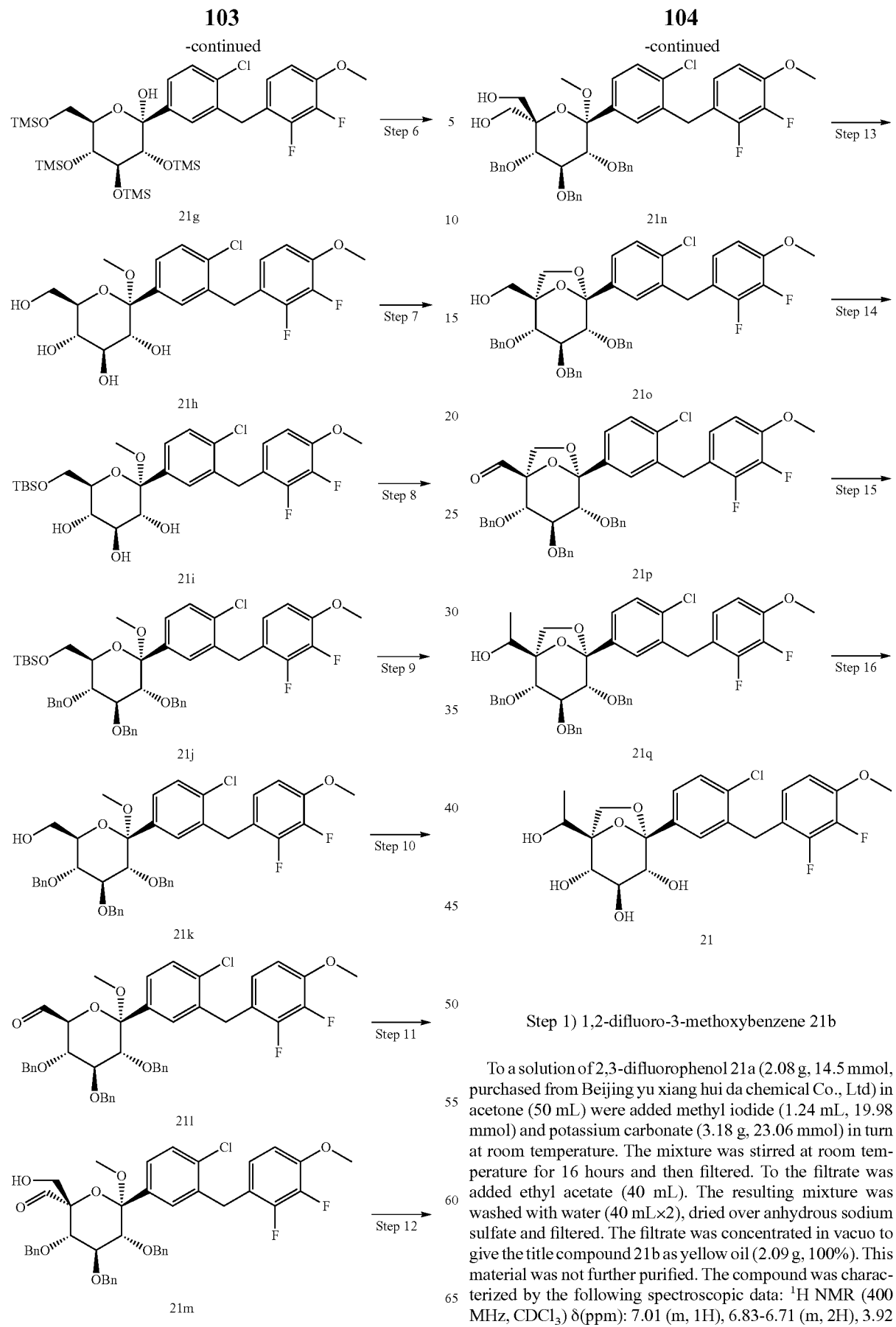

Step 1) 1,2-difluoro-3-methoxybenzene 21b

To a solution of 2,3-difluorophenol 21a (2.08 g, 14.5 mmol, purchased from Beijing yu xiang hui da chemical Co., Ltd) in acetone (50 mL) were added methyl iodide (1.24 mL, 19.98 mmol) and potassium carbonate (3.18 g, 23.06 mmol) in turn at room temperature. The mixture was stirred at room temperature for 16 hours and then filtered. To the filtrate was added ethyl acetate (40 mL). The resulting mixture was washed with water (40 mL×2), dried over anhydrous sodium sulfate and filtered. The filtrate was concentrated in vacuo to give the title compound 21b as yellow oil (2.09 g, 100%). This material was not further purified. The compound was characterized by the following spectroscopic data: $^1$H NMR (400 MHz, CDCl$_3$) δ(ppm): 7.01 (m, 1H), 6.83-6.71 (m, 2H), 3.92 (s, 3H).

Step 2) 5-bromo-2-chlorobenzoyl chloride 21d

To a solution of 5-bromo-2-chloro-benzoic acid 15a (7.24 g, 30.8 mmol) in toluene (100 mL) were added thionyl chloride (3.6 mL, 49.2 mmol) and N,N-dimethylformamide (0.2 mL, 2.6 mmol) in turn at 0° C. The mixture was warmed up to 100° C. and stirred for 4 hours. The reaction mixture was cooled to room temperature and concentrated in vacuo to give the title compound 21d as yellow oil (7.82 g, 100%). This material was not further purified.

Step 3) (5-bromo-2-chloro-phenyl)-(2,3-difluoro-4-methoxy-phenyl)methanone 21e To a solution of 5-bromo-2-chlorobenzoyl chloride 21d (3.4 g, 13.4 mmol) and 1,2-difluoro-3-methoxybenzene 21b (2.4 g, 16.7 mmol) in dichloromethane (40 mL) was added anhydrous aluminium chloride (1.82 g, 13 mmol) at 0° C. The mixture was stirred at 0° C. for 16 hours. Then the reaction mixture was quenched with hydrochloric acid (4 mL, 2 M) and warmed up to room temperature. The mixture was extracted with dichloromethane (40 mL×4). The combined organic layers were dried over anhydrous sodium sulfate and filtered. The filtrate was concentrated in vacuo to give the title compound 21e as yellow liquid (5.4 g, 96.4%). This material was not further purified.

Step 4) 1-[(5-bromo-2-chloro-phenyl)methyl]-2,3-difluoro-4-methoxy-benzene 21f To a solution of (5-bromo-2-chloro-phenyl)-(2,3-difluoro-4-methoxy-phenyl)methanone 21e (5.42 g, 14.9 mmol) in acetonitrile (100 mL) were added triethyl silicane (4.8 mL, 29.87 mmol) at 15° C., followed by boron trifluoride diethyl ether (7.4 mL, 59.74 mmol). The mixture was warmed up to room temperature and stirred for 15 hours. To the reaction mixture was added ethyl acetate (4 mL). The mixture was adjusted with saturated aqueous bicarbonate to pH 7, and then partitioned. The combined organic layers were dried over anhydrous sodium sulfate and filtered. The filtrate was concentrated in vacuo and the residue was purified by silica gel chromatography eluted with PE/EtOAc(v/v)=20/1 to give the title compound 21f as pale yellow oil (1.34 g, 25.8%). The compound was characterized by the following spectroscopic data: MS (ESI, pos. ion) m/z: 347.05 [M+H]$^+$; and $^1$H NMR (400 MHz, CDCl$_3$) δ (ppm): 7.33 (m, 1H), 7.28 (m, 2H), 6.84-6.76 (m, 1H), 6.75-6.62 (m, 1H), 4.05 (s, 2H), 3.91 (s, 3H).

Step 5) (2S,3R,4S,5R,6R)-2-[4-chloro-3-[(2,3-difluoro-4-methoxy-phenyl)methyl]phenyl]-3,4,5-tris(trimethylsilyloxy)-6-(trimethylsilyloxymethyetetrahydropyran-2-ol 21g To a solution of 1-[(5-bromo-2-chloro-phenyl)methyl]-2,3-difluoro-4-methoxy-benzene 21f (5.02 g, 14.4 mmol) in anhydrous tetrahydrofuran (50 mL) was added n-butyl-lithium (6.29 mL, 15.1 mmol, 2.4 M in hexane) dropwise at −78° C. The mixture was stirred at −78° C. for 1 hour and a solution of (3R,4S,5R,6R)-3,4,5-tris(trimethylsilyloxy)-6-(trimethylsilyloxymethyetetrahydropyran-2-one (7.39 g, 15.8 mmol) in anhydrous tetrahydrofuran (10 mL) was added dropwise. After the addition, the mixture was further stirred at −78° C. for 2 hours and quenched with saturated aqueous ammonium chloride (15 mL), and then partitioned. The aqueous layer was extracted with ethyl acetate (50 mL×3). The combined organic layers were washed with saturated aqueous sodium chloride (100 mL), dried over anhydrous sodium sulfate and filtered. The filtrated was concentrated in vacuo to give the title compound 21g as yellow oil (10.6 g, 100%). This material was not further purified.

Step 6) (2S,3R,4S,5S,6R)-2-[4-chloro-3-[(2,3-difluoro-4-methoxy-phenyl)methyl]phenyl]-6-(hydroxymethyl)-2-methoxy-tetrahydropyran-3,4,5-triol 21h To a solution of (2S,3R,4S,5R,6R)-2-[4-chloro-3-[(2,3-difluoro-4-methoxy-phenyl)methyl]phenyl]-3,4,5-tris(trimethylsilyloxy)-6-(trimethylsilyloxymethyetetrahydropyran-2-ol 21g (10.6 g, 14.4 mmol) in tetrahydrofuran (20 mL) was added a solution of methylsulfonic acid (0.47 mL, 7.2 mmol) in methanol (10 mL) at −78° C. The mixture was warmed up to room temperature and stirred for 24 hours. The reaction mixture was neutralized with saturated aqueous sodium bicarbonate till pH becomes 6-7 and partitioned. The organic layer was dried over anhydrous sodium sulfate and filtered. The filtrate was concentrated in vacuo and the residue was purified by re-crystallization from a toluene/petroleum ether mixture ((v/v)=2/1, 30 mL) to give the title compound 21h as a pale yellow solid (1.64 g, 12%).

Step 7) (2S,3R,4S,5S,6R)-6-[[tert-butyl(dimethyl)silyl]oxymethyl]-2-[4-chloro-3-[(2,3-difluoro-4-methoxy-phenyl)methyl]phenyl]-2-methoxy-tetrahydropyran-3,4,5-triol 21i To a solution of (2S,3R,4S,5S,6R)-2-[4-chloro-3-[(2,3-difluoro-4-methoxy-phenyl)methyl]phenyl]-6-(hydroxymethyl)-2-methoxy-tetrahydropyran-3,4,5-triol 21h (1.12 g, 2.38 mmol) in dichloromethane (20 mL) were added tert-butyldimethylsilyl chloride (0.54 g, 3.58 mmol) and imidazole (0.49 g, 7.16 mmol) in turn at room temperature. The mixture was stirred at room temperature for 3 hours. The mixture was partitioned between dichloromethane (40 mL) and water (40 mL). The organic layer was washed with saturated aqueous sodium chloride (30 mL), dried over anhydrous sodium sulfate and filtered. The filtrate was concentrated in vacuo to give the title compound 21i as yellow oil (1.37 g, 100%).

Step 8) tert-butyl-dimethyl-[[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methoxy]silane 21j To a suspension of sodium hydride (24.0 g, 0.6 mol, 60% dispersion in Mineral oil) in anhydrous tetrahydrofuran (150 mL) was added a solution of (2S,3R,4S,5S,6R)-6-[[tert-butyhdimethyl) silyl]oxymethyl]-2-[4-chloro-3-[(2,3-difluoro-4-methoxy-phenyl)methyl]phenyl]-2-methoxy-tetrahydropyran-3,4,5-triol 21i (49.5 g, 86 mmol) in anhydrous tetrahydrofuran (400 mL) slowly at 0° C. The mixture was stirred at 0° C. for 1 hour, and then benzyl bromide (81 mL, 690 mmol) was added. The mixture was warmed up to room temperature and further stirred for 12 hours. The reaction mixture was quenched with saturated aqueous ammonium chloride (1000 mL) and extracted with ethyl acetate (300 mL×2). The combined organic layers were dried over anhydrous sodium sulfate and filtered. The filtrate was concentrated in vacuo to give the title compound 21j as yellow oil (72.7 g, 100%). This material was not further purified.

Step 9) [(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methanol 21k To a solution of tert-butyl-dimethyl-[[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methoxy]silane 21j (72.7 g, 86 mmol) in tetrahydrofuran (300 mL) was added tetrabutylammonium fluoride (172 mL, 172 mmol, 1 M in tetrahydrofuran) at room temperature. The mixture was stirred at room temperature for 12 hours, and then ethyl acetate was added (300 mL). The resulting mixture was washed with water (400 mL×4), dried over anhydrous sodium sulfate and filtered. The filtrate was concentrated in vacuo and the residue was purified by silica gel chromatography eluted with PE/EtOAc(v/v)=20/1 to give the title compound 21k as yellow oil (21.0 g, 33.4%). The compound was characterized by the following spectroscopic data: $^1$H NMR (400 MHz, CDCl$_3$) δ(ppm): 7.42-7.29 (m, 13H), 7.27-7.17 (m, 3H), 7.01 (m, 2H), 6.74-6.66 (m, 1H), 6.63-6.53 (m, 1H), 4.99-4.88 (m, 3H), 4.72 (m, 1H), 4.54 (d, 1H), 4.15-4.09 (m, 2H), 3.99-3.89 (m, 3H), 3.87 (s, 3H), 3.83 (d, 1H), 3.78-3.66 (m, 2H), 3.34 (d, 1H), 3.10 (s, 3H).

Step 10) (2S,3S,4S,5R,6S)-3,4,5-tribenzyloxy-6-[4-chloro-3-[(2,3-difluoro-4-methoxy-phenyl)methyl]phenyl]-6-methoxy-tetrahydropyran-2-carbaldehyde 21l To a solution of [(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methanol 21k (3.05 g, 4.3 mmol) in dichloromethane (30 mL) was added 2-iodoxybenzoic acid (3.62 g, 12.94 mmol) at room temperature. The mixture was refluxed for 36 hours, then cooled to room temperature and filtered. The filtrate was washed with water (40 mL×4), dried over anhydrous sodium sulfate and filtered. The filtrate was concentrated in vacuo to give the title compound 21l as pale yellow oil (3.04 g, 100%). This material was not further purified.

Step 11) (2R,3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-carbaldehyde 21m To a solution of (2S,3S,4S,5R,6S)-3,4,5-tribenzyloxy-6-[4-chloro-3-[(2,3-difluoro-4-methoxy-phenyl)methyl]phenyl]-6-methoxy-tetrahydropyran-2-carbaldehyde 21l (0.52 g, 0.68 mmol) in N,N-dimethyl formamide (20 mL) were added 1,8-diazabicyclo[5.4.0]undec-7-ene (0.05 mL, 0.34 mmol) and formaldehyde (0.83 mL, 10.28 mmol, 37 wt % solution) in turn at room temperature. The mixture was stirred at room temperature for 16 hours, and then ethyl acetate (50 mL) was added. The resulting mixture was washed with water (60 mL×5), dried over anhydrous sodium sulfate and filtered. The filtrate was concentrated in vacuo to give the title compound 21m as yellow oil (0.52 g, 100%). This material was not further purified.

Step 12) [(3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-yl]methanol 21n To a solution of (2R,3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-carbaldehyde 21m (0.52 g, 0.68 mmol) in methanol (20 mL) was added sodium borohydride (52 mg, 1.37 mmol) at 0° C. The mixture was warmed up to room temperature and stirred for 4 hours. The reaction mixture was quenched with saturated aqueous ammonium chloride (15 mL) and 20 mL of water was added. The mixture was extracted with ethyl acetate (20 mL×4). The combined organic layers were dried over anhydrous sodium sulfate and filtered. The filtrate was concentrated in vacuo to give the title compound 21n as light yellow oil (0.52 g, 100%). This material was not further purified

Step 13) [(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]methanol 21o To a solution of [(3S,4S,5R,6S)-3,4,5-tribenzyloxy-6-[4-chloro-3-[(2,3-difluoro-4-methoxy-phenyl) methyl]phenyl]-2-(hydroxymethyl)-6-methoxy-tetrahydropyran-2-yl]methanol 21n (0.52 g, 0.68 mmol) in dichloromethane (30 mL) was added p-toluenesulfonic acid monohydrate (65 mg, 0.34 mmol) at room temperature. The mixture was stirred at room temperature for 12 hours. The reaction mixture was neutralized with saturated aqueous sodium bicarbonate to pH 6-7 and then water (40 mL) was added. The resulting mixture was partitioned. The aqueous layer was extracted with dichloromethane (25 mL×3). The combined organic layers were dried over anhydrous sodium sulfate and filtered. The filtrate was concentrated in vacuo and the residue was purified by silica gel chromatography eluted with PE/EtOAc(v/v)=10/1 to give the title compound 21o as pale yellow oil (0.22 g, 40%). The compound was characterized by the following spectroscopic data: $^1$H NMR (400 MHz, CDCl$_3$) δ(ppm): 7.46-7.40 (m, 3H), 7.40-7.29 (m, 10H), 7.23-7.15 (m, 3H), 6.96-6.86 (m, 2H), 6.72-6.63 (m, 1H), 6.57-6.49 (m, 1H), 4.88 (m, 3H), 4.77 (d, 1H), 4.31 (m, 2H), 4.10-4.01 (m, 3H), 3.97 (d, 1H), 3.89 (d, 1H), 3.86 (s, 3H), 3.82 (d, 1H), 3.77-3.65 (m, 3H).

Step 14) (1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octane-1-carbaldehyde 21p To a solution of [(1S,2S,3S,4R,5S)-2,3,4-tribenzyloxy-5-[4-chloro-3-[(2,3-difluoro-4-methoxy-phenyl)methyl]phenyl]-6,8-dioxa bicyclo[3.2.1]octan-1-yl]methanol 21o (0.52 g, 0.68 mmol) in ethyl acetate (20 mL) was added 2-iodoxybenzoic acid (0.58 g, 2.06 mmol) at room temperature. The mixture was refluxed for 20 hours and cooled to room temperature, then filtered. The filtrate was concentrated in vacuo to give the title compound 21p as a white solid (0.52 g, 100%). This material was not further purified.

Step 15) 1-[(1R,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]ethanol 21q To a solution of (1S,2S,3S,4R,5S)-2,3,4-tribenzyloxy-5-[4-chloro-3-[(2,3-difluoro-4-methoxy-phenyl)methyl]phenyl]-6,8-dioxa bicyclo[3.2.1]octane-1-carbaldehyde 21p (0.50 g, 0.69 mmol) in dry tetrahydrofuran (10 mL) was added dropwise methylmagnesium bromide (0.46 mL, 1.38 mmol, 3M in ethyl ether) under N$_2$ at 0° C. The mixture was stirred at room temperature for 2 hours and quenched with water (10 mL). The resulting mixture was extracted with ethyl acetate (10 mL×3). The combined organic layers were washed with saturated aqueous sodium chloride (15 mL), dried over anhydrous sodium sulfate and filtered. The filtrate was concentrated in vacuo and the residue was purified by silica gel chromatography eluted with PE/EtOAc(v/v)=15/1 to give the title compound 21q as a white solid (0.14 g, 19%). The compound was characterized by the following spectroscopic data: $^1$H NMR (400 MHz, CDCl$_3$) δ(ppm): 7.41 (s, 3H), 7.31 (m, 9H), 7.21 (m, 4H), 6.98-6.86 (m, 2H), 6.68 (m, 1H), 6.53 (m, 1H), 4.96 (m, 2H), 4.80 (m, 2H), 4.34-4.24 (m, 2H), 4.16-4.05 (m, 4H), 3.98 (m, 2H), 3.85 (s, 3H), 3.82 (dd, 1H), 3.70 (m, 1H), 1.27 (d, 3H).

Step 16) (1R,2S,3S,4R,5S)-5-[4-chloro-3-[(2,3-difluoro-4-methoxy-phenyl)methyl]phenyl]-1-(1-hydroxyethyl)-6,8-dioxabicyclo[3.2.1]octane-2,3,4-triol 21

To a solution of 1-[(1R,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]ethanol 21q (136 mg, 0.18 mmol) in a methanol/tetrahydrofuran mixture (v/v=4/1, 10 mL) were added o-dichlorobenzene (0.1 mL, 0.87 mmol) and 10% Pd/C (20 mg, 0.02 mmol) in turn at room temperature. The mixture was stirred at room temperature for 4 hours under H$_2$ and filtered. The filtrate was concentrated in vacuo and the residue was purified by silica gel chromatography eluted with PE/EtOAc(v/v)=10/1 to give the title compound 21 as colourless oil (34 mg, 39.3%, HPLC: 97.27%). The compound was characterized by the following spectroscopic data: MS (ESI, pos. ion) m/z: 517.2 [M+HCOO]$^-$; and $^1$H NMR (400 MHz, DMSO-d$_6$) δ(ppm): 7.43 (d, 1H), 7.40-7.23 (m, 2H), 6.96 (m 1H), 6.87 (m, 1H), 5.33 (s, 1H), 4.93 (s, 2H), 4.58 (s, 1H), 4.05 (s, 2H), 3.98 (d, 1H), 3.84 (s, 3H), 3.76 (d, 1H), 3.53 (d, 1H), 3.42 (m, 3H), 1.18-1.13 (d, 3H).

Example 22

(1S,2S,3S,4R,5S)-5-[4-Chloro-3-[(2,3-difluoro-4-methoxy-phenyl)methyl]phenyl]-1-(1-hydroxy-1-methyl-ethyl)-6,8-dioxabicyclo[3.2.1]octane-2,3,4-triol 22

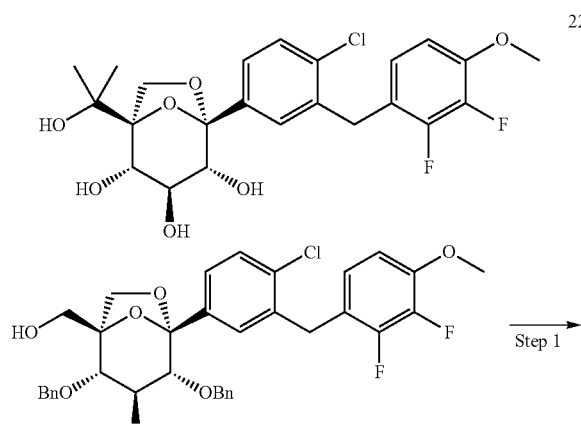

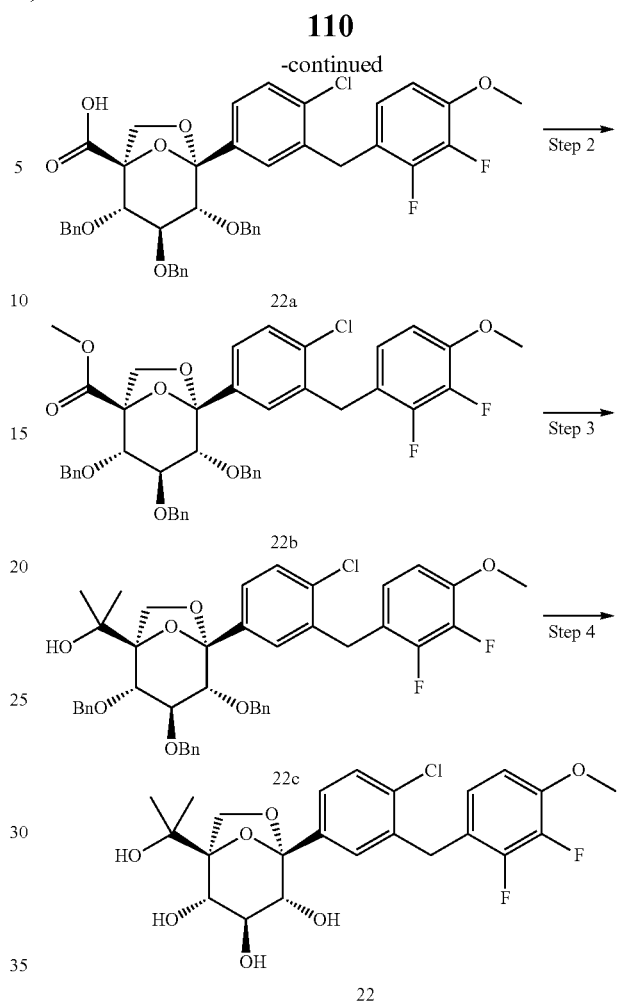

Step 1) (1S,2S,3 S,4R,5 S)-2,3,4-tribenzyloxy-5-[4-chloro-3-[(2,3-difluoro-4-methoxy-phenyl)methyl]phenyl]-6,8-dioxabicyclo[3.2.1]octane-1-carboxylic acid 22a To a solution of [(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]methanol 21o (0.38 g, 0.49 mmol, obtained from the synthetic method described in step 13 example 21) in tetrahydrofuran (10 mL) were added aqueous sodium bicarbonate (0.46 g, 5.43 mmol), potassium bromide (11.75 mg, 0.10 mmol) and 2,2,6,6-tetramethylpiperidinooxy (7.7 mg, 0.05 mmol) in turn at 0° C., and then sodium hypochlorite (6.8 mL, 8.5 mmol, available chlorine ≥3.5%) was added dropwise. The mixture was stirred at 0° C. for 3 hours and acidified with aqueous HCl (3 N) till pH becomes 6. The resulting mixture was extracted with ethyl acetate (40 mL×2). The combined organic layers were dried over anhydrous sodium sulfate and filtered. The filtrate was concentrated in vacuo to give the title compound 22a (0.37 g, 100%) as yellow oil. This material was not further purified.

Step 2) methyl (1S,2S,3S,4R,5S)-2,3,4-tribenzyloxy-5-[4-chloro-3-[(2,3-difluoro-4-methoxy-phenye methyl]phenyl]-6,8-dioxabicyclo[3.2.1]octane-1-carboxylate 22b To a solution of (1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octane-1-carboxylic acid 22a (0.38 g, 0.51 mmol) in a methanol/tetrahydrofuran mixture (v/v=4/1, 20 mL) was added concentrated sulphuric acid (0.03 mL, 0.56 mmol) at room temperature. The mixture was warmed up to 50° C. and stirred for 12 hours. The reaction mixture was cooled to room temperature and adjusted with saturated aqueous sodium bicarbonate to pH 7. The resulting mixture was extracted with ethyl acetate (30 mL×3). The combined organic layers were dried over anhydrous sodium sulfate and filtered. The filtrate was concentrated in vacuo and the residue was purified by silica gel chromatography eluted with PE/EtOAc(v/v)=10/1 to give the title compound 22b as pale yellow oil (0.11 g, 30%). The compound was characterized by the following spectroscopic data: $^1$H NMR (400 MHz, CDCl$_3$) δ(ppm): 7.48 (s, 1H), 7.43 (m, 2H), 7.32 (m, 7H), 7.21 (m, 6H), 6.90 (d, 2H), 6.65 (m, 1H), 6.57-6.47 (m, 1H), 4.83 (m, 3H), 4.64 (d, 1H), 4.54 (d, 1H), 4.32 (d, 1H), 4.23 (dd, 2H), 4.08 (s, 2H), 4.02 (t, 1H), 3.91 (m, 1H), 3.86 (s, 3H), 3.76 (d, 1H), 3.72 (s, 3H).

Step 3) 2-[(1S,2S,3S,4R,5S)-2,3,4-tribenzyloxy-5-[4-chloro-3-[(2,3-difluoro-4-methoxy-phenye methyl]phenyl]-6,8-dioxabicyclo[3.2.1]octan-1-yl]propan-2-ol 22c To a solution of methyl (1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octane-1-carboxylate 22b (70 mg, 0.092 mmol) in anhydrous tetrahydrofuran (5 mL) was added dropwise methylmagnesium bromide (0.22 mL, 0.65 mmol, 3M in ethyl ether) at 0° C. The mixture was stirred at room temperature for 12 hours. The reaction mixture was quenched with saturated aqueous ammonium chloride (5 mL) and extracted with ethyl acetate (10 mL×3). The combined organic layers were washed with saturated aqueous sodium chloride (10 mL), dried over anhydrous sodium sulfate and filtered. The filtrate was concentrated in vacuo and the residue was purified by silica gel chromatography eluted with PE/EtOAc(v/v)=15/1 to give the title compound 22c as pale yellow oil (70 mg, 100%). This material was not further purified. The compound was characterized by the following spectroscopic data: $^1$H NMR (400 MHz, CDCl$_3$) δ(ppm): 7.44 (s, 1H), 7.41 (m, 2H), 7.39-7.29 (m, 7H), 7.23 (m, 6H), 6.97 (d, 2H), 6.68 (m, 1H), 6.57-6.46 (m, 1H), 5.07 (d, 1H), 4.95 (d, 1H), 4.78 (d, 2H), 4.34 (d, 1H), 4.25 (d, 1H), 4.08 (m, 5H), 3.85 (s, 3H), 3.83 (m, 1H), 3.73 (d, 1H), 1.30 (s, 3H), 1.27 (s, 3H).

Step 4) (1S,2S,3S,4R,5S)-5-[4-chloro-3-[(2,3-difluoro-4-methoxy-phenyl)methyl]phenyl]-1-(1-hydroxy-1-methyl-ethyl)-6,8-dioxabicyclo[3.2.1]octane-2,3,4-triol 22

To a solution of 2-[(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]propan-2-ol 22c (86 mg, 0.11 mmol) in a methanol/tetrahydrofuran mixture (v/v=4/1, 10 mL) were added o-dichlorobenzene (0.064 mL, 0.57 mmol) and 10% Pd/C (13 mg, 0.01 mmol) at room temperature. The mixture was stirred at room temperature under H$_2$ for 4 hours and filtered. The filtrate was concentrated in vacuo and the residue was purified by silica gel chromatography eluted with PE/EtOAc(v/v)=1/3 to give the title compound 22 as white oil (43.9 mg, 79.8%, HPLC: 92.7%). The compound was characterized by the following spectroscopic data: MS (ESI, pos. ion) m/z: 531.0 [M+HCOO]$^-$; and $^1$H NMR (400 MHz, DMSO-d$_6$) δ(ppm):

7.42 (m, 1H), 7.37 (m, 2H), 6.96 (m, 1H), 6.93-6.85 (m, 1H), 5.51 (d, 1H), 5.05 (d, 1H), 5.00 (d, 1H), 4.24 (s, 1H), 4.05 (m, 3H), 3.85 (s, 3H), 3.79 (d, 1H), 3.75-3.65 (m, 1H), 3.50-3.36 (m, 2H), 1.20 (s, 3H), 1.15 (s, 3H).

Example 23

(1R,2S,3S,4R,5S)-5-[4-Chloro-3-[(4-ethoxy-2,3-difluoro-phenyl)methyl]phenyl]-1-(1-hydroxyethyl)-6,8-dioxabicyclo[3.2.1]octane-2,3,4-triol 23

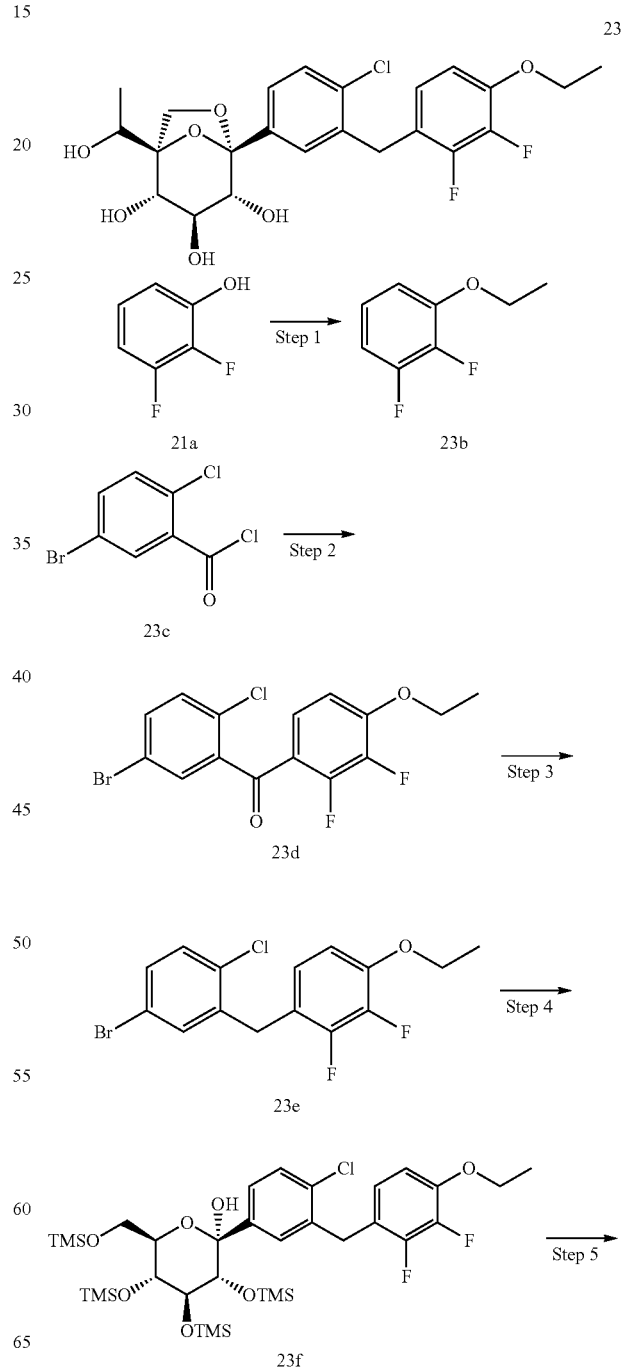

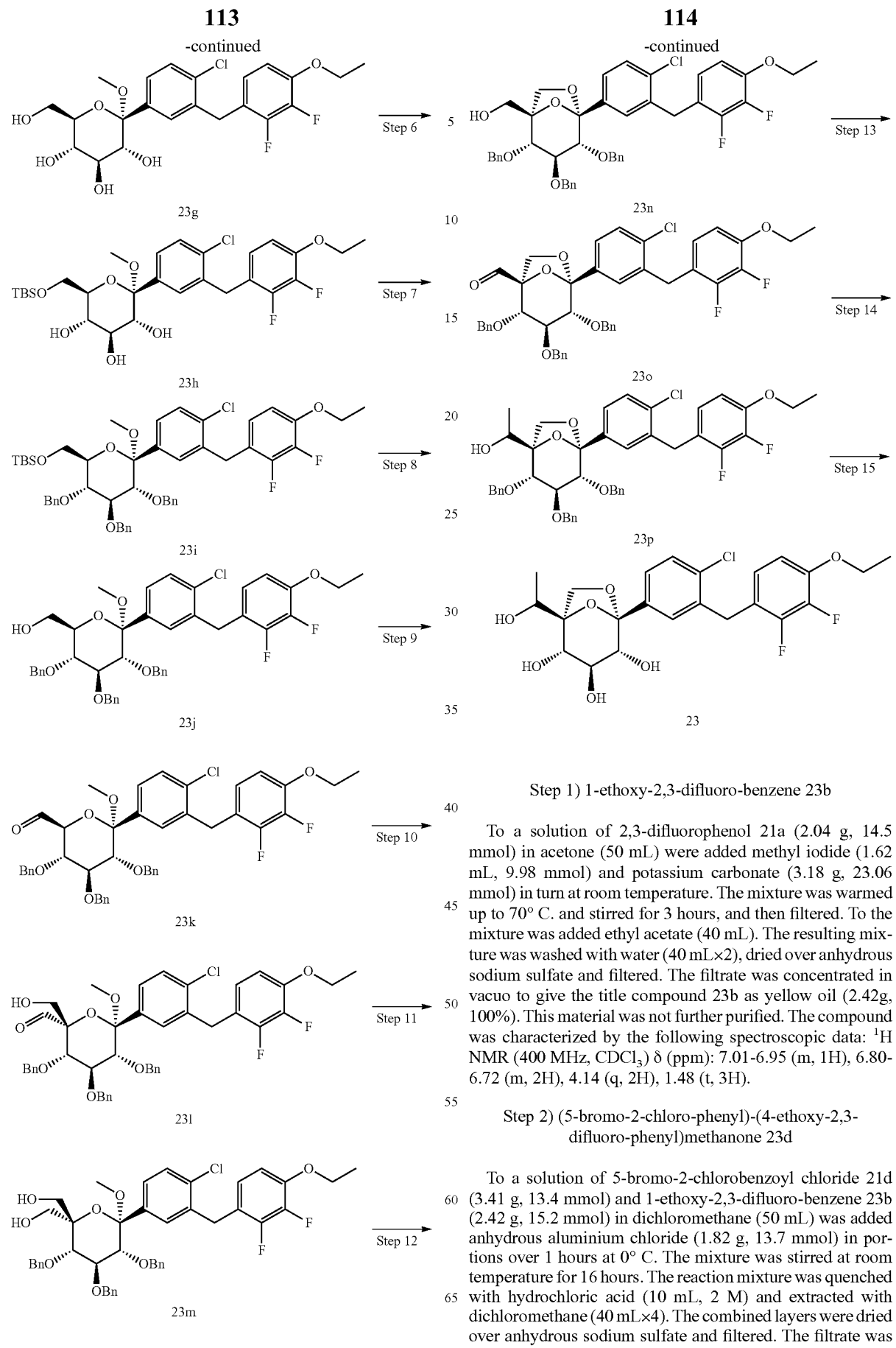

Step 1) 1-ethoxy-2,3-difluoro-benzene 23b

To a solution of 2,3-difluorophenol 21a (2.04 g, 14.5 mmol) in acetone (50 mL) were added methyl iodide (1.62 mL, 9.98 mmol) and potassium carbonate (3.18 g, 23.06 mmol) in turn at room temperature. The mixture was warmed up to 70° C. and stirred for 3 hours, and then filtered. To the mixture was added ethyl acetate (40 mL). The resulting mixture was washed with water (40 mL×2), dried over anhydrous sodium sulfate and filtered. The filtrate was concentrated in vacuo to give the title compound 23b as yellow oil (2.42g, 100%). This material was not further purified. The compound was characterized by the following spectroscopic data: $^1$H NMR (400 MHz, CDCl$_3$) δ (ppm): 7.01-6.95 (m, 1H), 6.80-6.72 (m, 2H), 4.14 (q, 2H), 1.48 (t, 3H).

Step 2) (5-bromo-2-chloro-phenyl)-(4-ethoxy-2,3-difluoro-phenyl)methanone 23d

To a solution of 5-bromo-2-chlorobenzoyl chloride 21d (3.41 g, 13.4 mmol) and 1-ethoxy-2,3-difluoro-benzene 23b (2.42 g, 15.2 mmol) in dichloromethane (50 mL) was added anhydrous aluminium chloride (1.82 g, 13.7 mmol) in portions over 1 hours at 0° C. The mixture was stirred at room temperature for 16 hours. The reaction mixture was quenched with hydrochloric acid (10 mL, 2 M) and extracted with dichloromethane (40 mL×4). The combined layers were dried over anhydrous sodium sulfate and filtered. The filtrate was concentrated in vacuo to give the title compound 23d as yellow oil (5.03 g, 100%). This material was not further purified.

Step 3) 1-[(5-bromo-2-chloro-phenyl)methyl]-4-ethoxy-2,3-difluoro-benzene 23e To a solution of (5-bromo-2-chloro-phenyl)-(4-ethoxy-2,3-difluoro-phenyl)methanone 23d (17.6 g, 46.8 mmol) in acetonitrile (100 mL) was added triethyl silicane (18.7 mL, 117.1 mmol) at 15° C., and then boron trifluoride diethyl ether (28.9 mL, 234.1 mmol) was added. The mixture was warmed up to room temperature and stirred for 15 hours. The reaction mixture was adjusted with saturated aqueous sodium bicarbonate to pH 7 and extracted with ethyl acetate (150 mL×3). The combined organic layers were dried over anhydrous sodium sulfate and filtered. The filtrate was concentrated in vacuo and the residue was purified by silica gel chromatography eluted with PE to give the title compound 23e as a white solid (9.45 g, 63%). The compound was characterized by the following spectroscopic data: $^1$H NMR (400 MHz, CDCl$_3$) δ(ppm): 7.34-7.30 (m, 1H), 7.29-7.26 (m, 2H), 6.79-6.75 (m, 1H), 6.71-6.66 (m, 1H), 4.12 (q, 2H), 4.04 (s, 2H), 1.47 (t, 3H).

Step 4) (2S,3R,4S,5R,6R)-2-[4-chloro-3-[(4-ethoxy-2,3-difluoro-phenyl)methyl]phenyl]-3,4,5-tris(trimethylsilyloxy)-6-(trimethylsilyloxymethyl)tetrahydropyran-2-ol 23f To a solution of 1-[(5-bromo-2-chloro-phenyl)methyl]-4-ethoxy-2,3-difluoro-benzene 23e (0.47 g, 1.3 mmol) in anhydrous tetrahydrofuran (15 mL) was added n-butyllithium (0.57 mL, 1.4 mmol, 2.4 M in hexane) dropwise at −78° C. The mixture was stirred at −78° C. for 1 hour, and then a solution of (3R,4S,5R,6R)-3,4,5-tris(trimethylsilyloxy)-6-(trimethylsilyloxymethyetetrahydropyran-2-one 1b (0.67 g, 1.4 mmol, obtained from the synthetic method described in step 1 of example 1) in anhydrous tetrahydrofuran (5 mL) was added dropwise. After the addition, the mixture was further stirred at −78° C. for 2 hours and quenched with saturated aqueous ammonium chloride (10 mL), and then partitioned. The aqueous layer was extracted with ethyl acetate (10 mL×3) and the combined organic layers were washed with saturated aqueous sodium chloride (30 mL), dried over anhydrous sodium sulfate and filtered. The filtrated was concentrated in vacuo to give the title compound 23f as yellow oil (0.97 g, 100%). This material was not further purified.

Step 5) (2S,3R,4S,5S,6R)-2-[4-chloro-3-[(4-ethoxy-2,3-difluoro-phenyl)methyl]phenyl]-6-(hydroxymethyl)-2-methoxy-tetrahydropyran-3,4,5-triol 23g To a solution of (2S,3R,4S,5R,6R)-2-[4-chloro-3-[(4-ethoxy-2,3-difluoro-phenyl)methyl]phenyl]-3,4,5-tris(trimethylsilyloxy)-6-(trimethylsilyloxymethyetetrahydropyran-2-ol 23f (0.97 g, 1.3 mmol) in tetrahydrofuran (10 mL) was added a solution of methylsulfonic acid (0.05 mL, 0.65 mmol) in methanol (2 mL) at −70° C. The mixture was warmed up to room temperature and stirred for 16 hours. The reaction mixture was neutralized with saturated aqueous sodium bicarbonate till pH becomes 6-7 and extracted with ethyl acetate (10 mL×3). The combined organic layers were dried over anhydrous sodium sulfate and filtered. The filtrate was concentrated in vacuo and the residue was purified by re-crystallization from a toluene/petroleum ether mixture ((v/v)=1/1, 30 mL) at −5° C. to give the title compound 23g as a pale yellow sticky solid (0.33 g, 54%).

Step 6) (2S,3R,4S,5S,6R)-6-[[tert-butyl(dimethyl)silyl]oxymethyl]-2-[4-chloro-3-[(4-ethoxy-2,3-difluoro-phenyl) methyl]phenyl]-2-methoxy-tetrahydropyran-3,4,5-triol 23h To a solution of (2S,3R,4S,5S,6R)-2-[4-chloro-3-[(4-ethoxy-2,3-difluoro-phenyl)methyl]phenyl]-6-(hydroxymethyl)-2-methoxy-tetrahydropyran-3,4,5-triol 23g (9.02 g, 18.95 mmol) in dichloromethane (150 mL) were added tert-butyldimethylsilyl chloride (4.29 g, 28.43 mmol), imidazole (2.58 g, 37.9 mmol) and N,N-dimethylaminopyridine (0.23 g, 1.9 mmol) in turn at 0° C. The mixture was stirred at room temperature for 3 hours, and then washed with water (100 mL×3) and saturated aqueous sodium chloride (100 mL) in turn. The resulting mixture was dried over anhydrous sodium sulfate and filtered. The filtrate was concentrated in vacuo to give the title compound 23h as a yellow solid (12.0 g, 100%). This material was not further purified.

Step 7) tert-butyl-dimethyl-[[(2R,3R,4S,5R,6S)-3,4,5-tribenzyloxy-6-[4-chloro-3-[(4-ethoxy-2,3-difluoro-phenyl) methyl]phenyl]-6-methoxy-tetrahydropyran-2-yl]methoxy]silane 23i To a suspension of sodium hydride (3.18 g, 32.65 mmol, 60% dispersion in Mineral oil) in anhydrous tetrahydrofuran (15 mL) was added a solution of (2S,3R,4S,5S,6R)-6-[[tert-butyl (dimethyl)silyl]oxymethyl]-2-[4-chloro-3-[(4-ethoxy-2,3-difluoro-phenyl)methyl]phenyl]-2-methoxy-tetrahydropyran-3,4,5-triol 23h (11.16 g, 18.95 mmol) in anhydrous tetrahydrofuran (80 mL) slowly at 0° C. The mixture was stirred at 0° C. for 1 hour, and then benzyl bromide (20.3 mL, 170.55 mmol) was added. The mixture was warmed up to room temperature and tetrabutylammonium iodide (0.70 g, 1.90 mmol) was added. The mixture was stirred for 12 hours. The reaction mixture was quenched with water (100 mL) at 0° C. and extracted with ethyl acetate (100 mL×2). The combined organic layers were dried over anhydrous sodium sulfate and filtered. The filtrate was concentrated in vacuo to give the title compound 23i as yellow oil (36.90 g, 100%). This material was not further purified.

Step 8) [(2R,3R,4S,5R,6S)-3,4,5-tribenzyloxy-6-[4-chloro-3-[(4-ethoxy-2,3-difluoro-phenyl)methyl] phenyl]-6-methoxy-tetrahydropyran-2-yl]methanol 23j To a solution of tert-butyl-dimethyl-[[(2R,3R,4S,5R,6S)-3,4,5-tribenzyloxy-6-[4-chloro-3-[(4-ethoxy-2,3-difluoro-phenyl)methyl]phenyl]-6-methoxy-tetrahydropyran-2-yl]methoxy]silane 23i (16.29 g, 18.95 mmol) in tetrahydrofuran (100 mL) was added tetrabutylammonium fluoride (37.9 mL, 37.9 mmol, 1 M in tetrahydrofuran) at room temperature. The mixture was stirred at room temperature for 12 hours, and then ethyl acetate (200 mL) was added. The resulting mixture was washed with saturated aqueous sodium chloride (100 mL×3), dried over anhydrous sodium sulfate and filtered. The filtrate was concentrated in vacuo and the residue was purified by silica gel chromatography eluted with PE/EtOAc(v/v) =15/1 to give the title compound 23j as a yellow solid (4.42 g, 31%). The compound was characterized by the following spectroscopic data: $^1$H NMR (400 MHz, CDCl$_3$) δ(ppm): 7.29 (m, 10H), 7.22 (s, 2H), 7.5 (m, 4H), 6.95 (m, 2H), 6.76 (m, 1H), 6.51 (m, 1H), 4.92 (m, 3H), 4.66 (d, 1H), 4.47 (d, 1H), 4.14 (m, 1H), 4.03 (m, 3H), 3.88 (m, 3H), 3.77 (m, 1H), 3.66 (m, 2H), 3.27 (d, 1H), 3.05 (s, 3H), 1.39 (t, 3H).

Step 9) (2S,3S,4S,5R,6S)-3,4,5-tribenzyloxy-6-[4-chloro-3-[ (4-ethoxy-2,3-difluoro-phenyl)methyl]phenyl]-6-methoxy-tetrahydropyran-2-carbaldehyde 23k To a solution of [(2R,3R,4S,5R,6S)-3,4,5-tribenzyloxy-6-[4-chloro-3-[(4-ethoxy-2,3-difluoro-phenyl) methyl]phenyl]-6-methoxy-tetrahydropyran-2-yl]methanol 23j (4.20 g, 5.64 mmol) in dichloromethane (70 mL) was added 2-iodoxybenzoic acid (4.70 g, 16.91 mmol) at room temperature. The mixture was refluxed for 36 hours. The reaction mixture was cooled to room temperature and filtered. The filtrate was washed with saturated sodium chloride (50 mL×3), dried over anhydrous sodium sulfate and filtered. The filtrate was concentrated in vacuo to give the title compound 23k as a yellow solid (4.12 g, 97.8%). This material was not further purified.

Step 10) (2R,3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-carbaldehyde 23l To a solution of (2S,3S,4S,5R,6S)-3,4,5-tribenzyloxy-6-[4-chloro-3-[(4-ethoxy-2,3-difluoro-phenye methyl]phenyl]-6-methoxy-tetrahydropyran-2-carbaldehyde 23k (3.21 g, 4.31 mmol) in N,N-dimethyl formamide (60 mL) were added 1,8-diazabicyclo[5.4.0]undec-7-ene (328 mg, 2.16 mmol) and formaldehyde (6.5 mL, 86.11 mmol, 37 wt % solution) in turn at room temperature. The mixture was stirred at room temperature for 16 hours, and then ethyl acetate (60 mL) was added. The resulting mixture was washed with water (30 mL×3), dried over anhydrous sodium sulfate and filtered. The filtrate was concentrated in vacuo to give the title compound 23l as yellow oil (5.02 g, 100%). This material was not further purified.

Step 11) [(3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-yl]methanol 23m To a solution of (2R,3S,4S,5R,6S)-3,4,5-tribenzyloxy-6-[4-chloro-3-[(4-ethoxy-2,3-difluoro-phenyl) methyl]phenyl]-2-(hydroxymethyl)-6-methoxy-tetrahydropyran-2-carbaldehyde 23l (3.30 g, 4.31 mmol) in methanol (60 mL) was added sodium borohydride (326 mg, 8.62 mmol) at 0° C. The mixture was warmed up to room temperature and stirred for 30 min. The reaction mixture was quenched with saturated aqueous ammonium chloride (15 mL), and then water (20 mL) was added. The mixture was extracted with ethyl acetate (30 mL×3). The combined organic layers were dried over anhydrous sodium sulfate and filtered. The filtrate was concentrated in vacuo to give the title compound 23m as yellow oil (3.41 g, 100%). This material was not further purified. The compound was characterized by the following spectroscopic data: $^1$H NMR (400 MHz, DMSO-d$_6$) δ(ppm): 7.57 (m, 1H), 7.45 (m, 2H), 7.28 (m, 13H), 7.03 (m, 2H), 6.78 (t, 1H), 6.60 (t, 1H), 4.87 (s, 1H), 4.79 (m, 3H), 4.68 (d, 1H), 4.51 (d, 1H), 4.39 (s, 1H), 4.06 (m, 5H), 3.93 (t, 3H), 3.77 (m, 2H), 3.52 (d, 1H), 3.18 (d, 1H), 3.09 (s, 3H), 1.32 (t, 3H).

Step 12) [(1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]methanol 23n To a solution of [(3S,4S,5R,6S)-3,4,5-tribenzyloxy-6-[4-chloro-3-[(4-ethoxy-2,3-difluoro-phenyl) methyl]phenyl]-2-(hydroxymethyl)-6-methoxy-tetrahydropyran-2-yl]methanol 23m (3.30 g, 4.26 mmol) in dichloromethane (70 mL) was added trifluoroacetic acid (1.26 mL, 17.03 mmol) at 0° C. The mixture was warmed up to room temperature and stirred for 12 hours. The reaction mixture was neutralized with saturated aqueous sodium bicarbonate to pH 7 and 40 mL of water was added, and then the mixture was partitioned. The aqueous layer was extracted with dichloromethane (20 mL×3). The combined organic layers were dried over anhydrous sodium sulfate and filtered. The filtrate was concentrated in vacuo and the residue was purified by silica gel chromatography eluted with PE/EtOAc(v/v)=10/1 to give the title compound 23n as yellow oil (1.62 g, 50%). The compound was characterized by the following spectroscopic data: $^1$H NMR (400 MHz, CDCl$_3$) δ(ppm): 7.36 (m, 13H), 7.20 (m, 3H), 6.92 (m, 2H), 6.66 (m, 1H), 6.53 (m, 1H), 4.88 (m, 3H), 4.78 (d, 1H), 4.31 (m, 2H), 4.06 (m, 5H), 3.98 (d, 1H), 3.89 (d, 1H), 3.83 (d, 1H), 3.72 (m, 3H), 1.45 (t, 3H).

Step 13) (1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octane-1-carbaldehyde 23o To a solution of [(1S,2S,3S,4R,5S)-2,3,4-tribenzyloxy-5-[4-chloro-3-[(4-ethoxy-2,3-difluoro-phenye methyl]phenyl]-6,8-dioxabicyclo[3.2.1]octan-1-yl]methanol 23n (1.36 g, 1.75 mmol) in ethyl acetate (30 mL) was added 2-iodoxybenzoic acid (735 mg, 2.62 mmol) at room temperature. The mixture was refluxed for 20 hours and cooled to room temperature. The reaction mixture was filtered and the filtrate was concentrated in vacuo to give the title compound 23o as a yellow soild (1.32 g, 100%). This material was not further purified.

Step 14) 1-[(1R,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]ethanol 23p To a solution of (1S,2S,3S,4R,5S)-2,3,4-tribenzyloxy-5-[4-chloro-3-[(4-ethoxy-2,3-difluoro-phenyl) methyl]phenyl]-6,8-dioxabicyclo[3.2.1]octane-1-carbaldehyde 23o (1.30 g, 1.75 mmol) in dry tetrahydrofuran (20 mL) was added dropwise methylmagnesium bromide (1.75 mL, 5.25 mmol, 3 M in ethyl ether) under N$_2$ at 0° C. The mixture was stirred at room temperature for 4 hours. The reaction mixture was quenched with water (10 mL) and extracted with ethyl acetate (15 mL×3). The combined organic layers were washed with saturated aqueous sodium chloride (30 mL), dried over anhydrous sodium sulfate and filtered. The filtrate was concentrated in vacuo and the residue was purified by silica gel chromatography eluted with PE/EtOAc(v/v)=12/1 to give the title compound 23p as a white solid (0.48 g, 36%). The compound was characterized by the following spectroscopic data: $^1$H NMR (600 MHz, CDCl$_3$) δ(ppm): 7.38 (m, 11H), 7.22 (m, 5H), 6.93 (m, 2H), 6.66 (s, 1H), 6.53 (m, 1H), 4.99 (m, 1H), 4.94 (d, 1H), 4.80 (m, 2H), 4.31 (m, 2H), 4.04 (m, 5H), 3.95 (m, 2H), 3.83 (m, 2H), 3.70 (m, 1H), 1.45 (t, 3H), 1.28 (d, 3H).

Step 15) (1R,2S,3S,4R,5S)-5-[4-chloro-3-[(4-ethoxy-2,3-difluoro-phenyl)methyl]phenyl]-1-(1-hydroxyethyl)-6,8-dioxabicyclo[3.2.1]octane-2,3,4-triol 23

To a solution of 1-[(1R,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]ethanol 23p (530 mg, 0.67 mmol) in a methanol/tetrahydrofuran mixture (v/v=4/1, 10 mL) were added o-dichlorobenzene (0.4 mL, 3.5 mmol) and 10% Pd/C (212 mg, 0.2 mmol) at room temperature. The mixture was stirred at room temperature for 4 hours under $H_2$ and filtered. The filtrate was concentrated in vacuo and the residue was purified by silica gel chromatography eluted with PE/EtOAc(v/v)=3/1 to give a few white solid. Then the solid was further purified by prep-HPLC to give the title compound 23 as a white solid (142 mg, 43%, HPLC: 97.3%). The compound was characterized by the following spectroscopic data: MS (ESI, pos. ion) m/z: 487.1 $[M+H]^+$; and $^1H$ NMR (600 MHz, $CDCl_3$) δ(ppm): 7.43-7.36 (m, 1H), 7.33 (m, 2H), 6.72 (m, 1H), 6.60 (m, 1H), 4.25-4.17 (m, 1H), 4.03 (m, 4H), 3.95 (m, 1H), 3.87 (m, 1H), 3.75 (m, 3H), 1.42 (t, 3H), 1.27 (d, 3H).

Examle 24

(1S,2S,3S,4R,5S)-5-[4-Chloro-3-[(4-ethoxy-2,3-difluoro-phenyl)methyl]phenyl]-1-(1-hydroxy-1-methyl-ethyl)-6,8-dioxabicyclo[3.2.1]octane-2,3,4-triol 24

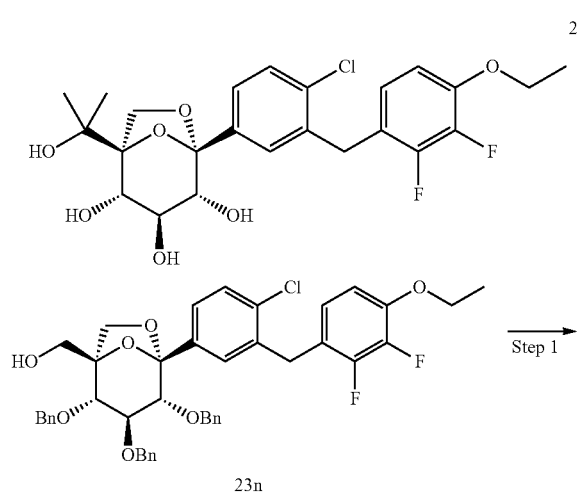

23n

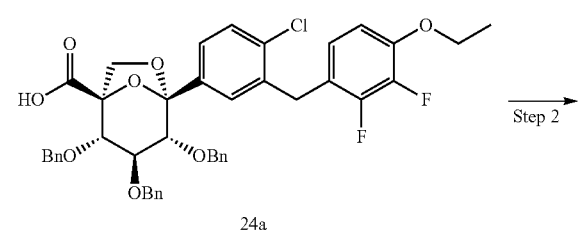

24a

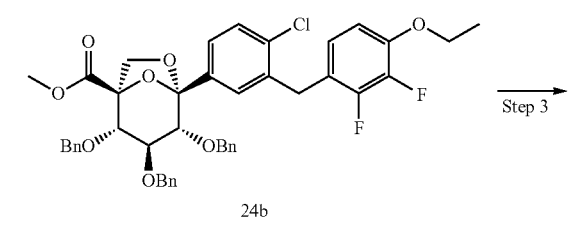

24b

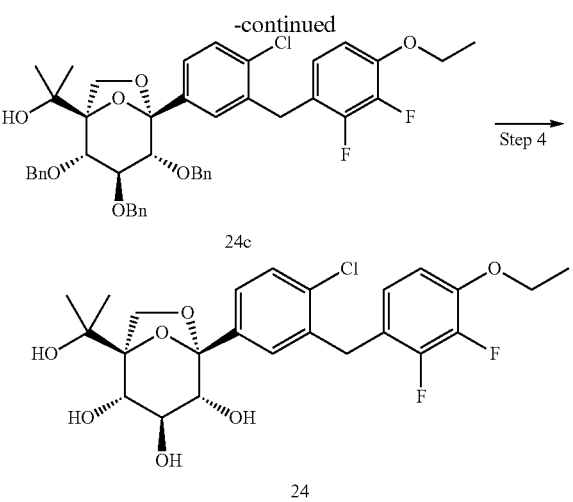

24c

24

Step 1) (1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octane-1-carboxylic acid 24a To a solution of [(1S,2S,3S,4R,5S)-2,3,4-tribenzyloxy-5-[4-chloro-3-[(4-ethoxy-2,3-difluoro-phenyl) methyl]phenyl]-6,8-dioxabicyclo[3.2.1]octan-1-yl]methanol 23n (0.56 g, 0.67 mmol, obtained from the synthetic method described in step 12 of example 23) in tetrahydrofuran (12 mL) were added aqueous sodium bicarbonate (12 mL, 7.4 mmol, 0.6 M), potassium bromide (16 mg, 0.13 mmol) and 2,2,6,6-tetramethylpiperidinooxy (10 mg, 0.07 mmol) in turn at 0° C., and then sodium hypochlorite (9 mL, 10.60 mmol, 3.5% available chlorine) was added dropwise. The mixture was stirred at 0° C. for 2 hours and acidified with aqueous HCl (1 N) till pH becomes 4. The resulting mixture was extracted with ethyl acetate (30 mL×3). The combined organic layers were washed with saturated brine (50 mL), dried over anhydrous sodium sulfate and filtered. The filtrate was concentrated in vacuo to give the title compound 24a (0.6 g, 100%) as yellow oil. This material was not further purified.

Step 2) methyl (1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octane-1-carboxylate 24b To a solution of (1S,2S,3S,4R,5S)-2,3,4-tribenzyloxy-5-[4-chloro-3-[(4-ethoxy-2,3-difluoro-phenyl) methyl]phenyl]-6,8-dioxabicyclo[3.2.1]octane-1-carboxylic acid 24a (507 mg, 0.67 mmol) in methanol (10 mL) was added concentrated sulphuric acid (0.04 mL, 0.74 mmol) at room temperature. The mixture was warmed up to 40° C. and stirred for 7 hours. The reaction mixture was cooled to room temperature and adjusted with saturated aqueous sodium bicarbonate to pH 7. To the mixture was added 10 mL of water and the resulting mixture was extracted with ethyl acetate (15 mL×3). The combined organic layers were dried over anhydrous sodium sulfate and filtered. The filtrate was concentrated in vacuo and the residue was purified by silica gel chromatography eluted with PE/EtOAc(v/v)=15/1 to give the title compound 24b as colorless oil (320 mg, 62%). The compound was characterized by the following spectroscopic data: $^1H$ NMR (400 MHz, $CDCl_3$) δ(ppm): 7.39 (m, 10H), 7.20 (m, 6H), 6.89 (d, 2H), 6.63 (t, 1H), 6.51 (t, 1H), 4.83 (m, 3H), 4.63

(d, 1H), 4.53 (d, 1H), 4.30 (d, 1H), 4.20 (d, 2H), 4.08-3.97 (m, 5H), 3.90 (d, 1H), 3.75 (m, 1H), 3.71 (s, 3H), 1.44 (t, 3H).

Step 3) 2-[(1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]propan-2-ol 24c To a solution of (1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octane-1-carboxylate 24b (320 mg, 0.42 mmol) in anhydrous tetrahydrofuran (15 mL) was added dropwise methylmagnesium bromide (0.83 mL, 2.49 mmol, 3M in ethyl ether) under N₂ at 0° C. The mixture was stirred at room temperature for 12 hours. The reaction mixture was quenched with water (10 mL) and extracted with ethyl acetate (10 mL×3). The combined organic layers were washed with saturated brine (15 mL), dried over anhydrous sodium sulfate and filtered. The filtrate was concentrated in vacuo and the residue was purified by silica gel chromatography eluted with PE/EtOAc(v/v)=20/1 to give the title compound 24c as colourless oil (250 mg, 78%). The compound was characterized by the following spectroscopic data: ¹H NMR (400 MHz, CDCl₃) δ (ppm): 7.36 (m, 11H), 7.22 (m, 5H), 6.96 (m 2H), 6.67 (m, 1H), 6.51 (m, 1H), 5.07 (d, 1H), 4.96 (d, 1H), 4.78 (d, 2H), 4.34 (d, 1H), 4.26 (d, 1H), 4.08 (m, 7H), 3.85 (d, 1H), 3.72 (d, 1H), 1.44 (t, 3H), 1.30 (s, 3H), 1.27 (s, 3H).

Step 4) (1S,2S,3S,4R,5S)-5-[4-chloro-3-[(4-ethoxy-2,3-difluoro-phenyl)methyl]phenyl]-1-(1-hydroxy-1-methyl-ethyl)-6,8-dioxabicyclo[3.2.1]octane-2,3,4-triol 24

To a solution of 2-[(1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]propan-2-ol 24c (250 mg, 0.32 mmol) in a methanol/tetrahydrofuran mixture (v/v=4/1, 10 mL) were added o-dichlorobenzene (0.18 mL, 1.62 mmol) and 10% Pd/C (100 mg, 0.09 mmol) at room temperature. The mixture was stirred at room temperature under H₂ for 4 hours and filtered. The filtrate was concentrated in vacuo and the residue was purified by silica gel chromatography eluted with PE/EtOAc(v/v)=1/2 to give the title compound 24 as a white solid (160 mg, 98.7%, HPLC: 96.6%). The compound was characterized by the following spectroscopic data: MS (ESI, pos. ion) m/z: 545 [M+HCOO]⁻; and ¹H NMR (600 MHz, DMSO-d₆) δ(ppm): 7.42 (d, 1H), 7.36 (m, 2H), 6.94 (t, 1H), 6.87 (t, 1H), 5.51 (s, 1H), 4.98 (s, 2H), 4.23 (d, 1H), 4.11 (q, 2H), 4.03 (m, 3H), 3.79 (d, 1H), 3.71 (d, 1H), 3.46 (t, 2H), 1.34 (t, 3H), 1.20 (s, 3H), 1.15 (s, 3H).

Examle 25

(1S,2S,3S,4R,5S)-5-[4-Chloro-3-[[4-(2,2-difluoroethoxyl)phenyl]methyl]phenyl]-1-(1-hydroxy-1-methyl-ethyl)-6,8-dioxabicyclo[3.2.1]octane-2,3,4-triol 25

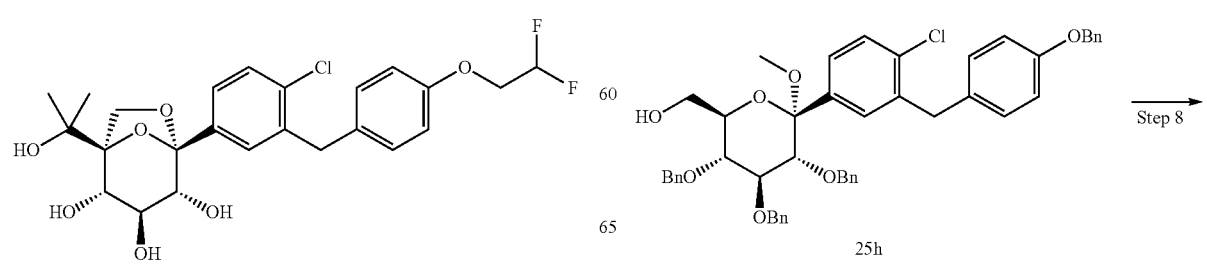

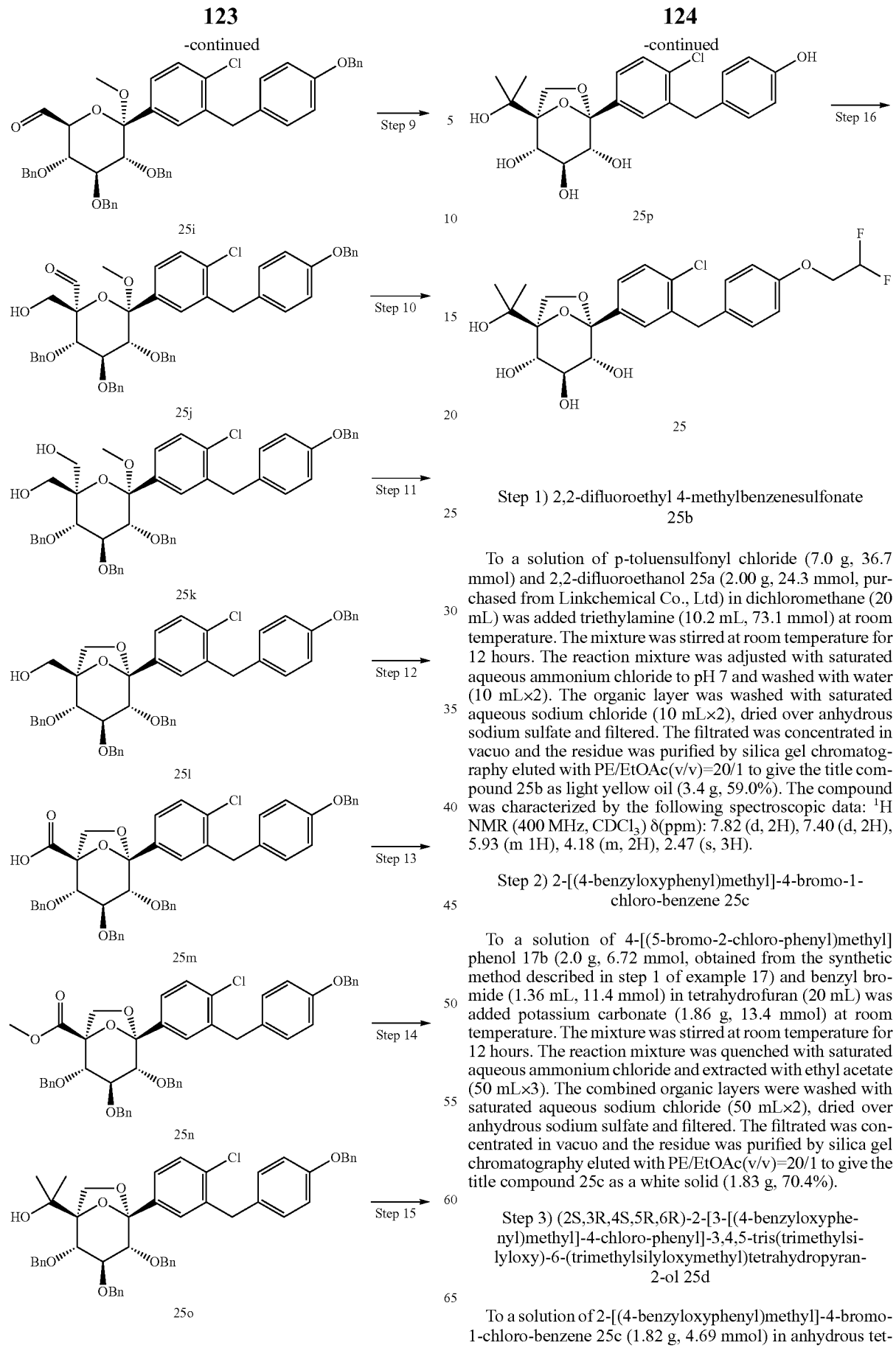

Step 1) 2,2-difluoroethyl 4-methylbenzenesulfonate 25b

To a solution of p-toluensulfonyl chloride (7.0 g, 36.7 mmol) and 2,2-difluoroethanol 25a (2.00 g, 24.3 mmol, purchased from Linkchemical Co., Ltd) in dichloromethane (20 mL) was added triethylamine (10.2 mL, 73.1 mmol) at room temperature. The mixture was stirred at room temperature for 12 hours. The reaction mixture was adjusted with saturated aqueous ammonium chloride to pH 7 and washed with water (10 mL×2). The organic layer was washed with saturated aqueous sodium chloride (10 mL×2), dried over anhydrous sodium sulfate and filtered. The filtrated was concentrated in vacuo and the residue was purified by silica gel chromatography eluted with PE/EtOAc(v/v)=20/1 to give the title compound 25b as light yellow oil (3.4 g, 59.0%). The compound was characterized by the following spectroscopic data: $^1$H NMR (400 MHz, CDCl$_3$) δ(ppm): 7.82 (d, 2H), 7.40 (d, 2H), 5.93 (m 1H), 4.18 (m, 2H), 2.47 (s, 3H).

Step 2) 2-[(4-benzyloxyphenyl)methyl]-4-bromo-1-chloro-benzene 25c

To a solution of 4-[(5-bromo-2-chloro-phenyl)methyl] phenol 17b (2.0 g, 6.72 mmol, obtained from the synthetic method described in step 1 of example 17) and benzyl bromide (1.36 mL, 11.4 mmol) in tetrahydrofuran (20 mL) was added potassium carbonate (1.86 g, 13.4 mmol) at room temperature. The mixture was stirred at room temperature for 12 hours. The reaction mixture was quenched with saturated aqueous ammonium chloride and extracted with ethyl acetate (50 mL×3). The combined organic layers were washed with saturated aqueous sodium chloride (50 mL×2), dried over anhydrous sodium sulfate and filtered. The filtrated was concentrated in vacuo and the residue was purified by silica gel chromatography eluted with PE/EtOAc(v/v)=20/1 to give the title compound 25c as a white solid (1.83 g, 70.4%).

Step 3) (2S,3R,4S,5R,6R)-2-[3-[(4-benzyloxyphenyl)methyl]-4-chloro-phenyl]-3,4,5-tris(trimethylsilyloxy)-6-(trimethylsilyloxymethyl)tetrahydropyran-2-ol 25d To a solution of 2-[(4-benzyloxyphenyl)methyl]-4-bromo-1-chloro-benzene 25c (1.82 g, 4.69 mmol) in anhydrous tetrahydrofuran (20 mL) was added n-butyllithium (2.35 mL, 5.63 mmol, 2.4 M in hexane) dropwise at −78° C. The mixture was stirred at −78° C. for 1 hour and a solution of (3R,4S,5R, 6R)-3,4,5-tris(trimethylsilyloxy)-6-(trimethylsilyloxymethyetetrahydropyran-2-one 1b (2.63 g, 5.63 mmol, obtained from the synthetic method described in step 1 of example 1) in anhydrous tetrahydrofuran (20 mL) was added dropwise. After the addition, the mixture was further stirred at −78° C. for 2 hours. When the reaction was complete, the reaction mixture was not further purified and used for the next step.

Step 4) (2S,3R,4S,5S,6R)-2-[3-[(4-benzyloxyphenyl) methyl]-4-chloro-phenyl]-6-(hydroxymethyl)-2-methoxy-tetrahydropyran-3,4,5-triol 25e To a solution of (2S,3R,4S,5R,6R)-2-[3-[(4-benzyloxyphenyl)methyl]-4-chloro-phenyl]-3,4,5-tris(trimethylsilyloxy)-6-(trimethylsilyloxymethyl)tetrahydropyran-2-ol 25d in anhydrous tetrahydrofuran was added a solution of methylsulfonic acid (0.2 mL, 2.82 mmol) in methanol (20 mL) at −78° C. The mixture was warmed up to room temperature and stirred for 12 hours. The reaction mixture was neutralized with saturated aqueous sodium bicarbonate till pH becomes 6-7 and extracted with ethyl acetate (50 mL×4). The combined organic layers were washed with water (60 mL×2) and saturated aqueous sodium chloride (60 mL×2) in turn, dried over anhydrous sodium sulfate and filtered. The filtrate was concentrated in vacuo and the residue was purified by re-crystallization from a toluene/n-hexane mixture ((v/v)=1/20, 500 mL) to give the title compound 25e as a white solid (1.28 g, 54.5%). The compound was characterized by the following spectroscopic data: MS (ESI, pos. ion) m/z: 545.3[M+HCOO]$^-$.

Step 5) (2S,3R,4S,5S,6R)-2-[3-[(4-benzyloxyphenyl) methyl]-4-chloro-phenyl]-6-[[tert-butyl(dimethyesilyl]oxymethyl]-2-methoxy-tetrahydropyran-3,4,5-triol 25f To a solution of (2S,3R,4S,5S,6R)-2-[3-[(4-benzyloxyphenyl)methyl]-4-chloro-phenyl]-6-(hydroxymethyl)-2-methoxy-tetrahydropyran-3,4,5-triol 25e (1.28 g, 2.56 mmol) and tert-butyldimethylsilyl chloride (0.58 g, 3.85 mmol) in dichloromethane (15 mL) was added triethylamine (1.07 mL, 7.69 mmol) at 0° C. The mixture was stirred at room temperature for 1 hour, and then quenched with saturated aqueous ammonium chloride (10 mL) and extracted with ethyl acetate (60 mL×3). The combined organic layers were washed with water (30 mL×2) and saturated aqueous sodium chloride (30 mL×2) in turn, dried over anhydrous sodium sulfate and filtered. The filtrate was concentrated in vacuo to give the title compound 25f as yellow oil (1.57 g, 100%). This material was not further purified.

Step 6) tert-butyl-dimethyl-[[(2R,3R,4S,5R,6S)-3,4, 5-tribenzyloxy-6-[3-[(4-benzyloxyphenyl)methyl]-4-chloro-phenyl]-6-methoxy-tetrahydropyran-2-yl] methoxy]silane 25g To a solution of (2S,3R,4S,5S,6R)-2-[3-[(4-benzyloxyphenyl)methyl]-4-chloro-phenyl]-6-[[tert-butyl(dimethyesilyl]oxymethyl]-2-methoxy-tetrahydropyran-3,4,5-triol 25f (1.57 g, 2.56 mmol) in anhydrous tetrahydrofuran (20 mL) was added sodium hydride (0.77 g, 19.2 mmol, 60% dispersion in Mineral oil) slowly at 0° C. The mixture was stirred at 0° C. for 1 hour, and then benzyl bromide (2.2 mL, 18.53 mmol) was added. The mixture was warmed up to room temperature and further stirred for 12 hours. The reaction mixture was quenched with saturated aqueous ammonium chloride (100 mL) and extracted with ethyl acetate (60 mL×2). The combined organic layers were washed with saturated aqueous sodium chloride (30 mL×2), dried over anhydrous sodium sulfate and filtered. The filtrate was concentrated in vacuo to give the title compound 25g as yellow oil (2.26 g, 100%). This material was not further purified.

Step 7) [(2R,3R,4S,5R,6S)-3,4,5-tribenzyloxy-6-[3-[(4-benzyloxyphenyl)methyl]-4-chloro-phenyl]-6-methoxy-tetrahydropyran-2-yl]methanol 25h To a solution of tert-butyl-dimethyl-[[(2R,3R,4S,5R,6S)-3,4,5-tribenzyloxy-6-[3-[(4-benzyloxyphenyl)methyl]-4-chloro-phenyl]-6-methoxy-tetrahydropyran-2-yl]methoxy] silane 25g (2.26 g, 2.56 mmol) in anhydrous tetrahydrofuran (20 mL) was added tetrabutylammonium fluoride (5.12 mL, 5.12 mmol, 1 M in tetrahydrofuran) at room temperature. The mixture was stirred at room temperature for 12 hours, then quenched with water (60 mL) and partitioned. The aqueous layer was extracted with ethyl acetate (100 mL×2). The combined organic layers were washed with water (100 mL×2) and saturated aqueous sodium chloride (100 mL×2) in turn, dried over anhydrous sodium sulfate and filtered. The filtrate was concentrated in vacuo and the residue was purified by silica gel chromatography eluted with PE/EtOAc(v/v)=10/1 to give the title compound 25h as a light yellow solid (0.54 g, 27.4%). The compound was characterized by the following spectroscopic data: $^1$H NMR (600 MHz, DMSO-d$_6$) δ (ppm): 7.46 (m, 2H), 7.42 (m, 2H), 7.35-7.24 (m, 17H), 7.01 (m, 4H), 6.84 (m, 2H), 5.02 (s, 2H), 4.82-4.75 (m, 3H), 4.69 (d, 1H), 4.41 (d, 1H), 4.04 (m, 1H), 3.97 (t, 1H), 3.88 (d, 1H), 3.77 (d, 1H), 3.70 (m, 3H), 3.53 (m, 1H), 3.23 (d, 1H), 2.97 (s, 3H).

Step 8) (2S,3S,4S,5R,6S)-3,4,5-tribenzyloxy-6-[3-[(4-benzyloxyphenyl)methyl]-4-chloro-phenyl]-6-methoxy-tetrahydropyran-2-carbaldehyde 25i To a solution of [(2R,3R,4S,5R,6S)-3,4,5-tribenzyloxy-6-[3-[(4-benzyloxyphenyl)methyl]-4-chloro-phenyl]-6-methoxy-tetrahydropyran-2-yl]methanol 25h (1.0 g, 1.3 mmol) in dichloromethane (20 mL) was added 2-iodoxybenzoic acid (1.09 g, 3.9 mmol) at room temperature. The mixture was refluxed for 16 hours. The reaction mixture was cooled to room temperature and filtered. The filtrate was concentrated in vacuo to give the title compound 25i as a yellow solid (1.0 g, 100%). This material was not further purified.

Step 9) (2R,3S,4S,5R,6S)-3,4,5-tribenzyloxy-6-[3-[(4-benzyloxyphenyl)methyl]-4-chloro-phenyl]-2-(hydroxymethyl)-6-methoxy-tetrahydropyran-2-carbaldehyde 25j To a solution of (2S,3S,4S,5R,6S)-3,4,5-tribenzyloxy-6-[3-[(4-benzyloxyphenyl)methyl]-4-chloro-phenyl]-6-methoxy-tetrahydropyran-2-carbaldehyde 25i (1.0 g, 1.3 mmol) in N,N-dimethyl formamide (20 mL) was added formaldehyde (2.6 mL, 32.5 mmol, 37 wt % solution) at room temperature, and then 1,8-diazabicyclo[5.4.0]undec-7-ene (0.3 mL, 0.78 mmol) was added to adjust the pH to 9. The mixture was stirred at room temperature for 16 hours and extracted with ethyl acetate (50 mL×2). The combined organic layers were washed with water (30 mL×2) and saturated aqueous sodium chloride (30 mL×2) in turn, dried over anhydrous sodium sulfate and filtered. The filtrate was concentrated in vacuo to give the title compound 25j as yellow oil (1.04 g, 100%). This material was not further purified.

Step 10) [(3S,4S,5R,6S)-3,4,5-tribenzyloxy-6-[3-[(4-benzyloxyphenyl)methyl]-4-chloro-phenyl]-2-(hydroxymethyl)-6-methoxy-tetrahydropyran-2-yl]methanol 25k To a solution of (2R,3S,4S,5R,6S)-3,4,5-tribenzyloxy-6-[3-[(4-benzyloxyphenyl)methyl]-4-chloro-phenyl]-2-(hydroxymethyl)-6-methoxy-tetrahydropyran-2-carbaldehyde 25j (1.04 g, 1.3 mmol) in methanol (20 mL) was added sodium borohydride (98 mg, 2.6 mmol) slowly at 0° C. The mixture was stirred at 0° C. for 5 min. The reaction mixture was quenched with saturated aqueous ammonium chloride (15 mL) and extracted with ethyl acetate (50 mL×2). The combined organic layers were washed with water (30 mL×2) and saturated aqueous sodium chloride (30 mL×2) in turn, dried over anhydrous sodium sulfate and filtered. The filtrate was concentrated in vacuo to give the title compound 25k as yellow oil (1.04 g, 100%). This material was not further purified.

Step 11) [(1S,2S,3S,4R,5S)-2,3,4-tribenzyloxy-5-[3-[(4-benzyloxyphenyl)methyl]-4-chloro-phenyl]-6,8-dioxabicyclo[3.2.1]octan-1-yl]methanol 25l To a solution of [(3S,4S,5R,6S)-3,4,5-tribenzyloxy-6-[3-[(4-benzyloxyphenyl)methyl]-4-chloro-phenyl]-2-(hydroxymethyl)-6-methoxy-tetrahydropyran-2-yl]methanol 25k (1.04 g, 13 mmol) in dichloromethane (100 mL) was added p-toluenesulfonic acid monohydrate (123 mg, 0.65 mmol) at 0° C. The mixture was warmed up to room temperature and stirred for 16 hours. The reaction mixture was quenched with saturated aqueous sodium bicarbonate (10 mL) and partitioned. The organic layer was washed with water (30 mL×2) and saturated aqueous sodium chloride (30 mL×2) in turn, dried over anhydrous sodium sulfate and filtered. The filtrate was concentrated in vacuo and the residue was purified by silica gel chromatography eluted with PE/EtOAc(v/v)=10/1 to give the title compound 25l as pale yellow oil (0.59 g, 58.7%). The compound was characterized by the following spectroscopic data: $^1$H NMR (600 MHz, CDCl$_3$) δ(ppm): 7.44 (m, 3H), 7.35 (m, 15H), 7.19 (m, 3H), 7.09 (m, 2H), 6.89 (m, 2H), 6.85 (m, 2H), 5.02 (s, 2H), 4.90 (d, 2H), 4.86 (d, 1H), 4.77 (d, 1H), 4.30 (d, 1H), 4.27 (d, 1H), 4.07 (d, 1H), 4.03 (m, 2H), 3.97 (d, 1H), 3.86 (d, 1H), 3.82 (d, 1H), 3.74 (d, 1H), 3.70 (d, 1H), 3.68 (d, 1H).

Step 12) (1S,2S,3S,4R,5S)-2,3,4-tribenzyloxy-5-[3-[(4-benzyloxyphenyl)methyl]-4-chloro-phenyl]-6,8-dioxabicyclo[3.2.1]octane-1-carboxylic acid 25m To a solution of [(1S,2S,3S,4R,5S)-2,3,4-tribenzyloxy-5-[3-[(4-benzyloxyphenyl)methyl]-4-chloro-phenyl]-6,8-dioxabicyclo[3.2.1]octan-1-yl]methanol 25l (0.45 g, 0.58 mmol) in tetrahydrofuran (20 mL) was added sodium bicarbonate (0.49 g, 5.8 mmol) at room temperature, and then potassium bromide (6.9 mg, 0.06 mmol), 2,2,6,6-tetramethylpiperidinooxy (9 mg, 0.06 mmol) and sodium hypochlorite (9 mL, available chlorine ≥5.5%) were added in turn at 0° C. The mixture was stirred at 0° C. for 40 min and acidified with aqueous HCl (1 N) till pH becomes 4. The resulting mixture was extracted with ethyl acetate (30 mL×2). The combined organic layers were washed with water (20 mL×2) and saturated brine (20 mL×2) in turn, dried over anhydrous sodium sulfate and filtered. The filtrate was concentrated in vacuo to give the title compound 25m (0.46 g, 100%) as a white solid. This material was not further purified.

Step 13) methyl (1S,2S,3S,4R,5S)-2,3,4-tribenzyloxy-5-[3-[(4-benzyloxyphenyl)methyl]-4-chloro-phenyl]-6,8-dioxabicyclo[3.2.1]octane-1-carboxylate 25n To a solution of (1S,2S,3S,4R,5S)-2,3,4-tribenzyloxy-5-[3-[(4-benzyloxyphenyl)methyl]-4-chloro-phenyl]-6,8-dioxabicyclo[3.2.1]octane-1-carboxylic acid 25m (0.45 g, 0.57 mmol) in a methanol/tetrahydrofuran mixture (v/v=6/5, 22 mL) was added concentrated sulphuric acid (0.05 mL) at room temperature. The mixture was warmed up to 60° C. and stirred for 14 hours. The reaction mixture was adjusted with saturated aqueous sodium bicarbonate to pH 7 at room temperature and extracted with ethyl acetate (60 mL). The organic layer was washed with saturated brine (20 mL×2), dried over anhydrous sodium sulfate and filtered. The filtrate was concentrated in vacuo and the residue was purified by silica gel chromatography eluted with PE/EtOAc(v/v)=6/1 to give the title compound 25n as a pale yellow solid (0.38 g, 84.4%). The compound was characterized by the following spectroscopic data: $^1$H NMR (600 MHz, CDCl$_3$) δ(ppm): 7.48 (m, 1H), 7.47 (m, 2H), 7.41 (m, 4H), 7.33 (m, 7H), 7.25 (m, 3H), 7.21 (m, 4H), 7.16 (m, 2H), 7.08 (m, 2H), 6.87 (m, 2H), 5.01 (s, 2H), 4.81-4.75 (m, 3H), 4.78 (m, 1H), 4.63 (d, 1H), 4.52 (d, 1H), 4.26 (d, 1H), 4.19 (m, 2H), 4.09 (m, 1H), 4.01 (m, 2H), 3.87 (m, 1H), 3.74 (d, 1H), 3.71 (s, 3H).

Step 14) 2-[(1S,2S,3S,4R,5S)-2,3,4-tribenzyloxy-5-[3-[(4-benzyloxyphenyl)methyl]-4-chloro-phenyl]-6,8-dioxabicyclo[3.2.1]octan-1-yl]propan-2-ol 25o To a solution of methyl (1S,2S,3S,4R,5S)-2,3,4-tribenzyloxy-5-[3-[(4-benzyloxyphenyl)methyl]-4-chloro-phenyl]-6,8-dioxabicyclo[3.2.1]octane-1-carboxylate 25n (0.38 g, 0.48 mmol) in dry tetrahydrofuran (15 mL) was added dropwise methylmagnesium bromide (0.79 mL, 2.38 mmol, 3 M in tertrahydrofuran) at 0° C., and then the mixture was stirred at room temperature for 12 hours. The reaction mixture was quenched with 20 mL of saturated aqueous ammonium chloride and extracted with ethyl acetate (30 mL×2). The combined organic layers were washed with saturated aqueous sodium chloride (20 mL×2), dried over anhydrous sodium sulfate and filtered. The filtrate was concentrated in vacuo and the residue was purified by silica gel chromatography eluted with PE/EtOAc(v/v)=20/1 to give the title compound 25o as a white solid (100 mg, 26.3%). The compound was characterized by the following spectroscopic data: $^1$H NMR (600 MHz, CDCl$_3$) δ(ppm): 7.44 (m, 3H), 7.36 (m, 12H), 7.21 (m, 6H), 7.10 (d, 2H), 6.93 (d, 2H), 6.85 (d, 2H), 5.07 (d, 1H), 5.01 (s, 2H), 4.96 (d, 1H), 4.78 (d, 2H), 4.34 (d, 1H), 4.22 (d, 1H), 4.06 (m, 5H), 3.82 (d, 1H), 3.71 (d, 1H), 1.30 (s, 3H), 1.26 (s, 3H).

Step 15) (1S,2S,3S,4R,5S)-5-[4-chloro-3-[(4-hydroxyphenyl)methyl]phenyl]-1-(1-hydroxy-1-methyl-ethyl)-6,8-dioxabicyclo[3.2.1]octane-2,3,4-triol 25p To a solution of 2-[(1S,2S,3S,4R,5S)-2,3,4-tribenzyloxy-5-[3-[(4-benzyloxyphenyl)methyl]-4-chloro-phenyl]-6,8-dioxabicyclo[3.2.1]octan-1-yl]propan-2-ol 25o (100 mg, 0.12 mmol) in a methanol/tetrahydrofuran mixture (v/v=4/1, 10 mL) were added o-dichlorobenzene (0.07 mL, 0.63 mmol) and 10% Pd/C (20 mg, 0.02 mmol) at room temperature. The mixture was stirred under H₂ at room temperature for 4 hours and filtered. The filtrate was concentrated in vacuo to give the title compound 25p as a white solid (54.8 mg, 100%). The compound was characterized by the following spectroscopic data: MS (ESI, pos. ion) m/z: 481.0[M+HCOO]⁻.

Step 16) (1S,2S,3S,4R,5S)-5-[4-chloro-3-[[4-(2,2-difluoroethoxyl)phenyl]methyl]phenyl]-1-(1-hydroxy-1-methyl-ethyl)-6,8-dioxabicyclo[3.2.1]octane-2,3,4-triol 25

To a solution of (1S,2S,3S,4R,5S)-5-[4-chloro-3-[(4-hydroxyphenyl)methyl]phenyl]-1-(1-hydroxy-1-methyl-ethyl)-6,8-dioxabicyclo[3.2.1]octane-2,3,4-triol 25p (150 mg, 0.34 mmol) in N,N-dimethylformamide (10 mL) was added cesium carbonate (169 mg, 0.52 mmol) at room temperature. The mixture was warmed up to 75° C. and stirred for 12 hours. The mixture was partitioned between water (30 mL) and ethyl acetate (30 mL). The aqueous layer was extracted with ethyl acetate (20 mL×4). The combined organic layers were washed with water (20 mL×2) and saturated aqueous sodium chloride (10 mL×2), dried over anhydrous sodium sulfate and filtered. The filtrate was concentrated in vacuo and the residue was purified by silica gel chromatography eluted with PE/EtOAc(v/v)=1/1 to give the title compound 25 as a white solid (69 mg, 40.5%, HPLC: 93.6%). The compound was characterized by the following spectroscopic data: MS (ESI, pos. ion) m/z: 545 [M+Na]⁺; and ¹H NMR (600 MHz, DMSO-d₆) δ(ppm): 7.43 (d, 1H), 7.39 (d, 1H), 7.33 (m, 1H), 7.14 (d, 2H), 6.92 (d, 2H), 6.47-6.25 (m, 1H), 5.51 (d, 1H), 5.05 (d, 1H), 5.00 (d, 1H), 4.30-4.22 (m, 3H), 4.07-3.95 (m, 4H), 3.80 (d, 1H), 3.73-3.68 (t, 1H), 1.21 (s, 3H), 1.14 (s, 3H).

Examle 26

(1S,2S,3S,4R,5S)-5-[4-Chloro-3-[(4-ethoxyphenyl) methyl]phenyl]-1-(oxiran-2-yl)-6,8-dioxabicyclo [3.2.1]octan e-2,3,4-triol 26

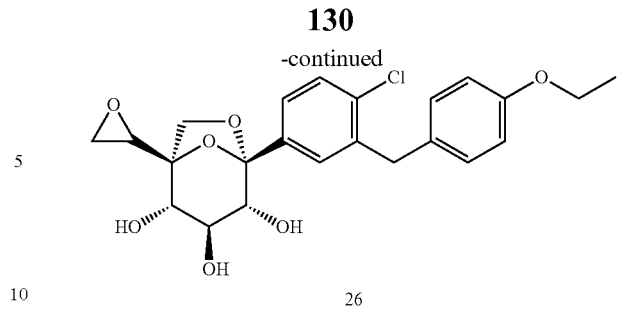

26

Step 1) (1S,2S,3S,4R,5S)-5-[4-chloro-3-[(4-ethoxyphenyl)methyl]phenyl]-1-(oxiran-2-yl)-6,8-dioxabicyclo[3.2.1]octane-2,3,4-triol 26

To a solution of (1S,2S,3S,4R,5S)-2,3,4-tribenzyloxy-5-[4-chloro-3-[(4-ethoxyphenyl)methyl]phenyl]-1-(oxiran-2-yl)-6,8-dioxabicyclo[3.2.1]octane 10a (310 mg, 0.43 mmol, obtained from the synthetic method described in step 1 example 10) in a methanol/tetrahydrofuran mixture (v/v=4/1, 15 mL) were added o-dichlorobenzene (0.25 mL, 2.15 mmol) and 10% Pd/C (30 mg, 0.03 mmol) at room temperature. The mixture was stirred under H₂ at room temperature for 6 hours and filtered. The filter cake was washed with an ethyl acetate/tetrahydrofuran mixture (v/v=4/1, 10 mL×2) and the filtrate was concentrated in vacuo. The residue was purified by silica gel chromatography eluted with PE/EtOAc(v/v)=1/1 to give the title compound 26 as a white solid (34 mg, 17.6%, HPLC: 97.5%). The compound was characterized by the following spectroscopic data: MS (ESI, pos. ion) m/z: 449.1[M+H]⁺; and ¹H NMR (400 MHz, DMSO-d₆) δ(ppm): 7.38 (m, 2H), 7.27 (m, 1H), 7.09 (d, 2H), 6.83 (d, 2H), 5.54 (d, 1H), 5.10 (d, 1H), 4.99 (d, 1H), 3.97 (m, 5H), 3.45 (t, 1H), 3.40 (m, 2H), 3.26 (m, 3H), 2.78 (t, 1H), 1.29 (t, 3H).

Examle 27

5-((1S,2S,3S,4R,5S)-5-(4-Chloro-3-(4-ethoxybenzyl)phenyl)-2,3,4-trihydroxy-6,8-dioxabicyclo[3.2.1] octan-1-yl)oxazolidin-2-one

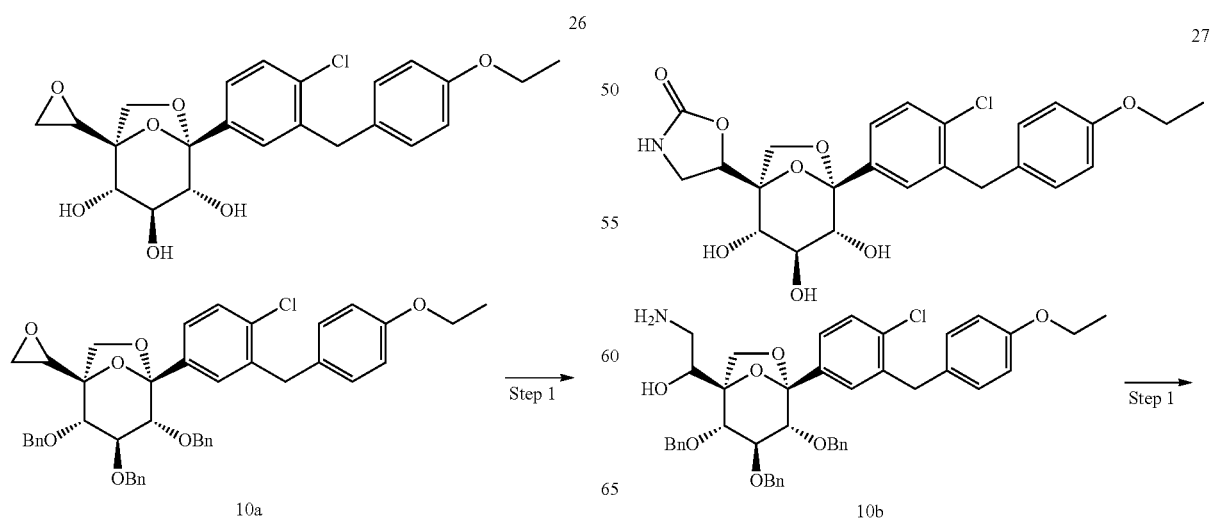

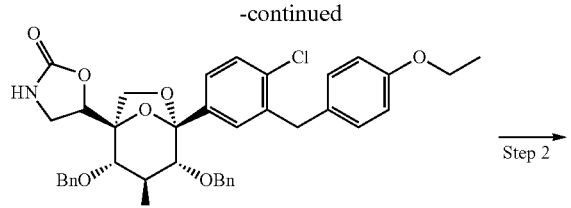

27a

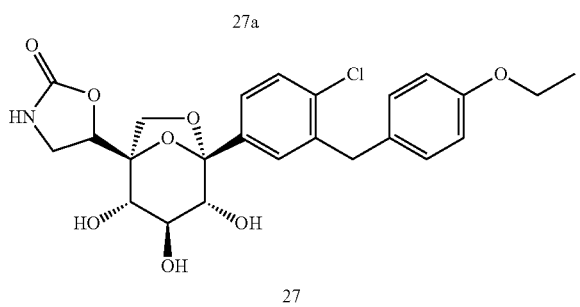

27

Step 1) 5-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]oxazolidin-2-one 27a To a solution of 2-amino-1-[(1R,2S,3S,4R,5S)-2,3,4-tribenzyloxy-5-[4-chloro-3-[(4-ethoxyphenyl) methyl]phenyl]-6,8-dioxabicyclo[3.2.1]octan-1-yl]ethanol 10b (50 mg, 0.07 mmol, obtained from the synthetic method described in step 2 of example 10) in tetrahydrofuran (10 mL) was added N,N'-carbonyldiimidazole (14.3 mg, 0.09 mmol) at room temperature. The mixture was stirred at room temperature for 4 hours. The reaction mixture was quenched with water (5 mL) and extracted with ethyl acetate (20 mL×2). The combined organic layers were washed with water (10 mL×2) and then saturated aqueous sodium chloride (10 mL×2), dried over anhydrous sodium sulfate and filtered. The filtrate was concentrated in vacuo and the residue was purified by silica gel chromatography eluted with PE/EtOAc(v/v)=10/1 to give the title compound 27a as a white solid (36 mg, 69.5%). The compound was characterized by the following spectroscopic data: $^1$H NMR (400 MHz, CDCl$_3$) δ(ppm): 7.42 (m, 1H), 7.34 (m, 12H), 7.20 (m, 3H), 7.10 (m, 2H), 6.91 (m, 2H), 6.78 (m, 2H), 5.46 (s, 1H), 4.95 (t, 2H), 4.84 (t, 2H), 4.30 (dd, 2H), 4.22 (d, 1H), 4.11 (m, 1H), 4.02 (m, 5H), 3.85 (d, 1H), 3.70 (d, 1H), 3.54 (m, 2H), 3.36 (d, 1H), 1.45 (t, 3H).

Step 2) 5-[(1S,2S,3S,4R,5S)-5-[4-chloro-3-[(4-ethoxyphenyl)methyl]phenyl]-2,3,4-trihydroxy-6,8-dioxabicyclo[3.2.1]octan-1-yl]oxazolidin-2-one 27

To a solution of 5-[(1R,2S,3S,4R,5S)-2,3,4-tribenzyloxy-5-[4-chloro-3-[(4-ethoxyphenyl)methyl]phenyl]-6,8-dioxabicyclo[3.2.1]octan-1-yl]oxazolidin-2-one 27a (113 mg, 0.17 mmol) in a methanol/tetrahydrofuran mixture (v/v=4/1, 10 mL) were added o-dichlorobenzene (0.1 mL, 0.85 mmol) and 10% Pd/C (20 mg, 0.02 mmol) at room temperature. The mixture was stirred at room temperature under H$_2$ for 4 hours and filtered. The filter cake was washed with a methanol/tetrahydrofuran mixture (v/v=4/1, 10 mL×2). The filtrate was concentrated in vacuo and the residue was purified by silica gel chromatography eluted with PE/EtOAc(v/v)=1/1 to give the title compound 27 as a white solid (66.2 mg, 78.8%, HPLC: 90.1%). The compound was characterized by the following spectroscopic data: MS (ESI, pos. ion) m/z: 492.2 [M+H]$^+$; and $^1$H NMR (400 MHz, DMSO-d$_6$) δ(ppm): 7.54 (s, 1H), 7.42 (m, 2H), 7.31 (m, 1H), 7.16 (m, 2H), 7.34 (m, 2H), 5.68 (d, 1H), 5.18 (d, 2H), 4.81 (t, 1H), 4.11 (m, 1H), 3.98 (m, 4H), 3.69 (t, 1H), 3.48 (m, 3H), 3.30 (m, 1H), 3.21 (m, 1H), 1.32 (t, 3H).

Example 28

(1R,2R,3S,4R,5S)-5-[4-Chloro-3-[(4-ethoxyphenyl)methyl]phenyl]-1-(1-hydroxyethyl)-6,8-dioxabicyclo[3.2.1]octane-2,3,4-triol 28

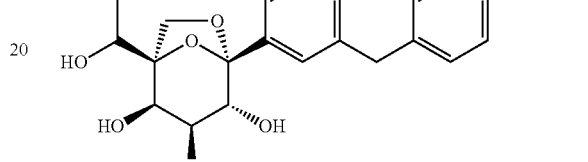

28

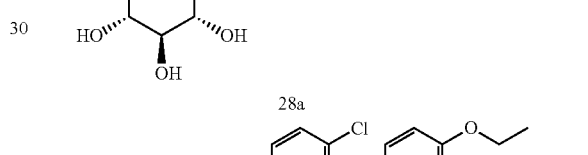

28a

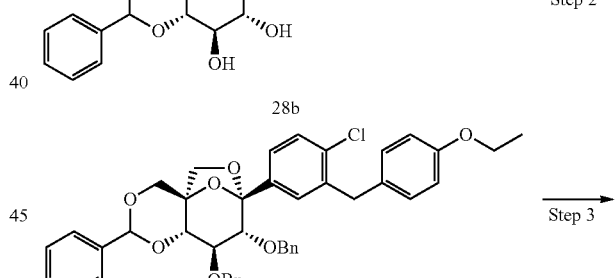

28b

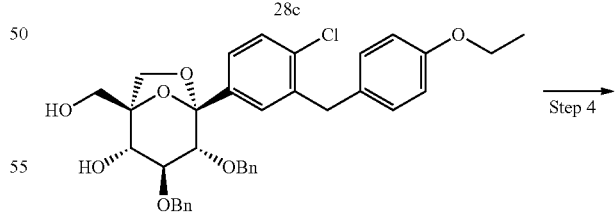

28c

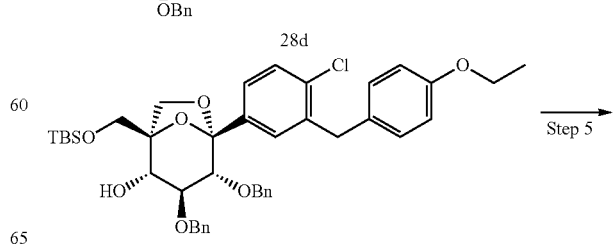

28d

28e

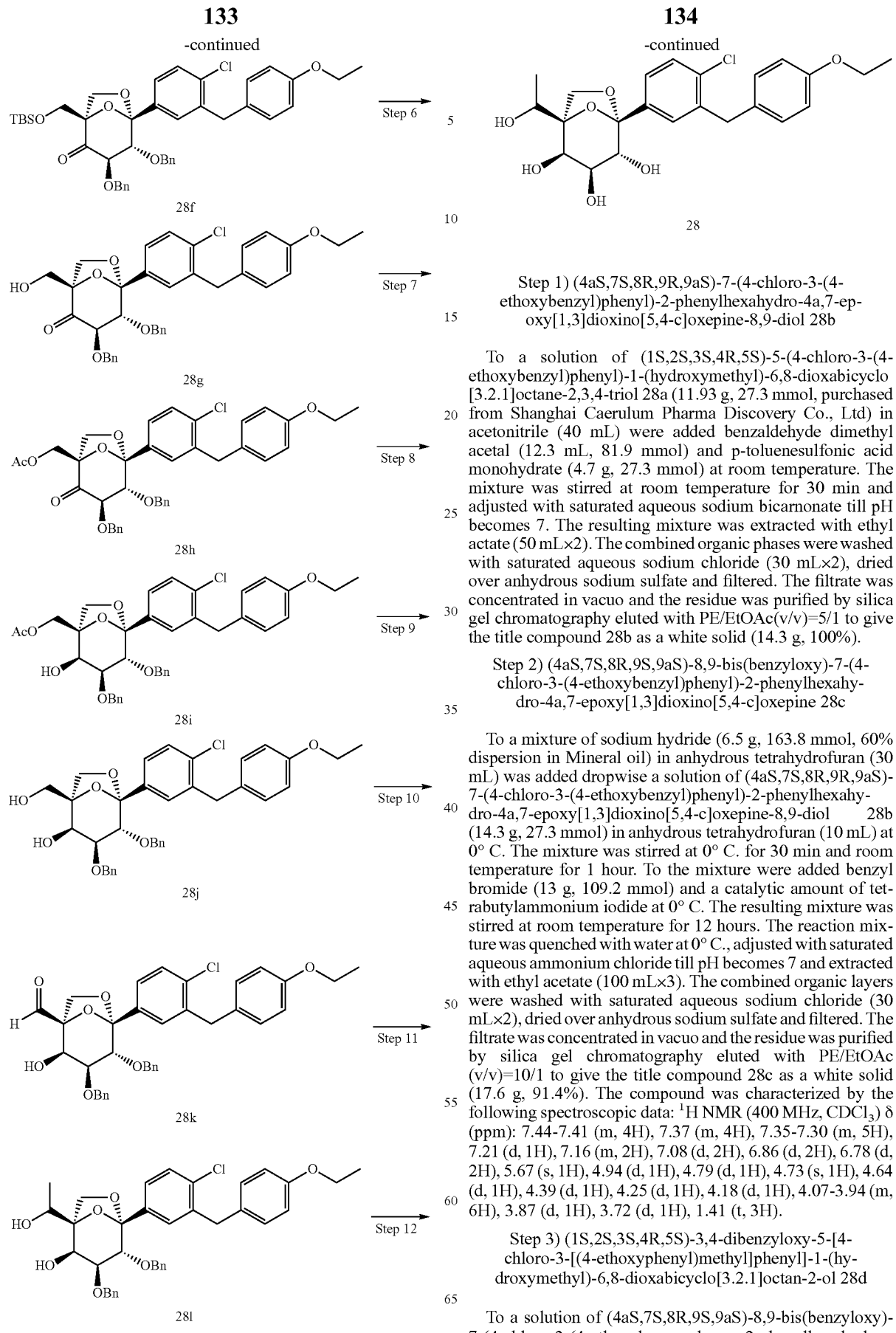

Step 1) (4aS,7S,8R,9R,9aS)-7-(4-chloro-3-(4-ethoxybenzyl)phenyl)-2-phenylhexahydro-4a,7-epoxy[1,3]dioxino[5,4-c]oxepine-8,9-diol 28b To a solution of (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol 28a (11.93 g, 27.3 mmol, purchased from Shanghai Caerulum Pharma Discovery Co., Ltd) in acetonitrile (40 mL) were added benzaldehyde dimethyl acetal (12.3 mL, 81.9 mmol) and p-toluenesulfonic acid monohydrate (4.7 g, 27.3 mmol) at room temperature. The mixture was stirred at room temperature for 30 min and adjusted with saturated aqueous sodium bicarnonate till pH becomes 7. The resulting mixture was extracted with ethyl actate (50 mL×2). The combined organic phases were washed with saturated aqueous sodium chloride (30 mL×2), dried over anhydrous sodium sulfate and filtered. The filtrate was concentrated in vacuo and the residue was purified by silica gel chromatography eluted with PE/EtOAc(v/v)=5/1 to give the title compound 28b as a white solid (14.3 g, 100%).

Step 2) (4aS,7S,8R,9S,9aS)-8,9-bis(benzyloxy)-7-(4-chloro-3-(4-ethoxybenzyl)phenyl)-2-phenylhexahydro-4a,7-epoxy[1,3]dioxino[5,4-c]oxepine 28c To a mixture of sodium hydride (6.5 g, 163.8 mmol, 60% dispersion in Mineral oil) in anhydrous tetrahydrofuran (30 mL) was added dropwise a solution of (4aS,7S,8R,9R,9aS)-7-(4-chloro-3-(4-ethoxybenzyl)phenyl)-2-phenylhexahydro-4a,7-epoxy[1,3]dioxino[5,4-c]oxepine-8,9-diol 28b (14.3 g, 27.3 mmol) in anhydrous tetrahydrofuran (10 mL) at 0° C. The mixture was stirred at 0° C. for 30 min and room temperature for 1 hour. To the mixture were added benzyl bromide (13 g, 109.2 mmol) and a catalytic amount of tetrabutylammonium iodide at 0° C. The resulting mixture was stirred at room temperature for 12 hours. The reaction mixture was quenched with water at 0° C., adjusted with saturated aqueous ammonium chloride till pH becomes 7 and extracted with ethyl acetate (100 mL×3). The combined organic layers were washed with saturated aqueous sodium chloride (30 mL×2), dried over anhydrous sodium sulfate and filtered. The filtrate was concentrated in vacuo and the residue was purified by silica gel chromatography eluted with PE/EtOAc (v/v)=10/1 to give the title compound 28c as a white solid (17.6 g, 91.4%). The compound was characterized by the following spectroscopic data: $^1$H NMR (400 MHz, CDCl$_3$) δ (ppm): 7.44-7.41 (m, 4H), 7.37 (m, 4H), 7.35-7.30 (m, 5H), 7.21 (d, 1H), 7.16 (m, 2H), 7.08 (d, 2H), 6.86 (d, 2H), 6.78 (d, 2H), 5.67 (s, 1H), 4.94 (d, 1H), 4.79 (d, 1H), 4.73 (s, 1H), 4.64 (d, 1H), 4.39 (d, 1H), 4.25 (d, 1H), 4.18 (d, 1H), 4.07-3.94 (m, 6H), 3.87 (d, 1H), 3.72 (d, 1H), 1.41 (t, 3H).

Step 3) (1S,2S,3S,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-ol 28d To a solution of (4aS,7S,8R,9S,9aS)-8,9-bis(benzyloxy)-7-(4-chloro-3-(4-ethoxybenzyephenye-2-phenylhexahydro- 4a,7-epoxy[1,3]dioxino[5,4-c]oxepine 28c (17.56 g, 27.3 mmol) in acetonitrile (40 mL) was added p-toluenesulfonic acid monohydrate (9.4 g, 54.6 mmol) at room temperature. The mixture was stirred at room temperature for 12 hours and adjusted with saturated aqueous sodium bicarnonate till pH becomes 7. The resulting mixture was extracted with ethyl actate (100 mL×3). The combined organic phases were washed with saturated aqueous sodium chloride (30 mL×2), dried over anhydrous sodium sulfate and filtered. The filtrate was concentrated in vacuo and the residue was purified by silica gel chromatography eluted with PE/EtOAc(v/v)=3/1 to give the title compound 28d as a yellow solid (11.68 g, 76.0%). The compound was characterized by the following spectroscopic data: $^1$H NMR (600 MHz, CDCl$_3$) δ (ppm): 7.35 (d, 1H), 7.29-7.26 (m, 4H), 7.24 (d, 3H), 7.11 (m, 3H), 6.99 (d, 2H), 6.82 (d, 2H), 6.67 (d, 2H), 4.79 (d, 1H), 4.62 (d, 1H), 4.15 (m, 2H), 3.99 (d, 1H), 3.90 (m, 4H), 3.76 (m, 4H), 3.57 (d, 2H), 1.31 (t, 3H).

Step 4) (1R,2S,3S,4R,5S)-3,4-dibenzyloxy-1-[(tert-butyl(dimethyl)silyl)oxymethyl]-5-[4-chloro-3-[(4-ethoxyphenyl)methyl]phenyl]-6,8-dioxabicyclo[3.2.1]octan-2-ol 28e To a solution of (1S,2S,3S,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-ol 28d (11.68 g, 18.9 mmol) in dichloromethane (40 mL) were added tert-butyldimethylsilyl chloride (3.4 g, 22.68 mmol), imidazole (2.57 g, 37.8 mmol) and a catalytic amount of 4-dimethylaminopyridine in turn at 0° C. The mixture was stirred at room temperature for 30 min and adjusted with saturated aqueous sodium bicarnonate till pH becomes 7. The resulting mixture was extracted with dichloromethane (50 mL×3). The combined organic phases were washed with saturated aqueous sodium chloride (30 mL×2), dried over anhydrous sodium sulfate and filtered. The filtrate was concentrated in vacuo to give the title compound 28e as a white solid (15.9 g, 100%). The crude product was used for next step without further purification.

Step 5) (1R,3R,4R,5S)-3,4-dibenzyloxy-1-[(tert-butyl(dimethyl)silyl)oxymethyl]-5-[4-chloro-3-[(4-ethoxyphenyl)methyl]phenyl]-6,8-dioxabicyclo[3.2.1]octan-2-one 28f To a solution of (1R,2S,3S,4R,5S)-3,4-dibenzyloxy-1-[(tert-butyl(dimethyl) silyl)oxymethyl]-5-[4-chloro-3-[(4-ethoxyphenyl)methyl]phenyl]-6,8-dioxabicyclo[3.2.1]octan-2-ol 28e (15.9 g, 21.7 mmol) in dichloromethane (40 mL) was added Dess-Martin periodinane (18.4 g, 43.5 mmol) at 0° C. The mixture was stirred at 0° C. for 3 hours and adjusted with saturated aqueous sodium bicarnonate till pH becomes 7. The resulting mixture was extracted with dichloromethane (100 mL×2). The combined organic phases were washed with saturated aqueous sodium chloride (100 mL×2), dried over anhydrous sodium sulfate and filtered. The filtrate was concentrated in vacuo to give the title compound 28f as colorless oil (15.9 g, 100%). The crude product was used for next step without further purification.

Step 6) (1S,3R,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-one 28g To a solution of (1R,3R,4R,5S)-3,4-dibenzyloxy-1-[(tert-butyl(dimethyl)silyl)oxymethyl]-5-[4-chloro-3-[(4-ethoxyphenyl)methyl]phenyl]-6,8-dioxabicyclo[3.2.1]octan-2-one 28f (15.9 g, 21.8 mmol) in tetrahydrofuran (40 mL) was added tetrabutylammonium fluoride (48 mL, 43.6 mmol, 1 M in tetrahydrofuran) at room temperature. The mixture was stirred at room temperature for 2 hours and extracted with ethyl acetate (100 mL×2). The combined organic phases were washed with water (100 mL×3) and then saturated aqueous sodium chloride (100 mL×3), dried over anhydrous sodium sulfate and filtered. The filtrate was concentrated in vacuo to give the title compound 28g as colorless oil (13.4 g, 100%). The crude product was used for next step without further purification. The compound was characterized by the following spectroscopic data: $^1$H NMR (600 MHz, CDCl$_3$) δ (ppm): 7.31 (d, 2H), 7.29-7.22 (m, 6H), 7.13 (m, 1H), 7.07 (m, 2H), 6.98 (d, 2H), 6.75 (d, 2H), 6.68 (d, 2H), 5.28 (s, 1H), 4.93 (d, 1H), 4.59 (d, 1H), 4.31 (m, 2H), 4.10 (d, 1H), 3.99 (m, 2H), 3.96-3.92 (m, 3H), 3.88 (m, 3H), 1.31 (t, 3H).

Step 7) [(1R,3R,4R,5S)-3,4-dibenzyloxy-5-[4-chloro-3-[(4-ethoxyphenyl)methyl]phenyl]-2-oxo-6,8-dioxabicyclo[3.2.1]octan-1-yl]methyl acetate 28h To a solution of (1S,3R,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-one 28g (13.4 g, 21.8 mmol) in dichloromethane (40 mL) were added acetic anhydride (3.0 mL, 32.7 mmol) and triethylamine (6.0 mL, 43.6 mmol) at room temperature. The mixture was stirred at room temperature for 2 hours and quenched with water (100 mL). The resulting mixture was extracted with dichloromethane (100 mL×2). The combined organic phases were washed with saturated aqueous sodium chloride (100 mL×3), dried over anhydrous sodium sulfate and filtered. The filtrate was concentrated in vacuo. The residue was purified by silica gel chromatography eluted with PE/EtOAc(v/v)=10/1 to give the title compound 28h as a pale yellow solid (12.1 g, 84.6%). The compound was characterized by the following spectroscopic data: $^1$H NMR (600 MHz, CDCl$_3$) δ (ppm): 7.29 (m, 4H), 7.24 (m, 3H), 7.19 (s, 1H), 7.12 (d, 1H), 7.07 (m, 2H), 6.99 (d, 2H), 6.76 (m, 2H), 6.68 (d, 2H), 4.94 (d, 1H), 4.58 (d, 1H), 4.47 (d, 1H), 4.37 (d, 1H), 4.31 (m, 2H), 4.07 (d, 1H), 3.95 (m, 3H), 3.88 (m, 5H), 1.97 (s, 3H), 1.31 (t, 3H).

Step 8) [(1R,2R,3S,4R,5S)-3,4-dibenzyloxy-5-[4-chloro-3-[(4-ethoxyphenyl)methyl]phenyl]-2-hydroxy-6,8-dioxabicyclo[3.2.1]octan-1-yl]methyl acetate 28i To a solution of [(1R,3R,4R,5S)-3,4-dibenzyloxy-5-[4-chloro-3-[(4-ethoxyphenyl)methyl]phenyl]-2-oxo-6,8-dioxabicyclo[3.2.1]octan-1-yl]methyl acetate 28h (4.09 g, 6.2 mmol) in an anhydrous methanol/tetrahydrofuran mixture (v/v=3/1, 20 mL) was added sodium borohydride (278 mg, 7.5 mmol) at 0° C. The mixture was stirred at 0° C. for 5 min, then quenched with water at 0° C. and adjusted with saturated aqueous ammonium chloride till pH becomes 7. The mixture was concentrated in vacuo to remove parts of the solvent. The resulting mixture was extracted with ethyl acetate (100 mL×3). The combined organic layers were washed with saturated aqueous sodium chloride (100 mL×3), dried over anhydrous sodium sulfate and filtered. The filtrate was concentrated in vacuo to give the title compound 28i as pale yellow oil (4.08 g, 100%). The compound was characterized by the following spectroscopic data: $^1$H NMR (400 MHz, DMSO-d$_6$) δ (ppm): 7.50 (m, 2H), 7.38 (d, 3H), 7.30 (m, 3H), 7.21 (m, 3H), 7.03 (d, 2H), 6.80 (d, 2H), 6.74 (d, 2H), 5.17 (d, 1H), 4.75 (d, 1H), 4.52 (d, 1H), 4.41 (d, 1H), 4.34 (d, 1H), 4.27 (d, 1H), 4.13 (d, 1H), 3.99 (m, 2H), 3.94 (m, 3H), 3.85 (m, 3H), 3.71 (d, 1H), 2.01 (s, 3H), 1.28 (t, 3H).

Step 9) (1S,2R,3S,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-ol 28j To a solution of [(1R,2R,3S,4R,5S)-3,4-dibenzyloxy-5-[4-chloro-3-[(4-ethoxyphenyl)methyl]phenyl]-2-hydroxy-6,8-dioxabicyclo[3.2.1]octan-1-yl]methyl acetate 28i (237 mg, 0.36 mmol) in methanol (20 mL) was added potassium carbonate (199 mg, 1.44 mmol) at room temperature. The mixture was stirred at room temperature for 5 min and adjusted with saturated aqueous ammonium chloride till pH becomes 7. The resulting mixture was extracted with ethyl acetate (10 mL×3). The combined organic layers were washed with saturated aqueous sodium chloride (10 mL×3), dried over anhydrous sodium sulfate and filtered. The filtrate was concentrated in vacuo to give the title compound 28j as a white solid (222 mg, 100%).

Step 10) (1S,2R,3S,4R,5S)-3,4-dibenzyloxy-5-[4-chloro-3-[(4-ethoxyphenyl)methyl]phenyl]-2-hydroxy-6,8-dioxabicyclo[3.2.1]octane-1-carbaldehyde 28k To a solution of (1S,2R,3S,4R,5S)-3,4-dibenzyloxy-5-[4-chloro-3-[(4-ethoxyphenyl)methyl]phenyl]-1-(hydroxymethyl)-6,8-dioxabicyclo[3.2.1]octan-2-ol 28j (0.22 g, 0.36 mmol) in dichloromethane (20 mL) was added saturated aqueous sodium bicarbonate (0.3 g, 3.6 mmol) at room temperature. To the mixture was added potassium bromide (25.7 mg, 0.22 mmol), 2,2,6,6-tetramethylpiperidinooxy (5.6 mg, 0.04 mmol) and sodium hypochlorite (0.8 mL, 0.94 mmol, 3.14% available chlorine) in turn at 0° C. The resulting mixture was stirred at 0° C. for 10 min and adjusted with saturated aqueous ammonium chloride till pH becomes 7. The resulting mixture was extracted with dichloromethane (15 mL×2). The combined organic layers were washed with water (10 mL×2) and saturated aqueous sodium chloride (10 mL×2), dried over anhydrous sodium sulfate and filtered. The filtrate was concentrated in vacuo to give the title compound 28k as a white solid (221 mg, 100%).

Step 11) (1R,2R,3S,4R,5S)-3,4-dibenzyloxy-5-[4-chloro-3-[(4-ethoxyphenyl)methyl]phenyl]-1-(1-hydroxyethyl)-6,8-dioxabicyclo[3.2.1]octan-2-ol 28l To a solution of (1S,2R,3S,4R,5S)-3,4-dibenzyloxy-5-[4-chloro-3-[(4-ethoxyphenyl)methyl]phenyl]-2-hydroxy-6,8-dioxabicyclo[3.2.1]octane-1-carbaldehyde 28k (221 mg, 0.36 mmol) in anhydrous tetrahydrofuran (20 mL) was added methylmagnesium bromide (0.48 mL, 1.44 mmol, 3 M in tetrahydrofuran) at 0° C. The mixture was stirred at room temperature for 18 hours and quenched with water (10 mL). The resulting mixture was extracted with ethyl acetate (20 mL×3). The combined organic layers were washed with saturated aqueous sodium chloride (20 mL×2), dried over anhydrous sodium sulfate and filtered. The filtrate was concentrated in vacuo. The residue was purified by silica gel chromatography eluted with PE/EtOAc(v/v)=10/1 to give the title compound 28l as a white solid (24 mg, 11.0%).

Step 12) (1R,2R,3S,4R,5S)-5-[4-chloro-3-[(4-ethoxyphenyl)methyl]phenyl]-1-(1-hydroxyethyl)-6,8-dioxabicyclo[3.2.1]octane-2,3,4-triol 28

To a solution of (1R,2R,3S,4R,5S)-3,4-dibenzyloxy-5-[4-chloro-3-[(4-ethoxyphenyl)methyl]phenyl]-1-(1-hydroxyethyl)-6,8-dioxabicyclo[3.2.1]octan-2-ol 281 (140 mg, 0.22 mmol) in a methanol/tetrahydrofuran mixture (v/v=4/1, 20 mL) were added hydrochloric acid (0.03 mL, 1.1 lmmol) and Pd/C (23 mg, 0.02 mmol, 10%) at room temperature. The mixture was stirred at room temperature under H$_2$ for 1 hour and filtered. The filtrate was adjusted with saturated aqueous sodium bicarbonate till pH becomes 7 and extracted with ethyl acetate (10 mL×3). The combined organic layers were washed with water (10 mL×3) and saturated aqueous sodium chloride (10 mL×2), dried over anhydrous sodium sulfate and filtered. The filtrate was concentrated in vacuo. The residue was purified by silica gel chromatography eluted with EtOAc to give the title compound 28 as a white solid (14 mg, 14.1%, HPLC: 86.0%). The compound was characterized by the following spectroscopic data: $^1$H NMR (600 MHz, DMSO-d$_6$) δ(ppm): 7.45 (s, 1H), 7.40 (m, 1H), 7.34 (m, 1H), 7.10 (d, 2H), 6.83 (d, 2H), 5.35-5.30 (m, 1H), 4.78 (d, 1H), 4.68 (s, 2H), 4.60 (d, 1H), 4.21-4.16 (m, 1H), 4.02-3.95 (m, 4H), 3.82-3.75 (m, 1H), 3.71 (d, 1H), 3.66-3.55 (m, 2H), 1.30 (t, 3H), 1.02 (d, 3H); and MS (ESI, pos. ion) m/z: 451.1[M+H]$^+$.

Example 29

(1R,2S,3S,4R,5S)-5-[4-Chloro-3-[(4-ethoxyphenyl)-hydroxy-methyl]phenyl]-[(1-hydroxyethyl]-6,8-dioxabicyclo[3.2.1]octane-2,3,4-triol 29

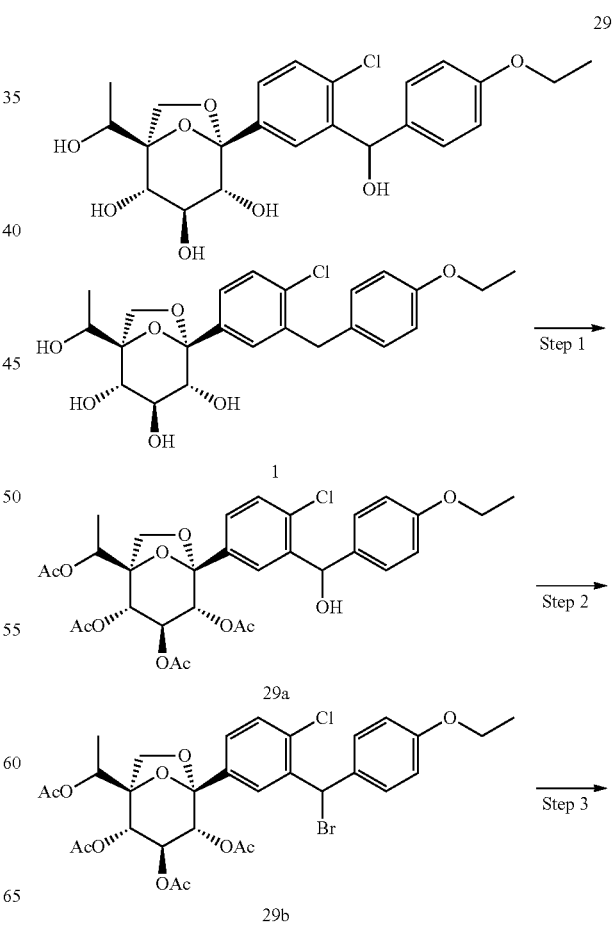

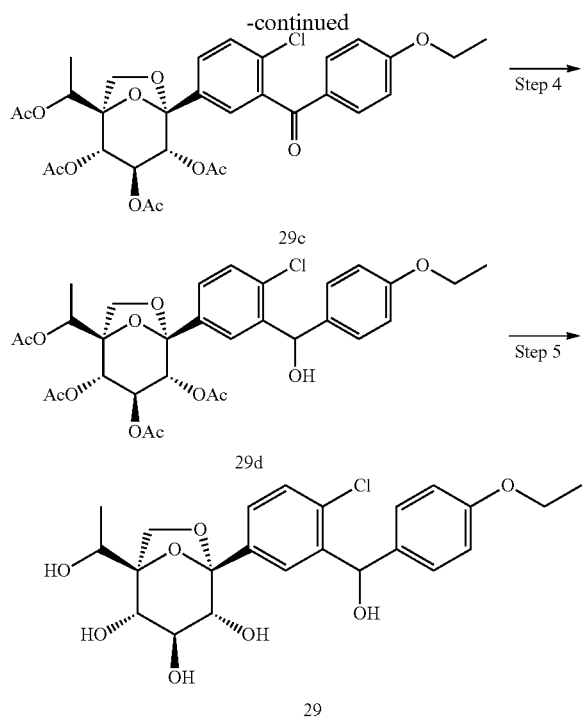

Step 1) [(1R,2S,3S,4R,5S)-2,4-diacetoxy-1-(1-acetoxyethyl)-5-[4-chloro-3-[(4-ethoxyphenyl)methyl]phenyl]-6,8-dioxabicyclo[3.2.1]octan-3-yl]acetate 29a To a solution of acetic anhydride (4.0 g, 39.1 mmol) and (1R,2S,3S,4R,5S)-5-[4-chloro-3-[(4-ethoxyphenyl)methyl]phenyl]-1-(1-hydroxyethyl)-6,8-dioxabicyclo[3.2.1]octane-2,3,4-triol 1 (1.96 g, 4.3 mmol) in dichloromethane (150 mL) was added triethylamine (9.0 mL, 64.5 mmol) at room temperature, and then a catalytic amount of 4-dimethylaminopyridine was added. The mixture was stirred at room temperature for 12 hours and adjusted with saturated aqueous ammonium chloride till pH becomes 7. The organic layer was washed with water (50 mL×2) and saturated aqueous sodium chloride (50 mL×2), dried over anhydrous sodium sulfate and filtered. The filtrate was concentrated in vacuo. The residue was purified by silica gel chromatography eluted with PE/EtOAc(v/v)=4/1 to give the title compound 29a as a white solid (2.64 g, 99.2%). The compound was characterized by the following spectroscopic data: $^1$H NMR (600 MHz, CDCl$_3$) δ (ppm): 7.38 (d, 1H), 7.34 (d, 1H), 7.32 (d, 1H), 7.09 (d, 2H), 6.83 (d, 2H), 5.49 (m, 1H), 5.41 (t, 1H), 5.25 (d, 1H), 5.09 (m, 1H), 4.40 (d, 1H), 4.10 (m, 1H), 4.04-3.98 (m, 3H), 3.84 (m, 1H), 2.10 (s, 3H), 2.07 (s, 3H), 2.00 (s, 3H), 1.71 (s, 3H), 1.41 (t, 3H), 1.34 (d, 3H).

Step 2) [(1R,2S,3S,4R,5S)-2,4-diacetoxy-1-(1-acetoxyethyl)-5-[3-[bromo-(4-ethoxyphenyl)methyl]-4-chloro-phenyl]-6,8-dioxabicyclo[3.2.1]octan-3-yl]acetate 29b To a solution of [(1R,2S,3S,4R,5S)-2,4-diacetoxy-1-(1-acetoxyethyl)-5-[4-chloro-3-[(4-ethoxyphenye methyl]phenyl]-6,8-dioxabicyclo[3.2.1]octan-3-yl]acetate 29a (0.5 g, 0.8 mmol) in tetrachloromethane (15 mL) were added N-bromosuccinimide (158 mg, 0.88 mmol) and 2,2'-azobis(2-methylpropionitrile) (11.8 mg, 0.07 mmol) in turn at room temperature under N$_2$. The mixture was refluxed for 12 hours and filtered. To the filtrate was added water (20 mL) and the mixture was partitioned. The aqueous layer was extracted with dichloromethane (20 mL×2). The combined organic layers were washed with water (20 mL×2) and then saturated aqueous sodium chloride (20 mL×2), dried over anhydrous sodium sulfate and filtered. The filtrate was concentrated in vacuo. The residue was purified by silica gel chromatography eluted with PE/EtOAc(v/v)=4/1 to give the title compound 29b as a white solid (278 mg, 49.8%). The compound was characterized by the following spectroscopic data: $^1$H NMR (600 MHz, CDCl$_3$) δ (ppm): 7.89 (d, 1H), 7.41-7.31 (m, 3H), 7.27 (d, 1H), 6.86 (m, 2H), 6.18-6.11 (m, 1H), 5.52 (t, 1H), 5.49-5.42 (m, 1H), 5.37-5.30 (m, 1H), 5.11 (m, 1H), 4.43 (t, 1H), 4.03 (m, 2H), 3.88 (d, 1H), 2.11 (s, 3H), 2.09 (s, 3H), 2.02 (s, 3H), 1.71 (s, 3H), 1.41 (t, 3H), 1.36 (d, 3H).

Step 3) [(1R,2S,3S,4R,5S)-2,4-diacetoxy-1-(1-acetoxyethyl)-5-[4-chloro-3-(4-ethoxybenzoyephenyl]-6,8-dioxabicyclo[3.2.1]octan-3-yl]acetate 29c To a solution of [(1R,2S,3S,4R,5S)-2,4-diacetoxy-1-(1-acetoxyethyl)-5-[3-[bromo-(4-ethoxyphenye methyl]-4-chloro-phenyl]-6,8-dioxabicyclo[3.2.1]octan-3-yl]acetate 29b (242 mg, 0.34 mmol) in dichloromethane (20 mL) was added Dess-Martin periodinane (220 mg, 0.52 mmol) at 0° C. The mixture was stirred at 0° C. for 3 hours and then to the reaction mixture were added saturated aqueous sodium bicarbonate (10 mL) and aqueous sodium thiosulfate (10 mL). The resulting mixture was further stirred for 30 min at 0° C. and partitioned. The aqueous layer was extracted with dichloromethane (20 mL×2). The combined organic layers were washed with water (20 mL×2) and then saturated aqueous sodium chloride (20 mL×2), dried over anhydrous sodium sulfate and filtered. The filtrate was concentrated in vacuo. The residue was purified by silica gel chromatography eluted with PE/EtOAc(v/v)=4/1 to give the title compound 29c as a white solid (411 mg, 87.2%). The compound was characterized by the following spectroscopic data: $^1$H NMR (600 MHz, CDCl$_3$) δ (ppm): 7.77 (d, 2H), 7.57-7.51 (m, 2H), 7.46 (d, 1H), 6.95 (d, 2H), 5.49 (d, 1H), 5.44 (t, 1H), 5.26 (d, 1H), 5.13-5.07 (m, 1H), 4.41 (d, 1H), 4.13 (m, 2H), 3.86 (d, 1H), 2.10 (s, 3H), 2.08 (s, 3H), 2.01 (s, 3H), 1.89 (s, 3H), 1.47 (t, 3H), 1.36 (d, 3H).

Step 4) [(1R,2S,3S,4R,5S)-2,4-diacetoxy-1-(1-acetoxyethyl)-5-[4-chloro-3-[(4-ethoxyphenyl)-hydroxy-methyl]phenyl]-6,8-dioxabicyclo[3.2.1]octan-3-yl]acetate 29d To a solution of [(1R,2S,3S,4R,5S)-2,4-diacetoxy-1-(1-acetoxyethyl)-5-[4-chloro-3-(4-ethoxybenzoyl) phenyl]-6,8-dioxabicyclo[3.2.1]octan-3-yl]acetate 29c (411 mg, 0.65 mmol) in anhydrous methanol (20 mL) was added sodium borohydride (98 mg, 2.5 mmol) at 0° C. The mixture was stirred at 0° C. for 10 min and quenched with water. Part of the solvent was removed in vacuo. The residue was extracted with ethyl acetate (10 mL×2). The combined organic layers were washed with water (10 mL×2) and then saturated aqueous sodium chloride (10 mL×2), dried over anhydrous sodium sulfate and filtered. The filtrate was concentrated in vacuo to give the title compound 29d as a white solid (377 mg, 91.5%). The crude product was used for next step without further purification.

Step 5) (1R,2S,3S,4R,5S)-5-[4-chloro-3-[(4-ethoxyphenyl)-hydroxy-methyl]phenyl]-1-(1-hydroxyethyl)-6,8-dioxabicyclo[3.2.1]octane-2,3,4-triol 29

To a solution of [(1R,2S,3S,4R,5S)-2,4-diacetoxy-1-(1-acetoxyethyl)-5-[4-chloro-3-[(4-ethoxyphenyl)-hydroxy-methyl]phenyl]-6,8-dioxabicyclo[3.2.1]octan-3-yl]acetate 29d (316 mg, 0.5 mmol) in methanol (20 mL) was added potassium carbonate (344 mg, 2.5 mmol) at room temperature. The mixture was stirred at room temperature for 2 hours. Part of the solvent was removed in vacuo. The residue was extracted with ethyl acetate (10 mL×2). The combined organic layers were washed with water (10 mL×2) and then saturated aqueous sodium chloride (10 mL×2), dried over anhydrous sodium sulfate and filtered. The filtrate was concentrated in vacuo. The residue was purified by silica gel chromatography eluted with EtOAc to give the title compound 29 as a white solid (47 mg, 20.0%, HPLC: 99.2%). The compound was characterized by the following spectroscopic data: $^1$H NMR (400 MHz, DMSO-$d_6$) δ (ppm): 7.84 (s, 1H), 7.32 (d, 2H), 7.19 (d, 2H), 6.84 (d, 2H), 5.93 (d, 1H), 5.90 (d, 1H), 5.31 (d, 1H), 5.02 (d, 1H), 4.91 (d, 1H), 4.65 (d, 1H), 4.04 (m, 1H), 4.01-3.96 (m, 2H), 3.88-3.82 (m, 1H), 3.79 (d, 1H), 3.61-3.55 (m, 1H), 3.46 (d, 1H), 3.44-3.39 (m, 1H), 1.30 (t, 3H), 1.17 (d, 3H); and MS (ESI, pos. ion) m/z: 5112[M+HCOO]$^-$.

Example 30

(1R,2S,3S,4R,5S)-5-[3-[(4-Ethoxyphenyl)methyl]phenyl]-1-(1-hydroxyethyl)-6,8-dioxabicyclo[3.2.1]octane-2,3,4-triol 30

To a solution of (1R,2S,3S,4R,5S)-5-[4-chloro-3-[(4-ethoxyphenyl)methyl]phenyl]-1-(1-hydroxyethyl)-6,8-dioxabicyclo[3.2.1]octane-2,3,4-triol 1 (10.0 g, 21.6 mmol, HPLC: 97.5%) in methanol (80 mL) were added Pd/C (1.5 g, 0.705 mmol, 5%) and triethylamine (5 mL, 32.4 mmol) at room temperature in turn. The mixture was stirred at room temperature under H$_2$ for 20 hours and filtered. The filtrate was concentrated in vacuo. To the residue were added ethyl acetate (80 mL) and water (50 mL) and the resulting mixture was stirred at room temperature for 5 min, then stood for a few minutes and partitioned. The organic layer was washed with saturated aqueous sodium chloride (50 mL×2), dried over anhydrous sodium sulfate and filtered. The filtrate was concentrated in vacuo to give the title compound 30 as a white solid (9.2 g, 99.6%, HPLC: 97.1%). The compound was characterized by the following spectroscopic data: $^1$H NMR (600 MHz, CD$_3$OD) δ (ppm): 7.43 (s, 1H), 7.38 (d, 1H), 7.26 (t, 1H), 7.15 (d, 1H), 7.11 (d, 2H), 6.82 (d, 2H), 4.18 (d, 1H), 4.01 (m, 3H), 3.95-3.91 (m, 3H), 3.80 (dd, 1H), 3.68 (t, 1H), 3.60 (d, 1H), 1.37 (t, 3H), 1.33 (d, 3H); and MS (ESI, pos. ion) m/z: 417.1[M+H]$^+$.

Example 31

(1R,2S,3S,4R,5S)-5-[4-chloro-3-[[4-(1,1,2,2,2-pentadeuterioethoxy)phenyl]methyl]phenyl]-1-(1-hydroxyethyl)-6,8-dioxabicyclo[3.2.1]octane-2,3,4-triol 31

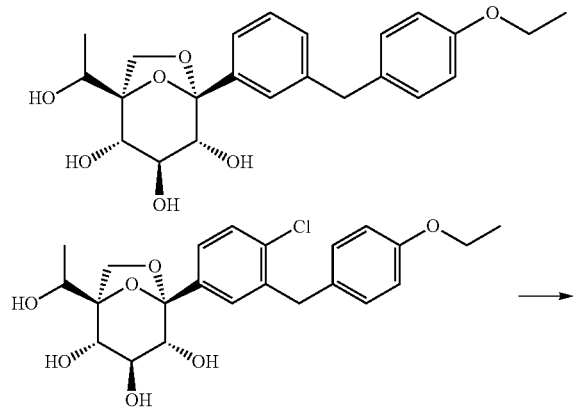

-continued

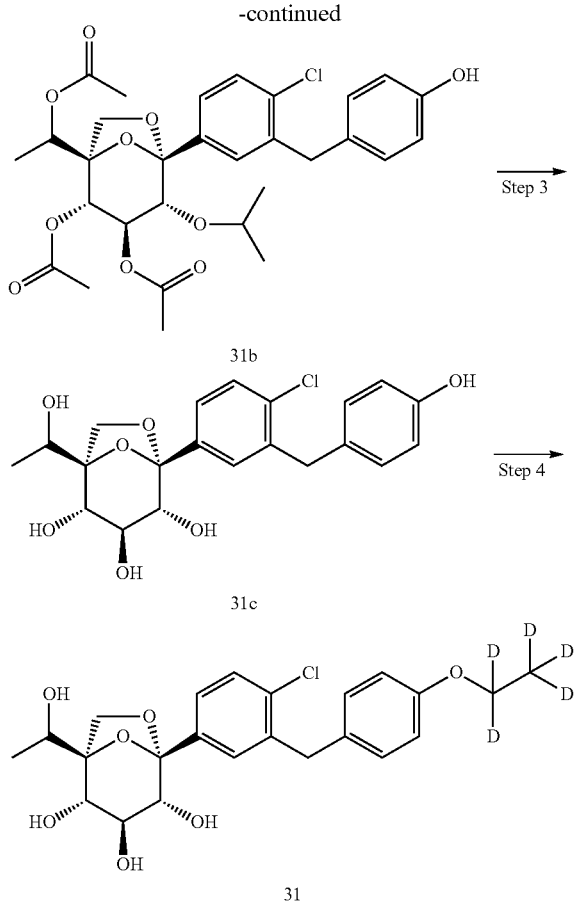

Step 1) [(1R,2S,3S,4R,5S)-2,4-diacetoxy-1-(1-acetoxyethyl)-5-[4-chloro-3-[(4-ethoxyphenyl)methyl]phenyl]-6,8-dioxabicyclo[3.2.1]octan-3-yl]acetate 31a To a dichloromethane solution (2 mL) were added acetic anhydride (0.5 mL, 5.3 mmol), (1R,2S,3S,4R,5S)-5-(4-chloro-3-(4-ethoxybenzyl)phenyl)-1-(1-hydroxyethyl)-6,8-dioxabicyclo[3.2.1]octane-2, 3,4-triol 1 (0.2 g, 0.44 mmol), 4-dimethylaminopyridine (6 mg, 0.05 mmol) and pyridine (0.4 mL, 5.0 mmol) at 0° C. The mixture was stirred at 0° C. for 30 min and then at room temperature for 2 hours. The reaction mixture was concentrated in vacuo. To the residue was added isopropyl ether (10 mL), the resulting mixture was washed with hydrochloric acid (10 mL×2, 1 N), saturated aqueous sodium bicarbonate (10 mL×2) and saturated aqueous sodium chloride (10 mL×2), dried over anhydrous sodium sulfate and filtered. The filtrate was concentrated in vacuo to give the title compound 31a as a white solid (0.27 g, 98.0%). The compound was characterized by the following spectroscopic data: $^1$H NMR (400 MHz, CDCl$_3$) δ (ppm): 7.35 (d, 1H), 7.31 (d, 1H), 7.29 (dd, 1H), 7.08 (d, 2H), 6.80 (d, 2H), 5.47 (dd, 1H), 5.39 (t, 1H), 5.23 (d, 1H), 5.07 (q, 1H), 4.37 (d, 1H), 4.08 (d, 1H), 3.99 (m, 3H), 3.82 (dd, 1H), 2.07 (s, 3H), 2.05 (s, 3H), 1.98 (s, 3H), 1.69 (s, 3H), 1.39 (t, 3H), 1.31 (d, 3H).

Step 2) [(1R,2S,3S,4R,5S)-2,4-diacetoxy-1-(1-acetoxyethyl)-5-[4-chloro-3-[(4-hydroxyphenyl)methyl]phenyl]-6,8-dioxabicyclo[3.2.1]octan-3-yl]acetate 31b To a solution of [(1R,2S,3S,4R,5S)-2,4-diacetoxy-1-(1-acetoxyethyl)-5-[4-chloro-3-[(4-ethoxyphenyl) methyl]phenyl]-6,8-dioxabicyclo[3.2.1]octan-3-yl]acetate 31a (4.8 g, 7.75 mmol) in dichloromethane (80 mL) were added boron tribromide (54 mL, 54 mmol, 1.0 M in dichloromethane) dropwsie at −78° C. under N$_2$. The mixture was stirred at −78° C. for 1 hour and then at −40° C. for 30 min, additional at −30° C. for 30 min. The reaction mixture was poured into ice water (100 g). The resulting mixture was adjusted with saturated aqueous sodium bicarbonate to pH 7, separated, and the organic layer was washed with saturated aqueous sodium chloride (50 mL×2), dried over anhydrous sodium sulfate and filtered. The filtrate was concentrated in vacuo. The residue was purified by silica gel chromatography eluted with PE/EtOAc(v/v)=2/1 to give the title compound 31b as a white foam (1.2 g, 23.0%, HPLC: 87.9%). The compound was characterized by the following spectroscopic data: MS m/z (ESI): 613.2 [M+Na]$^+$; and $^1$H NMR (400 MHz, CDCl$_3$) δ (ppm): 7.35 (d, 1H), 7.32-7.27 (m, 2H), 7.03 (d, 2H), 6.74 (d, 2H), 5.47 (d, 1H), 5.39 (t, 1H), 5.23 (d, 1H), 5.07 (q, 1H), 4.86 (s, 1H), 4.38 (d, 1H), 4.02 (dd, 2H), 3.85-3.77 (m, 1H), 2.07 (s, 3H), 2.05 (s, 3H), 1.98 (s, 3H), 1.69 (s, 3H), 1.31 (d, 3H).

Step 3) (1R,2S,3S,4R,5S)-5-[4-chloro-3-[(4-hydroxyphenyl)methyl]phenyl]-1-(1-hydroxyethyl)-6,8-dioxabicyclo[3.2.1]octane-2,3,4-triol 31c To a solution of [(1R,2S,3S,4R,5S)-2,4-diacetoxy-1-(1-acetoxyethyl)-5-[4-chloro-3-[(4-hydroxyphenyl)methyl]phenyl]-6,8-dioxabicyclo[3.2.1]octan-3-yl]acetate 31b (1.17 g, 1.98 mmol) in methanol (20 mL) was added sodium methoxide (85 mg, 1.57 mmol) at rt. The mixture was stirred at rt for 4 hours, and then acetic acid (0.1 mL) was added. The resulting mixture was concentrated in vacuo. The residue was purified by silica gel chromatography eluted with EtOAc to give the title compound 31c as a white foam (0.78 g, 93.2%). The compound was characterized by the following spectroscopic data: $^1$H NMR (400 MHz, MeOD) δ(ppm): 7.44 (d, 1H), 7.42-7.34 (m, 2H), 7.03 (d, 2H), 6.70 (d, 2H), 4.17 (d, 1H), 4.06-3.98 (m, 3H), 3.92 (d, 1H), 3.78 (d, 1H), 3.66 (t, 1H), 3.55 (d, 1H), 1.33 (d, 3H).

Step 4) (1R,2S,3S,4R,5S)-5-[4-chloro-3-[[4-(1,1,2,2,2-pentadeuterioethoxy)phenyl]methyl]phenyl]-1-(1-hydroxyethyl)-6,8-dioxabicyclo[3.2.1]octane-2,3,4-triol 31

To a solution of (1R,2S,3S,4R,5S)-5-[4-chloro-3-[(4-hydroxyphenyl)methyl]phenyl]-1-(1-hydroxyethyl)-6,8-dioxabicyclo[3.2.1]octane-2,3,4-triol 31c (790 mg, 1.87 mmol) in N,N-dimethylformamide (10 mL) were added cesium carbonate (790 mg, 2.42 mmol) and 1,1,2,2,2-pentadeuterioethoxy-4-methylbenzenesulfonate (570 mg, 2.78 mmol) at rt. The mixture was stirred at 75° C. under N$_2$ for 16 hours and then cooled to rt. The mixture was partitioned between water (30 mL) and ethyl acetate (20 mL). The organic layer was washed with saturated aqueous sodium chloride (20 mL×2), dried over anhydrous sodium sulfate and filtered. The filtrate was concentrated in vacuo. The residue was purified by silica gel chromatography eluted with EtOAc to give the title compound 31 as a white foam (0.54 g, HPLC: 94.1%).

A suspension of (1R,2S,3S,4R,5S)-5-[4-chloro-3-[[4-(1,1,2,2,2-pentadeuterioethoxy)phenyl]methyl]phenyl]-1-(1-hydroxyethyl)-6,8-dioxabicyclo[3.2.1]octane-2,3,4-triol 31 (0.54 g, 1.11 mmol) in anhydrous ethanol (2 mL) was stirred at rt for 1 hour and filtered. The filter cake was washed with water (1 mL) and dried in vacuo to give the title compound 31 as a white solid (0.34 g, 99.0%). The compound was characterized by the following spectroscopic data: MS m/z (ESI): 456.3 [M+H]$^+$; $^1$H NMR (600 MHz, DMSO-$d_6$) δ(ppm): 7.40 (dd, 2H), 7.30 (dd, 1H), 7.09 (d, 2H), 6.85-6.80 (m, 2H), 5.26 (d, 1H), 4.97 (d, 1H), 4.88 (d, 1H), 4.61 (d, 1H), 4.02-3.95 (m, 3H), 3.83 (p, 1H), 3.78-3.74 (m, 1H), 3.56-3.52 (m, 1H), 3.43 (td, 1H), 3.39-3.35 (m, 1H), 1.16 (d, 3H).

Biological Activity

SGLT-1 and SGLT-2 Activity Measurement

Test Purpose

The following methods can be used to determine the inhibitory activity of the compounds described in the invention for SGLT-1 and SGLT-2.

Test Materials $^{14}$C-AMG solution was purchased from PerkinElmer, Cat. No. NEZ080001MC.

α-Methylglucoside was purchased from Sigma, Cat. No. M9376-100G.

N-methyl-D-glucosamine was purchased from Sigma, Cat. No. M2004-100G.

Phloridzin was purchased from Sigma, Cat. No. P3449-1G.

96-Well plate was purchased from Corning, Cat. No. 3903.

Test Method

Mock-transfected FIP-in CHO cells (3×10$^4$ cells) and expressing human SGLT1/SGLT2 CHO cells were seeded into 96-well plates respectively. The cells were incubated for 12 hours. Each well of the 96-well plates was washed with 150 μL of sodium-free buffer once. To each well was added 50 μL of sodium-containing buffer containing test compounds having different concentrations and 0.5 μm [$^{14}$C]-AMG. The incubation mixture was incubated at 37° C. for 1 hour. To each well was added 150 μL of precooled sodium-free buffer to terminate the reaction. The cell pellet was washed with sodium-free buffer three times and the residual liquid in well was removed. To each well was added 20 μL of precooled 100 mM NaOH. The 96-well plates were vibrated at 900 rpm for 5 minutes. Scintillation fluid (80 μL) was added to each well which was then vibrated at 600 rpm for 5 minutes. The amount of $^{14}$C-AMG was quantitatively detected using liquid scintillation. The results are shown in table 1:

TABLE 1

| Example Number | IC$_{50}$(SGLT-2)/nM | IC$_{50}$(SGLT-1)/nM |
|---|---|---|
| 1 | 1.65 | 260 |
| 2 | 1.14 | 110 |
| 3 | 9.8 | — |
| 4 | 9.39 | 4210 |
| 5 | — | 840 |
| 6 | 3.60 | 26810 |
| 7 | 4.96 | — |
| 8 | 51.8 | |
| 10 | 3729 | |
| 11 | 498.1 | |
| 12 | 12.7 | — |
| 13 | 44.15 | 3760 |
| 15 | 1.96 | 290 |
| 16 | 2.95 | 1310 |

TABLE 1-continued

| Example Number | IC$_{50}$(SGLT-2)/nM | IC$_{50}$(SGLT-1)/nM |
|---|---|---|
| 17 | 1.22 | 820 |
| 18 | 3.66 | 350 |
| 19 | 1.27 | 180 |
| 20 | 0.85 | 170 |
| 21 | 0.81 | 120 |
| 22 | 1.84 | 1040 |
| 23 | 2.28 | 560 |
| 24 | 2.19 | — |
| 25 | 3.48 | 5560 |
| 26 | 6.85 | — |
| 27 | 13.8 | — |
| 28 | 12.59 | 3400 |
| 29 | 1.46 | — |
| 30 | 12.1 | |

Conclusions: The compounds described in the present invention have high selectivity and significant inhibitory effect on SGLT-2.

OGTT and Test of Glycosuria Excretion

Test Purpose

The following methods were used to evaluate the effects of the compounds of the invention in improving oral glucose tolerance and glycosuria excretion.

Test Materials

The glucose was purchased from Cheng Du Kelong Chemical Reagent Company.

Glycosuria test was determined on Roche Biochemistry Analyzer.

Blood glucose test was determined on Roche Accu-Chek Performa Blood Glucose Meter.

Test Method

The weight and the blood glucose levels of C57BL/6 mice were measured after an overnight 15-hour fast. The mice were grouped by their weights and fasting plasma glucose levels. Each test group was administered the corresponding test compound once by gavage, and the blank control group was administered solvent. After 15 minutes, the blood glucose level (i.e. zero point blood glucose) of each group was measured, and each group was administered glucose (2.5 g/kg) immediately by gavage. The blood was drawn from the caudal vein of the C57BL/6 mice at 15, 30, 45, 60 and 120 minutes after glucose administration and the blood glucose levels were measured continuously on blood-glucose meter. After blood glucose level at 120 min time point was measured, each group was placed in a metabolism cage, and the urine was collected during 2.25 hours to 6 hours and 6 hours to 24 hours after drug administration with the metabolism cage as the unit. The urine volume of each metabolism cage at each point was measured and the glycosuria level was determined on automatic biochemical analyzer. The mice had free access to food and water during the urine collection.

The results of the test indicated that the compounds of the present invention have distinct effects in the improvement of oral glucose tolerance and glycosuria excretion.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples,"

in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, a racemate, an N-oxide, a hydrate, a solvate, or a pharmaceutically acceptable salt thereof,

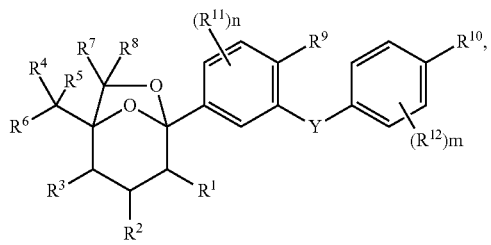

wherein each of $R^1$, $R^2$ and $R^3$ is OH;
wherein $R^6$ is —$OR^{6a}$ or —$OC(=O)R^{6b}$; and
each of $R^4$ and $R^5$ is independently —H, alkyl, alkylamino, alkynyl, alkenyl, cyano, cycloalkyl or heterocyclyl, and wherein optionally each of the alkyl, alkylamino, alkynyl, alkenyl, cycloalkyl and heterocyclyl is substituted by one or more substituents independently selected from —H, —F, —Cl, —Br, —I, hydroxy, cyano, amino, alkynyl, alkenyl, carboxy, mercapto, alkylamino, —$SR^{13}$, —$C(=O)R^{13}$, —$C(=O)OR^{13}$, —$OC(=O)R^{13}$, —$OC(=O)OR^{13}$, —$NHC(=O)R^{13}$, —$C(=O)NHR^{13}$, trifluoromethyl, —$S(=O)_2R^{13}$, —$S(=O)R^{13}$, aryl, heteroaryl, arylalkyl, heteroarylalkyl, arylalkoxy and heteroarylalkoxy, or
$R^4$ and $R^5$, together with the carbon atom to which they are attached, form a ring A, wherein the ring A is a saturated or unsaturated, 3- to 8-membered ring, and wherein the ring A optionally contains one or more atoms or atomic groups independently selected from —NH—, —O—, —S—, —C(=O)— and —S(=O)—, and wherein the ring A is optionally substituted by one or more substituents independently selected from —H, —F, —Cl, —Br and —I; or
wherein $R^4$ is —H; and
$R^5$ and $R^6$, together with the carbon atom to which they are attached, form a ring B, wherein the ring B is a saturated or unsaturated, 3- to 8-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;
wherein $R^{6a}$ is —H, alkyl, cycloalkyl, heterocyclyl, aryl, heteroaryl, arylalkyl or heteroarylalkyl, and wherein optionally each of the alkyl, cycloalkyl, heterocyclyl, aryl, heteroaryl, arylalkyl and heteroarylalkyl is substituted by one or more substituents independently selected from —H, —F, —Cl, —Br, —I, hydroxy, cyano, amino, alkynyl, alkenyl, carboxy, mercapto, trifluoromethyl, —$SR^{14}$, —$C(=O)R^{14}$, —$C(=O)OR^{14}$, —$OC(=O)R^{14}$, —$OC(=O)OR^{14}$, —$NHC(=O)R^{14}$, —$S(=O)_2R^{14}$ and —$S(=O)R^{14}$;
wherein $R^{6b}$ is alkyl, alkoxy, arylalkoxy or heteroarylalkoxy, and wherein optionally each of the alkoxy, arylalkoxy or heteroarylalkoxy is substituted by one or more substituents independently selected from —H, —F, —Cl, —Br, —I, hydroxy, cyano, amino, alkynyl, alkenyl, carboxy and mercapto;
wherein $R^7$ is —H, alkyl, alkylamino, alkynyl or alkenyl;
wherein $R^8$ is —H, alkylamino, alkynyl or alkenyl;
wherein at least one of $R^4$, $R^5$, $R^7$ and $R^8$ is not H;
wherein $R^9$ is —H, —F, —Cl, —Br, —I or $C_{1-6}$ alkyl;
wherein $R^{10}$ is $C_{1-6}$ alkoxy or $C_{1-6}$ haloalkoxy;
wherein Y is methylene, which is optionally substituted by one or more substituents independently selected from —H, —F, —Cl, —Br and hydroxy;
wherein each $R^{11}$ is independently —H, —F, —Cl, —Br, —I or $C_{1-6}$ alkoxy;
wherein n is 1, 2 or 3;
wherein each $R^{12}$ is independently —H, —F, —Cl or —I;
wherein m is 1, 2, 3 or 4; and
wherein each $R^{13}$ and $R^{14}$ is independently —H, alkyl, aryl, heteroaryl, cycloalkyl or heterocyclyl, and wherein optionally each of the alkyl, aryl, heteroaryl, cycloalkyl and heterocyclyl is substituted by one or more substituents independently selected from —H, —F, —Cl, —Br, —I, hydroxy, amino, cyano, alkyl, alkoxy, alkylamino, hydroxyalkyl, cycloalkoxy, aryloxy, heteroaryloxy, heterocycloalkoxy, trifluoromethyl, carboxy and —C(=O)O-alkyl.

2. The compound of claim 1, having Formula (II), or a stereoisomer, a geometric isomer, a tautomer, a racemate, an N-oxide, a hydrate, a solvate, or a pharmaceutically acceptable salt thereof,

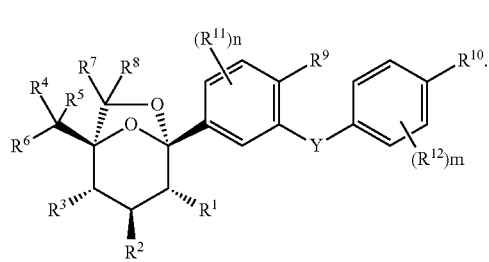

3. The compound of claim 1,
wherein each of $R^4$ and $R^5$ is independently —H, $C_{1-6}$ alkyl, $C_{1-4}$ alkylamino, $C_{2-4}$ alkynyl, $C_{2-4}$ alkenyl, cyano, $C_{3-6}$ cycloalkyl or $C_{2-6}$ heterocyclyl, and wherein optionally each of the $C_{1-6}$ alkyl, $C_{1-4}$ alkylamino, $C_{2-4}$ alkynyl, $C_{2-4}$ alkenyl, $C_{3-6}$ cycloalkyl and $C_{2-6}$ heterocyclyl is substituted by one or more substituents independently selected from —H, —F, —Cl, —Br, —I, hydroxy, cyano, amino, $C_{2-4}$ alkynyl, $C_{2-4}$ alkenyl, carboxy, mercapto, $C_{1-2}$ alkylamino, —$SR^{13}$, —$C(=O)R^{13}$, —$C(=O)OR^{13}$, —$OC(=O)R^{13}$, —$OC(=O)OR^{13}$, —$NHC(=O)R^{13}$, —$C(=O)NHR^{13}$, trifluoromethyl, —$S(=O)_2R^{13}$, —$S(=O)R^{13}$, $C_{6-10}$ aryl, $C_{1-9}$ heteroaryl, $C_{6-10}$ aryl-$C_{1-6}$-alkyl, $C_{1-9}$ heteroaryl-$C_{1-6}$-alkyl, $C_{6-10}$ aryl-$C_{1-6}$-alkoxy and $C_{1-9}$ heteroaryl-$C_{1-6}$-alkoxy, or $R^4$ and $R^5$, together with the carbon atom to which they are attached, form a ring A, wherein the ring A is a saturated or unsaturated, 3 to 6 membered ring, and wherein the ring A optionally contains one or more atoms or atomic groups independently selected from —NH—, —O—, —S—, —C(=O)— and —S(=O)—, and wherein the ring A is optionally substituted by one or more substituents independently selected from —H, —F, —Cl, —Br and —I.

4. The compound of claim 1,
wherein each of $R^4$ and $R^5$ is independently —H, methyl, ethyl, propyl, allyl, cyano, aminomethyl, methylamino, methylaminomethyl, dimethylaminomethyl, ethylamino, ethynyl, 1-propinyl, 2-propinyl, hydroxymethyl, chloromethyl, cyclopropyl or cyclobutyl, or $R^4$ and $R^5$, together with the carbon atom to which they are attached, form a ring A, wherein the ring A is a saturated or unsaturated, 3- to 4-membered ring, and wherein the ring A optionally contains one or more atoms or atomic groups selected from —NH—, —O—, —S—, —C(=O)— and —S(=O)—, and wherein the ring A is optionally substituted by one or more substituents independently selected from —H, —F, —Cl, —Br and —I.

5. The compound of claim 1,
wherein $R^6$ is —$OR^{6a}$ or —$OC(=O)R^{6b}$, or $R^5$ and $R^6$, together with the carbon atom to which they are attached, form a ring B, meanwhile $R^4$ is —H, wherein the ring B is a saturated or unsaturated, 3- to 6-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;

wherein $R^{6a}$ is —H, $C_{1-6}$ alkyl, $C_{3-6}$ cycloalkyl, $C_{2-6}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl, and wherein optionally each of the $C_{1-6}$ alkyl, $C_{3-6}$ cycloalkyl, $C_{2-6}$ heterocyclyl, $C_{6-10}$ aryl, $C_{1-9}$ heteroaryl, $C_{6-10}$ aryl-$C_{1-6}$-alkyl and $C_{1-9}$ heteroaryl-$C_{1-6}$-alkyl is substituted by one or more substituents independently selected from —H, —F, —Cl, —Br, —I, hydroxy, cyano, amino, $C_{2-4}$ alkynyl, $C_{2-4}$ alkenyl, carboxy, mercapto, trifluoromethyl, —$SR^{14}$, —$C(=O)R^{14}$, —$C(=O)OR^{14}$, —$OC(=O)R^{14}$, —$OC(=O)OR^{14}$, —$NHC(=O)R^{14}$, —$S(=O)_2R^{14}$ and —$S(=O)R^{14}$; and wherein $R^{6b}$ is $C_{1-6}$ alkyl, $C_{1-6}$ alkoxy, $C_{6-10}$ aryl-$C_{1-6}$-alkoxy or $C_{1-9}$ heteroaryl-$C_{1-6}$-alkoxy, and wherein optionally each of the $C_{1-6}$ alkoxy, $C_{6-10}$ aryl-$C_{1-6}$-alkoxy and $C_{1-9}$ heteroaryl-$C_{1-6}$-alkoxy is substituted by one or more substituents independently selected from —H, —F, —Cl, —Br, —I, hydroxy, cyano, amino, $C_{2-4}$ alkynyl, $C_{2-4}$ alkenyl, carboxy and mercapto.

6. The compound of claim 1,
wherein $R^6$ is —$OR^{6a}$ or —$OC(=O)R^{6b}$, or wherein $R^4$ is —H, and $R^5$ and $R^6$, together with the carbon atom to which they are attached, form a ring B, wherein the ring B is a saturated or unsaturated, 3- to 6-membered ring, and wherein the ring B optionally contains one or more atoms or atomic groups independently selected from —NH—, —O—, —S—, —C(=O)— and —S(=O)—, and wherein the ring B is optionally substituted by one or more substituents independently selected from —H, —F, —Cl, —Br and —I;

wherein $R^{6a}$ is —H, methyl, ethyl, iso-propyl, tert-butyl, chloromethyl or dichloromethyl; and wherein $R^{6b}$ is methyl, ethyl, iso-propyl, tert-butyl, methoxy, ethoxy, iso-propoxy or tert-butoxy.

7. The compound of claim 1, wherein $R^7$ is —H, $C_{1-4}$ alkyl, $C_{1-4}$ alkylamino, $C_{2-4}$ alkynyl or $C_{2-4}$ alkenyl; and $R^8$ is —H, $C_{1-4}$ alkylamino, $C_{2-4}$ alkynyl or $C_{2-4}$ alkenyl.

8. The compound of claim 1, wherein $R^7$ is —H, methyl, ethyl or isopropyl; and $R^8$ is —H.

9. The compound of claim 1, wherein $R^{10}$ is methoxy, ethoxy, isopropoxy, difluoromethoxy, trifluoromethoxy, 2,2-difluoroethoxy, 2,2,2-trifluoroethoxy or perfluoroethoxy.

10. The compound of claim 1, wherein each $R^{13}$ and $R^{14}$ is independently —H, $C_{1-6}$ alkyl, $C_{6-10}$ aryl, $C_{1-9}$ heteroaryl, $C_{3-8}$ cycloalkyl or $C_{2-8}$ heterocyclyl, and wherein optionally each of the $C_{1-6}$ alkyl, $C_{6-10}$ aryl, $C_{1-9}$ heteroaryl, $C_{3-8}$ cycloalkyl and $C_{2-8}$ heterocyclyl is substituted by one or more substituents independently selected from —H, —F, —Cl, —Br, —I, hydroxy, amino, cyano, $C_{1-4}$ alkyl, $C_{1-4}$ alkoxy, $C_{1-6}$ alkylamino, $C_{1-6}$ hydroxyalkyl, $C_{3-6}$ cycloalkoxy, $C_{6-10}$ aryloxy, $C_{1-9}$ heteroaryloxy, $C_{2-8}$ heterocyclyloxy, trifluoromethyl, carboxy and —$C(=O)O$—$C_{1-4}$ alkyl.

11. The compound of claim 1, having one of the following structures:

(1)

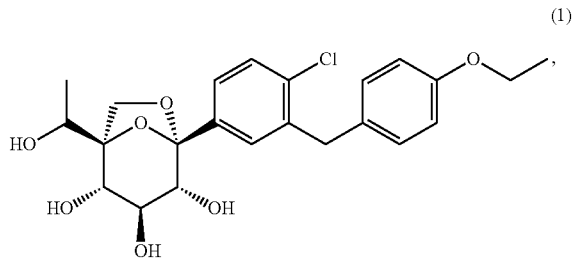

(2)

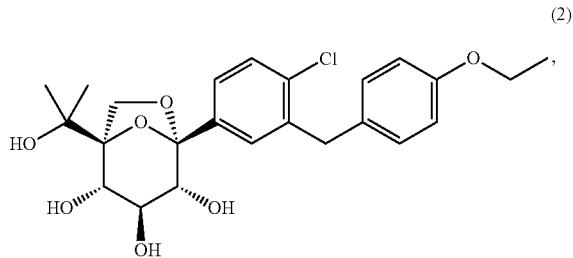

(3)

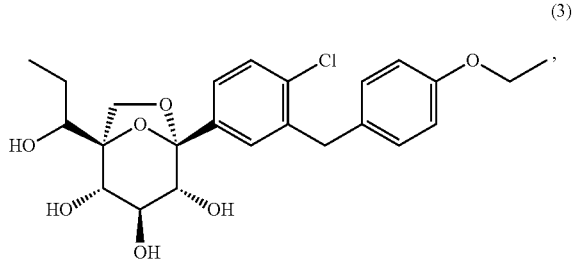

(4)

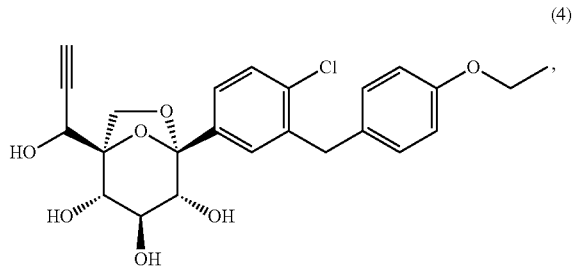

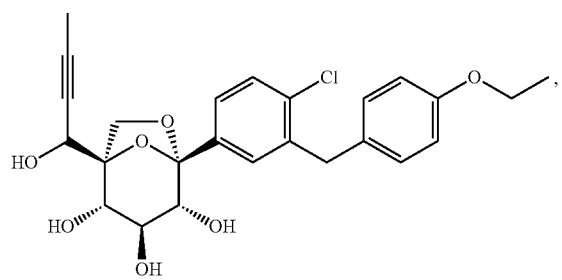 (5)
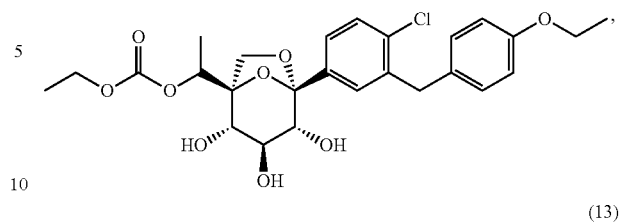 (12)
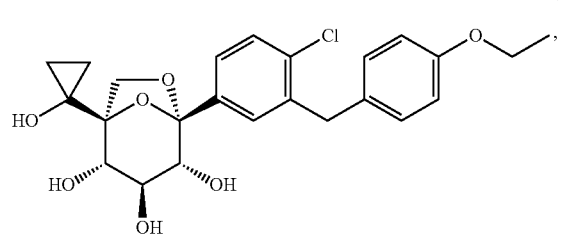 (6)
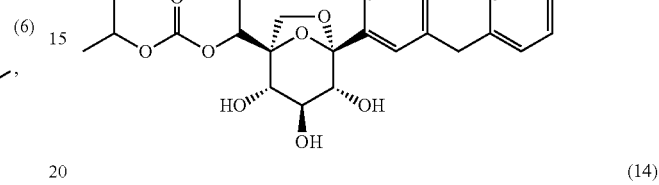 (13)
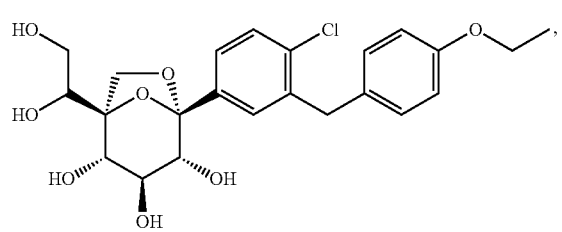 (7)
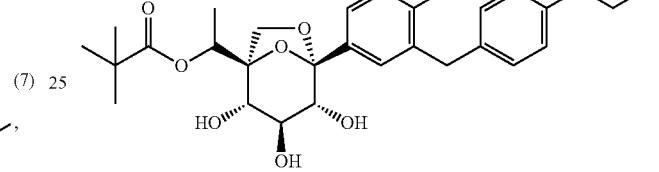 (14)
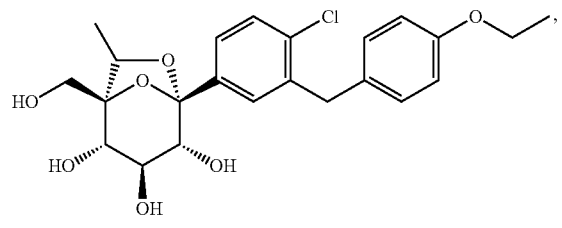 (8)
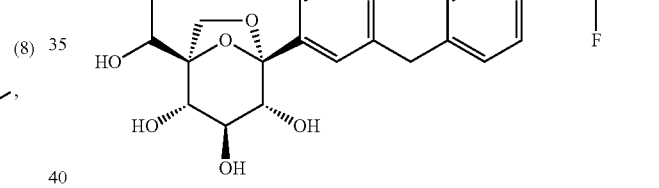 (15)
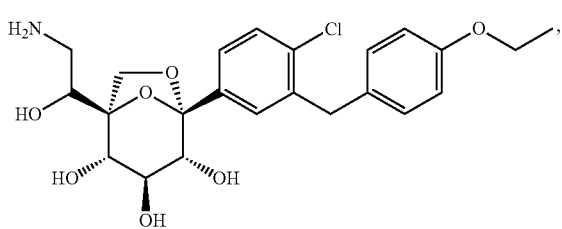 (10)
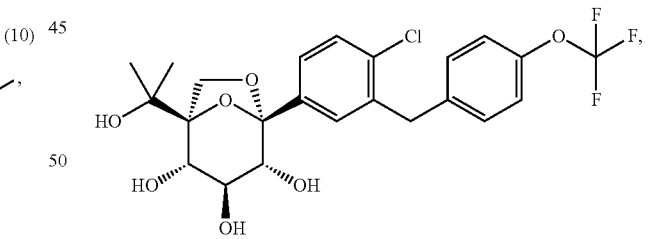 (16)
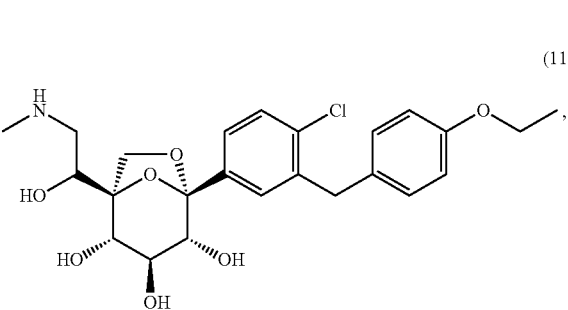 (11)
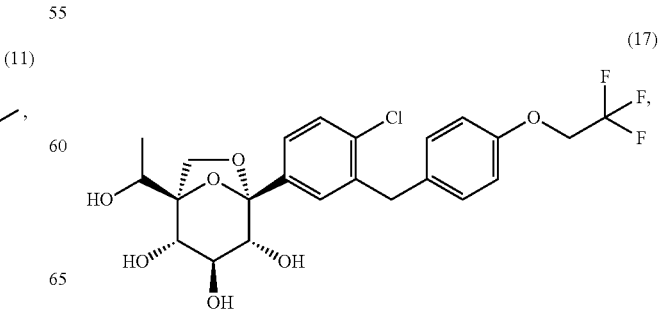 (17)

-continued
(18)
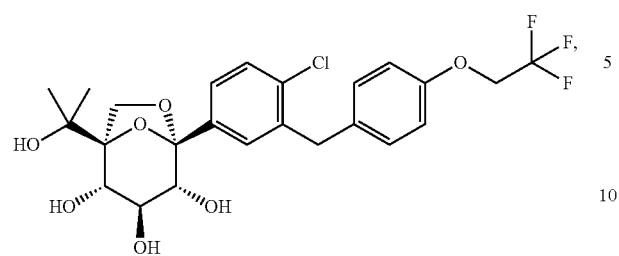
(19)
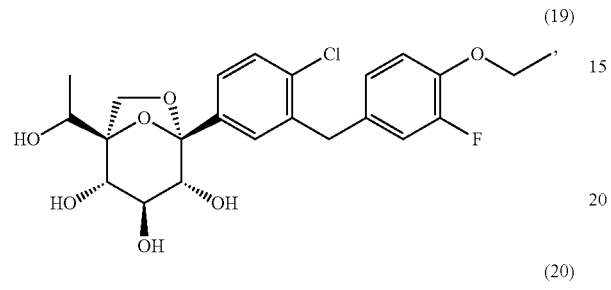
(20)
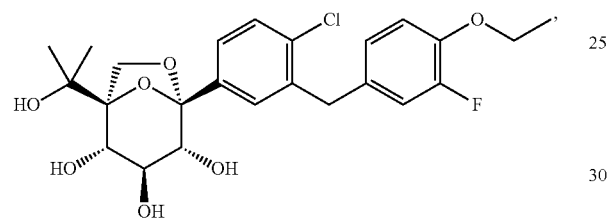
(21)
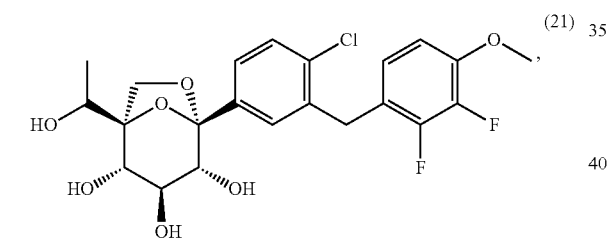
(22)
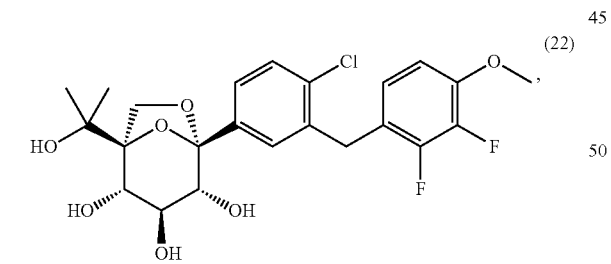
(23)
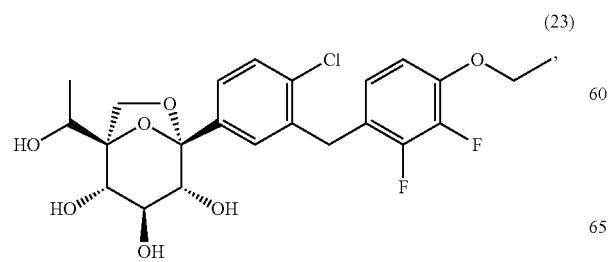
-continued
(24)
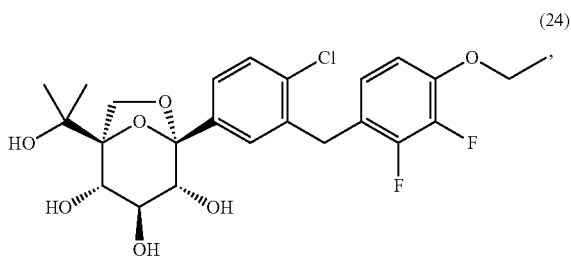
(25)
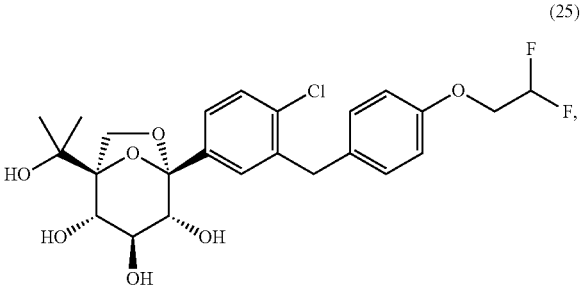
(26)
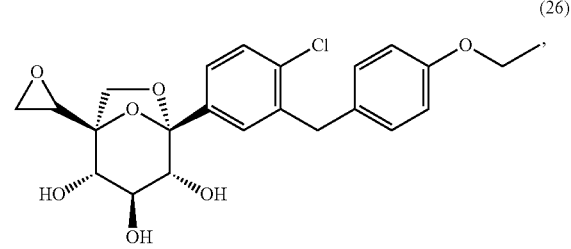
(27)
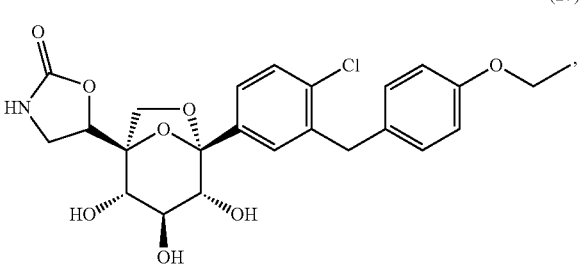
(28)
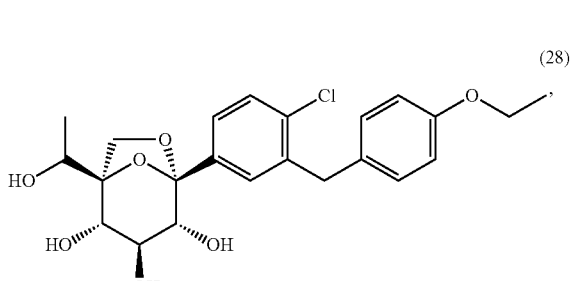
(29)
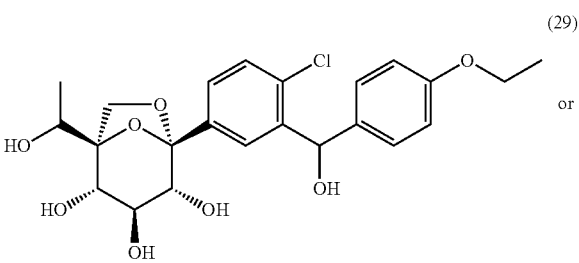 or -continued (30)

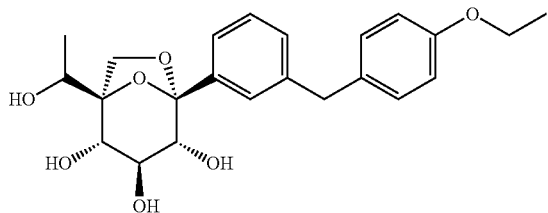

or a stereoisomer, a geometric isomer, a tautomer, a racemate, a hydrate, a solvate, or a pharmaceutically acceptable salt thereof.

12. A process for preparing a compound of Formula (I-b), comprising reacting a compound of Formula (I-a) with formaldehyde in the presence of 1,8-diazabicyclo[5.4.0]undec-7-ene in a polar solvent to afford the compound of Formula (I-b):

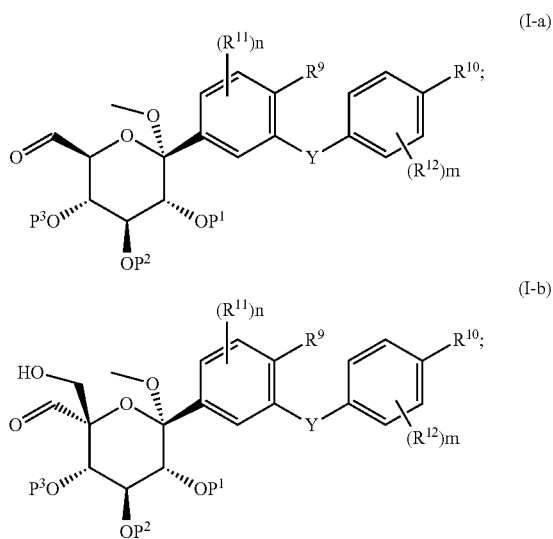

wherein each of $P^1$, $P^2$ and $P^3$ is independently a hydroxy-protecting group, and wherein the hydroxy-protecting group is trimethylsilyl, tert-butyldimethylsilyl, tert-butyldiphenylsilyl, triethylsilyl, triisopropylsilyl, 4-methoxybenzyl, benzyl, benzyloxycarbonyl, trimethylsilylethoxymethyl, tetrahydropyranyl, allyl, ethoxycarbonyl or acetyl;

wherein $R^9$ is —H, —F, —Cl, —Br, —I or $C_{1-6}$ alkyl;

$R^{10}$ is $C_{1-6}$ alkoxy or $C_{1-6}$ haloalkoxy;

Y is methylene, which is optionally substituted by one or two substituents independently selected from —H, —F, —Cl, —Br and hydroxy;

each is independently —H, —F, —Cl, —Br, —I or $C_{1-6}$ alkoxy;

n is 1, 2 or 3;

each $R^{12}$ is independently —H, —F, —Cl or I; and m is 1, 2, 3 or 4; or wherein $R^9$ is Cl;

$R^{10}$ is $C_{1-4}$ alkoxy or $C_{1-4}$ haloalkoxy;

each $R^{11}$ is independently —H; and each $R^{12}$ is independently —H or —F.

13. A pharmaceutical composition comprising the compound of claim 1 and a pharmaceutically acceptable carrier, excipient, diluent, adjuvant, vehicle or a combination thereof.

14. The pharmaceutical composition of claim 13 further comprising an additional therapeutic agent, wherein the additional therapeutic agent is an anti-diabetic agent other than an SGLT-2 inhibitor, an antihyperglycemic agent, an antiadipositas drug, an antihypertensive agent, an antiplatelet agent, an antiatherosclerotic drug, a lipid-lowering agent, an anti-inflammatory or a combination thereof.

15. The pharmaceutical composition of claim 14, wherein the anti-diabetic agent other than an SGLT-2 inhibitor or antihyperglycemic agent is a biguanide, a sulfonylurea, a glucosidase inhibitor, a PPAR agonist, an αP2 inhibitor, a PPARα/γ dual agonist, a dipeptidyl peptidase IV (DPP-IV) inhibitor, a meglitinide, insulin, a glucagon-like peptide-1 (GLP-1) inhibitor, a PTP1B inhibitor, a glycogen phosphorylase inhibitor, a glucose-6-phosphatase inhibitor or a combination thereof.

16. The pharmaceutical composition of claim 14, wherein the lipid-lowering agent is an MTP inhibitor, an HMGCoA reductase inhibitor, a squalene synthase inhibitor, a fabric acid derivative, an ACAT inhibitor, a lipoxygenase inhibitor, a cholesterol absorption inhibitor, an ileal Na(+)/bile acid cotransporter inhibitor, an upregulator of LDL receptor activity, niacin or a derivative thereof, a bile acid sequestrant or a combination thereof.

17. The pharmaceutical composition of claim 14, wherein the lipid-lowering agent is pravastatin, simvastatin, atorvastatin, fluvastatin, cerivastatin, atavastatin, rosuvastatin or a combination thereof.

18. A method for inhibiting the activity of SGLT-2, comprising administering to a patient in need thereof a therapeutically effective amount of the compound of claim 1.

19. A method for treating a disease, lessening a disease symptoms, or delaying the progression or onset of a disease or increasing HDL level, comprising administering to a patient in need thereof a therapeutically effective amount of the compound of claim 1, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis or hypertension.

20. A method for inhibiting the activity of SGLT-2, comprising administering to a patient in need thereof a therapeutically effective amount of the pharmaceutical composition of claim 13.

21. A method for treating a disease, lessening a disease symptoms, or delaying the progression or onset of a disease or increasing HDL level, comprising administering to a patient in need thereof a therapeutically effective amount of the pharmaceutical composition of claim 13, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis or hypertension.

22. A compound prepared by the process of claim 12, wherein the compound has Formula (I-b):

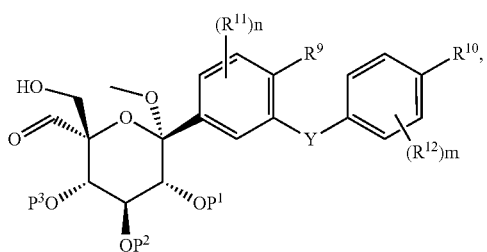

(I-b)

wherein each of $P^1$, $P^2$ and $P^3$ is independently a hydroxy-protecting group, and wherein the hydroxy-protecting group is trimethylsilyl, tert-butyldimethylsilyl, tert-butyldiphenylsilyl, triethylsilyl, triisopropylsilyl, 4-methoxybenzyl, benzyl, benzyloxycarbonyl, trimethylsilylethoxymethyl, tetrahydropyranyl, allyl, ethoxycarbonyl or acetyl;

wherein $R^9$ is —H, —F, —Cl, —Br, —I or $C_{1-6}$ alkyl;

$R^{10}$ is $C_{1-6}$ alkoxy or $C_{1-6}$ haloalkoxy;

Y is methylene, which is optionally substituted by one or more substituents independently selected from —H, —F, —Cl, —Br and hydroxy;

each is independently —H, —F, —Cl, —Br, —I or $C_{1-6}$ alkoxy;

n is 1, 2 or 3;

each $R^{12}$ is independently —H, —F, —Cl or I; and m is 1, 2, 3 or 4; or wherein $R^9$ is Cl;

$R^{10}$ is $C_{1-4}$ alkoxy or $C_{1-4}$ haloalkoxy;

each $R^{11}$ is independently —H; and each $R^{12}$ is independently —H or —F.

\* \* \* \* \*